(12) United States Patent
Chen et al.

(10) Patent No.: US 12,102,643 B2
(45) Date of Patent: Oct. 1, 2024

(54) AQUEOUS PHARMACEUTICAL FORMULATION OF HYDROCORTISONE SODIUM PHOSPHATE AND MONOTHIOGLYCEROL

(71) Applicant: ANTARES PHARMA, INC., Ewing, NJ (US)

(72) Inventors: Xiaoming Chen, Westfield, NJ (US); Shaowei Ong, Belle Mead, NJ (US)

(73) Assignee: Antares Pharma, Inc., Ewing, NJ (US)

( * ) Notice: Subject to any disclaimer, the term of this patent is extended or adjusted under 35 U.S.C. 154(b) by 0 days.

(21) Appl. No.: 18/189,613

(22) Filed: Mar. 24, 2023

(65) Prior Publication Data

US 2023/0302016 A1     Sep. 28, 2023

Related U.S. Application Data

(63) Continuation of application No. PCT/US2023/064771, filed on Mar. 21, 2023.

(60) Provisional application No. 63/321,997, filed on Mar. 21, 2022, provisional application No. 63/322,934, filed on Mar. 23, 2022, provisional application No. 63/387,727, filed on Dec. 16, 2022.

(51) Int. Cl.
*A61K 31/573*    (2006.01)
*A61K 47/18*    (2017.01)
*A61K 47/20*    (2006.01)

(52) U.S. Cl.
CPC .......... *A61K 31/573* (2013.01); *A61K 47/183* (2013.01); *A61K 47/20* (2013.01)

(58) Field of Classification Search
CPC ..... A61K 31/573; A61K 47/20; A61K 47/183
See application file for complete search history.

(56) References Cited

U.S. PATENT DOCUMENTS

| | | |
|---|---|---|
| 2,970,944 A | 2/1961 | Charnicki et al. |
| 3,696,195 A * | 10/1972 | Crivellaro ............. A61K 31/66 514/973 |
| 5,173,488 A | 12/1992 | Haeger |
| 5,733,572 A | 3/1998 | Unger |
| 6,028,066 A | 2/2000 | Unger |
| 8,021,335 B2 | 9/2011 | Lesch, Jr. |
| 8,814,834 B2 | 8/2014 | Sund et al. |
| 8,945,063 B2 | 2/2015 | Wotton et al. |
| 10,300,207 B2 | 5/2019 | Newton et al. |
| 10,456,355 B1 * | 10/2019 | Bardonnaud ........... A61P 11/06 |
| 10,653,839 B2 | 5/2020 | Vigot |
| 2001/0018072 A1 | 8/2001 | Unger |
| 2007/0105761 A1 | 5/2007 | Chappell |
| 2020/0255462 A1 | 8/2020 | Siddiqui-Jain et al. |
| 2022/0096496 A1 | 3/2022 | Chen et al. |

FOREIGN PATENT DOCUMENTS

| | | | |
|---|---|---|---|
| EP | 3189855 B1 | 3/2018 | |
| WO | WO-2018078285 A1 * | 5/2018 | ............. A61K 31/10 |
| WO | 2019213662 A1 | 11/2019 | |
| WO | 2023083825 A1 | 5/2023 | |

OTHER PUBLICATIONS

Solu-Cortef label(hydrocortisone sodiumsuccinate for injection,USP;Apr. 2010; Pharmacia & Upjohn Company a division of Pfizer,Inc.(2010) pp. 1-15. (Year: 2010).*
Efcortesol hydrocortisone sodium phosphate injection, Patient Information Leaflet, 102451-52/LF/057/03, Amdipharm, 1 page.
"How to give an emergency injection of Efcortesol" Information for families, Great Ormond Street Hospital for Children NHS Foundation Trust University College London Hospitals NHS Trust, 4 pages.
Solu-Cortef label (hydrocortisone sodium succinate for injection, USP; Apr. 2010; Pharmacia & Upjohn Company division of Pfizer, Inc. (2010), 15 pages.
International Search Report and Written Opinion issued in PCT/US2021/051349, mailed Jan. 20, 2022, 13 pages.
Office Action issued in U.S. Appl. No. 17/494,340, mailed Apr. 29, 2022, 9 pages.
Final Office Action issued in U.S. Appl. No. 17/494,340, mailed Sep. 28, 2022, 18 pages.
International Search Report and Written Opinion for PCT/US2023/064771, dated Jul. 5, 2023, 14 pages.

* cited by examiner

*Primary Examiner* — Theodore R. Howell
*Assistant Examiner* — George W Kosturko
(74) *Attorney, Agent, or Firm* — Morgan, Lewis & Bockius LLP

(57) ABSTRACT

The present disclosure provides aqueous formulations comprising hydrocortisone sodium phosphate and monothioglycerol. In some embodiments, the formulations comprise monobasic sodium phosphate, dibasic sodium phosphate, or disodium EDTA. The present disclosure further provides a method of treating a disease or disorder in a subject by administering the aqueous formulation.

15 Claims, 31 Drawing Sheets

AQUEOUS PHARMACEUTICAL FORMULATION OF HYDROCORTISONE SODIUM PHOSPHATE AND MONOTHIOGLYCEROL

CROSS-REFERENCE TO RELATED APPLICATIONS

The present application is a continuation application claiming priority to International Application No. PCT/US2023/064771, filed Mar. 21, 2023, which claims priority to U.S. Provisional Application Nos. 63/321,997, filed Mar. 21, 2022, 63/322,934, filed Mar. 23, 2022, and 63/387,727, filed Dec. 16, 2022, each of which applications is incorporated by reference herein in its entirety.

FIELD

The invention relates generally to hydrocortisone and hydrocortisone prodrugs, and pharmaceutically acceptable salts thereof, and related formulations.

BACKGROUND

Hydrocortisone is the name for the hormone cortisol when supplied as a medication. It is used in oral administration, intravenous injection, or topical application. It is used as an immunosuppressive drug, given by injection in the treatment of severe allergic reactions such as anaphylaxis and angioedema. It may be used topically for allergic rashes, eczema, psoriasis, itching and other inflammatory skin conditions.

Therapeutic hydrocortisone is a synthetic or semisynthetic analog of natural hydrocortisone hormone produced by the adrenal glands with primary glucocorticoid and minor mineralocorticoid effects. As a glucocorticoid receptor agonist, hydrocortisone promotes protein catabolism, gluconeogenesis, capillary wall stability, renal excretion of calcium, and suppresses immune and inflammatory responses.

SUMMARY

In one aspect, the present disclosure provides an aqueous pharmaceutical formulation comprising from about 50 to about 150 mg/mL hydrocortisone sodium phosphate, from about 2.5 to about 50 mg/mL monothioglycerol, and water. In one embodiment, the aqueous pharmaceutical formulation comprises from about 120 to about 130 mg/mL hydrocortisone sodium phosphate, from about 127 mg/mL to about 141 mg/mL hydrocortisone sodium phosphate, from about 130 to about 140 mg/mL hydrocortisone sodium phosphate, or from about 140 to about 150 mg/mL hydrocortisone sodium phosphate. In one embodiment, the aqueous pharmaceutical formulation comprises from about 127 mg/mL to about 141 mg/mL hydrocortisone sodium phosphate. In one embodiment, the aqueous pharmaceutical formulation comprises from about 130 to about 135 mg/mL hydrocortisone sodium phosphate, or from about 135 to about 140 mg/mL hydrocortisone sodium phosphate. In one embodiment, the aqueous pharmaceutical formulation comprises about 127 mg/mL mg/mL hydrocortisone sodium phosphate, about 128 mg/mL hydrocortisone sodium phosphate, about 129 mg/mL hydrocortisone sodium phosphate, about 130 mg/mL hydrocortisone sodium phosphate, about 131 mg/mL hydrocortisone sodium phosphate, about 132 mg/mL hydrocortisone sodium phosphate, about 133 mg/mL hydrocortisone sodium phosphate, about 134 mg/mL hydrocortisone sodium phosphate, about 135 mg/mL hydrocortisone sodium phosphate, about 136 mg/mL hydrocortisone sodium phosphate, about 137 mg/mL hydrocortisone sodium phosphate, about 138 mg/mL hydrocortisone sodium phosphate, about 139 mg/mL hydrocortisone sodium phosphate, about 140 mg/mL hydrocortisone sodium phosphate, or about 141 mg/mL hydrocortisone sodium phosphate. In one embodiment, the aqueous pharmaceutical formulation comprises about 134 mg/mL hydrocortisone sodium phosphate, about 134.1 mg/mL hydrocortisone sodium phosphate, about 134.2 mg/mL hydrocortisone sodium phosphate, about 134.3 mg/mL hydrocortisone sodium phosphate, about 134.4 mg/mL hydrocortisone sodium phosphate, about 134.5 mg/mL hydrocortisone sodium phosphate, about 134.6 mg/mL hydrocortisone sodium phosphate, about 134.7 mg/mL hydrocortisone sodium phosphate, about 134.8 mg/mL hydrocortisone sodium phosphate, about 134.9 mg/mL hydrocortisone sodium phosphate, or about 135 mg/mL hydrocortisone sodium phosphate. In one embodiment, the aqueous pharmaceutical formulation comprises from about 2.5 to about 3.5 mg/mL monothioglycerol, from about 3.5 to about 4.5 mg/mL monothioglycerol, from about 3.5 to about 5.5 mg/mL monothioglycerol, from about 4.5 to about 5.5 mg/mL monothioglycerol, from about 5.5 to about 6.5 mg/mL monothioglycerol, from about 6.5 to about 7.5 mg/mL monothioglycerol, from about 7.5 to about 8.5 mg/mL monothioglycerol, from about 8.5 to about 9.5 mg/mL monothioglycerol, from about 9.5 to about 10.5 mg/mL monothioglycerol, from about 10.5 to about 11.5 mg/mL monothioglycerol, or from about 11.5 to about 12.5 mg/mL monothioglycerol. In one embodiment, the aqueous pharmaceutical formulation comprises from about 4 to about 4.25 mg/mL monothioglycerol, from about 4.25 to about 4.5 mg/mL monothioglycerol, from about 4.5 to about 4.75 mg/mL monothioglycerol, from about 4.75 to about 5 mg/mL monothioglycerol, from about 5 to about 5.25 mg/mL monothioglycerol, from about 5.25 to about 5.5 mg/mL monothioglycerol, from about 5.5 to about 5.75 mg/mL monothioglycerol, or from about 5.75 to about 6 mg/mL monothioglycerol. In one embodiment, the aqueous pharmaceutical formulation comprises about 4.5 mg/mL monothioglycerol, about 4.6 mg/mL monothioglycerol, about 4.7 mg/mL monothioglycerol, about 4.8 mg/mL monothioglycerol, about 4.9 mg/mL monothioglycerol, about 5 mg/mL monothioglycerol, about 5.1 mg/mL monothioglycerol, about 5.2 mg/mL monothioglycerol, about 5.3 mg/mL monothioglycerol, about 5.4 mg/mL monothioglycerol, or about 5.5 mg/mL monothioglycerol. In one embodiment, the aqueous pharmaceutical formulation comprises from about 0.5 to about 2.5 mg/mL monobasic sodium phosphate. In one embodiment, the aqueous pharmaceutical formulation comprises from about 5 to about 25 mg/mL dibasic sodium phosphate. In one embodiment, the aqueous pharmaceutical formulation comprises from about 0.1 to about 1 mg/mL disodium EDTA. In one embodiment, the aqueous pharmaceutical formulation comprises from about 0.1 to about 0.22 mg/mL disodium EDTA.

In one embodiment, the aqueous pharmaceutical formulation has a pH from about 7.5 to about 9.5 or about 7.5 to about 8.5. In one embodiment, the aqueous pharmaceutical formulation has a pH of about 7.5, about 7.6, about 7.7, about 7.8, about 7.9, about 8.0, about 8.1, about 8.2, about 8.3, about 8.4, about 8.5, about 8.6, about 8.7, about 8.8, about 8.9, or about 9. In one embodiment, upon formulation, the pharmaceutical formulation comprises from no organic impurities to less than, or no more than 0.2% organic impurities, from no organic impurities to less than, or no more than 0.15% organic impurities, from no organic impurities to less than, or no more than 0.10% organic impurities, or from no organic impurities to less than, or no more than 0.05% organic impurities. In one embodiment, upon storage at about 25° C. for about 3 months, the formulation comprises from no organic impurities to less than, or no more than 0.2% organic impurities or from no organic impurities to less than, or no more than 0.07% organic impurities. In one embodiment, upon storage at about 25° C. for about 6 months, the formulation comprises from no organic impurities to less than, or no more than 0.60% organic impurities or from no organic impurities to less than, or no more than 0.20% organic impurities. In one embodiment, the formulation is stored at about 60% relative humidity. In one embodiment, the formulation is stored against at least one non-glass pharmaceutically acceptable surface selected from a stopper surface, a needle surface, a needle tip cap surface, a needle shield surface, a septa surface, a syringe plunger surface, a plastic syringe surface, an injector surface, or a rubber surface.

In one embodiment, the aqueous pharmaceutical formulation described above is for use in the treatment of a disease, a condition, or a disorder that is alleviated by hydrocortisone or hydrocortisone sodium phosphate. In one embodiment, the disease, condition, or disorder comprises one or more of asthma, an allergic reaction, severe shock due to injury or infection, failure of the adrenal glands, inflammation, atopic dermatitis, contact dermatitis, a drug hypersensitivity reaction, perennial or seasonal allergic rhinitis, serum sickness, a transfusion reaction, a gastrointestinal disease, trichinosis with neurologic or myocardial involvement, tuberculous meningitis with subarachnoid block or impending block, a neoplastic disease, palliative management of a leukemia and/or lymphoma, a renal disease, proteinuria in idiopathic nephrotic syndrome, proteinuria due to lupus erythematosus, dermatomyositis, temporal arteritis, polymyositis, swollen joints and/or tendons, painful joints and/or tendons, tennis elbow, golfer's elbow, and systemic lupus erythematosus. In one embodiment, the disease, condition, or disorder comprises dermatologic diseases selected from bullous dermatitis herpetiformis, exfoliative erythroderma, mycosis fungoides, pemphigus, and severe erythema multiforme (Stevens-Johnson syndrome); endocrine disorders selected from primary or secondary adrenocortical insufficiency, congenital adrenal hyperplasia, hypercalcemia associated with cancer, and nonsuppurative thyroiditis; hematologic disorders selected from acquired (autoimmune) hemolytic anemia, congenital (erythroid) hypoplastic anemia (Diamond-Blackfan anemia), idiopathic thrombocytopenic purpura in adults, pure red cell aplasia, and selected cases of secondary thrombocytopenia; nervous system conditions selected from acute exacerbations of multiple sclerosis; cerebral edema associated with primary or metastatic brain tumor, and craniotomy; ophthalmic diseases selected from sympathetic ophthalmia, uveitis, and ocular inflammatory conditions; respiratory diseases selected from berylliosis, fulminating or disseminated pulmonary tuberculosis, idiopathic eosinophilic pneumonias, and symptomatic sarcoidosis; rheumatic disorders selected from acute gouty arthritis, acute rheumatic carditis, ankylosing spondylitis, psoriatic arthritis, and rheumatoid arthritis; and adrenal insufficiency selected from primary adrenal insufficiency, acute adrenal insufficiency, and secondary adrenal insufficiency. In one embodiment, the disease, condition, or disorder comprises adrenal insufficiency selected from primary adrenal insufficiency, acute adrenal insufficiency, and secondary adrenal insufficiency. In one embodiment, the disease, condition, or disorder comprises acute adrenal insufficiency occurring in a patient with primary adrenal insufficiency or secondary adrenal insufficiency.

In another aspect, the present disclosure provides a method of treating a disease, condition, or disorder alleviated by administering hydrocortisone or hydrocortisone sodium phosphate in a patient in need thereof, the method comprising administering to the patient a therapeutically effective amount of the aqueous pharmaceutical formulation described above. In one embodiment, the disease, condition, or disorder comprises one or more of asthma, acute exacerbations of asthma, an allergic reaction, severe shock due to injury or infection, failure of the adrenal glands, inflammation, atopic dermatitis, contact dermatitis, a drug hypersensitivity reaction, perennial or seasonal allergic rhinitis, serum sickness, a transfusion reaction, a gastrointestinal disease, trichinosis with neurologic or myocardial involvement, tuberculous meningitis with subarachnoid block or impending block, a neoplastic disease, palliative management of a leukemia and/or lymphoma, a renal disease, proteinuria in idiopathic nephrotic syndrome, proteinuria due to lupus erythematosus, dermatomyositis, temporal arteritis, polymyositis, swollen joints and/or tendons, painful joints and/or tendons, tennis elbow, golfer's elbow, systemic lupus erythematosus, acute exacerbations of inflammatory bowel disease, and infantile spasms. In one embodiment, the disease, condition, or disorder comprises dermatologic diseases selected from bullous dermatitis herpetiformis, exfoliative erythroderma, mycosis fungoides, pemphigus, and severe erythema multiforme (Stevens-Johnson syndrome); endocrine disorders selected from primary or secondary adrenocortical insufficiency, congenital adrenal hyperplasia, hypercalcemia associated with cancer, and nonsuppurative thyroiditis; hematologic disorders selected from acquired (autoimmune) hemolytic anemia, congenital (erythroid) hypoplastic anemia (Diamond-Blackfan anemia), idiopathic thrombocytopenic purpura in adults, pure red cell aplasia, and selected cases of secondary thrombocytopenia; nervous system conditions selected from acute exacerbations of multiple sclerosis; cerebral edema associated with primary or metastatic brain tumor, and craniotomy; ophthalmic diseases selected from sympathetic ophthalmia, uveitis, and ocular inflammatory conditions; respiratory diseases selected from berylliosis, fulminating or disseminated pulmonary tuberculosis, idiopathic eosinophilic pneumonias, and symptomatic sarcoidosis; rheumatic disorders selected from acute gouty arthritis, acute rheumatic carditis, ankylosing spondylitis, psoriatic arthritis, and rheumatoid arthritis; and adrenal insufficiency selected from primary adrenal insufficiency, acute adrenal insufficiency, and secondary adrenal insufficiency. In one embodiment, the disease, condition, or disorder comprises adrenal insufficiency selected from primary adrenal insufficiency, acute adrenal insufficiency, and secondary adrenal insufficiency. In one embodiment, the disease, condition, or disorder comprises acute adrenal insufficiency occurring in a patient with primary adrenal insufficiency or secondary adrenal insufficiency. In one embodiment, the therapeutic amount is about 0.5 mL to about 0.6 mL, about 0.6 mL to about 0.7 mL, about 0.7 mL to about 0.8 mL, about 0.8 mL to about 0.9 mL, about 0.9 mL to about 1.0 mL, about 1.0 mL to about 1.2 mL, about 1.0 mL to about 1.1 mL, about 1.1 mL to about 1.2 mL, about 1.2 mL to about 1.3 mL, about 1.3 mL to about 1.4 mL, or about 1.4 mL to about 1.5 mL of the aqueous pharmaceutical formulation. In one embodiment, the therapeutic amount is about 0.5 mL, about 0.6 mL, about 0.7 mL, about 0.8 mL, about 0.9 mL, about 1.0 mL, about 1.1 mL, about 1.2 mL, about 1.3 mL, about 1.4 mL, or about 1.5 mL of the aqueous pharmaceutical formulation. In one embodiment, the therapeutic amount is administered to the patient using an emergency-use/rescue autoinjector device. In one embodiment, the patient cannot be administered hydrocortisone or a drug thereof by oral therapy. In one embodiment, the therapeutic amount is administered intravenously. In one embodiment, the therapeutic amount is administered intramuscularly. In one embodiment, the therapeutic amount provides an in vivo plasma profile for hydrocortisone that includes a mean $AUC_{0-inf}$ of about 5,500 to 5,575 h*ng/mL. In one embodiment, the therapeutic amount provides an in vivo plasma profile for hydrocortisone that includes a mean $AUC_{0-t}$ of about 5,275 to 5,375 h*ng/mL, wherein t is between about 0.5 and 12.5 hours. In one embodiment, the patient has a $C_{max}$ of hydrocortisone that is about 800 to 1600 ng/mL, about 900 to 1600 ng/mL, about 1000 to 1600 ng/mL, about 1000 to 1500 ng/mL, about 1100 to 1500 ng/mL, about 1100 to 1400 ng/mL, or about 1200 to 1300 ng/mL about 30 minutes, about 45 minutes, about 1.0 hour, about 1.25 hours, about 1.5 hours, about 1.75 hours, about 2.0 hours, about 2.25 hours, about 2.5 hours, about 2.75 hours, about 3.0 hours, about 3.25 hours, about 3.5 hours, or about 4.0 hours after the therapeutic amount is administered. In one embodiment, the therapeutic amount provides a hydrocortisone median $T_{max}$ of about 0.5 to 2.5 hours. In one embodiment, hydrocortisone is eliminated from the patient with a mean $T_{1/2\ el}$ of about 1.8 to 2.1 hours. In one embodiment, the aqueous pharmaceutical formulation exhibits higher exposure after administration to the patient compared to a hydrocortisone reference formulation. In one embodiment, the aqueous pharmaceutical formulation achieves a higher area under the curve (AUC) after administration to the patient compared to a hydrocortisone reference listed formulation. In one embodiment, the aqueous pharmaceutical formulation achieves a higher maximum (or peak) serum concentration ($C_{max}$) after administration to the patient compared to a hydrocortisone reference formulation. In one embodiment, the aqueous pharmaceutical formulation achieves a maximum (or peak) serum concentration ($C_{max}$) after administration to the patient faster than a hydrocortisone reference formulation. In one embodiment, the hydrocortisone reference formulation is administered intravenously to a patient. In one embodiment, the hydrocortisone reference formulation is administered intramuscularly to a patient. In one embodiment, the hydrocortisone reference formulation comprises hydrocortisone sodium succinate. In one embodiment, the hydrocortisone reference formulation does not comprise an antioxidant. In one embodiment, the hydrocortisone reference formulation comprises an aqueous formulation comprising about 67 mg/mL hydrocortisone sodium succinate, about 4.4 mg/mL dibasic sodium phosphate, about 0.4 mg/mL monobasic sodium phosphate, and water, wherein about 2.0 mL is administered to the patient.

BRIEF DESCRIPTION OF THE DRAWINGS

The foregoing summary, as well as the following detailed description of embodiments of the invention, will be better understood when read in conjunction with the appended drawings and figures.

Figure 1:
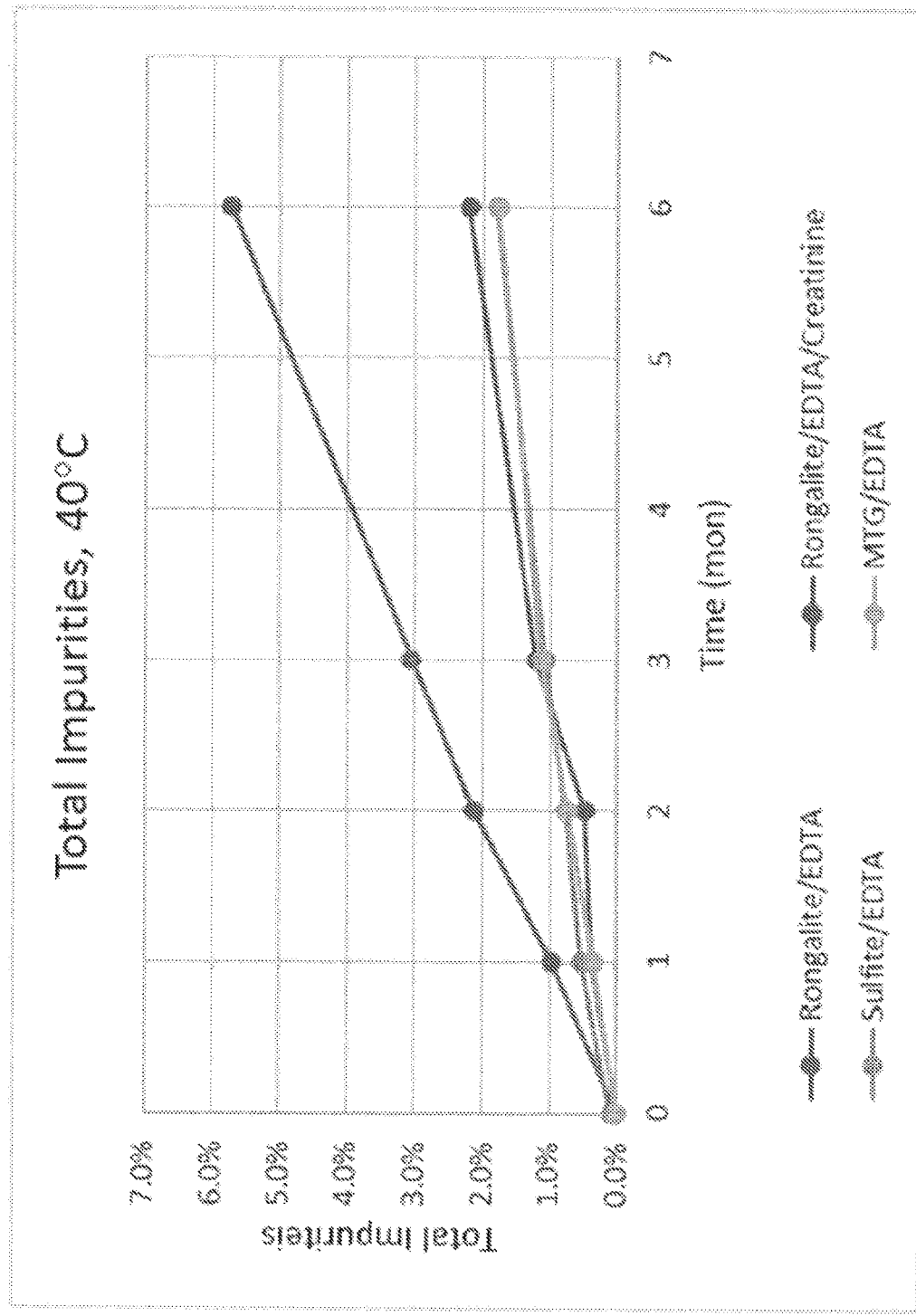
FIG. 1 illustrates the stability of three lead formulations.

While the above-identified drawings set forth presently disclosed embodiments, other embodiments are also contemplated, as noted in the discussion. This disclosure presents illustrative embodiments by way of representation and not limitation. Numerous other modifications and embodiments can be devised by those skilled in the art which fall within the scope and spirit of the principles of the presently disclosed embodiments.

DETAILED DESCRIPTION

The present invention is directed to pharmaceutical formulations including hydrocortisone, one or more hydrocortisone prodrugs, e.g., hydrocortisone esters, and/or any salts thereof, including, without limitation, stable liquid formulations using hydrocortisone sodium phosphate as the active ingredient.

Definitions

Unless defined otherwise, all technical and scientific terms used herein have the same meaning as is commonly understood by one of skill in the art to which this invention belongs.

All patents and publications referred to herein are incorporated by reference in their entireties.

As used herein, the terms "administer," "administration," or "administering" refer to (1) providing, giving, dosing, and/or prescribing by either a health practitioner or his authorized agent or under his or her direction according to the disclosure, and/or (2) putting into, taking, or consuming by a subject, for example a mammal, including a human, according to the disclosure.

The terms "co-administration," "co-administering," "administered in combination with," "administering in combination with," "simultaneous," and "concurrent," as used herein, encompass administration of two or more active pharmaceutical ingredients to a subject so that both active pharmaceutical ingredients and/or their metabolites are present in the subject at the same time. Co-administration includes simultaneous administration in separate compositions, administration at different times in separate compositions, or administration in a composition in which two or more active pharmaceutical ingredients are present. In some embodiments, simultaneous administration in separate compositions and administration in a composition in which both agents are present are preferred.

The term "effective amount" or "therapeutically effective amount" refers to that amount of a compound or combination of compounds as described herein that is sufficient to effect the intended application including, but not limited to, disease treatment. A therapeutically effective amount may vary depending upon the intended application (in vitro or in vivo), or the subject and disease condition being treated (e.g., the weight, age and gender of the subject), the severity of the disease condition, the manner of administration, etc., which can readily be determined by one of ordinary skill in the art. The term also applies to a dose that will induce a particular response in target cells (e.g., the reduction of platelet adhesion and/or cell migration). The specific dose will vary depending on the subject to whom the dose is to be administered, the particular compounds chosen, the dosing regimen to be followed, whether the compound is administered in combination with other compounds, timing of administration, the tissue to which it is administered, and the physical delivery system in which the compound is carried.

A "therapeutic effect" as that term is used herein, encompasses a therapeutic benefit and/or a prophylactic benefit. A prophylactic effect includes delaying or eliminating the appearance of a disease or condition, delaying or eliminating the onset of symptoms of a disease or condition, slowing, halting, or reversing the progression of a disease or condition, or any combination thereof.

As used herein, the terms "treat," "treatment," and/or "treating" may refer to the management of a disease, disorder, or pathological condition, or symptom thereof with the intent to cure, ameliorate, stabilize, and/or control the disease, disorder, pathological condition or symptom thereof. Regarding control of the disease, disorder, or pathological condition more specifically, "control" may include the absence of condition progression, as assessed by the response to the methods recited herein, where such response may be complete (e.g., placing the disease in remission) or partial (e.g., lessening or ameliorating any symptoms associated with the condition). As used herein, the terms "prevent," "preventing," and/or "prevention" may refer to reducing the risk of developing a disease, disorder, or pathological condition.

The term "pharmaceutically acceptable salt" refers to salts derived from a variety of organic and inorganic counter ions known in the art. Pharmaceutically acceptable acid addition salts can be formed with inorganic acids and organic acids. Preferred inorganic acids from which salts can be derived include, for example, hydrochloric acid, hydrobromic acid, sulfuric acid, nitric acid and phosphoric acid. Preferred organic acids from which salts can be derived include, for example, acetic acid, propionic acid, glycolic acid, pyruvic acid, oxalic acid, maleic acid, malonic acid, phosphoric acid, succinic acid, fumaric acid, tartaric acid, citric acid, benzoic acid, cinnamic acid, mandelic acid, methanesulfonic acid, ethanesulfonic acid, p-toluenesulfonic acid and salicylic acid. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese and aluminum. Organic bases from which salts can be derived include, for example, primary, secondary, and tertiary amines, substituted amines including naturally occurring substituted amines, cyclic amines and basic ion exchange resins. Specific examples include isopropylamine, trimethylamine, diethylamine, triethylamine, tripropylamine, and ethanolamine. In some embodiments, the pharmaceutically acceptable base addition salt is chosen from ammonium, potassium, sodium, calcium, and magnesium salts. The term "cocrystal" refers to a molecular complex derived from a number of cocrystal formers known in the art. Unlike a salt, a cocrystal typically does not involve hydrogen transfer between the cocrystal and the drug, and instead involves intermolecular interactions, such as hydrogen bonding, aromatic ring stacking, or dispersive forces, between the cocrystal former and the drug in the crystal structure.

"Pharmaceutically acceptable carrier" or "pharmaceutically acceptable excipient" or "physiologically compatible" carrier or carrier medium is intended to include any and all solvents, dispersion media, coatings, antibacterial and antifungal agents, isotonic and absorption delaying agents, and inert ingredients. The use of such pharmaceutically acceptable carriers or pharmaceutically acceptable excipients for active pharmaceutical ingredients is well known in the art. Except insofar as any conventional pharmaceutically acceptable carrier or pharmaceutically acceptable excipient is incompatible with the active pharmaceutical ingredient, its use in the therapeutic compositions of the invention is contemplated. Additional active pharmaceutical ingredients, such as other drugs, can also be incorporated into the described compositions and methods.

A "prodrug" refers to a derivative of a compound described herein, the pharmacologic action of which results from the conversion by chemical or metabolic processes in vivo to the active compound. Prodrugs include, without limitation, compounds wherein an amino acid residue, or a polypeptide chain of two or more (e.g., two, three or four) amino acid residues is covalently joined through an amide or ester bond to a free amino, hydroxyl or carboxylic acid group of hydrocortisone. The amino acid residues include but are not limited to the 20 naturally occurring amino acids commonly designated by one or three letter symbols but also include, for example, 4-hydroxyproline, hydroxylysine, desmosine, isodesmosine, 3-methylhistidine, beta-alanine, gamma-aminobutyric acid, citrulline, homocysteine, homoserine, ornithine and methionine sulfone. Additional types of prodrugs are also encompassed. For instance, free carboxyl groups can be derivatized as amides or alkyl esters (e.g., methyl esters and acetoxy methyl esters). Prodrug esters as employed herein includes esters and carbonates formed by reacting one or more hydroxyls of compounds of the method of the invention with alkyl, alkoxy, or aryl substituted acylating agents employing procedures known to those skilled in the art to generate acetates, phosphates, succinates, butyrates, pivalates, methylcarbonates, benzoates and the like. As further examples, free hydroxyl groups may be derivatized using groups including but not limited to hemisuccinates, phosphate esters, dimethylaminoacetates, and phosphoryloxymethyloxycarbonyls, as outlined in Advanced Drug Delivery Reviews, 1996, 19, 115. Carbamate prodrugs of hydroxyl and amino groups are also included, as are carbonate prodrugs, sulfonate prodrugs, sulfonate esters and sulfate esters of hydroxyl groups. Free amines can also be derivatized to amides, sulfonamides or phosphonamides. All of the stated prodrug moieties may incorporate groups including but not limited to ether, amine and carboxylic acid functionalities. Moreover, any compound that can be converted in vivo to provide the bioactive agent (e.g., hydrocortisone) is a prodrug within the scope of the invention. Various forms of prodrugs are well known in the art. A comprehensive description of prodrugs and prodrug derivatives are described in: (a) The Practice of Medicinal Chemistry, Camille G. Wermuth et al., (Academic Press, 1996); (b) Design of Prodrugs, edited by H. Bundgaard, (Elsevier, 1985); (c) A Textbook of Drug Design and Development, P. Krogsgaard-Larson and H. Bundgaard, eds., (Harwood Academic Publishers, 1991). In general, prodrugs may be designed to improve the penetration of a drug across biological membranes in order to obtain improved drug absorption, to prolong duration of action of a drug (slow release of the parent drug from a prodrug, decreased first-pass metabolism of the drug), to target the drug action (e.g., organ or tumor-targeting, lymphocyte targeting), to modify or improve aqueous solubility of a drug (e.g., i.v. preparations and eyedrops), to improve topical drug delivery (e.g., dermal and ocular drug delivery), to improve the chemical/enzymatic stability of a drug, or to decrease off-target drug effects, and more generally in order to improve the therapeutic efficacy of the compounds utilized in the invention.

Unless otherwise stated, the chemical structures depicted herein are intended to include compounds which differ only in the presence of one or more isotopically enriched atoms. For example, compounds where one or more hydrogen atoms is replaced by deuterium or tritium, or wherein one or more carbon atoms is replaced by $^{13}$C-enriched or $^{14}$C-enriched carbons, are within the scope of this invention.

When ranges are used herein to describe, for example, physical or chemical properties such as molecular weight or chemical formulae, all combinations and subcombinations of ranges and specific embodiments therein are intended to be included. Use of the term "about" when referring to a number or a numerical range means that the number or numerical range referred to is an approximation within experimental variability (or within statistical experimental error), and thus the number or numerical range may vary. The variation is typically from 0% to 15%, from 0% to 10%, from 0% to 5%, or the like, of the stated number or numerical range.

As used herein, the term "about" means that amounts, sizes, formulations, parameters, shapes and other quantities and characteristics are not, and need not be exact, but may be approximate and/or larger or smaller, as desired, reflecting tolerances, conversion factors, rounding off, measurement error and the like, and other factors known to those of skill in the art. In general, an amount, size, formulation, parameter, shape or other quantity or characteristic is "about" or "approximate" whether or not expressly stated to be such. The term "about" generally refers to a particular numeric value that is within an acceptable error range as determined by one of ordinary skill in the art, which will depend in part on how the numeric value is measured or determined, i.e., the limitations of the measurement system. For example, "about" can mean a range of ±20%, ±10%, or ±5% of a given numeric value. The transitional terms "comprising", "consisting essentially of" and "consisting of", when used in the appended claims, in original and amended form, define the claim scope with respect to what unrecited additional claim elements or steps, if any, are excluded from the scope of the claim(s). The term "comprising" is intended to be inclusive or open-ended and does not exclude any additional, unrecited element, method, step or material. The term "consisting of" excludes any element, step or material other than those specified in the claim and, in the latter instance, impurities ordinarily associated with the specified material(s). The term "consisting essentially of" limits the scope of a claim to the specified elements, steps or material(s) and those that do not materially affect the basic and novel characteristic(s) of the claimed invention. All compounds, compositions, formulations, and methods described herein that embody the present invention can, in alternate embodiments, be more specifically defined by any of the transitional terms "comprising," "consisting essentially of," and "consisting of." The term "comprising" (and related terms such as "comprise" or "comprises" or "having" or "including") includes those embodiments such as, for example, an embodiment of any composition of matter, method, or process that "consist of" or "consist essentially of" the described features.

"Alkyl" refers to a straight or branched hydrocarbon chain radical consisting solely of carbon and hydrogen atoms, containing no unsaturation, having from one to ten carbon atoms (e.g., $(C_{1-10})$alkyl or $C_{1-10}$ alkyl). Whenever it appears herein, a numerical range such as "1 to 10" refers to each integer in the given range, e.g., "1 to 10 carbon atoms" means that the alkyl group may consist of 1 carbon atom, 2 carbon atoms, 3 carbon atoms, etc., up to and including 10 carbon atoms, although the definition is also intended to cover the occurrence of the term "alkyl" where no numerical range is specifically designated. Typical alkyl groups include, but are in no way limited to, methyl, ethyl, propyl, isopropyl, n-butyl, isobutyl, sec-butyl isobutyl, tertiary butyl, pentyl, isopentyl, neopentyl, hexyl, septyl, octyl, nonyl and decyl. The alkyl moiety may be attached to the rest of the molecule by a single bond, such as for example, methyl (Me), ethyl (Et), n-propyl (Pr), 1-methylethyl (isopropyl), n-butyl, n-pentyl, 1,1-dimethylethyl (t-butyl) and 3-methylhexyl. Unless stated otherwise specifically in the specification, an alkyl group is optionally substituted by one or more of substituents which are independently heteroalkyl, acylsulfonamido, alkenyl, alkynyl, cycloalkyl, heterocycloalkyl, hydroxamate, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —S(O)$_t$R$^a$-(where t is 1 or 2), —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(N-R$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$ where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl. The alkyl moiety, whether saturated or unsaturated, may be branched, straight chain, or cyclic.

An "alkene" or "alkenyl" moiety refers to a group consisting of at least two carbon atoms and at least one carbon-carbon double bond, and an "alkyne" moiety refers to a group consisting of at least two carbon atoms and at least one carbon-carbon triple bond.

"Alkenyl" refers to a straight or branched hydrocarbon chain radical group consisting solely of carbon and hydrogen atoms, containing at least one double bond, and having from two to ten carbon atoms (i.e., ($C_{2-10}$)alkenyl or $C_{2-10}$ alkenyl). Whenever it appears herein, a numerical range such as "2 to 10" refers to each integer in the given range—e.g., "2 to 10 carbon atoms" means that the alkenyl group may consist of 2 carbon atoms, 3 carbon atoms, etc., up to and including 10 carbon atoms. The alkenyl moiety may be attached to the rest of the molecule by a single bond, such as for example, ethenyl (i.e., vinyl), prop-1-enyl (i.e., allyl), but-1-enyl, pent-1-enyl and penta-1,4-dienyl. Unless stated otherwise specifically in the specification, an alkenyl group is optionally substituted by one or more substituents which are independently alkyl, heteroalkyl, acylsulfonamido, alkenyl, alkynyl, cycloalkyl, heterocycloalkyl, hydroxamate, aryl, arylalkyl, heteroaryl, heteroarylalkyl, hydroxy, halo, cyano, trifluoromethyl, trifluoromethoxy, nitro, trimethylsilanyl, —$OR^a$, —$SR^a$, —$S(O)_tR^a$— (where t is 1 or 2), —OC(O)— $R^a$, —$N(R^a)_2$, —$C(O)R^a$, —$C(O)OR^a$, —$OC(O)N(R^a)_2$, —$OC(O)N(R^a)_2$, —$C(O)N(R^a)_2$, —$N(R^a)C(O)OR^a$, —$N(R^a)C(O)R^a$, —$N(R^a)C(O)N(R^a)_2$, $N(R^a)C(NR^a)N(R^a)_2$, —$N(R^a)S(O)_tR^a$ (where t is 1 or 2), —$S(O)_tOR^a$ (where t is 1 or 2), —$S(O)_tN(R^a)_2$ (where t is 1 or 2), or $PO_3(R^a)_2$, where each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Alkenyl-cycloalkyl" refers to an -(alkenyl)cycloalkyl radical where alkenyl and cycloalkyl are as disclosed herein and which are optionally substituted by one or more of the substituents described as suitable substituents for alkenyl and cycloalkyl respectively.

"Cycloalkyl" refers to a monocyclic or polycyclic radical that contains only carbon and hydrogen, and may be saturated, or partially unsaturated. Cycloalkyl groups include groups having from 3 to 10 ring atoms (i.e., ($C_{3-10}$)cycloalkyl or $C_{3-10}$ cycloalkyl). Whenever it appears herein, a numerical range such as "3 to 10" refers to each integer in the given range—e.g., "3 to 10 carbon atoms" means that the cycloalkyl group may consist of 3 carbon atoms, etc., up to and including 10 carbon atoms. Illustrative examples of cycloalkyl groups include, but are not limited to the following moieties: cyclopropyl, cyclobutyl, cyclopentyl, cyclopentenyl, cyclohexyl, cyclohexenyl, cycloheptyl, cyclooctyl, cyclononyl, cyclodecyl, norbornyl, and the like. Unless stated otherwise specifically in the specification, a cycloalkyl group is optionally substituted by one or more substituents which independently are: alkyl, heteroalkyl, alkenyl, alkynyl, cycloalkyl, acylsulfonamido, heterocycloalkyl, hydroxamate, aryl, arylalkyl, heteroaryl, heteroarylalkyl, hydroxy, halo, cyano, trifluoromethyl, trifluoromethoxy, nitro, trimethylsilanyl, —$OR^a$, —$SR^a$, —$S(O)_tR^a$— (where t is 1 or 2), —$S(O)_tR^a$— (where t is 1 or 2), —OC(O)—$R^a$, —$N(R^a)_2$, —$C(O)R^a$, —$C(O)OR^a$, —$OC(O)N(R^a)_2$, —$C(O)N(R^a)_2$, —$N(R^a)C(O)OR^a$, —$N(R^a)C(O)R^a$, —$N(R^a)C(O)N(R^a)_2$, $N(R^a)C(NR^a)N(R^a)_2$, —$N(R^a)S(O)_tR^a$ (where t is 1 or 2), —$S(O)_tOR^a$ (where t is 1 or 2), —$S(O)_tN(R^a)_2$ (where t is 1 or 2), or $PO_3(R^a)_2$, where each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Cycloalkyl-alkenyl" refers to a -(cycloalkyl)alkenyl radical where cycloalkyl and alkenyl are as disclosed herein and which are optionally substituted by one or more of the substituents described as suitable substituents for cycloalkyl and alkenyl, respectively.

"Acyl" refers to the groups (alkyl)-C(O)—, (aryl)-C(O)—, (heteroaryl)-C(O)—, (heteroalkyl)-C(O)— and (heterocycloalkyl)-C(O)—, wherein the group is attached to the parent structure through the carbonyl functionality. If the R radical is heteroaryl or heterocycloalkyl, the hetero ring or chain atoms contribute to the total number of chain or ring atoms. Unless stated otherwise specifically in the specification, the alkyl, aryl or heteroaryl moiety of the acyl group is optionally substituted by one or more substituents which are independently alkyl, heteroalkyl, acylsulfonamido, alkenyl, alkynyl, cycloalkyl, heterocycloalkyl, hydroxamate, aryl, arylalkyl, heteroaryl, heteroarylalkyl, hydroxy, halo, cyano, trifluoromethyl, trifluoromethoxy, nitro, trimethylsilanyl, —$OR^a$, —$SR^a$, —$S(O)_tR^a$— (where t is 1 or 2), —OC(O)— $R^a$, —$N(R^a)_2$, —$C(O)R^a$, —$C(O)OR^a$, —$OC(O)N(R^a)_2$, —$C(O)N(R^a)_2$, —$N(R^a)C(O)OR^a$, —$N(R^a)C(O)R^a$, —$N(R^a)C(O)N(R^a)_2$, $N(R^a)C(NR^a)N(R^a)_2$, —$N(R^a)S(O)_tR^a$ (where t is 1 or 2), —$S(O)_tOR^a$ (where t is 1 or 2), —$S(O)_tN(R^a)_2$ (where t is 1 or 2), or $PO_3(R^a)_2$, where each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Ester" refers to, without limitation, a chemical radical of formula —COOR, where R is selected from the group consisting of alkyl, cycloalkyl, aryl, heteroaryl (bonded through a ring carbon) and heteroalicyclic (bonded through a ring carbon). The procedures and specific groups to make esters are known to those of skill in the art and can readily be found in seminal sources such as Greene and Wuts, Protective Groups in Organic Synthesis, $3^{rd}$ Ed., John Wiley & Sons, New York, N.Y., 1999, which is incorporated herein by reference in its entirety. Unless stated otherwise specifically in the specification, an ester group is optionally substituted by one or more substituents which independently are: alkyl, acylsulfonamido, heteroalkyl, alkenyl, alkynyl, cycloalkyl, heterocycloalkyl, hydroxamate, aryl, arylalkyl, heteroaryl, heteroarylalkyl, hydroxy, halo, cyano, trifluoromethyl, trifluoromethoxy, nitro, trimethylsilanyl, —$OR^a$, —$SR^a$, —$S(O)_tR^a$— (where t is 1 or 2), —OC(O)—$R^a$, —$N(R^a)_2$, —$C(O)R^a$, —$C(O)OR^a$, —$OC(O)N(R^a)_2$, —$C(O)N(R^a)_2$, —$N(R^a)C(O)OR^a$, —$N(R^a)C(O)R^a$, —$N(R^a)C(O)N(R^a)_2$, $N(R^a)C(NR^a)N(R^a)_2$, —$N(R^a)S(O)_tR^a$ (where t is 1 or 2), —$S(O)_tOR^a$ (where t is 1 or 2), —$S(O)_tN(R^a)_2$ (where t is 1 or 2), or $PO_3(R^a)_2$, where each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Ester" also refers to, without limitation, a phosphate.

"Fluoroalkyl" refers to an alkyl radical, as defined above, that is substituted by one or more fluoro radicals, as defined above, for example, trifluoromethyl, difluoromethyl, 2,2,2-trifluoroethyl, 1-fluoromethyl-2-fluoroethyl, and the like. The alkyl part of the fluoroalkyl radical may be optionally substituted as defined above for an alkyl group.

"Isomers" are different compounds that have the same molecular formula.

"Stereoisomers" are isomers that differ only in the way the atoms are arranged in space—i.e., having a different stereochemical configuration. "Enantiomers" are a pair of stereoisomers that are non-superimposable mirror images of each other. A 1:1 mixture of a pair of enantiomers is a "racemic" mixture. The term "(±)" is used to designate a racemic mixture where appropriate.

"Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon can be specified by either (R) or (S). Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers and can thus give rise to enantiomers, diastereomers, and other stereoisomeric forms that can be defined, in terms of absolute stereochemistry, as (R) or (S). The present chemical entities, pharmaceutical compositions and methods are meant to include all such possible isomers, including racemic mixtures, optically pure forms and intermediate mixtures. Optically active (R)- and (S)-isomers can be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers.

"Moiety" refers to a specific segment or functional group of a molecule. Chemical moieties are often recognized chemical entities embedded in or appended to a molecule.

"Tautomers" are structurally distinct isomers that interconvert by tautomerization. "Tautomerization" is a form of isomerization and includes prototropic or proton-shift tautomerization, which is considered a subset of acid-base chemistry. "Prototropic tautomerization" or "proton-shift tautomerization" involves the migration of a proton accompanied by changes in bond order, often the interchange of a single bond with an adjacent double bond. Where tautomerization is possible (e.g., in solution), a chemical equilibrium of tautomers can be reached. An example of tautomerization is keto-enol tautomerization. A specific example of keto-enol tautomerization is the interconversion of pentane-2,4-dione and 4-hydroxypent-3-en-2-one tautomers. Another example of tautomerization is phenol-keto tautomerization. A specific example of phenol-keto tautomerization is the interconversion of pyridin-4-ol and pyridin-4(1H)-one tautomers.

"Substituted" means that the referenced group may have attached one or more additional groups, radicals or moieties individually and independently selected from, for example, acyl, alkyl, alkylaryl, cycloalkyl, aralkyl, aryl, carbohydrate, carbonate, heteroaryl, heterocycloalkyl, hydroxamate, hydroxy, alkoxy, aryloxy, mercapto, alkylthio, arylthio, cyano, halo, carbonyl, ester, thiocarbonyl, isocyanato, thiocyanato, isothiocyanato, nitro, oxo, perhaloalkyl, perfluoroalkyl, phosphate, silyl, sulfinyl, sulfonyl, sulfonamidyl, sulfoxyl, sulfonate, urea, and amino, including mono- and di-substituted amino groups, and protected derivatives thereof. The substituents themselves may be substituted, for example, a cycloalkyl substituent may itself have a halide substituent at one or more of its ring carbons. The term "optionally substituted" means optional substitution with the specified groups, radicals or moieties.

DETAILED DESCRIPTION

Formulations

In one embodiment, the invention relates to a pharmaceutical formulation including hydrocortisone, one or more hydrocortisone prodrugs, e.g., a hydrocortisone ester, and/or any salts thereof.

Hydrocortisone is the name for the hormone cortisol when supplied as a medication. It is used in oral administration, intravenous injection, or topical application. It is used as an immunosuppressive drug, given by injection in the treatment of severe allergic reactions such as anaphylaxis and angioedema. It may be used topically for allergic rashes, eczema, psoriasis, itching and other inflammatory skin conditions.

Therapeutic hydrocortisone is a synthetic or semisynthetic analog of natural hydrocortisone hormone produced by the adrenal glands with primary glucocorticoid and minor mineralocorticoid effects. As a glucocorticoid receptor agonist, hydrocortisone promotes protein catabolism, gluconeogenesis, capillary wall stability, renal excretion of calcium, and suppresses immune and inflammatory responses.

The empirical formula of Hydrocortisone is $C_{21}H_{30}O_5$. The molecular weight is 362.46 g/mol. The structural formula is:

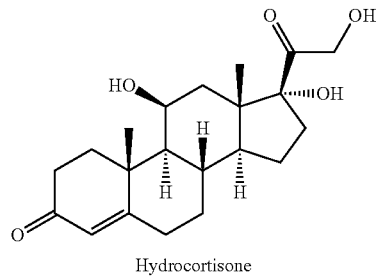

Hydrocortisone

Hydrocortisone is available as a crystalline, white powder and has bitter taste. Its melting point is 220° C. It is a water insoluble with a reported solubility of about 0.32 mg/mL in water. Reported solubility in propylene glycol is 12.7 mg/mL. The octanol/water partition coefficient value of hydrocortisone is 1.61. It is sensitive to light and unstable in strong acids and alkalies.

Hydrocortisone sodium phosphate is an organic salt. Its molecular formula is $C_{21}H_{29}Na_2O_8P$ and its molecular weight is 486.4 g/mol, and it has the following structure:

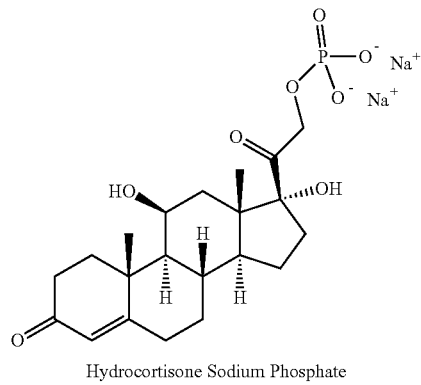

Hydrocortisone Sodium Phosphate

Any antioxidant suitable for parenteral administration can be used in the formulations of the invention. In some embodiments, the antioxidant is one or more of butylated hydroxy toluene (BHT), tocopherol, butylated hydroxy anisole (BHA), ascorbyl palmitate, ascorbic acid and salts thereof, vitamin E, niacinamide, methionine, monothioglycerol, sodium bisulfite, cysteine, dithionite sodium, gentisic acid, and/or glutamate monosodium. In one embodiment, the antioxidant allows an aqueous formulation of the invention to be stable at room temperature for a longer period of time than other aqueous hydrocortisone formulations without an antioxidant. In one embodiment, the antioxidant allows an aqueous formulation of the invention to be stable at elevated temperatures (i.e., above room temperature) for a longer period of time than other aqueous hydrocortisone formulations without an antioxidant. In one embodiment, the formulation of the disclosure comprises monothioglycerol antioxidant. In one embodiment, aqueous formulations of the disclosure comprising between about 0.50%-2.5% w/v monothioglycerol are stable for up to about 24 months at room temperature or elevated temperatures. In one embodiment, aqueous hydrocortisone formulations without an antioxidant are not stable at elevated temperatures and stable at room temperature only for a short period of time. Specifically, formulations comprising hydrocortisone sodium succinate, anhydrous monobasic sodium phosphate, and dried dibasic sodium phosphate without an antioxidant, when reconstituted with sterile water, are only FDA approved for storage at room temperature for three days.

Pharmaceutical Compositions

In some embodiments, the concentration of the hydrocortisone, hydrocortisone prodrug, i.e., hydrocortisone ester, or pharmaceutically acceptable salts of thereof, described herein is less than, or no more than, for example, 100%, 90%, 80%, 70%, 60%, 50%, 40%, 30%, 20%, 19%, 18%, 17%, 16%, 15%, 14%, 13%, 12%, 11%, 10%, 9%, 8%, 7%, 6%, 5%, 4%, 3%, 2%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002% or 0.0001% w/w, w/v, or v/v of the pharmaceutical formulations described herein.

In some embodiments, the concentration of the hydrocortisone, hydrocortisone prodrug, i.e., hydrocortisone ester, or pharmaceutically acceptable salts of thereof, described herein is greater than 90%, 80%, 70%, 60%, 50%, 40%, 30%, 20%, 19.75%, 19.50%, 19.25% 19%, 18.75%, 18.50%, 18.25% 18%, 17.75%, 17.50%, 17.25% 17%, 16.75%, 16.50%, 16.25% 16%, 15.75%, 15.50%, 15.25% 15%, 14.75%, 14.50%, 14.25% 14%, 13.75%, 13.50%, 13.25% 13%, 12.75%, 12.50%, 12.25% 12%, 11.75%, 11.50%, 11.25% 11%, 10.75%, 10.50%, 10.25% 10%, 9.75%, 9.50%, 9.25% 9%, 8.75%, 8.50%, 8.25% 8%, 7.75%, 7.50%, 7.25% 7%, 6.75%, 6.50%, 6.25% 6%, 5.75%, 5.50%, 5.25% 5%, 4.75%, 4.50%, 4.25%, 4%, 3.75%, 3.50%, 3.25%, 3%, 2.75%, 2.50%, 2.25%, 2%, 1.75%, 1.50%, 125%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002% or 0.0001% w/w, w/v, or v/v of the pharmaceutical formulations described herein.

In some embodiments, the concentration of the hydrocortisone, hydrocortisone prodrug, i.e., hydrocortisone ester, or pharmaceutically acceptable salts of thereof, described herein is in the range from about 0.0001% to about 50%, about 0.001% to about 40%, about 0.01% to about 30%, about 0.02% to about 29%, about 0.03% to about 28%, about 0.04% to about 27%, about 0.05% to about 26%, about 0.06% to about 25%, about 0.07% to about 24%, about 0.08% to about 23%, about 0.09% to about 22%, about 0.1% to about 21%, about 0.2% to about 20%, about 0.3% to about 19%, about 0.4% to about 18%, about 0.5% to about 17%, about 0.6% to about 16%, about 0.7% to about 15%, about 0.8% to about 14%, about 0.9% to about 12% or about 1% to about 10% w/w, w/v, or v/v of the pharmaceutical formulations described herein.

In some embodiments, the concentration of the hydrocortisone, hydrocortisone prodrug, i.e., hydrocortisone ester, or pharmaceutically acceptable salts of thereof, described herein is in the range from about 0.001% to about 10%, about 0.01% to about 5%, about 0.02% to about 4.5%, about 0.03% to about 4%, about 0.04% to about 3.5%, about 0.05% to about 3%, about 0.06% to about 2.5%, about 0.07% to about 2%, about 0.08% to about 1.5%, about 0.09% to about 1%, about 0.1% to about 0.9% w/w, w/v, or v/v of the pharmaceutical formulations described herein.

In some embodiments, the amount of each of the active and/or inactive pharmaceutical ingredients provided in the pharmaceutical compositions of the invention, such as a hydrocortisone, hydrocortisone prodrug, i.e., hydrocortisone ester, or pharmaceutically acceptable salts of thereof, and/or an antioxidant, is equal to or less than, or no more than 10 g, 9.5 g, 9.0 g, 8.5 g, 8.0 g, 7.5 g, 7.0 g, 6.5 g, 6.0 g, 5.5 g, 5.0 g, 4.5 g, 4.0 g, 3.5 g, 3.0 g, 2.5 g, 2.0 g, 1.5 g, 1.0 g, 0.95 g, 0.9 g, 0.85 g, 0.8 g, 0.75 g, 0.7 g, 0.65 g, 0.6 g, 0.55 g, 0.5 g, 0.45 g, 0.4 g, 0.35 g, 0.3 g, 0.25 g, 0.2 g, 0.15 g, 0.1 g, 0.09 g, 0.08 g, 0.07 g, 0.06 g, 0.05 g, 0.04 g, 0.03 g, 0.02 g, 0.01 g, 0.009 g, 0.008 g, 0.007 g, 0.006 g, 0.005 g, 0.004 g, 0.003 g, 0.002 g, 0.001 g, 0.0009 g, 0.0008 g, 0.0007 g, 0.0006 g, 0.0005 g, 0.0004 g, 0.0003 g, 0.0002 g, or 0.0001 g in a pharmaceutical formulation described herein.

In some embodiments, the amount of each of the active and/or inactive pharmaceutical ingredients provided in the pharmaceutical compositions of the invention, such as a hydrocortisone, hydrocortisone prodrug, i.e., hydrocortisone ester, or pharmaceutically acceptable salts of thereof, and/or an antioxidant, is more than 0.0001 g, 0.0002 g, 0.0003 g, 0.0004 g, 0.0005 g, 0.0006 g, 0.0007 g, 0.0008 g, 0.0009 g, 0.001 g, 0.0015 g, 0.002 g, 0.0025 g, 0.003 g, 0.0035 g, 0.004 g, 0.0045 g, 0.005 g, 0.0055 g, 0.006 g, 0.0065 g, 0.007 g, 0.0075 g, 0.008 g, 0.0085 g, 0.009 g, 0.0095 g, 0.01 g, 0.015 g, 0.02 g, 0.025 g, 0.03 g, 0.035 g, 0.04 g, 0.045 g, 0.05 g, 0.055 g, 0.06 g, 0.065 g, 0.07 g, 0.075 g, 0.08 g, 0.085 g, 0.09 g, 0.095 g, 0.1 g, 0.15 g, 0.2 g, 0.25 g, 0.3 g, 0.35 g, 0.4 g, 0.45 g, 0.5 g, 0.55 g, 0.6 g, 0.65 g, 0.7 g, 0.75 g, 0.8 g, 0.85 g, 0.9 g, 0.95 g, 1 g, 1.5 g, 2 g, 2.5 g, 3 g, 3.5, 4 g, 4.5 g, 5 g, 5.5 g, 6 g, 6.5 g, 7 g, 7.5 g, 8 g, 8.5 g, 9 g, 9.5 g, or 10 g in a pharmaceutical formulation described herein.

Each of the active pharmaceutical ingredients according to the invention is effective over a wide dosage range. For example, in the treatment of adult humans, dosages independently range from 0.01 to 1000 mg, from 0.5 to 100 mg, from 1 to 50 mg per day, and from 5 to 40 mg per day are examples of dosages that may be used. Effective dosages from 50 to 200 mg per week are also examples of dosages that may be used. In one embodiment, the effective weekly dosage is about 50 mg. In one embodiment, the effective weekly dosage is about 100 mg. In one embodiment, the effective weekly dosage is about 150 mg. In one embodiment, the effective weekly dosage is about 200 mg. In one embodiment, the effective weekly dosage is about 250 mg.

The exact dosage will depend upon the route of administration, the form in which the compound is administered, the gender and age of the subject to be treated, the body weight of the subject to be treated, and the preference and experience of the attending physician. The clinically-established dosages of hydrocortisone, hydrocortisone prodrug, i.e., hydrocortisone ester, or pharmaceutically acceptable salts of thereof, for example hydrocortisone phosphate, may also be used if appropriate.

In some embodiments, the concentration of hydrocortisone sodium phosphate ranges from 50 mg/mL to 200 mg/mL. In some embodiments, the concentration of BHT ranges from 0.01% to 0.1%. In some embodiments, the concentration of monothioglycerol ranges from 0.1 mg/mL to 10 mg/mL.

Pharmaceutical Compositions for Injection

In some embodiments, a pharmaceutical composition is provided for injection containing an active pharmaceutical ingredient or combination of active pharmaceutical ingredients, such as a hydrocortisone ester, for example hydrocortisone sodium phosphate, and a pharmaceutical excipient suitable for injection.

The forms in which the compositions of the present invention may be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles.

Aqueous solutions in saline are also conventionally used for injection. Ethanol, glycerol, propylene glycol and liquid polyethylene glycol (and suitable mixtures thereof), cyclodextrin derivatives, and vegetable oils may also be employed. The proper fluidity can be maintained, for example, by the use of a coating, such as lecithin, for the maintenance of the required particle size in the case of dispersion and by the use of surfactants. The prevention of the action of microorganisms can be brought about by various antibacterial and antifungal preservatives or preservative agents, for example, parabens, chlorobutanol, phenol, sorbic acid, and thimerosal.

Sterile injectable solutions are prepared by incorporating an active pharmaceutical ingredient or combination of active pharmaceutical ingredients in the required amounts in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, certain desirable methods of preparation are vacuum-drying and freeze-drying techniques which yield a powder of the active ingredient plus any additional desired ingredient from a previously sterile-filtered solution thereof.

Administration of an active pharmaceutical ingredient or combination of active pharmaceutical ingredients or a pharmaceutical composition thereof can be effected by any method that enables delivery of the compounds to the site of action. These methods include oral routes, intraduodenal routes, parenteral injection (including intravenous, intraarterial, subcutaneous, intramuscular, intradermal, intravascular, intraperitoneal or infusion), topical (e.g., transdermal application), rectal administration, via local delivery by catheter or stent or through inhalation. The active pharmaceutical ingredient or combination of active pharmaceutical ingredients can also be administered intraadiposally or intrathecally. In one embodiment, the hydrocortisone sodium phosphate formulations described herein can be administered via an emergency-use/rescue autoinjector device.

An injector may be used to inject the pharmaceutical formulation described herein. The formulation may be injected subcutaneously or intramuscularly. In some embodiments, the injector is a single use device that is discarded or recycled after administering a single dose. In other embodiments, the injector is a multi-dose injector. Some injectors that are contemplated for use with the formulation described herein are disclosed in U.S. Pat. Nos. 8,021,335; 8,814,834; 8,945,063; and 10,300,207, all incorporated herein by reference.

Referring to FIGS. 5-11, there is shown an injector, generally designated 30, in accordance with an exemplary embodiment of the present invention. Injector 30 may be an auto-injector. Injector 30 may include a housing 32. An end cap 34 may be coupled to housing 30. Injector 30 may include a needle 74 fluidly coupled to a formulation container 72 (e.g., syringe). A plunger 70 may be movable relative to formulation container 72 to force formulation out of needle 74 during an injection. A ram 58 may be operatively associated with plunger 70 such that axial movement of ram 58 causes movement of plunger 70. An energy source 66 (e.g., biasing element, spring) may move plunger 70 when injector 30 is triggered.

Figure 8:
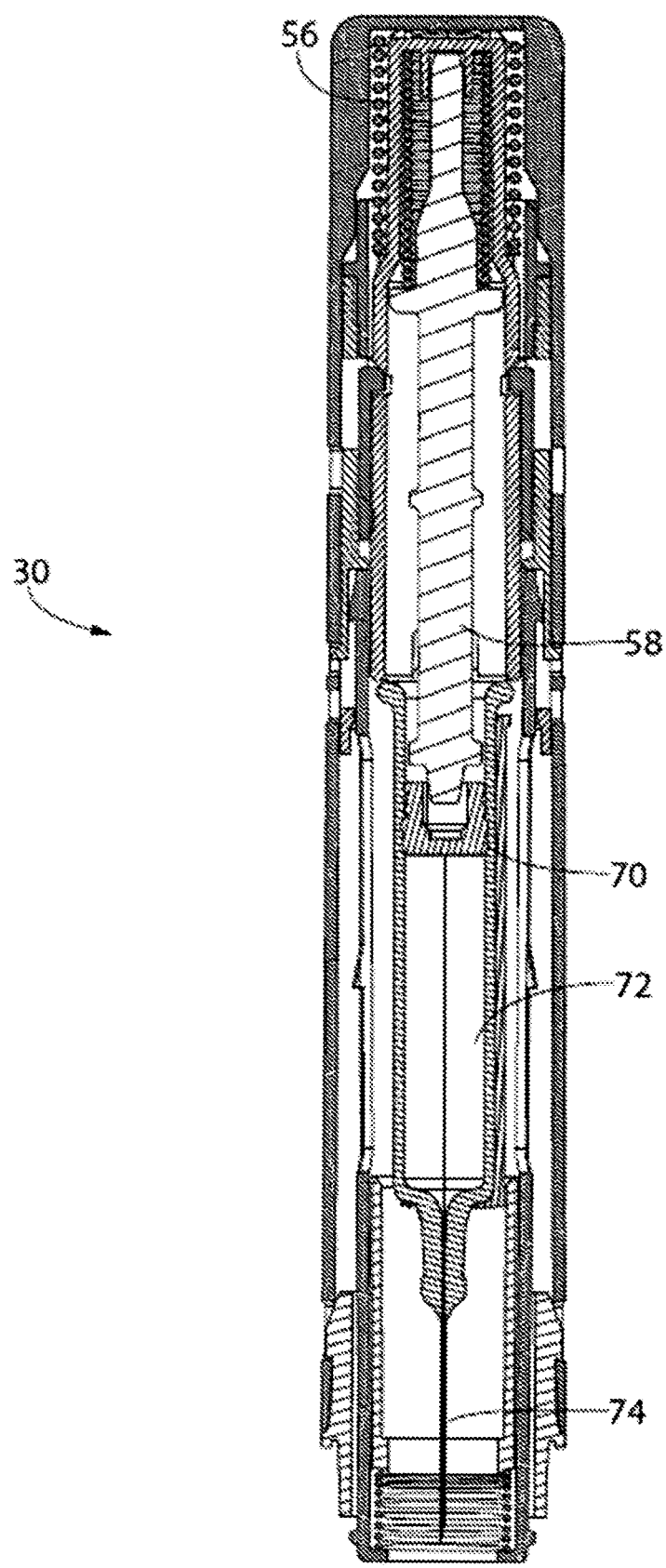
FIG. 8 is a sectional view of the injector of FIG. 6 with the needle guard in a retracted position.

A needle guard 78 may be movably coupled to housing 32. Needle guard 78 may be moveable between an extended position (FIG. 7) and a retracted position (FIG. 8). Needle guard 78 may be movable when a distal end of needle guard 78 is pressed against an injection site. Movement of needle guard 78 relative to housing 32 may trigger injector 30 to start an injection sequence.

Figure 9:
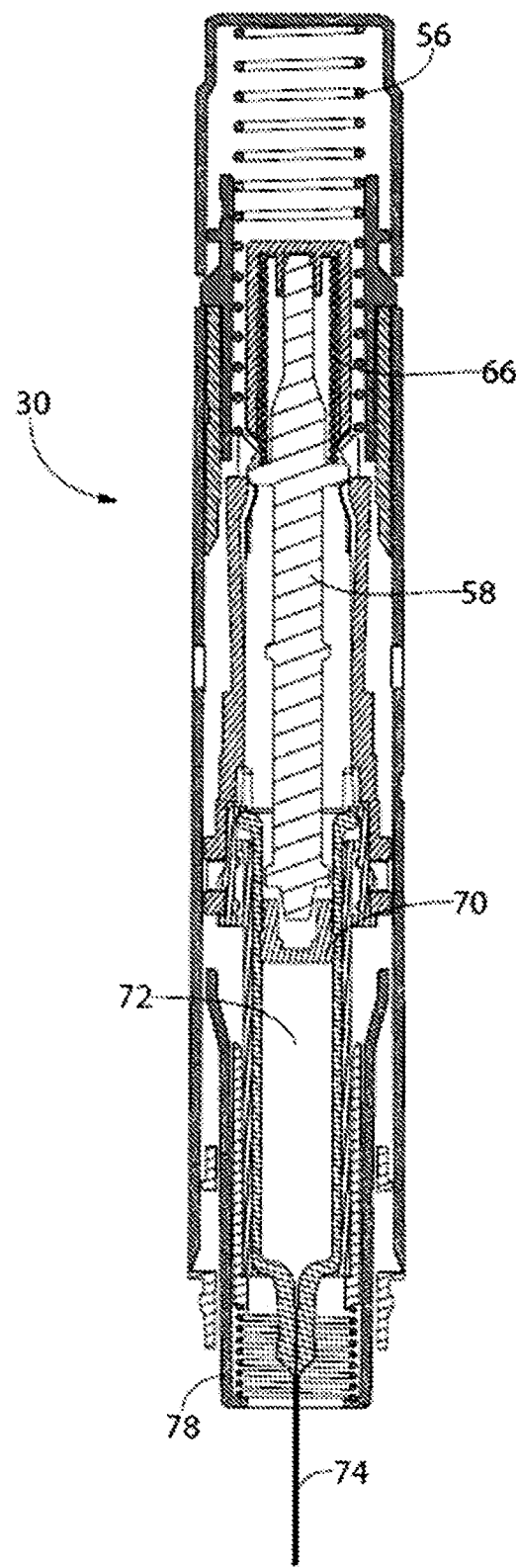
FIG. 9 is a sectional view of the injector of FIG. 6 with the medicament container in an injection position.
Figure 10:
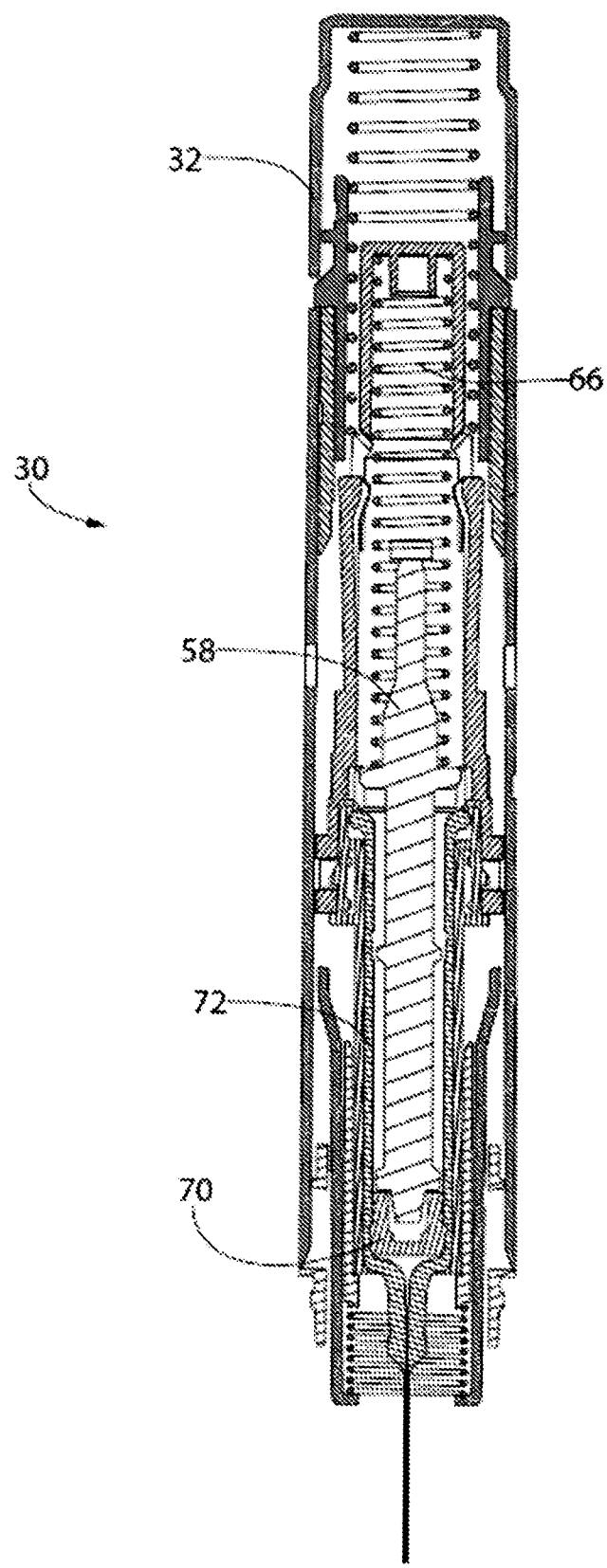
FIG. 10 is a sectional view of the injector of FIG. 6 after medicament has been injected.
Figure 11:
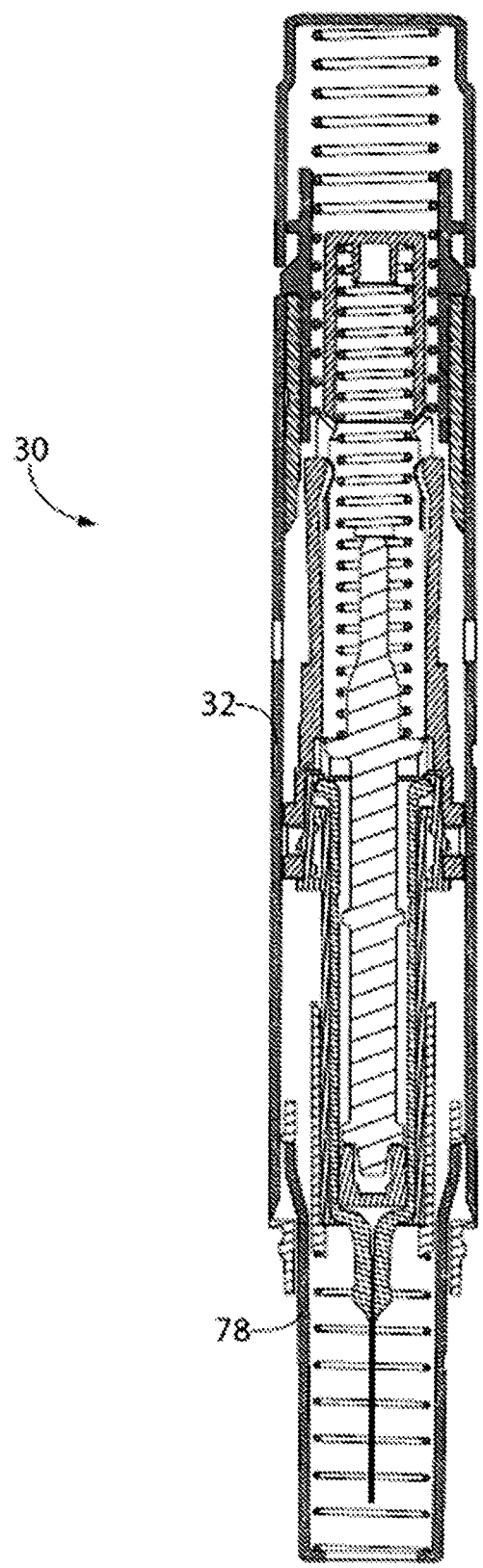
FIG. 11 is a sectional view of the injector of FIG. 6 after an injection with the needle guard in an extended position.

Formulation container 72 may be movable relative to housing 32 between a storage position (FIG. 7) and an injection position (FIG. 9). Formulation container 72 may be moved to the injection position after needle guard 78 triggers injector 30. A second energy source 56 (e.g., biasing element or spring) may move formulation container 72 from the storage position to the injection position. Energy source 66 may move ram 58 once formulation container 72 is in the injection position to dispense the formulation through needle 74. Needle guard 78 may return to the extended position (FIG. 11) once the formulation has been dispensed.

Kits

The invention also provides kits. The kits include an active pharmaceutical ingredient or combination of active pharmaceutical ingredients, either alone or in combination in suitable packaging, and written material that can include instructions for use, discussion of clinical studies and listing of side effects. Such kits may also include information, such as scientific literature references, package insert materials, clinical trial results, and/or summaries of these and the like, which indicate or establish the activities and/or advantages of the composition, and/or which describe dosing, administration, side effects, drug interactions, or other information useful to the health care provider. Such information may be based on the results of various studies, for example, studies using experimental animals involving in vivo models and studies based on human clinical trials. The kit may further contain another active pharmaceutical ingredient. In selected embodiments, an active pharmaceutical ingredient or combination of active pharmaceutical ingredients are provided as separate compositions in separate containers within the kit. In selected embodiments, an active pharmaceutical ingredient or combination of active pharmaceutical ingredients are provided as a single composition within a container in the kit. Suitable packaging and additional articles for use (e.g., measuring cup for liquid preparations, foil wrapping to minimize exposure to air, and the like) are known in the art and may be included in the kit.

Kits described herein can be provided, marketed and/or promoted to health providers, including physicians, nurses, pharmacists, formulary officials, and the like. Kits may also, in selected embodiments, be marketed directly to the consumer.

In some embodiments, the invention provides a kit including a composition including a therapeutically effective amount of an active pharmaceutical ingredient (e.g., a hydrocortisone sodium phosphate) or combination of active pharmaceutical ingredients or a pharmaceutically acceptable salt, solvate, hydrate, cocrystal, or prodrug thereof. These compositions are typically pharmaceutical compositions. The kit is for co-administration of the active pharmaceutical ingredient or combination of active pharmaceutical ingredients, either simultaneously or separately.

In some embodiments, the invention provides for a kit including a composition including a therapeutically effective amount of hydrocortisone sodium phosphate alone or in combination with active pharmaceutical ingredients or a pharmaceutically acceptable salt, solvate, hydrate, cocrystal, or prodrug in an oil combined with an antioxidant in a prefilled syringe (PFS) or vial. In some embodiments, the prefilled syringe or the vial are transparent.

The kit includes suitable packaging for protecting the prefilled syringe or vial from light. In some embodiments this includes an autoinjector. In other embodiments, this includes an autoinjector with a viewing window to allow inspection of the drug prior to injection. In yet other embodiments, the autoinjector is in a carton to prevent light access to the drug.

The prefilled syringe or the vial may include one dose or multiple doses. In some embodiments, a prefilled syringe or vial including multiple doses is bigger, i.e., has a larger volume than a prefilled syringe or vial including only one dose. In some embodiments, the surface area to the volume ratio of a prefilled syringe or vial gets smaller as the prefilled syringe or vial gets larger in volume.

Such kits may include information, such as scientific literature references, package insert materials, clinical trial results, and/or summaries of these and the like, which indicate or establish the activities and/or advantages of the composition, and/or which describe dosing, administration, side effects, drug interactions, or other information useful to the health care provider and/or the patient. Such information may instruct the user to keep the prefilled syringe or prefilled syringe and autoinjector in a carton to protect the pharmaceutical ingredients from light.

In some embodiments, the invention provides a kit including (1) a composition including a therapeutically effective amount of an active pharmaceutical ingredient (e.g., a hydrocortisone sodium phosphate) or combination of active pharmaceutical ingredients or a pharmaceutically acceptable salt, solvate, hydrate, cocrystal, or prodrug thereof, and (2) a diagnostic test for determining whether a patient is in need of hydrocortisone sodium phosphate administration.

Dosages and Dosing Regimens

The amounts of the pharmaceutical compositions administered using the methods herein, such as the dosages of hydrocortisone sodium phosphate, will be dependent on the subject, e.g., human or mammal being treated, the severity of the disorder or condition, the rate of administration, the disposition of the active pharmaceutical ingredients and the discretion of the prescribing physician. Dosage in the range of 50 to 100 mg per week for administration to a human may be adequate to achieve an effective therapeutic level. At times, dosages of 50 to 100 mg per week over several weeks may be required to achieve the desired therapeutic level. However, an effective dosage is in the range of about 0.001 to about 100 mg per kg body weight per day, such as about 1 to about 35 mg/kg/day, in single or divided doses. For a 70 kg human, this would amount to about 0.05 to 7 g/day, such as about 0.05 to about 2.5 g/day. In some instances, dosage levels below the lower limit of the aforesaid range may be more than adequate, while in other cases still larger doses may be employed without causing any harmful side effect— e.g., by dividing such larger doses into several small doses for administration throughout the day. The dosage of the pharmaceutical compositions and active pharmaceutical ingredients may be provided in units of mg/kg of body mass or in mg/m$^2$ of body surface area.

In some embodiments, a pharmaceutical composition or active pharmaceutical ingredient is administered in multiple doses. In an embodiment, a pharmaceutical composition is administered in multiple doses. Dosing may be once, twice, three times, four times, five times, six times, or more than six times per day. Dosing may be once a month, once every two weeks, once a week, or once every other day. In other embodiments, a pharmaceutical composition is administered about once per day to about 6 times per day. In some embodiments, a pharmaceutical composition is administered once daily, while in other embodiments, a pharmaceutical composition is administered twice daily, and in other embodiments a pharmaceutical composition is administered three times daily.

Administration of the active pharmaceutical ingredients may continue as long as necessary. In selected embodiments, a pharmaceutical composition is administered for more than 1, 2, 3, 4, 5, 6, 7, 14, or 28 day(s). Other embodiments require the pharmaceutical composition is administered for more than 1, 2, 3, 4, 5, 6, 7, 14, or 28 week(s). In some embodiments, a pharmaceutical composition is administered for less than, or no more than 28, 14, 7, 6, 5, 4, 3, 2, or 1 day(s). In some embodiments, a pharmaceutical composition is administered chronically on an ongoing basis—e.g., for the treatment of chronic effects. In some embodiments, the administration of a pharmaceutical composition continues for less than, or no more than about 7 days. In yet another embodiment the administration continues for more than about 6, 10, 14, 28 days, two months, six months, or one year. In some cases, continuous dosing is achieved and maintained as long as necessary.

In some embodiments, an effective dosage of an active pharmaceutical ingredient disclosed herein is in the range of about 1 mg to about 500 mg, about 10 mg to about 300 mg, about 20 mg to about 250 mg, about 25 mg to about 200 mg, about 50 mg to 200 mg, about 10 mg to about 200 mg, about 20 mg to about 150 mg, about 30 mg to about 120 mg, about 10 mg to about 90 mg, about 20 mg to about 80 mg, about 30 mg to about 70 mg, about 40 mg to about 60 mg, about 45 mg to about 55 mg, about 50 mg to about 100 mg, about 48 mg to about 52 mg, about 50 mg to about 150 mg, about 60 mg to about 140 mg, about 70 mg to about 130 mg, about 80 mg to about 120 mg, about 90 mg to about 110 mg, about 95 mg to about 105 mg, about 150 mg to about 250 mg, about 160 mg to about 240 mg, about 170 mg to about 230 mg, about 180 mg to about 220 mg, about 190 mg to about 210 mg, about 195 mg to about 205 mg, or about 198 to about 202 mg. In some embodiments, an effective dosage of an active pharmaceutical ingredient disclosed herein is less than, or no more than about 25 mg, less than, or no more than about 50 mg, less than, or no more than about 75 mg, less than, or no more than about 100 mg, less than, or no more than about 125 mg, less than, or no more than about 150 mg, less than, or no more than about 175 mg, less than, or no more than about 200 mg, less than, or no more than about 225 mg, or less than, or no more than about 250 mg. In some embodiments, an effective dosage of an active pharmaceutical ingredient disclosed herein is greater than about 25 mg, greater than about 50 mg, greater than about 75 mg, greater than about 100 mg, greater than about 125 mg, greater than about 150 mg, greater than about 175 mg, greater than about 200 mg, greater than about 225 mg, or greater than about 250 mg.

In some embodiments, an effective dosage of an active pharmaceutical ingredient disclosed herein is in the range of about 0.01 mg/kg to about 200 mg/kg, or about 0.1 to 100 mg/kg, or about 1 to 50 mg/kg. In some embodiments, an active pharmaceutical ingredient is administered at a dosage of 10 to 200 mg BID, including 50, 60, 70, 80, 90, 100, 150, or 200 mg BID. In some embodiments, an active pharmaceutical ingredient is administered at a dosage of 10 to 500 mg BID, including 1, 5, 10, 15, 25, 50, 75, 100, 150, 200, 300, 400, or 500 mg BID.

In some instances, dosage levels below the lower limit of the aforesaid ranges may be more than adequate, while in other cases still larger doses may be employed without causing any harmful side effect, e.g., by dividing such larger doses into several small doses for administration throughout the day. As those skilled in the art will appreciate, the dosage actually administered will depend upon the condition being treated, the age, health and weight of the recipient, the type of concurrent treatment, if any, and the frequency of treatment. Moreover, the effective dosage amount may be determined by one skilled in the art on the basis of routine empirical activity testing to measure the bioactivity of the compound(s) in a bioassay, and thus establish the appropriate dosage to be administered.

An effective amount of the combination of the active pharmaceutical ingredient may be administered in either single or multiple doses by any of the accepted modes of administration of agents having similar utilities, including rectal, buccal, intranasal and transdermal routes, by intra-arterial injection, intravenously, intraperitoneally, parenterally, intramuscularly, subcutaneously, intradermally, orally, topically, or as an inhalant. In some embodiments, the compositions described herein further include controlled-release, sustained release, or extended-release therapeutic dosage forms for administration of the compounds described herein, which involves incorporation of the compounds into a suitable delivery system in the formation of certain compositions. This dosage form controls release of the compound(s) in such a manner that an effective concentration of the compound(s) in the bloodstream may be maintained over an extended period of time, with the concentration in the blood remaining relatively constant, to improve therapeutic results and/or minimize side effects. Additionally, a controlled-release system would provide minimum peak to trough fluctuations in blood plasma levels of the compound.

The following clauses describe certain embodiments.

Clause 1. A pharmaceutical formulation comprising hydrocortisone, a hydrocortisone prodrug, and/or a pharmaceutically acceptable salt of any one thereof, and one or more inactive ingredients.

Clause 2. The pharmaceutical formulation of clause 1, wherein the hydrocortisone prodrug is a hydrocortisone ester.

Clause 3. The pharmaceutical formulation of clause 1 or 2, wherein the hydrocortisone prodrug or pharmaceutically acceptable salt thereof is selected from hydrocortisone sodium phosphate, hydrocortisone sodium succinate, hydrocortisone hydrogen succinate, hydrocortisone butyrate, hydrocortisone acetate.

Clause 4. The pharmaceutical formulation of clause 1 or 2, wherein the hydrocortisone prodrug or pharmaceutically acceptable salt thereof is hydrocortisone sodium phosphate.

Clause 5. The pharmaceutical formulation of clause 4, wherein the concentration of hydrocortisone sodium phosphate in the pharmaceutical formulation is between about 5 mg/mL and about 100 mg/mL.

Clause 6. The pharmaceutical formulation of clause 4, wherein the concentration of hydrocortisone sodium phosphate in the pharmaceutical formulation is between about 50 mg/mL and about 100 mg/mL.

Clause 7. The pharmaceutical formulation of clause 4, wherein the concentration of hydrocortisone sodium phosphate in the pharmaceutical formulation is between about 25 mg/mL and about 75 mg/mL.

Clause 8. The pharmaceutical formulation of clause 4, wherein the concentration of hydrocortisone sodium phosphate in the pharmaceutical formulation is about 50 mg/mL, about 51 mg/mL, about 52 mg/mL, about 53 mg/mL, about 54 mg/mL, about 55 mg/mL, about 56 mg/mL, about 57 mg/mL, about 58 mg/mL, about 59 mg/mL, about 60 mg/mL, about 61 mg/mL, about 62 mg/mL, about 63 mg/mL, about 64 mg/mL, about 65 mg/mL, about 66 mg/mL, about 67 mg/mL, about 68 mg/mL, about 69 mg/mL, or about 70 mg/mL.

Clause 9. The pharmaceutical formulation of any one of clauses 1 to 8, wherein the one or more inactive ingredients are selected from a buffer agent, a chelating agent, an antioxidant, a pH adjustor, and a solvent.

Clause 10. The pharmaceutical formulation of clause 9, wherein the buffer agent is selected from monobasic sodium phosphate anhydrous and dibasic sodium phosphate anhydrous.

Clause 11. The pharmaceutical formulation of clause 9, wherein the chelating agent is disodium EDTA.

Clause 12. The pharmaceutical formulation of clause 9, wherein the antioxidant is monothioglycerol.

Clause 13. The pharmaceutical formulation of clause 9, wherein the pH adjustor is selected from sodium hydroxide and HCl.

Clause 14. The pharmaceutical formulation of clause 9, wherein the solvent is water.

Clause 101. An aqueous pharmaceutical formulation comprising from about 50 to about 150 mg/mL hydrocortisone sodium phosphate, from about 2.5 to about 12.5 mg/mL monothioglycerol, and water.

Clause 102. An aqueous pharmaceutical formulation comprising from about 60 to about 135 mg/mL hydrocortisone sodium phosphate, from about 5 to about 10 mg/mL monothioglycerol, and water.

Clause 201. The aqueous pharmaceutical formulation of clause 101 or 102, comprising from about 50 to about 60 mg/mL hydrocortisone sodium phosphate, from about 60 to about 70 mg/mL hydrocortisone sodium phosphate, or from about 70 to about 80 mg/mL hydrocortisone sodium phosphate.

Clause 301. The aqueous pharmaceutical formulation of clause 101 or 102, comprising from about 60 to about 65 mg/mL hydrocortisone sodium phosphate, or from about 65 to about 70 mg/mL hydrocortisone sodium phosphate.

Clause 401. The aqueous pharmaceutical formulation of clauses 101 or 102, comprising from about 120 to about 130 mg/mL hydrocortisone sodium phosphate, from about 130 to about 140 mg/mL hydrocortisone sodium phosphate, or from about 140 to about 150 mg/mL hydrocortisone sodium phosphate.

Clause 501. The aqueous pharmaceutical formulation of clauses 101 or 102, comprising from about 130 to about 135 mg/mL hydrocortisone sodium phosphate, or from about 135 to about 140 mg/mL hydrocortisone sodium phosphate.

Clause 601. The aqueous pharmaceutical formulation of clauses 101 or 102, comprising about 50 mg/mL hydrocortisone sodium phosphate, about 55 mg/mL hydrocortisone sodium phosphate, about 60 mg/mL hydrocortisone sodium phosphate, about 65 mg/mL hydrocortisone sodium phosphate, about 70 mg/mL hydrocortisone sodium phosphate, about 75 mg/mL hydrocortisone sodium phosphate, about 80 mg/mL hydrocortisone sodium phosphate, about 85 mg/mL hydrocortisone sodium phosphate, about 90 mg/mL hydrocortisone sodium phosphate, about 95 mg/mL hydrocortisone sodium phosphate, about 100 mg/mL hydrocortisone sodium phosphate, about 105 mg/mL hydrocortisone sodium phosphate, about 110 mg/mL hydrocortisone sodium phosphate, about 115 mg/mL hydrocortisone sodium phosphate, about 120 mg/mL hydrocortisone sodium phosphate, about 125 mg/mL hydrocortisone sodium phosphate, about 130 mg/mL hydrocortisone sodium phosphate, about 135 mg/mL hydrocortisone sodium phosphate, about 140 mg/mL hydrocortisone sodium phosphate, about 145 mg/mL hydrocortisone sodium phosphate, or about 150 mg/mL hydrocortisone sodium phosphate.

Clause 701. An aqueous pharmaceutical formulation comprising about 60 mg/mL hydrocortisone sodium phosphate, from about 2.5 to about 12.5 mg/mL monothioglycerol, and water.

Clause 702. An aqueous pharmaceutical formulation comprising about 61 mg/mL hydrocortisone sodium phosphate, from about 2.5 to about 12.5 mg/mL monothioglycerol, and water.

Clause 703. An aqueous pharmaceutical formulation comprising about 62 mg/mL hydrocortisone sodium phosphate, from about 2.5 to about 12.5 mg/mL monothioglycerol, and water.

Clause 704. An aqueous pharmaceutical formulation comprising about 63 mg/mL hydrocortisone sodium phosphate, from about 2.5 to about 12.5 mg/mL monothioglycerol, and water.

Clause 705. An aqueous pharmaceutical formulation comprising about 64 mg/mL hydrocortisone sodium phosphate, from about 2.5 to about 12.5 mg/mL monothioglycerol, and water.

Clause 706. An aqueous pharmaceutical formulation comprising about 65 mg/mL hydrocortisone sodium phosphate, from about 2.5 to about 12.5 mg/mL monothioglycerol, and water.

Clause 707. An aqueous pharmaceutical formulation comprising about 66 mg/mL hydrocortisone sodium phosphate, from about 2.5 to about 12.5 mg/mL monothioglycerol, and water.

Clause 708. An aqueous pharmaceutical formulation comprising about 67 mg/mL hydrocortisone sodium phosphate, from about 2.5 to about 12.5 mg/mL monothioglycerol, and water.

Clause 709. An aqueous pharmaceutical formulation comprising about 68 mg/mL hydrocortisone sodium phosphate, from about 2.5 to about 12.5 mg/mL monothioglycerol, and water.

Clause 710. An aqueous pharmaceutical formulation comprising about 69 mg/mL hydrocortisone sodium phosphate, from about 2.5 to about 12.5 mg/mL monothioglycerol, and water.

Clause 711. An aqueous pharmaceutical formulation comprising about 70 mg/mL hydrocortisone sodium phosphate, from about 2.5 to about 12.5 mg/mL monothioglycerol, and water.

Clause 801. An aqueous pharmaceutical formulation comprising about 67 mg/mL hydrocortisone sodium phosphate, from about 2.5 to about 12.5 mg/mL monothioglycerol, and water.

Clause 802. An aqueous pharmaceutical formulation comprising about 67.1 mg/mL hydrocortisone sodium phosphate, from about 2.5 to about 12.5 mg/mL monothioglycerol, and water.

Clause 803. An aqueous pharmaceutical formulation comprising about 67.2 mg/mL hydrocortisone sodium phosphate, from about 2.5 to about 12.5 mg/mL monothioglycerol, and water.

Clause 804. An aqueous pharmaceutical formulation comprising about 67.3 mg/mL hydrocortisone sodium phosphate, from about 2.5 to about 12.5 mg/mL monothioglycerol, and water.

Clause 805. An aqueous pharmaceutical formulation comprising about 67.4 mg/mL hydrocortisone sodium phosphate, from about 2.5 to about 12.5 mg/mL monothioglycerol, and water.

Clause 806. An aqueous pharmaceutical formulation comprising about 67.5 mg/mL hydrocortisone sodium phosphate, from about 2.5 to about 12.5 mg/mL monothioglycerol, and water.

Clause 807. An aqueous pharmaceutical formulation comprising about 67.6 mg/mL hydrocortisone sodium phosphate, from about 2.5 to about 12.5 mg/mL monothioglycerol, and water.

Clause 808. An aqueous pharmaceutical formulation comprising about 67.7 mg/mL hydrocortisone sodium phosphate, from about 2.5 to about 12.5 mg/mL monothioglycerol, and water.

Clause 809. An aqueous pharmaceutical formulation comprising about 67.8 mg/mL hydrocortisone sodium phosphate, from about 2.5 to about 12.5 mg/mL monothioglycerol, and water.

Clause 810. An aqueous pharmaceutical formulation comprising about 67.9 mg/mL hydrocortisone sodium phosphate, from about 2.5 to about 12.5 mg/mL monothioglycerol, and water.

Clause 811. An aqueous pharmaceutical formulation comprising about 68 mg/mL hydrocortisone sodium phosphate, from about 2.5 to about 12.5 mg/mL monothioglycerol, and water.

Clause 901. An aqueous pharmaceutical formulation comprising about 130 mg/mL hydrocortisone sodium phosphate, from about 2.5 to about 12.5 mg/mL monothioglycerol, and water.

Clause 902. An aqueous pharmaceutical formulation comprising about 131 mg/mL hydrocortisone sodium phosphate, from about 2.5 to about 12.5 mg/mL monothioglycerol, and water.

Clause 903. An aqueous pharmaceutical formulation comprising about 132 mg/mL hydrocortisone sodium phosphate, from about 2.5 to about 12.5 mg/mL monothioglycerol, and water.

Clause 904. An aqueous pharmaceutical formulation comprising about 133 mg/mL hydrocortisone sodium phosphate, from about 2.5 to about 12.5 mg/mL monothioglycerol, and water.

Clause 905. An aqueous pharmaceutical formulation comprising about 134 mg/mL hydrocortisone sodium phosphate, from about 2.5 to about 12.5 mg/mL monothioglycerol, and water.

Clause 906. An aqueous pharmaceutical formulation comprising about 135 mg/mL hydrocortisone sodium phosphate, from about 2.5 to about 12.5 mg/mL monothioglycerol, and water.

Clause 907. An aqueous pharmaceutical formulation comprising about 136 mg/mL hydrocortisone sodium phosphate, from about 2.5 to about 12.5 mg/mL monothioglycerol, and water.

Clause 908. An aqueous pharmaceutical formulation comprising about 137 mg/mL hydrocortisone sodium phosphate, from about 2.5 to about 12.5 mg/mL monothioglycerol, and water.

Clause 909. An aqueous pharmaceutical formulation comprising about 138 mg/mL hydrocortisone sodium phosphate, from about 2.5 to about 12.5 mg/mL monothioglycerol, and water.

Clause 910. An aqueous pharmaceutical formulation comprising about 139 mg/mL hydrocortisone sodium phosphate, from about 2.5 to about 12.5 mg/mL monothioglycerol, and water.

Clause 911. An aqueous pharmaceutical formulation comprising about 140 mg/mL hydrocortisone sodium phosphate, from about 2.5 to about 12.5 mg/mL monothioglycerol, and water.

Clause 1001. An aqueous pharmaceutical formulation comprising about 134 mg/mL hydrocortisone sodium phosphate, about 134.1 mg/mL hydrocortisone sodium phosphate, about 134.2 mg/mL hydrocortisone sodium phosphate, about 134.3 mg/mL hydrocortisone sodium phosphate, about 134.4 mg/mL hydrocortisone sodium phosphate, about 134.5 mg/mL hydrocortisone sodium phosphate, about 134.6 mg/mL hydrocortisone sodium phosphate, about 134.7 mg/mL hydrocortisone sodium phosphate, about 134.8 mg/mL hydrocortisone sodium phosphate, about 134.9 mg/mL hydrocortisone sodium phosphate, or about 135 mg/mL hydrocortisone sodium phosphate, from about 2.5 to about 12.5 mg/mL monothioglycerol, and water.

Clause 1101. The aqueous pharmaceutical formulation of any one of clauses 101 to 1001, comprising from about 2.5 to about 3.5 mg/mL monothioglycerol, from about 3.5 to about 4.5 mg/mL monothioglycerol, from about 4.5 to about 5.5 mg/mL monothioglycerol, from about 5.5 to about 6.5 mg/mL monothioglycerol, from about 6.5 to about 7.5 mg/mL monothioglycerol, from about 7.5 to about 8.5 mg/mL monothioglycerol, from about 8.5 to about 9.5 mg/mL monothioglycerol, from about 9.5 to about 10.5 mg/mL monothioglycerol, from about 10.5 to about 11.5 mg/mL monothioglycerol, or from about 11.5 to about 12.5 mg/mL monothioglycerol.

Clause 1201. The aqueous pharmaceutical formulation of any one of clauses 101 to 1001, comprising from about 4 to about 4.25 mg/mL monothioglycerol, from about 4.25 to about 4.5 mg/mL monothioglycerol, from about 4.5 to about 4.75 mg/mL monothioglycerol, from about 4.75 to about 5 mg/mL monothioglycerol, from about 5 to about 5.25 mg/mL monothioglycerol, from about 5.25 to about 5.5 mg/mL monothioglycerol, from about 5.5 to about 5.75 mg/mL monothioglycerol, or from about 5.75 to about 6 mg/mL monothioglycerol.

Clause 1301. The aqueous pharmaceutical formulation of any one of clauses 101 to 1001, comprising from about 9 to about 9.25 mg/mL monothioglycerol, from about 9.25 to about 9.5 mg/mL monothioglycerol, from about 9.5 to about 9.75 mg/mL monothioglycerol, from about 9.75 to about 10 mg/mL monothioglycerol, from about 10 to about 10.25 mg/mL monothioglycerol, from about 10.25 to about 10.5 mg/mL monothioglycerol, from about 10.5 to about 10.75 mg/mL monothioglycerol, or from about 10.75 to about 11 mg/mL monothioglycerol.

Clause 1401. The aqueous pharmaceutical formulation of any one of clauses 101 to 1001, comprising about 4.5 mg/mL monothioglycerol.

Clause 1402. The aqueous pharmaceutical formulation of any one of clauses 101 to 1001, comprising about 4.6 mg/mL monothioglycerol.

Clause 1403. The aqueous pharmaceutical formulation of any one of clauses 101 to 1001, comprising about 4.7 mg/mL monothioglycerol.

Clause 1404. The aqueous pharmaceutical formulation of any one of clauses 101 to 1001, comprising about 4.8 mg/mL monothioglycerol.

Clause 1405. The aqueous pharmaceutical formulation of any one of clauses 101 to 1001, comprising about 4.9 mg/mL monothioglycerol.

Clause 1406. The aqueous pharmaceutical formulation of any one of clauses 101 to 1001, comprising about 5 mg/mL monothioglycerol.

Clause 1407. The aqueous pharmaceutical formulation of any one of clauses 101 to 1001, comprising about 5.1 mg/mL monothioglycerol.

Clause 1408. The aqueous pharmaceutical formulation of any one of clauses 101 to 1001, comprising about 5.2 mg/mL monothioglycerol.

Clause 1409. The aqueous pharmaceutical formulation of any one of clauses 101 to 1001, comprising about 5.3 mg/mL monothioglycerol.

Clause 1410. The aqueous pharmaceutical formulation of any one of clauses 101 to 1001, comprising about 5.4 mg/mL monothioglycerol.

Clause 1411. The aqueous pharmaceutical formulation of any one of clauses 101 to 1001, comprising about 5.5 mg/mL monothioglycerol.

Clause 1501. The aqueous pharmaceutical formulation of any one of clauses 101 to 1001, comprising about 9.5 mg/mL monothioglycerol.

Clause 1502. The aqueous pharmaceutical formulation of any one of clauses 101 to 1001, comprising about 9.6 mg/mL monothioglycerol.

Clause 1503. The aqueous pharmaceutical formulation of any one of clauses 101 to 1001, comprising about 9.7 mg/mL monothioglycerol.

Clause 1504. The aqueous pharmaceutical formulation of any one of clauses 101 to 1001, comprising about 9.8 mg/mL monothioglycerol.

Clause 1505. The aqueous pharmaceutical formulation of any one of clauses 101 to 1001, comprising about 9.9 mg/mL monothioglycerol.

Clause 1506. The aqueous pharmaceutical formulation of any one of clauses 101 to 1001, comprising about 10 mg/mL monothioglycerol.

Clause 1601. The aqueous pharmaceutical formulation of any one of clauses 101 to 1001, comprising about 10.1 mg/mL monothioglycerol.

Clause 1602. The aqueous pharmaceutical formulation of any one of clauses 101 to 1001, comprising about 10.2 mg/mL monothioglycerol.

Clause 1603. The aqueous pharmaceutical formulation of any one of clauses 101 to 1001, comprising about 10.3 mg/mL monothioglycerol.

Clause 1604. The aqueous pharmaceutical formulation of any one of clauses 101 to 1001, comprising about 10.4 mg/mL monothioglycerol.

Clause 1605. The aqueous pharmaceutical formulation of any one of clauses 101 to 1001, comprising about 10.5 mg/mL monothioglycerol.

Clause 1701. The aqueous pharmaceutical formulation of any one of clauses 101 to 1606, further comprising from about 0.5 to about 2.5 mg/mL monobasic sodium phosphate.

Clause 1702. The aqueous pharmaceutical formulation of any one of clauses 101 to 1606, further comprising about 0.5 mg/mL monobasic sodium phosphate.

Clause 1703. The aqueous pharmaceutical formulation of any one of clauses 101 to 1606, further comprising about 0.6 mg/mL monobasic sodium phosphate.

Clause 1704. The aqueous pharmaceutical formulation of any one of clauses 101 to 1606, further comprising about 0.7 mg/mL monobasic sodium phosphate.

Clause 1705. The aqueous pharmaceutical formulation of any one of clauses 101 to 1606, further comprising about 0.8 mg/mL monobasic sodium phosphate.

Clause 1706. The aqueous pharmaceutical formulation of any one of clauses 101 to 1606, further comprising about 0.9 mg/mL monobasic sodium phosphate.

Clause 1707. The aqueous pharmaceutical formulation of any one of clauses 101 to 1606, further comprising about 1 mg/mL monobasic sodium phosphate.

Clause 1708. The aqueous pharmaceutical formulation of any one of clauses 101 to 1606, further comprising about 1.1 mg/mL monobasic sodium phosphate.

Clause 1709. The aqueous pharmaceutical formulation of any one of clauses 101 to 1606, further comprising about 1.2 mg/mL monobasic sodium phosphate.

Clause 1710. The aqueous pharmaceutical formulation of any one of clauses 101 to 1606, further comprising about 1.3 mg/mL monobasic sodium phosphate.

Clause 1711. The aqueous pharmaceutical formulation of any one of clauses 101 to 1606, further comprising about 1.4 mg/mL monobasic sodium phosphate.

Clause 1712. The aqueous pharmaceutical formulation of any one of clauses 101 to 1606, further comprising about 1.5 mg/mL monobasic sodium phosphate.

Clause 1713. The aqueous pharmaceutical formulation of any one of clauses 101 to 1606, further comprising about 1.6 mg/mL monobasic sodium phosphate.

Clause 1714. The aqueous pharmaceutical formulation of any one of clauses 101 to 1606, further comprising about 1.7 mg/mL monobasic sodium phosphate.

Clause 1715. The aqueous pharmaceutical formulation of any one of clauses 101 to 1606, further comprising about 1.8 mg/mL monobasic sodium phosphate.

Clause 1716. The aqueous pharmaceutical formulation of any one of clauses 101 to 1606, further comprising about 1.9 mg/mL monobasic sodium phosphate.

Clause 1717. The aqueous pharmaceutical formulation of any one of clauses 101 to 1606, further comprising about 2 mg/mL monobasic sodium phosphate.

Clause 1718. The aqueous pharmaceutical formulation of any one of clauses 101 to 1606, further comprising about 2.1 mg/mL monobasic sodium phosphate.

Clause 1719. The aqueous pharmaceutical formulation of any one of clauses 101 to 1606, further comprising about 2.2 mg/mL monobasic sodium phosphate.

Clause 1720. The aqueous pharmaceutical formulation of any one of clauses 101 to 1606, further comprising about 2.3 mg/mL monobasic sodium phosphate.

Clause 1721. The aqueous pharmaceutical formulation of any one of clauses 101 to 1606, further comprising about 2.4 mg/mL monobasic sodium phosphate.

Clause 1722. The aqueous pharmaceutical formulation of any one of clauses 101 to 1606, further comprising about 2.5 mg/mL monobasic sodium phosphate.

Clause 1801. The aqueous pharmaceutical formulation of any one of clauses 101 to 1722, further comprising from about 5 to about 25 mg/mL dibasic sodium phosphate.

Clause 1802. The aqueous pharmaceutical formulation of any one of clauses 101 to 1722, further comprising about 5 mg/mL dibasic sodium phosphate.

Clause 1803. The aqueous pharmaceutical formulation of any one of clauses 101 to 1722, further comprising about 6 mg/mL dibasic sodium phosphate.

Clause 1804. The aqueous pharmaceutical formulation of any one of clauses 101 to 1722, further comprising about 7 mg/mL dibasic sodium phosphate.

Clause 1805. The aqueous pharmaceutical formulation of any one of clauses 101 to 1722, further comprising about 8 mg/mL dibasic sodium phosphate.

Clause 1806. The aqueous pharmaceutical formulation of any one of clauses 101 to 1722, further comprising about 9 mg/mL dibasic sodium phosphate.

Clause 1807. The aqueous pharmaceutical formulation of any one of clauses 101 to 1722, further comprising about 10 mg/mL dibasic sodium phosphate.

Clause 1808. The aqueous pharmaceutical formulation of any one of clauses 101 to 1722, further comprising about 11 mg/mL dibasic sodium phosphate.

Clause 1809. The aqueous pharmaceutical formulation of any one of clauses 101 to 1722, further comprising about 12 mg/mL dibasic sodium phosphate.

Clause 1810. The aqueous pharmaceutical formulation of any one of clauses 101 to 1722, further comprising about 13 mg/mL dibasic sodium phosphate.

Clause 1811. The aqueous pharmaceutical formulation of any one of clauses 101 to 1722, further comprising about 14 mg/mL dibasic sodium phosphate.

Clause 1812. The aqueous pharmaceutical formulation of any one of clauses 101 to 1722, further comprising about 15 mg/mL dibasic sodium phosphate.

Clause 1813. The aqueous pharmaceutical formulation of any one of clauses 101 to 1722, further comprising about 16 mg/mL dibasic sodium phosphate.

Clause 1814. The aqueous pharmaceutical formulation of any one of clauses 101 to 1722, further comprising about 17 mg/mL dibasic sodium phosphate.

Clause 1815. The aqueous pharmaceutical formulation of any one of clauses 101 to 1722, further comprising about 18 mg/mL dibasic sodium phosphate.

Clause 1816. The aqueous pharmaceutical formulation of any one of clauses 101 to 1722, further comprising about 19 mg/mL dibasic sodium phosphate.

Clause 1817. The aqueous pharmaceutical formulation of any one of clauses 101 to 1722, further comprising about 20 mg/mL dibasic sodium phosphate.

Clause 1818. The aqueous pharmaceutical formulation of any one of clauses 101 to 1722, further comprising about 21 mg/mL dibasic sodium phosphate.

Clause 1819. The aqueous pharmaceutical formulation of any one of clauses 101 to 1722, further comprising about 22 mg/mL dibasic sodium phosphate.

Clause 1820. The aqueous pharmaceutical formulation of any one of clauses 101 to 1722, further comprising about 23 mg/mL dibasic sodium phosphate.

Clause 1821. The aqueous pharmaceutical formulation of any one of clauses 101 to 1722, further comprising about 24 mg/mL dibasic sodium phosphate.

Clause 1822. The aqueous pharmaceutical formulation of any one of clauses 101 to 1722, further comprising about 25 mg/mL dibasic sodium phosphate.

Clause 1901. The aqueous pharmaceutical formulation of any one of clauses 101 to 1822, further comprising from about 0.1 to about 1 mg/mL disodium EDTA.

Clause 1902. The aqueous pharmaceutical formulation of any one of clauses 101 to 1822, further comprising about 0.1 mg/mL disodium EDTA.

Clause 1903. The aqueous pharmaceutical formulation of any one of clauses 101 to 1822, further comprising about 0.2 mg/mL disodium EDTA.

Clause 1904. The aqueous pharmaceutical formulation of any one of clauses 101 to 1822, further comprising about 0.3 mg/mL disodium EDTA.

Clause 1905. The aqueous pharmaceutical formulation of any one of clauses 101 to 1822, further comprising about 0.4 mg/mL disodium EDTA.

Clause 1906. The aqueous pharmaceutical formulation of any one of clauses 101 to 1822, further comprising about 0.5 mg/mL disodium EDTA.

Clause 1907. The aqueous pharmaceutical formulation of any one of clauses 101 to 1822, further comprising about 0.6 mg/mL disodium EDTA.

Clause 1908. The aqueous pharmaceutical formulation of any one of clauses 101 to 1822, further comprising about 0.7 mg/mL disodium EDTA.

Clause 1909. The aqueous pharmaceutical formulation of any one of clauses 101 to 1822, further comprising about 0.8 mg/mL disodium EDTA.

Clause 1910. The aqueous pharmaceutical formulation of any one of clauses 101 to 1822, further comprising about 0.9 mg/mL disodium EDTA.

Clause 1911. The aqueous pharmaceutical formulation of any one of clauses 101 to 1822, further comprising about 1 mg/mL disodium EDTA.

Clause 2001. The aqueous pharmaceutical formulation of any one of clauses 101 to 1911, wherein the pharmaceutical formulation has a pH from about 7.5 to about 9.5.

Clause 2002. The aqueous pharmaceutical formulation of any one of clauses 101 to 1911, wherein the pharmaceutical formulation has a pH from about 7.5 to about 8.

Clause 2003. The aqueous pharmaceutical formulation of any one of clauses 101 to 1911, wherein the pharmaceutical formulation has a pH from about 8 to about 8.5.

Clause 2004. The aqueous pharmaceutical formulation of any one of clauses 101 to 1911, wherein the pharmaceutical formulation has a pH from about 8.5 to about 9.

Clause 2101. The aqueous pharmaceutical formulation of any one of clauses 101 to 1911, wherein the pharmaceutical formulation has a pH of about 7.5.

Clause 2102. The aqueous pharmaceutical formulation of any one of clauses 101 to 1911, wherein the pharmaceutical formulation has a pH of about 7.6.

Clause 2103. The aqueous pharmaceutical formulation of any one of clauses 101 to 1911, wherein the pharmaceutical formulation has a pH of about 7.7.

Clause 2104. The aqueous pharmaceutical formulation of any one of clauses 101 to 1911, wherein the pharmaceutical formulation has a pH of about 7.8.

Clause 2105. The aqueous pharmaceutical formulation of any one of clauses 101 to 1911, wherein the pharmaceutical formulation has a pH of about 7.9.

Clause 2106. The aqueous pharmaceutical formulation of any one of clauses 101 to 1911, wherein the pharmaceutical formulation has a pH of about 8.

Clause 2107. The aqueous pharmaceutical formulation of any one of clauses 101 to 1911, wherein the pharmaceutical formulation has a pH of about 8.1.

Clause 2108. The aqueous pharmaceutical formulation of any one of clauses 101 to 1911, wherein the pharmaceutical formulation has a pH of about 8.2.

Clause 2109. The aqueous pharmaceutical formulation of any one of clauses 101 to 1911, wherein the pharmaceutical formulation has a pH of about 8.3.

Clause 2110. The aqueous pharmaceutical formulation of any one of clauses 101 to 1911, wherein the pharmaceutical formulation has a pH of about 8.4.

Clause 2111. The aqueous pharmaceutical formulation of any one of clauses 101 to 1911, wherein the pharmaceutical formulation has a pH of about 8.5.

Clause 2112. The aqueous pharmaceutical formulation of any one of clauses 101 to 1911, wherein the pharmaceutical formulation has a pH of about 8.6.

Clause 2113. The aqueous pharmaceutical formulation of any one of clauses 101 to 1911, wherein the pharmaceutical formulation has a pH of about 8.7.

Clause 2114. The aqueous pharmaceutical formulation of any one of clauses 101 to 1911, wherein the pharmaceutical formulation has a pH of about, 8.8.

Clause 2115. The aqueous pharmaceutical formulation of any one of clauses 101 to 1911, wherein the pharmaceutical formulation has a pH of about 8.9.

Clause 2116. The aqueous pharmaceutical formulation of any one of clauses 101 to 1911, wherein the pharmaceutical formulation has a pH of about 9.

Clause 2201. The aqueous pharmaceutical formulation of any one of clauses 1 to 2116, wherein the formulation comprises from no impurities to less than, or no more than 0.05% impurities upon formulation.

Clause 2202. The aqueous pharmaceutical formulation of any one of clauses 101 to 2116, wherein the formulation comprises from no impurities to less than, or no more than 0.04% impurities upon formulation.

Clause 2203. The aqueous pharmaceutical formulation of any one of clauses 101 to 2116, wherein the formulation comprises from no impurities to less than, or no more than 0.03% impurities upon formulation.

Clause 2204. The aqueous pharmaceutical formulation of any one of clauses 101 to 2116, wherein the formulation comprises from no impurities to less than, or no more than 0.02% impurities upon formulation.

Clause 2205. The aqueous pharmaceutical formulation of any one of clauses 101 to 2116, wherein the formulation comprises from no impurities to less than, or no more than 0.01% impurities upon formulation.

Clause 2206. The aqueous pharmaceutical formulation of any one of clauses 1 to 2116, wherein the formulation comprises from no impurities to less than, or no more than 0.1% impurities upon formulation.

Clause 2207. The aqueous pharmaceutical formulation of any one of clauses 101 to 2116, wherein the formulation comprises from no impurities to less than, or no more than 0.09% impurities upon formulation.

Clause 2208. The aqueous pharmaceutical formulation of any one of clauses 101 to 2116, wherein the formulation comprises from no impurities to less than, or no more than 0.08% impurities upon formulation.

Clause 2209. The aqueous pharmaceutical formulation of any one of clauses 101 to 2116, wherein the formulation comprises from no impurities to less than, or no more than 0.07% impurities upon formulation.

Clause 2210. The aqueous pharmaceutical formulation of any one of clauses 101 to 2116, wherein the formulation comprises from no impurities to less than, or no more than 0.06% impurities upon formulation.

Clause 2211. The aqueous pharmaceutical formulation of any one of clauses 1 to 2116, wherein the formulation comprises from no impurities to less than, or no more than 0.5% impurities upon formulation.

Clause 2212. The aqueous pharmaceutical formulation of any one of clauses 101 to 2116, wherein the formulation comprises from no impurities to less than, or no more than 0.45% impurities upon formulation.

Clause 2213. The aqueous pharmaceutical formulation of any one of clauses 101 to 2116, wherein the formulation comprises from no impurities to less than, or no more than 0.4% impurities upon formulation.

Clause 2214. The aqueous pharmaceutical formulation of any one of clauses 101 to 2116, wherein the formulation comprises from no impurities to less than, or no more than 0.35% impurities upon formulation.

Clause 2215. The aqueous pharmaceutical formulation of any one of clauses 101 to 2116, wherein the formulation comprises from no impurities to less than, or no more than 0.3% impurities upon formulation.

Clause 2216. The aqueous pharmaceutical formulation of any one of clauses 1 to 2116, wherein the formulation comprises from no impurities to less than, or no more than 0.25% impurities upon formulation.

Clause 2217. The aqueous pharmaceutical formulation of any one of clauses 101 to 2116, wherein the formulation comprises from no impurities to less than, or no more than 0.2% impurities upon formulation.

Clause 2218. The aqueous pharmaceutical formulation of any one of clauses 101 to 2116, wherein the formulation comprises from no impurities to less than, or no more than 0.15% impurities upon formulation.

Clause 2219. The aqueous pharmaceutical formulation of any one of clauses 101 to 2116, wherein the formulation comprises from no impurities to less than, or no more than 0.14% impurities upon formulation.

Clause 2220. The aqueous pharmaceutical formulation of any one of clauses 101 to 2116, wherein the formulation comprises from no impurities to less than, or no more than 0.13%, 0.12%, or 0.11% impurities upon formulation.

Clause 2301. The aqueous pharmaceutical formulation of any one of clauses 101 to 2205, wherein the formulation comprises from no impurities to less than, or no more than 0.07% impurities upon storage at 25° C. for about 3 months.

Clause 2302. The aqueous pharmaceutical formulation of any one of clauses 101 to 2205, wherein the formulation comprises from no impurities to less than, or no more than 0.06% impurities upon storage at 25° C. for about 3 months.

Clause 2303. The aqueous pharmaceutical formulation of any one of clauses 101 to 2205, wherein the formulation comprises from no impurities to less than, or no more than 0.05% impurities upon storage at 25° C. for about 3 months.

Clause 2304. The aqueous pharmaceutical formulation of any one of clauses 101 to 2205, wherein the formulation comprises from no impurities to less than, or no more than 0.04% impurities upon storage at 25° C. for about 3 months.

Clause 2305. The aqueous pharmaceutical formulation of any one of clauses 101 to 2205, wherein the formulation comprises from no impurities to less than, or no more than 0.03% impurities upon storage at 25° C. for about 3 months.

Clause 2306. The aqueous pharmaceutical formulation of any one of clauses 101 to 2205, wherein the formulation comprises from no impurities to less than, or no more than 0.02% impurities upon storage at 25° C. for about 3 months.

Clause 2307. The aqueous pharmaceutical formulation of any one of clauses 101 to 2205, wherein the formulation comprises from no impurities to less than, or no more than 0.01% impurities upon storage at 25° C. for about 3 months.

Clause 2308. The aqueous pharmaceutical formulation of any one of clauses 101 to 2205, wherein the formulation comprises from 0.01% impurities to less than, or no more than 0.07% impurities upon storage at 25° C. for about 3 months.

Clause 2309. The aqueous pharmaceutical formulation of any one of clauses 101 to 2205, wherein the formulation comprises from 0.01% impurities to less than, or no more than 0.06% impurities upon storage at 25° C. for about 3 months.

Clause 2310. The aqueous pharmaceutical formulation of any one of clauses 101 to 2205, wherein the formulation comprises from 0.01% impurities to less than, or no more than 0.05% impurities upon storage at 25° C. for about 3 months.

Clause 2311. The aqueous pharmaceutical formulation of any one of clauses 101 to 2205, wherein the formulation comprises from 0.01% impurities to less than, or no more than 0.04% impurities upon storage at 25° C. for about 3 months.

Clause 2312. The aqueous pharmaceutical formulation of any one of clauses 101 to 2205, wherein the formulation comprises from 0.01% impurities to less than, or no more than 0.03% impurities upon storage at 25° C. for about 3 months.

Clause 2313. The aqueous pharmaceutical formulation of any one of clauses 101 to 2205, wherein the formulation comprises from 0.01% impurities to less than, or no more than 0.02% impurities upon storage at 25° C. for about 3 months.

Clause 2314. The aqueous pharmaceutical formulation of any one of clauses 101 to 2205, wherein the formulation comprises from 0.01% impurities to less than, or no more than 0.1% impurities upon storage at 25° C. for about 3 months.

Clause 2315. The aqueous pharmaceutical formulation of any one of clauses 101 to 2205, wherein the formulation comprises from 0.01% impurities to less than, or no more than 0.15% impurities upon storage at 25° C. for about 3 months.

Clause 2316. The aqueous pharmaceutical formulation of any one of clauses 101 to 2205, wherein the formulation comprises from 0.01% impurities to less than, or no more than 0.2% impurities upon storage at 25° C. for about 3 months.

Clause 2317. The aqueous pharmaceutical formulation of any one of clauses 101 to 2205, wherein the formulation comprises from 0.01% impurities to less than, or no more than 0.25% impurities upon storage at 25° C. for about 3 months.

Clause 2318. The aqueous pharmaceutical formulation of any one of clauses 101 to 2205, wherein the formulation comprises from 0.01% impurities to less than, or no more than 0.3% impurities upon storage at 25° C. for about 3 months.

Clause 2319. The aqueous pharmaceutical formulation of any one of clauses 101 to 2205, wherein the formulation comprises from 0.01% impurities to less than, or no more than 0.35%, 0.4%, or 0.5% impurities upon storage at 25° C. for about 3 months.

Clause 2401. The aqueous pharmaceutical formulation of any one of clauses 101 to 2307, wherein the formulation comprises from no impurities to less than, or no more than 0.20% impurities upon storage at 25° C. for about 6 months.

Clause 2402. The aqueous pharmaceutical formulation of any one of clauses 101 to 2307, wherein the formulation comprises from no impurities to less than, or no more than 0.19% impurities upon storage at 25° C. for about 6 months.

Clause 2403. The aqueous pharmaceutical formulation of any one of clauses 101 to 2307, wherein the formulation comprises from no impurities to less than, or no more than 0.18% impurities upon storage at 25° C. for about 6 months.

Clause 2404. The aqueous pharmaceutical formulation of any one of clauses 101 to 2307, wherein the formulation comprises from no impurities to less than, or no more than 0.17% impurities upon storage at 25° C. for about 6 months.

Clause 2405. The aqueous pharmaceutical formulation of any one of clauses 101 to 2307, wherein the formulation comprises from no impurities to less than, or no more than 0.16% impurities upon storage at 25° C. for about 6 months.

Clause 2406. The aqueous pharmaceutical formulation of any one of clauses 101 to 2307, wherein the formulation comprises from no impurities to less than, or no more than 0.15% impurities upon storage at 25° C. for about 6 months.

Clause 2407. The aqueous pharmaceutical formulation of any one of clauses 101 to 2307, wherein the formulation comprises from no impurities to less than, or no more than 0.14% impurities upon storage at 25° C. for about 6 months.

Clause 2408. The aqueous pharmaceutical formulation of any one of clauses 101 to 2307, wherein the formulation comprises from no impurities to less than, or no more than 0.13% impurities upon storage at 25° C. for about 6 months.

Clause 2409. The aqueous pharmaceutical formulation of any one of clauses 101 to 2307, wherein the formulation comprises from no impurities to less than, or no more than 0.12% impurities upon storage at 25° C. for about 6 months.

Clause 2410. The aqueous pharmaceutical formulation of any one of clauses 101 to 2307, wherein the formulation comprises from no impurities to less than, or no more than 0.11% impurities upon storage at 25° C. for about 6 months.

Clause 2411. The aqueous pharmaceutical formulation of any one of clauses 101 to 2307, wherein the formulation comprises from no impurities to less than, or no more than 0.10% impurities upon storage at 25° C. for about 6 months.

Clause 2412. The aqueous pharmaceutical formulation of any one of clauses 101 to 2307, wherein the formulation comprises from no impurities to less than, or no more than 0.09% impurities upon storage at 25° C. for about 6 months.

Clause 2413. The aqueous pharmaceutical formulation of any one of clauses 101 to 2307, wherein the formulation comprises from no impurities to less than, or no more than 0.08% impurities upon storage at 25° C. for about 6 months.

Clause 2414. The aqueous pharmaceutical formulation of any one of clauses 101 to 2307, wherein the formulation comprises from no impurities to less than, or no more than 0.07% impurities upon storage at 25° C. for about 6 months.

Clause 2415. The aqueous pharmaceutical formulation of any one of clauses 101 to 2307, wherein the formulation comprises from 0.01% impurities to less than, or no more than 0.20% impurities upon storage at 25° C. for about 6 months.

Clause 2416. The aqueous pharmaceutical formulation of any one of clauses 101 to 2307, wherein the formulation comprises from 0.01% impurities to less than, or no more than 0.19% impurities upon storage at 25° C. for about 6 months.

Clause 2417. The aqueous pharmaceutical formulation of any one of clauses 101 to 2307, wherein the formulation comprises from 0.01% impurities to less than, or no more than 0.18% impurities upon storage at 25° C. for about 6 months.

Clause 2418. The aqueous pharmaceutical formulation of any one of clauses 101 to 2307, wherein the formulation comprises from 0.01% impurities to less than, or no more than 0.17% impurities upon storage at 25° C. for about 6 months.

Clause 2419. The aqueous pharmaceutical formulation of any one of clauses 101 to 2307, wherein the formulation comprises from 0.01% impurities to less than, or no more than 0.16% impurities upon storage at 25° C. for about 6 months.

Clause 2420. The aqueous pharmaceutical formulation of any one of clauses 101 to 2307, wherein the formulation comprises from 0.01% impurities to less than, or no more than 0.15% impurities upon storage at 25° C. for about 6 months.

Clause 2421. The aqueous pharmaceutical formulation of any one of clauses 101 to 2307, wherein the formulation comprises from 0.01% impurities to less than, or no more than 0.14% impurities upon storage at 25° C. for about 6 months.

Clause 2422. The aqueous pharmaceutical formulation of any one of clauses 101 to 2307, wherein the formulation comprises from 0.01% impurities to less than, or no more than 0.13% impurities upon storage at 25° C. for about 6 months.

Clause 2423. The aqueous pharmaceutical formulation of any one of clauses 101 to 2307, wherein the formulation comprises from 0.01% impurities to less than, or no more than 0.12% impurities upon storage at 25° C. for about 6 months.

Clause 2424. The aqueous pharmaceutical formulation of any one of clauses 101 to 2307, wherein the formulation comprises from 0.01% impurities to less than, or no more than 0.11% impurities upon storage at 25° C. for about 6 months.

Clause 2425. The aqueous pharmaceutical formulation of any one of clauses 101 to 2307, wherein the formulation comprises from 0.01% impurities to less than, or no more than 0.10% impurities upon storage at 25° C. for about 6 months.

Clause 2426. The aqueous pharmaceutical formulation of any one of clauses 101 to 2307, wherein the formulation comprises from 0.01% impurities to less than, or no more than 0.09% impurities upon storage at 25° C. for about 6 months.

Clause 2427. The aqueous pharmaceutical formulation of any one of clauses 101 to 2307, wherein the formulation comprises from 0.01% impurities to less than, or no more than 0.08% impurities upon storage at 25° C. for about 6 months.

Clause 2428. The aqueous pharmaceutical formulation of any one of clauses 101 to 2307, wherein the formulation comprises from 0.01% impurities to less than, or no more than 0.07% impurities upon storage at 25° C. for about 6 months.

Clause 2429. The aqueous pharmaceutical formulation of any one of clauses 101 to 2307, wherein the formulation comprises from 0.01% impurities to less than, or no more than 0.25% impurities upon storage at 25° C. for about 6 months.

Clause 2430. The aqueous pharmaceutical formulation of any one of clauses 101 to 2307, wherein the formulation comprises from 0.01% impurities to less than, or no more than 0.3% impurities upon storage at 25° C. for about 6 months.

Clause 2431. The aqueous pharmaceutical formulation of any one of clauses 101 to 2307, wherein the formulation comprises from 0.01% impurities to less than, or no more than 0.35% impurities upon storage at 25° C. for about 6 months.

Clause 2432. The aqueous pharmaceutical formulation of any one of clauses 101 to 2307, wherein the formulation comprises from 0.01% impurities to less than, or no more than 0.4% impurities upon storage at 25° C. for about 6 months.

Clause 2433. The aqueous pharmaceutical formulation of any one of clauses 101 to 2307, wherein the formulation comprises from 0.01% impurities to less than, or no more than 0.45% impurities upon storage at 25° C. for about 6 months.

Clause 2434. The aqueous pharmaceutical formulation of any one of clauses 101 to 2307, wherein the formulation comprises from 0.01% impurities to less than, or no more than 0.5% impurities upon storage at 25° C. for about 6 months.

Clause 2501. The aqueous pharmaceutical formulation of any one of clauses 101 to 2428, wherein upon storage at 40° C. for about 1 month, the formulation comprises from no impurities to less than, or no more than 0.35% impurities.

Clause 2601. The aqueous pharmaceutical formulation of any one of clauses 101 to 2428, wherein upon storage at 40° C. for about 2 months, the formulation comprises from no impurities to less than, or no more than 0.7% impurities.

Clause 2701. The aqueous pharmaceutical formulation of any one of clauses 101 to 2428, wherein upon storage at 40° C. for about 3 months, the formulation comprises from no impurities to less than, or no more than 1.5% impurities.

Clause 2801. The aqueous pharmaceutical formulation of any one of clauses 101 to 2428, wherein upon storage at 40° C. for about 6 months, the formulation comprises from no impurities to less than, or no more than 2% impurities.

Clause 2901. The aqueous pharmaceutical formulation of any one of clauses 2301 to 2801, wherein impurities concentration is measured upon storage against at least one pharmaceutically acceptable surface selected from a stopper surface, a needle surface, a needle tip cap surface, a needle shield surface, a septa surface, a syringe plunger surface, a glass syringe surface, a plastic syringe surface, (e.g. neoprene, polyisoprene, silicone), an injector surface, a rubber surface, and the like. Any surface may include any material known in the art, for example and without limitation, neoprene, polyisoprene, silicone, and the like.

Clause 3001. The aqueous pharmaceutical formulation of any one of clauses 2201 to 2901, wherein impurities comprise hydrocortisone.

Clause 3002. The aqueous pharmaceutical formulation of any one of clauses 2201 to 2901, wherein impurities consist essentially of hydrocortisone.

Clause 3003. The aqueous pharmaceutical formulation of any one of clauses 2201 to 2901, wherein the formulation comprises from no hydrocortisone to less than, or no more than 0.01% hydrocortisone; from no hydrocortisone to less than, or no more than 0.025% hydrocortisone; from no hydrocortisone to less than, or no more than 0.05% hydrocortisone; from no hydrocortisone to less than, or no more than 0.1% hydrocortisone; from no hydrocortisone to less than, or no more than 0.15% hydrocortisone; from no hydrocortisone to less than, or no more than 0.2% hydrocortisone; from no hydrocortisone to less than, or no more than 0.25% hydrocortisone; from no hydrocortisone to less than, or no more than 0.3% hydrocortisone; from no hydrocortisone to less than, or no more than 0.35% hydrocortisone; from no hydrocortisone to less than, or no more than 0.4% hydrocortisone; from no hydrocortisone to less than, or no more than 0.45% hydrocortisone; or from no hydrocortisone to less than, or no more than 0.5% hydrocortisone.

Clause 3101. The aqueous pharmaceutical formulation of any one of clauses 101 to 3003, wherein any formulation component concentration can be expressed as % w/v, using a conversion factor of 1 mg/mL=0.1% w/v.

Clause 3201. A method of treating a disease, condition, or disorder alleviated by administering hydrocortisone or hydrocortisone sodium phosphate in a patient in need thereof, the method comprising administering to the patient a therapeutically effective amount of the aqueous pharmaceutical formulation of any one of clauses 101 to 3101.

Clause 3301. The method of clause 3201, wherein the disease, condition, or disorder comprises one or more of swollen joints and/or tendons, painful joints and/or tendons, tennis elbow, and/or golfer's elbow.

Clause 3401. The method of clause 3201, wherein the disease, condition, or disorder comprises one or more of asthma, an allergic reaction, severe shock due to injury or infection, and/or or failure of the adrenal glands.

Clause 3501. The method of clause 3201, wherein the disease, condition, or disorder comprises inflammation.

Clause 3601. The method of clause 3201, wherein the disease, condition, or disorder comprises asthma, atopic dermatitis, contact dermatitis, drug hypersensitivity reactions, perennial or seasonal allergic rhinitis, serum sickness, and/or transfusion reactions.

Clause 3701. The method of clause 3201, wherein the disease, condition, or disorder comprises dermatologic diseases selected from bullous dermatitis herpetifornis, exfoliative erythroderma, mycosis fungoides, pemphigus, severe erythema multiforme (Stevens-Johnson syndrome).

Clause 3801. The method of clause 3201, wherein the disease, condition, or disorder comprises endocrine disorders selected from primary or secondary adrenocortical insufficiency, congenital adrenal hyperplasia, hypercalcemia associated with cancer, and/or nonsuppurative thyroiditis.

Clause 3901. The method of clause 3201, wherein the disease, condition, or disorder comprises gastrointestinal diseases.

Clause 4001. The method of clause 3201, wherein the disease, condition, or disorder comprises gastrointestinal diseases selected from regional enteritis (systemic therapy) and ulcerative colitis.

Clause 4101. The method of clause 3201, wherein the disease, condition, or disorder comprises hematologic disorders selected from acquired (autoimmune) hemolytic anemia, congenital (erythroid) hypoplastic anemia (Diamond-Blackfan anemia), idiopathic thrombocytopenic purpura in adults, pure red cell aplasia, selected cases of secondary thrombocytopenia.

Clause 4201. The method of clause 3201, wherein the disease, condition, or disorder comprises one or more of trichinosis with neurologic or myocardial involvement, tuberculous meningitis with subarachnoid block or impending block.

Clause 4301. The method of clause 3201, wherein the disease, condition, or disorder comprises neoplastic diseases.

Clause 4401. The method of clause 3201, wherein the disease, condition, or disorder comprises palliative management of leukemias and/or lymphomas.

Clause 4501. The method of clause 3201, wherein the disease, condition, or disorder comprises nervous system conditions selected from acute exacerbations of multiple sclerosis; cerebral edema associated with primary or metastatic brain tumor, or craniotomy.

Clause 4601. The method of clause 3201, wherein the disease, condition, or disorder comprises ophthalmic diseases selected from sympathetic ophthalmia, uveitis and ocular inflammatory conditions.

Clause 4701. The method of clause 3201, wherein the disease, condition, or disorder comprises renal diseases.

Clause 4801. The method of clause 3201, wherein the disease, condition, or disorder comprises inducing diuresis or remission of proteinuria in idiopathic nephrotic syndrome or that due to lupus erythematosus.

Clause 4901. The method of clause 3201, wherein the disease, condition, or disorder comprises respiratory diseases selected from berylliosis, fulminating or disseminated pulmonary tuberculosis, idiopathic eosinophilic pneumonias, symptomatic sarcoidosis.

Clause 5001. The method of clause 3201, wherein the disease, condition, or disorder comprises rheumatic disorders selected from acute gouty arthritis; acute rheumatic carditis; ankylosing spondylitis; psoriatic arthritis; rheumatoid arthritis, including juvenile rheumatoid arthritis.

Clause 5101. The method of clause 3201, wherein the disease, condition, or disorder comprises dermatomyositis, temporal arteritis, polymyositis, and systemic lupus erythematosus.

Clause 5201. The method of clause 3201, wherein the disease, condition, or disorder comprises adrenal insufficiency selected from primary adrenal insufficiency, acute adrenal insufficiency, and secondary adrenal insufficiency.

Clause 6001. An aqueous pharmaceutical formulation comprising from about 50 to about 150 mg/mL hydrocortisone sodium phosphate, from about 2.5 to about 12.5 mg/mL monothioglycerol, and water.

Clause 6002. The aqueous pharmaceutical formulation of clause 6001, comprising from about 50 to about 60 mg/mL hydrocortisone sodium phosphate, from about 60 to about 70 mg/mL hydrocortisone sodium phosphate, or from about 70 to about 80 mg/mL hydrocortisone sodium phosphate.

Clause 6003. The aqueous pharmaceutical formulation of clause 6001, comprising from about 60 to about 65 mg/mL hydrocortisone sodium phosphate, or from about 65 to about 70 mg/mL hydrocortisone sodium phosphate.

Clause 6004. The aqueous pharmaceutical formulation of clause 6001, comprising from about 120 to about 130 mg/mL hydrocortisone sodium phosphate, from about 130 to about 140 mg/mL hydrocortisone sodium phosphate, or from about 140 to about 150 mg/mL hydrocortisone sodium phosphate.

Clause 6005. The aqueous pharmaceutical formulation of clause 6001, comprising from about 130 to about 135 mg/mL hydrocortisone sodium phosphate, or from about 135 to about 140 mg/mL hydrocortisone sodium phosphate.

Clause 6006. The aqueous pharmaceutical formulation of clause 6001, comprising about 50 mg/mL hydrocortisone sodium phosphate, about 55 mg/mL hydrocortisone sodium phosphate, about 60 mg/mL hydrocortisone sodium phosphate, about 65 mg/mL hydrocortisone sodium phosphate, about 70 mg/mL hydrocortisone sodium phosphate, about 75 mg/mL hydrocortisone sodium phosphate, about 80 mg/mL hydrocortisone sodium phosphate, about 85 mg/mL hydrocortisone sodium phosphate, about 90 mg/mL hydrocortisone sodium phosphate, about 95 mg/mL hydrocortisone sodium phosphate, about 100 mg/mL hydrocortisone sodium phosphate, about 105 mg/mL hydrocortisone sodium phosphate, about 110 mg/mL hydrocortisone sodium phosphate, about 115 mg/mL hydrocortisone sodium phosphate, about 120 mg/mL hydrocortisone sodium phosphate, about 125 mg/mL hydrocortisone sodium phosphate, about 130 mg/mL hydrocortisone sodium phosphate, about 135 mg/mL hydrocortisone sodium phosphate, about 140 mg/mL hydrocortisone sodium phosphate, about 145 mg/mL hydrocortisone sodium phosphate, or about 150 mg/mL hydrocortisone sodium phosphate.

Clause 6007. The aqueous pharmaceutical formulation of clause 6001, comprising about 60 mg/mL hydrocortisone sodium phosphate, about 61 mg/mL hydrocortisone sodium phosphate, about 62 mg/mL hydrocortisone sodium phosphate, about 63 mg/mL hydrocortisone sodium phosphate, about 64 mg/mL hydrocortisone sodium phosphate, about 65 mg/mL hydrocortisone sodium phosphate, about 66 mg/mL hydrocortisone sodium phosphate, about 67 mg/mL hydrocortisone sodium phosphate, about 68 mg/mL hydrocortisone sodium phosphate, about 69 mg/mL hydrocortisone sodium phosphate, or about 70 mg/mL hydrocortisone sodium phosphate.

Clause 6008. The aqueous pharmaceutical formulation of clause 6001, comprising about 67 mg/mL hydrocortisone sodium phosphate, about 67.1 mg/mL hydrocortisone sodium phosphate, about 67.2 mg/mL hydrocortisone sodium phosphate, about 67.3 mg/mL hydrocortisone sodium phosphate, about 67.4 mg/mL hydrocortisone sodium phosphate, about 67.5 mg/mL hydrocortisone sodium phosphate, about 67.6 mg/mL hydrocortisone sodium phosphate, about 67.7 mg/mL hydrocortisone sodium phosphate, about 67.8 mg/mL hydrocortisone sodium phosphate, about 67.9 mg/mL hydrocortisone sodium phosphate, or about 68 mg/mL hydrocortisone sodium phosphate.

Clause 6009. The aqueous pharmaceutical formulation of clause 6001, comprising about 130 mg/mL hydrocortisone sodium phosphate, about 131 mg/mL hydrocortisone sodium phosphate, about 132 mg/mL hydrocortisone sodium phosphate, about 133 mg/mL hydrocortisone sodium phosphate, about 134 mg/mL hydrocortisone sodium phosphate, about 135 mg/mL hydrocortisone sodium phosphate, about 136 mg/mL hydrocortisone sodium phosphate, about 137 mg/mL hydrocortisone sodium phosphate, about 138 mg/mL hydrocortisone sodium phosphate, about 139 mg/mL hydrocortisone sodium phosphate, or about 140 mg/mL hydrocortisone sodium phosphate.

Clause 6010. The aqueous pharmaceutical formulation of clause 6001, comprising about 134 mg/mL hydrocortisone sodium phosphate, about 134.1 mg/mL hydrocortisone sodium phosphate, about 134.2 mg/mL hydrocortisone sodium phosphate, about 134.3 mg/mL hydrocortisone sodium phosphate, about 134.4 mg/mL hydrocortisone sodium phosphate, about 134.5 mg/mL hydrocortisone sodium phosphate, about 134.6 mg/mL hydrocortisone sodium phosphate, about 134.7 mg/mL hydrocortisone sodium phosphate, about 134.8 mg/mL hydrocortisone sodium phosphate, about 134.9 mg/mL hydrocortisone sodium phosphate, or about 135 mg/mL hydrocortisone sodium phosphate.

Clause 6011. The aqueous pharmaceutical formulation of any one of clauses 6001 to 6010, comprising from about 2.5 to about 3.5 mg/mL monothioglycerol, from about 3.5 to about 4.5 mg/mL monothioglycerol, from about 4.5 to about 5.5 mg/mL monothioglycerol, from about 5.5 to about 6.5 mg/mL monothioglycerol, from about 6.5 to about 7.5 mg/mL monothioglycerol, from about 7.5 to about 8.5 mg/mL monothioglycerol, from about 8.5 to about 9.5 mg/mL monothioglycerol, from about 9.5 to about 10.5 mg/mL monothioglycerol, from about 10.5 to about 11.5 mg/mL monothioglycerol, or from about 11.5 to about 12.5 mg/mL monothioglycerol.

Clause 6012. The aqueous pharmaceutical formulation of any one of clauses 6001 to 6010, comprising from about 4 to about 4.25 mg/mL monothioglycerol, from about 4.25 to about 4.5 mg/mL monothioglycerol, from about 4.5 to about 4.75 mg/mL monothioglycerol, from about 4.75 to about 5 mg/mL monothioglycerol, from about 5 to about 5.25 mg/mL monothioglycerol, from about 5.25 to about 5.5 mg/mL monothioglycerol, from about 5.5 to about 5.75 mg/mL monothioglycerol, or from about 5.75 to about 6 mg/mL monothioglycerol.

Clause 6013. The aqueous pharmaceutical formulation of any one of clauses 6001 to 6010, comprising from about 9 to about 9.25 mg/mL monothioglycerol, from about 9.25 to about 9.5 mg/mL monothioglycerol, from about 9.5 to about 9.75 mg/mL monothioglycerol, from about 9.75 to about 10 mg/mL monothioglycerol, from about 10 to about 10.25 mg/mL monothioglycerol, from about 10.25 to about 10.5 mg/mL monothioglycerol, from about 10.5 to about 10.75 mg/mL monothioglycerol, or from about 10.75 to about 11 mg/mL monothioglycerol.

Clause 6014. The aqueous pharmaceutical formulation of any one of clauses 6001 to 6010, comprising about 4.5 mg/mL monothioglycerol, about 4.6 mg/mL monothioglycerol, about 4.7 mg/mL monothioglycerol, about 4.8 mg/mL monothioglycerol, about 4.9 mg/mL monothioglycerol, about 5 mg/mL monothioglycerol, about 5.1 mg/mL monothioglycerol, about 5.2 mg/mL monothioglycerol, about 5.3 mg/mL monothioglycerol, about 5.4 mg/mL monothioglycerol, or about 5.5 mg/mL monothioglycerol.

Clause 6015. The aqueous pharmaceutical formulation of any one of clauses 6001 to 6010, comprising about 9.5 mg/mL monothioglycerol, about 9.6 mg/mL monothioglycerol, about 9.7 mg/mL monothioglycerol, about 9.8 mg/mL monothioglycerol, about 9.9 mg/mL monothioglycerol, about 10 mg/mL monothioglycerol, about 10.1 mg/mL monothioglycerol, about 10.2 mg/mL monothioglycerol, about 10.3 mg/mL monothioglycerol, about 10.4 mg/mL monothioglycerol, or about 10.5 mg/mL monothioglycerol.

Clause 6016. The aqueous pharmaceutical formulation of any one of clauses 6001 to 6015, further comprising from about 0.5 to about 2.5 mg/mL monobasic sodium phosphate.

Clause 6017. The aqueous pharmaceutical formulation of any one of clauses 6001 to 6016, further comprising from about 5 to about 25 mg/mL dibasic sodium phosphate.

Clause 6018. The aqueous pharmaceutical formulation of any one of clauses 6001 to 6017, further comprising from about 0.1 to about 1 mg/mL disodium EDTA.

Clause 6019. The aqueous pharmaceutical formulation of any one of clauses 6001 to 6018, wherein the pharmaceutical formulation has a pH from about 7.5 to about 9.5.

Clause 6020. The aqueous pharmaceutical formulation of any one of clauses 6001 to 6018, wherein the pharmaceutical formulation has a pH of about 7.5, about 7.6, about 7.7, about 7.8, about 7.9, about 8, about 8.1, about 8.2, about 8.3, about 8.4, about 8.5, about 8.6, about 8.7, about, 8.8, about 8.9, or about 9.

Clause 6021. The aqueous pharmaceutical formulation of any one of clauses 6001 to 6020, wherein the formulation comprises from no impurities to less than, or no more than 0.05% impurities upon formulation.

Clause 6022. The aqueous pharmaceutical formulation of any one of clauses 6001 to 6020, wherein the formulation comprises from no impurities to less than, or no more than 0.07% impurities upon storage at 25° C. for about 3 months.

Clause 6023. The aqueous pharmaceutical formulation of any one of clauses 6001 to 6020, wherein upon storage at 25° C. for about 3 months, the formulation comprises from no impurities to less than, or no more than 0.01% impurities, from no impurities to less than, or no more than 0.02% impurities, from no impurities to less than, or no more than 0.03% impurities, from no impurities to less than, or no more than 0.04% impurities, from no impurities to less than, or no more than 0.05% impurities, from no impurities to less than, or no more than 0.06% impurities, or from no impurities to less than, or no more than 0.07% impurities.

Clause 6024. The aqueous pharmaceutical formulation of any one of clauses 6001 to 6023, wherein the formulation comprises from no impurities to less than, or no more than 0.20% impurities upon storage at 25° C. for about 6 months.

Clause 6025. The aqueous pharmaceutical formulation of any one of clauses 6001 to 6023, wherein upon storage at 25° C. for about 6 months, the formulation comprises from no impurities to less than, or no more than 0.1% impurities, from no impurities to less than, or no more than 0.11% impurities, from no impurities to less than, or no more than 0.12% impurities, from no impurities to less than, or no more than 0.13% impurities, from no impurities to less than, or no more than 0.14% impurities, from no impurities to less than, or no more than 0.15% impurities, from no impurities to less than, or no more than 0.16% impurities, from no impurities to less than, or no more than 0.17% impurities, from no impurities to less than, or no more than 0.18% impurities, from no impurities to less than, or no more than 0.19% impurities, or from no impurities to less than, or no more than 0.2% impurities.

Clause 6026. The aqueous pharmaceutical formulation of any one of clauses 6001 to 6025, wherein upon storage at 40° C. for about 1 month, the formulation comprises from no impurities to less than, or no more than 0.35% impurities.

Clause 6027. The aqueous pharmaceutical formulation of any one of clauses 6001 to 6025, wherein upon storage at 40° C. for about 2 months, the formulation comprises from no impurities to less than, or no more than 0.7% impurities.

Clause 6028. The aqueous pharmaceutical formulation of any one of clauses 6001 to 6025, wherein upon storage at 40° C. for about 3 months, the formulation comprises from no impurities to less than, or no more than 1.5% impurities.

Clause 6029. The aqueous pharmaceutical formulation of any one of clauses 6001 to 6025, wherein upon storage at 40° C. for about 6 months, the formulation comprises from no impurities to less than, or no more than 2% impurities.

Clause 6030. A method of treating a disease, condition, or disorder alleviated by administering hydrocortisone or hydrocortisone sodium phosphate in a patient in need thereof, the method comprising administering to the patient a therapeutically effective amount of the aqueous pharmaceutical formulation of any one of clauses 6001 to 6029.

Clause 6031. The method of clause 6030, wherein the disease, condition, or disorder comprises one or more of swollen joints and/or tendons, painful joints and/or tendons, tennis elbow, and/or golfer's elbow.

Clause 6032. The method of clause 6030, wherein the disease, condition, or disorder comprises one or more of asthma, an allergic reaction, severe shock due to injury or infection, and/or or failure of the adrenal glands.

Clause 6033. The method of clause 6030, wherein the disease, condition, or disorder comprises inflammation.

Clause 6034. The method of clause 6030, wherein the disease, condition, or disorder comprises asthma, atopic dermatitis, contact dermatitis, drug hypersensitivity reactions, perennial or seasonal allergic rhinitis, serum sickness, and/or transfusion reactions.

Clause 6035. The method of clause 6030, wherein the disease, condition, or disorder comprises dermatologic diseases selected from bullous dermatitis herpetiformis, exfoliative erythroderma, mycosis fungoides, pemphigus, severe erythema multiforme (Stevens-Johnson syndrome).

Clause 6036. The method of clause 6030, wherein the disease, condition, or disorder comprises endocrine disorders selected from primary or secondary adrenocortical insufficiency, congenital adrenal hyperplasia, hypercalcemia associated with cancer, and/or nonsuppurative thyroiditis.

Clause 6037. The method of clause 6030, wherein the disease, condition, or disorder comprises gastrointestinal diseases.

Clause 6038. The method of clause 6030, wherein the disease, condition, or disorder comprises gastrointestinal diseases selected from regional enteritis (systemic therapy) and ulcerative colitis.

Clause 6039. The method of clause 6030, wherein the disease, condition, or disorder comprises hematologic disorders selected from acquired (autoimmune) hemolytic anemia, congenital (erythroid) hypoplastic anemia (Diamond-Blackfan anemia), idiopathic thrombocytopenic purpura in adults, pure red cell aplasia, selected cases of secondary thrombocytopenia.

Clause 6040. The method of clause 6030, wherein the disease, condition, or disorder comprises one or more of trichinosis with neurologic or myocardial involvement, tuberculous meningitis with subarachnoid block or impending block.

Clause 6041. The method of clause 6030, wherein the disease, condition, or disorder comprises neoplastic diseases.

Clause 6042. The method of clause 6030, wherein the disease, condition, or disorder comprises palliative management of leukemias and/or lymphomas.

Clause 6043. The method of clause 6030, wherein the disease, condition, or disorder comprises nervous system conditions selected from acute exacerbations of multiple sclerosis; cerebral edema associated with primary or metastatic brain tumor, or craniotomy.

Clause 6044. The method of clause 6030, wherein the disease, condition, or disorder comprises ophthalmic diseases selected from sympathetic ophthalmia, uveitis and ocular inflammatory conditions.

Clause 6045. The method of clause 6030, wherein the disease, condition, or disorder comprises renal diseases.

Clause 6046. The method of clause 6030, wherein the disease, condition, or disorder comprises inducing diuresis or remission of proteinuria in idiopathic nephrotic syndrome or that due to lupus erythematosus.

Clause 6047. The method of clause 6030, wherein the disease, condition, or disorder comprises respiratory diseases selected from berylliosis, fulminating or disseminated pulmonary tuberculosis, idiopathic eosinophilic pneumonias, symptomatic sarcoidosis.

Clause 6048. The method of clause 6030, wherein the disease, condition, or disorder comprises rheumatic disorders selected from acute gouty arthritis; acute rheumatic carditis; ankylosing spondylitis; psoriatic arthritis; rheumatoid arthritis, including juvenile rheumatoid arthritis.

Clause 6049. The method of clause 6030, wherein the disease, condition, or disorder comprises dermatomyositis, temporal arteritis, polymyositis, and systemic lupus erythematosus.

Clause 6050. The method of clause 6030, wherein the disease, condition, or disorder comprises adrenal insufficiency selected from primary adrenal insufficiency, acute adrenal insufficiency, and secondary adrenal insufficiency.

Clause 6051. The method of clause 6050, wherein the disease, condition, or disorder comprises acute adrenal insufficiency occurring in a patient with primary adrenal insufficiency or secondary adrenal insufficiency.

Clause 6052. The method of any one of clauses 6030 to 6051, wherein the therapeutic amount is about 0.5 mL to about 0.6 mL, about 0.6 mL to about 0.7 mL, about 0.7 mL to about 0.8 mL, about 0.8 mL to about 0.9 mL, about 0.9 mL to about 1.0 mL, about 1.0 mL to about 1.1 mL, about 1.1 mL to about 1.2 mL, about 1.2 mL to about 1.3 mL, about 1.3 mL to about 1.4 mL, or about 1.4 mL to about 1.5 mL of the aqueous pharmaceutical formulation.

Clause 6053. The method of any one of clauses 6030 to 6051, wherein the therapeutic amount is about 0.5 mL, about 0.6 mL, about 0.7 mL, about 0.8 mL, about 0.9 mL, about 1.0 mL, about 1.1 mL, about 1.2 mL, about 1.3 mL, about 1.4 mL, or about 1.5 mL of the aqueous pharmaceutical formulation.

Clause 6054. The method of any one of clauses 6030 to 6051, wherein the therapeutic amount is administered to the patient using an emergency-use/rescue autoinjector device.

Clause 6055. The method of any one of clauses 6030 to 6054, wherein the patient cannot be administered hydrocortisone or a drug thereof by oral therapy.

Clause 6056. The method of any one of clauses 6030 to 6055, wherein the therapeutic amount is administered intravenously.

Clause 6057. The method of any one of clauses 6030 to 6055, wherein the therapeutic amount is administered intramuscularly.

Clause 6058. The method of any one of clauses 6054 to 6057, wherein the aqueous pharmaceutical formulation exhibits higher exposure after administration to the patient compared to a hydrocortisone reference listed drug.

Clause 6059. The method of any one of clauses 6054 to 6058, wherein the aqueous pharmaceutical formulation achieves a higher area under the curve (AUC) after administration to the patient compared to a hydrocortisone reference listed drug.

Clause 6060. The method of any one of clauses 6054 to 6059, wherein the aqueous pharmaceutical formulation achieves a higher maximum (or peak) serum concentration ($C_{max}$) after administration to the patient compared to a hydrocortisone reference listed drug.

Clause 6061. The method of any one of clauses 6054 to 6060, wherein the aqueous pharmaceutical formulation achieves a maximum (or peak) serum concentration ($C_{max}$) after administration to the patient faster than a hydrocortisone reference listed drug.

Clause 6062. The method of any one of clauses 6058 to 6061, wherein the hydrocortisone reference listed drug is administered intravenously to a patient.

Clause 6063. The method of any one of clauses 6058 to 6061, wherein the hydrocortisone reference listed drug is administered intramuscularly to a patient.

Clause 6064. The method of any one of clauses 6058 to 6063, wherein the hydrocortisone reference listed drug comprises hydrocortisone sodium succinate.

Clause 6065. The method of any one of clauses 6058 to 6064, wherein the hydrocortisone reference listed drug does not comprise an antioxidant.

Clause 6066. The method of any one of clauses 6058 to 6065, wherein the hydrocortisone reference listed drug is Solu-Cortef.

Clause 7001. An aqueous pharmaceutical formulation comprising from about 50 to about 150 mg/mL hydrocortisone sodium phosphate, from about 2.5 to about 50 mg/mL monothioglycerol, and water.

Clause 7002. The aqueous pharmaceutical formulation of clause 7001, comprising from about 120 to about 130 mg/mL hydrocortisone sodium phosphate, from about 127 mg/mL to about 141 mg/mL hydrocortisone sodium phosphate, from about 130 to about 140 mg/mL hydrocortisone sodium phosphate, or from about 140 to about 150 mg/mL hydrocortisone sodium phosphate.

Clause 7003. The aqueous pharmaceutical formulation of clause 7001, comprising from about 127 mg/mL to about 141 mg/mL hydrocortisone sodium phosphate.

Clause 7004. The aqueous pharmaceutical formulation of clause 7001, comprising from about 130 to about 135 mg/mL hydrocortisone sodium phosphate, or from about 135 to about 140 mg/mL hydrocortisone sodium phosphate.

Clause 7005. The aqueous pharmaceutical formulation of clause 7001, comprising about 127 mg/mL mg/mL hydrocortisone sodium phosphate, about 128 mg/mL hydrocortisone sodium phosphate, about 129 mg/mL hydrocortisone sodium phosphate, about 130 mg/mL hydrocortisone sodium phosphate, about 131 mg/mL hydrocortisone sodium phosphate, about 132 mg/mL hydrocortisone sodium phosphate, about 133 mg/mL hydrocortisone sodium phosphate, about 134 mg/mL hydrocortisone sodium phosphate, about 135 mg/mL hydrocortisone sodium phosphate, about 136 mg/mL hydrocortisone sodium phosphate, about 137 mg/mL hydrocortisone sodium phosphate, about 138 mg/mL hydrocortisone sodium phosphate, about 139 mg/mL hydrocortisone sodium phosphate, about 140 mg/mL hydrocortisone sodium phosphate, or about 141 mg/mL hydrocortisone sodium phosphate.

Clause 7006. The aqueous pharmaceutical formulation of clause 7001, comprising about 134 mg/mL hydrocortisone sodium phosphate, about 134.1 mg/mL hydrocortisone sodium phosphate, about 134.2 mg/mL hydrocortisone sodium phosphate, about 134.3 mg/mL hydrocortisone sodium phosphate, about 134.4 mg/mL hydrocortisone sodium phosphate, about 134.5 mg/mL hydrocortisone sodium phosphate, about 134.6 mg/mL hydrocortisone sodium phosphate, about 134.7 mg/mL hydrocortisone sodium phosphate, about 134.8 mg/mL hydrocortisone sodium phosphate, about 134.9 mg/mL hydrocortisone sodium phosphate, or about 135 mg/mL hydrocortisone sodium phosphate.

Clause 7007. The aqueous pharmaceutical formulation of any one of clauses 7001 to 7006, comprising from about 2.5 to about 3.5 mg/mL monothioglycerol, from about 3.5 to about 4.5 mg/mL monothioglycerol, from about 3.5 to about 5.5 mg/mL monothioglycerol, from about 4.5 to about 5.5 mg/mL monothioglycerol, from about 5.5 to about 6.5 mg/mL monothioglycerol, from about 6.5 to about 7.5 mg/mL monothioglycerol, from about 7.5 to about 8.5 mg/mL monothioglycerol, from about 8.5 to about 9.5 mg/mL monothioglycerol, from about 9.5 to about 10.5 mg/mL monothioglycerol, from about 10.5 to about 11.5 mg/mL monothioglycerol, or from about 11.5 to about 12.5 mg/mL monothioglycerol.

Clause 7008. The aqueous pharmaceutical formulation of any one of clauses 7001 to 7007, comprising from about 4 to about 4.25 mg/mL monothioglycerol, from about 4.25 to about 4.5 mg/mL monothioglycerol, from about 4.5 to about 4.75 mg/mL monothioglycerol, from about 4.75 to about 5 mg/mL monothioglycerol, from about 5 to about 5.25 mg/mL monothioglycerol, from about 5.25 to about 5.5 mg/mL monothioglycerol, from about 5.5 to about 5.75 mg/mL monothioglycerol, or from about 5.75 to about 6 mg/mL monothioglycerol.

Clause 7009. The aqueous pharmaceutical formulation of any one of clauses 7001 to 7008, comprising about 4.5 mg/mL monothioglycerol, about 4.6 mg/mL monothioglycerol, about 4.7 mg/mL monothioglycerol, about 4.8 mg/mL monothioglycerol, about 4.9 mg/mL monothioglycerol, about 5 mg/mL monothioglycerol, about 5.1 mg/mL monothioglycerol, about 5.2 mg/mL monothioglycerol, about 5.3 mg/mL monothioglycerol, about 5.4 mg/mL monothioglycerol, or about 5.5 mg/mL monothioglycerol.

Clause 7010. The aqueous pharmaceutical formulation of any one of clauses 7001 to 7009, further comprising from about 0.5 to about 2.5 mg/mL monobasic sodium phosphate.

Clause 7011. The aqueous pharmaceutical formulation of any one of clauses 7001 to 7010, further comprising from about 5 to about 25 mg/mL dibasic sodium phosphate.

Clause 7012. The aqueous pharmaceutical formulation of any one of clauses 7001 to 7011, further comprising from about 0.1 to about 1 mg/mL disodium EDTA.

Clause 7013. The aqueous pharmaceutical formulation of any one of clauses 7001 to 7011, further comprising from about 0.1 to about 0.22 mg/mL disodium EDTA.

Clause 7014. The aqueous pharmaceutical formulation of any one of clauses 7001 to 7013, wherein the pharmaceutical formulation has a pH from about 7.5 to about 9.5 or about 7.5 to about 8.5.

Clause 7015. The aqueous pharmaceutical formulation of any one of clauses 7001 to 7013, wherein the pharmaceutical formulation has a pH of about 7.5, about 7.6, about 7.7, about 7.8, about 7.9, about 8.0, about 8.1, about 8.2, about 8.3, about 8.4, about 8.5, about 8.6, about 8.7, about, 8.8, about 8.9, or about 9.

Clause 7016. The aqueous pharmaceutical formulation of any one of clauses 7001 to 7015, wherein upon formulation, the pharmaceutical formulation comprises from no organic impurities to less than, or no more than 0.2% organic impurities, from no organic impurities to less than, or no more than 0.15% organic impurities, from no organic impurities to less than, or no more than 0.10% organic impurities, or from no organic impurities to less than, or no more than 0.05% organic impurities.

Clause 7017. The aqueous pharmaceutical formulation of any one of clauses 7001 to 7016, wherein upon storage at about 25° C. for about 3 months, the formulation comprises from no organic impurities to less than, or no more than 0.2% organic impurities or from no organic impurities to less than, or no more than 0.07% organic impurities.

Clause 7018. The aqueous pharmaceutical formulation of any one of clauses 7001 to 7017, wherein upon storage at about 25° C. for about 6 months, the formulation comprises from no organic impurities to less than, or no more than 0.60% organic impurities or from no organic impurities to less than, or no more than 0.20% organic impurities.

Clause 7019. The aqueous pharmaceutical formulation of any clause 7017 or 7018, wherein the formulation is stored at about 60% relative humidity.

Clause 7020. The aqueous pharmaceutical formulation of any one of clauses 7017 to 7019, wherein the formulation is stored against at least one non-glass pharmaceutically acceptable surface selected from a stopper surface, a needle surface, a needle tip cap surface, a needle shield surface, a septa surface, a syringe plunger surface, a plastic syringe surface, an injector surface, or a rubber surface.

Clause 7021. The aqueous pharmaceutical formulation of any one of clauses 7001 to 7020 for use in the treatment of a disease, a condition, or a disorder that is alleviated by hydrocortisone or hydrocortisone sodium phosphate.

Clause 7022. The aqueous pharmaceutical formulation for the use of clause 7021, wherein the disease, condition, or disorder comprises one or more of asthma, an allergic reaction, severe shock due to injury or infection, failure of the adrenal glands, inflammation, atopic dermatitis, contact dermatitis, a drug hypersensitivity reaction, perennial or seasonal allergic rhinitis, serum sickness, a transfusion reaction, a gastrointestinal disease, trichinosis with neurologic or myocardial involvement, tuberculous meningitis with subarachnoid block or impending block, a neoplastic disease, palliative management of a leukemia and/or lymphoma, a renal disease, proteinuria in idiopathic nephrotic syndrome, proteinuria due to lupus erythematosus, dermatomyositis, temporal arteritis, polymyositis, swollen joints and/or tendons, painful joints and/or tendons, tennis elbow, golfer's elbow, and systemic lupus erythematosus.

Clause 7023. The aqueous pharmaceutical formulation for the use of clause 7021, wherein the disease, condition, or disorder comprises dermatologic diseases selected from bullous dermatitis herpetiformis, exfoliative erythroderma, mycosis fungoides, pemphigus, and severe erythema multiforme (Stevens-Johnson syndrome); endocrine disorders selected from primary or secondary adrenocortical insufficiency, congenital adrenal hyperplasia, hypercalcemia associated with cancer, and nonsuppurative thyroiditis; hematologic disorders selected from acquired (autoimmune) hemolytic anemia, congenital (erythroid) hypoplastic anemia (Diamond-Blackfan anemia), idiopathic thrombocytopenic purpura in adults, pure red cell aplasia, and selected cases of secondary thrombocytopenia; nervous system conditions selected from acute exacerbations of multiple sclerosis; cerebral edema associated with primary or metastatic brain tumor, and craniotomy; ophthalmic diseases selected from sympathetic ophthalmia, uveitis, and ocular inflammatory conditions; respiratory diseases selected from berylliosis, fulminating or disseminated pulmonary tuberculosis, idiopathic eosinophilic pneumonias, and symptomatic sarcoidosis; rheumatic disorders selected from acute gouty arthritis, acute rheumatic carditis, ankylosing spondylitis, psoriatic arthritis, and rheumatoid arthritis; and adrenal insufficiency selected from primary adrenal insufficiency, acute adrenal insufficiency, and secondary adrenal insufficiency.

Clause 7024. The aqueous pharmaceutical formulation for the use of clause 7023, wherein the disease, condition, or disorder comprises adrenal insufficiency selected from primary adrenal insufficiency, acute adrenal insufficiency, and secondary adrenal insufficiency.

Clause 7025. The aqueous pharmaceutical formulation for the use of clause 7023, wherein the disease, condition, or disorder comprises acute adrenal insufficiency occurring in a patient with primary adrenal insufficiency or secondary adrenal insufficiency.

Clause 7026. A method of treating a disease, condition, or disorder alleviated by administering hydrocortisone or hydrocortisone sodium phosphate in a patient in need thereof, the method comprising administering to the patient a therapeutically effective amount of the aqueous pharmaceutical formulation of any one of clauses 7001 to 7020.

Clause 7027. The method of clause 7026, wherein the disease, condition, or disorder comprises one or more of asthma, acute exacerbations of asthma, an allergic reaction, severe shock due to injury or infection, failure of the adrenal glands, inflammation, atopic dermatitis, contact dermatitis, a drug hypersensitivity reaction, perennial or seasonal allergic rhinitis, serum sickness, a transfusion reaction, a gastrointestinal disease, trichinosis with neurologic or myocardial involvement, tuberculous meningitis with subarachnoid block or impending block, a neoplastic disease, palliative management of a leukemia and/or lymphoma, a renal disease, proteinuria in idiopathic nephrotic syndrome, proteinuria due to lupus erythematosus, dermatomyositis, temporal arteritis, polymyositis, swollen joints and/or tendons, painful joints and/or tendons, tennis elbow, golfer's elbow, systemic lupus erythematosus, acute exacerbations of inflammatory bowel disease, and infantile spasms.

Clause 7028. The method of clause 7026, wherein the disease, condition, or disorder comprises dermatologic diseases selected from bullous dermatitis herpetiformis, exfoliative erythroderma, mycosis fungoides, pemphigus, and severe erythema multiforme (Stevens-Johnson syndrome); endocrine disorders selected from primary or secondary adrenocortical insufficiency, congenital adrenal hyperplasia, hypercalcemia associated with cancer, and nonsuppurative thyroiditis; hematologic disorders selected from acquired (autoimmune) hemolytic anemia, congenital (erythroid) hypoplastic anemia (Diamond-Blackfan anemia), idiopathic thrombocytopenic purpura in adults, pure red cell aplasia, and selected cases of secondary thrombocytopenia; nervous system conditions selected from acute exacerbations of multiple sclerosis; cerebral edema associated with primary or metastatic brain tumor, and craniotomy; ophthalmic diseases selected from sympathetic ophthalmia, uveitis, and ocular inflammatory conditions; respiratory diseases selected from berylliosis, fulminating or disseminated pulmonary tuberculosis, idiopathic eosinophilic pneumonias, and symptomatic sarcoidosis; rheumatic disorders selected from acute gouty arthritis, acute rheumatic carditis, ankylosing spondylitis, psoriatic arthritis, and rheumatoid arthritis; and adrenal insufficiency selected from primary adrenal insufficiency, acute adrenal insufficiency, and secondary adrenal insufficiency.

Clause 7029. The method of clause 7028, wherein the disease, condition, or disorder comprises adrenal insufficiency selected from primary adrenal insufficiency, acute adrenal insufficiency, and secondary adrenal insufficiency.

Clause 7030. The method of clause 7028, wherein the disease, condition, or disorder comprises acute adrenal insufficiency occurring in a patient with primary adrenal insufficiency or secondary adrenal insufficiency.

Clause 7031. The method of any one of clauses 7026 to 7030, wherein the therapeutic amount is about 0.5 mL to about 0.6 mL, about 0.6 mL to about 0.7 mL, about 0.7 mL to about 0.8 mL, about 0.8 mL to about 0.9 mL, about 0.9 mL to about 1.0 mL, about 1.0 mL to about 1.2 mL, about 1.0 mL to about 1.1 mL, about 1.1 mL to about 1.2 mL, about 1.2 mL to about 1.3 mL, about 1.3 mL to about 1.4 mL, or about 1.4 mL to about 1.5 mL of the aqueous pharmaceutical formulation.

Clause 7032. The method of any one of clauses 7026 to 7030, wherein the therapeutic amount is about 0.5 mL, about 0.6 mL, about 0.7 mL, about 0.8 mL, about 0.9 mL, about 1.0 mL, about 1.1 mL, about 1.2 mL, about 1.3 mL, about 1.4 mL, or about 1.5 mL of the aqueous pharmaceutical formulation.

Clause 7033. The method of any one of clauses 7026 to 7032, wherein the therapeutic amount is administered to the patient using an emergency-use/rescue autoinjector device.

Clause 7034. The method of any one of clauses 7026 to 7033, wherein the patient cannot be administered hydrocortisone or a drug thereof by oral therapy.

Clause 7035. The method of any one of clauses 7026 to 7034, wherein the therapeutic amount is administered intravenously.

Clause 7036. The method of any one of clauses 7026 to 7034, wherein the therapeutic amount is administered intramuscularly.

Clause 7037. The method of any one of clauses 7026 to 7036, wherein the therapeutic amount provides an in vivo plasma profile for hydrocortisone that includes a mean $AUC_{0-inf}$ of about 5,500 to 5,575 h*ng/mL.

Clause 7038. The method of any one of clauses 7026 to 7037, wherein the therapeutic amount provides an in vivo plasma profile for hydrocortisone that includes a mean $AUC_{0-t}$ of about 5,275 to 5,375 h*ng/mL, wherein t is between about 0.5 and 12.5 hours.

Clause 7039. The method of any one of clauses 7026 to 7038, wherein the patient has a $C_{max}$ of hydrocortisone that is about 800 to 1600 ng/mL, about 900 to 1600 ng/mL, about 1000 to 1600 ng/mL, about 1000 to 1500 ng/mL, about 1100 to 1500 ng/mL, about 1100 to 1400 ng/mL, or about 1200 to 1300 ng/mL about 30 minutes, about 45 minutes, about 1.0 hour, about 1.25 hours, about 1.5 hours, about 1.75 hours, about 2.0 hours, about 2.25 hours, about 2.5 hours, about 2.75 hours, about 3.0 hours, about 3.25 hours, about 3.5 hours, or about 4.0 hours after the therapeutic amount is administered.

Clause 7040. The method of any one of clauses 7026 to 7039, wherein the therapeutic amount provides a hydrocortisone median $T_{max}$ of about 0.5 to 2.5 hours.

Clause 7041. The method of any one of clauses 7026 to 7040, wherein hydrocortisone is eliminated from the patient with a mean $T_{1/2\ el}$ of about 1.8 to 2.1 hours.

Clause 7042. The method of any one of clauses 7026 to 7041, wherein the aqueous pharmaceutical formulation exhibits higher exposure after administration to the patient compared to a hydrocortisone reference formulation.

Clause 7043. The method of any one of clauses 7026 to 7042, wherein the aqueous pharmaceutical formulation achieves a higher area under the curve (AUC) after administration to the patient compared to a hydrocortisone reference listed formulation.

Clause 7044. The method of any one of clauses 7026 to 7043, wherein the aqueous pharmaceutical formulation achieves a higher maximum (or peak) serum concentration ($C_{max}$) after administration to the patient compared to a hydrocortisone reference formulation.

Clause 7045. The method of any one of clauses 7026 to 7044, wherein the aqueous pharmaceutical formulation achieves a maximum (or peak) serum concentration ($C_{max}$) after administration to the patient faster than a hydrocortisone reference formulation.

Clause 7046. The method of any one of clauses 7042 to 7045, wherein the hydrocortisone reference formulation is administered intravenously to a patient.

Clause 7047. The method of any one of clauses 7042 to 7045, wherein the hydrocortisone reference formulation is administered intramuscularly to a patient.

Clause 7048. The method of any one of clauses 7042 to 7047, wherein the hydrocortisone reference formulation comprises hydrocortisone sodium succinate.

Clause 7049. The method of any one of clauses 7042 to 7048, wherein the hydrocortisone reference formulation does not comprise an antioxidant.

Clause 7050. The method of any one of clauses 7042 to 7049, wherein the hydrocortisone reference formulation comprises an aqueous formulation comprising about 67 mg/mL hydrocortisone sodium succinate, about 4.4 mg/mL dibasic sodium phosphate, about 0.4 mg/mL monobasic sodium phosphate, and water, wherein about 2.0 mL is administered to the patient.

A number of patent and non-patent publications are cited herein in order to describe the state of the art to which this invention pertains. The entire disclosure of each of these publications is incorporated by reference herein.

The following examples describe the invention in further detail. These examples are provided for illustrative purposes only, and should in no way be considered as limiting the invention.

EXAMPLES

Example 1

Antioxidants, chelating agent, buffer agents used in the stability study are listed in the following table:

Inactive Ingredients Used in the Formulation Development;

TABLE 1

| Inactive ingredient | Functionality | Quality Standard | Level used in the study | FDA IIG Limit for IM |
|---|---|---|---|---|
| Edetate disodium | Chelating agent | USP | 0.02% w/v | 10% w/v |
| Sodium sulfite | Antioxidant | USP | 0.2% w/v | 0.2% w/v |
| Sodium formaldehyde sulfoxylate | Antioxidant | USP-NF | 0.2% w/v | 0.2% w/v |
| Monothioglycerol | Antioxidant | USP-NF | 0.5% w/v | 0.5% w/v |
| Ascorbic acid | Antioxidant | USP | 0.2% w/v | 0.2% w/v |
| Methionine | Antioxidant | USP | 0.05% w/v | 0.05% w/v |
| Niacinamide | Stabilizer | USP | 2.5% w/v | 2.5% w/v |
| Creatinine | Stabilizer | USP | 0.8% w/v | 0.8% w/v |
| Hydroxylpropyl beta cyclodextrin | Stabilizer | USP-NF | 10% w/v | 33.33% w/v |

TABLE 1-continued

| Inactive ingredient | Functionality | Quality Standard | Level used in the study | FDA IIG Limit for IM |
|---|---|---|---|---|
| Sodium phosphate dibasic | Buffer agent | USP-NF | 0.1-0.8% | 27.8% |
| Sodium phosphate monobasic | Buffer agent | USP-NF | 0.01-0.08% | 2.56% |

Procedure for formulation preparation: add ~90% of water to a container; turn on the mixer; add Monobasic sodium phosphate anhydrous, Dibasic sodium phosphate anhydrous, Disodium EDTA, an antioxidant, or a third stabilizer, use a portion of water to rinse if needed, mix for at least 15 min or until dissolved; weigh hydrocortisone sodium phosphate and charge to the container from previous step, mix for at least 30 min and until dissolved; measure pH, adjust pH to approx. 8.0 using 0.1 N HCl or 0.1 N NaOH; Q.S. to final volume (weight) using water, mix for at least 15 min.

A stability indicating HPLC method was developed, suitable for monitoring hydrolysis of hydrocortisone sodium phosphate and other degradations based on literature methods for hydrocortisone prodrugs and other similar products. A detailed description of the HPLC method with information such as chromatography conditions and sample preparation, is described herein. in 5.0 Analytical method development Primary Packaging Materials

| Material | Description |
|---|---|
| Syringe Barrel | Ompi Article #7600007.6977, Syringe EZ-Fill 1 mL Long, 22G ⅝ 3B, NS 4800GS, NE160, EB, IUP |
| Stopper | West Stoppers Item # 10149656, Article 2340 4432/50 Gry B2-40 Westar RU |

The pH effect was evaluated for Formulations F #6 to F #4 at 13.42% hydrocortisone sodium phosphate with disodium edetate and sodium formaldehyde included at level typically used in injectable products. The effect of drug concentration on stability was studied in F #5, which has a concentration at 6.71% (50 mg/mL hydrocortisone) in comparison to 13.42% (100 mg/mL hydrocortisone) for the other formulations.

Prototype Formulations to Evaluate pH and Concentration:

TABLE 2

| Ingredient | F #1 | F#2 | F#3 | F#4 | F#5 |
|---|---|---|---|---|---|
| Hydrocortisone sodium phosphate (w/v) | 13.42% | 13.42% | 13.42% | 13.42% | 6.71% |
| Monobasic sodium phosphate anhydrous | 0.1% | 0.1% | 0.1% | 0.1% | 0.1% |
| Dibasic sodium phosphate anhydrous | 1.09% | 1.09% | 1.09% | 1.09% | 1.09% |
| Disodium EDTA | 0.02% | 0.02% | 0.02% | 0.02% | 0.02% |
| Sodium formaldehyde sulfoxylate | 0.2% | 0.2% | 0.2% | 0.2% | 0.2% |
| Sodium hydroxide/HCl | q.s. to pH 7.0 | q.s. to pH 7.5 | q.s. to pH 8.0 | q.s. to pH 8.5 | q.s. to pH 8.0 |
| Water | q.s. to 1 mL | q.s. to 1 mL | q.s. to 1 mL | q.s. to 1 mL | q.s. to 1 mL |

A second group of formulations were designed to study alternative antioxidants to sodium formaldehyde sulfoxylate, such as sodium sulfite, monothioglycerol, ascorbic acid, and methionine, whether better stabilization effect can be achieved (F #6-9):

Prototype formulations to evaluate the effect of antioxidants:

TABLE 3

| Ingredient | F #6 | F#7 | F#8 | F#9 |
|---|---|---|---|---|
| Hydrocortisone sodium phosphate | 13.42% | 13.42% | 13.42% | 13.42% |

TABLE 3-continued

| Ingredient | F #6 | F#7 | F#8 | F#9 |
|---|---|---|---|---|
| Monobasic sodium phosphate anhydrous | 0.1% | 0.1% | 0.1% | 0.1% |
| Dibasic sodium phosphate anhydrous | 1.09% | 1.09% | 1.09% | 1.09% |
| Disodium EDTA | 0.02% | 0.02% | 0.02% | 0.02% |
| Sodium sulfite | 0.2% | | | |
| Monothioglycerol | | 0.5% | | |
| Ascorbic acid | | | 0.2% | |
| Methionine | | | | 0.05% |
| Sodium hydroxide/HCl | q.s to pH 8.0 | q.s to pH 8.0 | q.s to pH 8.0 | q.s to pH 8.0 |
| Water | q.s to 1 mL | q.s to 1 mL | q.s to 1 mL | q.s to 1 mL |

As disclosed by U.S. Pat. No. 2,970,944, incorporated herein in its entirety, the stability of aqueous steroid phosphates including hydrocortisone sodium phosphates can be increased by incorporation of a small amount of a nitrogen containing compound such as niacinamide and creatinine. The main instability for steroid phosphates is the formation of precipitate during storage, which is due to the hydrolysis to form free hydrocortisone with much less aqueous solubility. It is possible that niacinamide and creatinine increase the solubility of hydrocortisone and thus, prevent precipitation after formation from hydrolysis.

The purpose to study Formulation F #10 to F #13 was to evaluate whether solubilizing agents like niacinamide, creatinine, hydroxylpropyl beta cyclodextrin can stabilize hydrocortisone sodium phosphate injection to maintain as clear solutions during stability test.

Prototype Formulations to Evaluate Solubilizing Agents

TABLE 4

| Ingredient | F#10 | F#11 | F#12 | F#13 | F#14 | F#15 |
|---|---|---|---|---|---|---|
| Hydrocortisone sodium phosphate | 13.42% w/v | 13.42% w/v | 13.42% w/v | 13.42% w/v | 13.42% w/v | 13.42% w/v |
| Monobasic sodium phosphate anhydrous | 0.1% w/v | 0.1% w/v | 0.1% w/v | 0.1% w/v | 0.1% w/v | 0.1% w/v |
| Dibasic sodium phosphate anhydrous | 1.09% w/v | 1.09% w/v | 1.09% w/v | 1.09% w/v | 1.09% w/v | 1.09% w/v |
| Disodium EDTA | 0.02% w/v | 0.02% w/v | 0.02% w/v | 0.02% w/v | 0.02% w/v | 0.02% w/v |
| Sodium formaldehyde sulfoxylate | 0.2% w/v | 0.2% w/v | 0.2% w/v | 0.2% w/v | 0.2% w/v | 0.2% w/v |
| Creatinine | 0.8% w/v | | | | | |
| Niacinamide | | 2.5% w/v | | | | |
| Hydroxypropyl beta cyclodextrin | | | 5.0% w/v | 10.0% w/v | | |
| Lactobionic acid | | | | | 0.2% w/v | |
| Sodium hydroxide/HCl | q.s to pH 8.0 | q.s to pH 8.0 | q.s to pH 8.0 | q.s to pH 8.0 | q.s to pH 8.0 | q.s to pH 8.0 |
| Water | q.s to 1 mL | q.s to 1 mL | q.s to 1 mL | q.sto 1 mL | q.s to 1 mL | q.s to 1 ml |

The needle shield in PFS is permeable to oxygen. Without wishing to be bound by any particular theory, it is believed that the use of barrier packaging such as foil pouch has the potential to enhance the stability of hydrocortisone sodium phosphate injection in PFS. The foil pouch to be evaluated is from Glenroy with film structure EFS 477-001. Two sets of formulation F #8 and F #15 PFS were packed with foil pouch purged with nitrogen, one PFS per pouch, while another set were packed the foil pouch with StabilOx oxygen scavenger, one PFS/two packs of oxygen scavenger per pouch, as described herein, to evaluate whether barrier packaging offer any stabilizing effect.

Specification of Glenroy Foil Pouch:

| Criteria | Details |
|---|---|
| Product Name | Glenroy Foil Pouch |
| Supplier Item # | EFS 477-001 |
| Dimensions | Width - 3.246-inch, Length - 9.75 inch, and Seal - ⅜ inch |
| Material Construction | Coated Polyester (PET) - 0.48 mm, LDPE white - 0.75 mm, Aluminum foil - 0.5 mm, HPC - 0.75 mm, LLDPE - 1.25 mm |

Details of StabilOx, D100-H60 Oxygen Absorber Packets:

TABLE 5

| Criteria | Details |
|---|---|
| Product Name | StabilOx ®, D-100-H60, is an oxygen absorbing packet in cut strip form. |
| Part Number | 02-02937CG10 |
| DESCRIPTION | StabilOx ®, D-100-H60 oxygen absorbers are designed to absorb a minimum of 100 cc of oxygen for modified atmosphere packaging of dry or semi-moist products with water activity less than 0.7 intended for storage and distribution at ambient or refrigerated temperatures down to 30 degrees F. The rate of absorption is dependent upon the equilibrium relative humidity and the composition of the atmosphere within the package. |
| Physical Attributes | 0.76" wide ± 0.04" × 1.83" long ± 0.07", The D-100-H60 is active in air and will begin to react within one-half hour after removal of the protective barrier pouch |
| MATERIALS | Product contact surface is Tyvek ® and suitable for direct food contact |

Study of Packaging Control on Stability of HCP Injection in PFS:

TABLE 6

| Sublot# Formulation | F#-A | F#-B Formulation F#8 and F#15 | F#-C |
|---|---|---|---|
| Pouch | None | One PFS, Purging nitrogen, pouching | One PFS, Two oxygen scavengers, Pouching |

All the formulations were prepared together, filled in PFS and were placed on stability. There are different sets of formulations. Formulations for each set were prepared on a separate day, PFS were filled and the zero time analysis was conducted on the next day. Information on actual composition of 15 prototype formulations is described herein. Stability program for the stability work are defined below:

TABLE 7

| Storage Condition | Intervals | | | | | | | | | Contingency samples |
| | Initial | 1M | 2M | 3M | 6M | 9M | 12M | 18M | 24M | |
|---|---|---|---|---|---|---|---|---|---|---|
| 25° C. | | | | X | X | (X) | (X) | (X) | (X) | 5 |
| 40° C. | X | X | X | X | X | | — | | — | 2 |

X = Appearance, Color/Clarity, pH, Assay and Related substances
(X) The decision to analyze these samples is to be made at 6M time point Following HPLC method was developed to determine the potency of Hydrocortisone sodium Phosphate and the area % of Hydrocortisone impurity and other unknown impurities in Hydrocortisone sodium Phosphate injection. This method employs High Performance Liquid Chromatography (HPLC) to determine the potency of Hydrocortisone sodium Phosphate and the area % of Hydrocortisone impurity and other unknown impurities in Hydrocortisone sodium Phosphate injection.

Equipment and Materials:
HPLC: Waters Alliance 2695 with Waters 2998 PDA detector; a data handling system with Empower 2 software.
Reagents:
1) Trifluoroacetic acid
2) Distilled water
3) Acetonitrile, HPLC grade
4) Hydrocortisone sodium Phosphate standard (in-house)
5) Hydrocortisone impurity standard (in-house)
Chromatography Conditions:
Column: Waters Sunfire C18, 250×4.6 mm, 5 µm
Column temperature: Ambient
Mobile Phase A: 0.2% v/v TFA in water
Mobile Phase B: 0.2% v/v TFA in ACN
Diluent: Water: ACN (80:20)
Pump wash & Needle wash: Diluent
Flow Rate: 1.5 mL/min
Injection volume: 10 µL
Run time: 45 minutes
Detection wavelength: 254 nm
Elution technique: Gradient (Linear):

TABLE 8

| Time in Minutes | % Mobile Phase A | % Mobile Phase B |
|---|---|---|
| 0.00 | 85 | 15 |
| 10.00 | 85 | 15 |
| 22.40 | 55 | 45 |
| 38.00 | 30 | 70 |
| 38.10 | 85 | 15 |
| 45.00 | 85 | 15 |

Preparation of Hydrocortisone Sodium Phosphate Standard Solution:
Prepared a 0.5 mg/mL solution of Hydrocortisone Sodium Phosphate using the diluent. Weighed required amount of standard in a clean empty and dry volumetric flask. Added ~80% volume diluent to the flask to dissolve standard. Sonicated, if necessary. Made up volume to the mark using diluent, mixed well and used in analysis. Prepared standards in duplicate.

Preparation of Hydrocortisone Impurity Stock Solution:
Prepared a stock solution of Hydrocortisone impurity using ACN for qualitative purpose.
Preparation of Peak Identification Solution:
Spiked the Hydrocortisone impurity stock solution to one of the two Hydrocortisone Sodium Phosphate standard solutions separately to prepare the Peak Identification solution. Injected this solution in HPLC sequence to find out the peak shape, peak symmetry and actual retention times of Hydrocortisone Sodium Phosphate and Hydrocortisone impurity on Chromatogram. Used this solution for qualitative purpose only.
Preparation of Hydrocortisone Sodium Phosphate Injection Test Solution:
Prepared a test solution of Hydrocortisone Sodium Phosphate injection in diluent. Weighed required amount of formulation equivalent to 0.5 mg/mL of Hydrocortisone Sodium Phosphate in a clean empty and dry volumetric flask. Added ~80% volume diluent to the flask to dissolve formulation. Sonicated, if necessary. Made up volume to the mark using diluent, mixed well and used in analysis. Prepared test solutions for zero time analysis in duplicate.
System Suitability Criteria for Analysis:
1) Accuracy of response between 2 HCP standards should be in 98-102%. The accuracy of response is calculated using following equation:

$$\% \text{ Accuracy of response} = \left(\frac{\text{Peak area of Std 2}}{\text{Peak area of Std 1}}\right) \times \left(\frac{\text{Concentration of Std 1}}{\text{Concentration of Std 2}}\right) \times 100$$

2) % relative standard deviation of peak areas for 5 repeated injections of HCP standard should be less than 2%.

3) Chromatogram of blank (Diluent) should be without unwanted peaks or humps.
4) Note the retention times of Hydrocortisone Sodium Phosphate and Hydrocortisone impurity at zero time analysis. These retention times should not change more than 1 minute range (i.e. +0.5 minutes)

Figure 2:
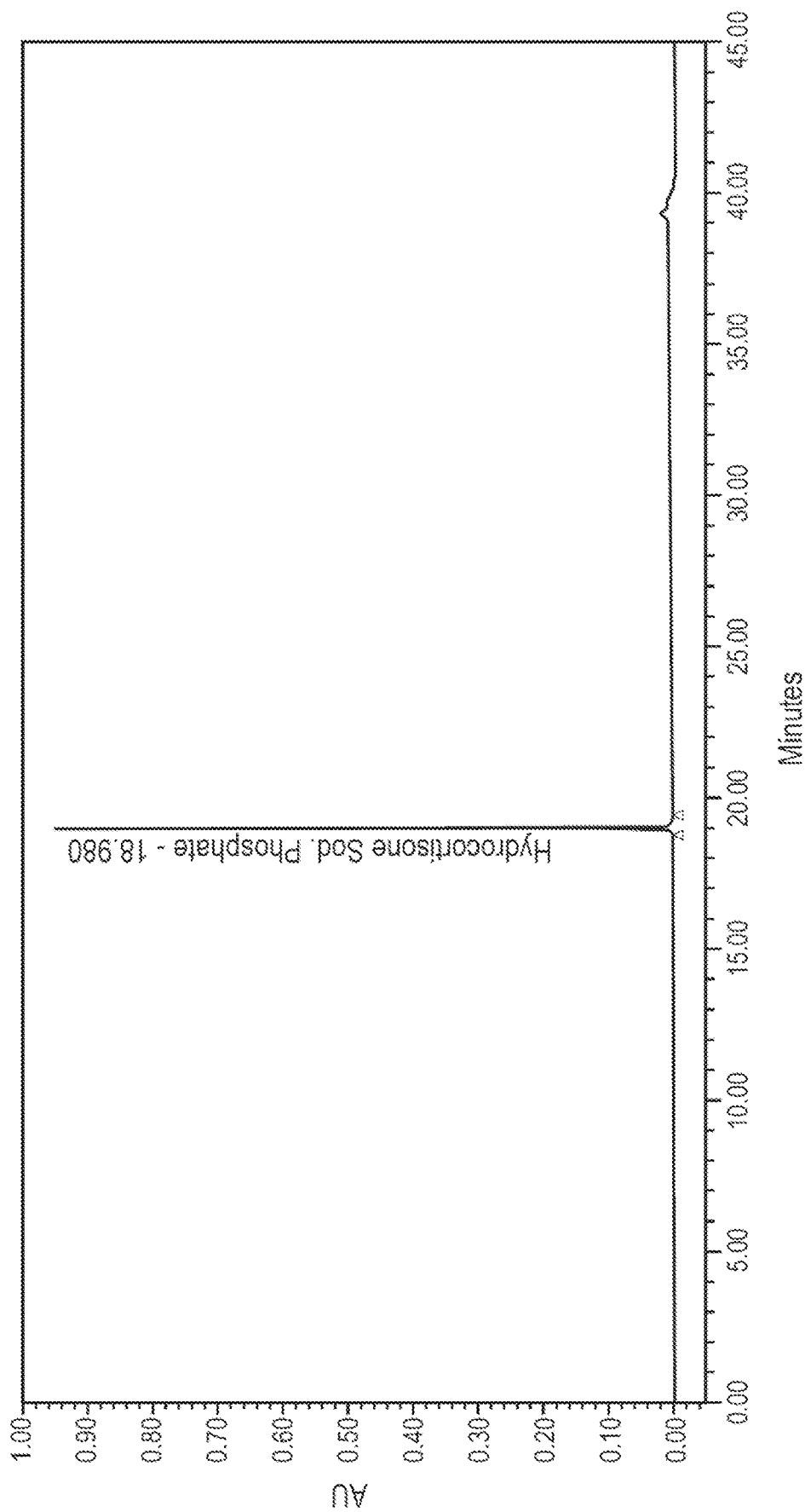
FIG. 2 illustrates a typical chromatogram of HCP using the developed analytical method described herein.

A typical chromatogram of HCP using the developed analytical method is as depicted in FIG. 2.

15 formulations were evaluated under stability study at 40° C. and 25° C. in PFS, to evaluate pH effect, combination of antioxidants, for 6 months. Results from stability data at 40° C. and 25° C.:

- Optimum pH range 7.5 to 8.5, in agreement with USP monograph spec
- Combinations of EDTA/Monothiolglycerol, EDTA/sulfite show better stability than the combination of EDTA/Rongalite, which is covered by a U.S. Pat. No. 10,456,355, incorporated in its entirety herein
- The addition of a third stabilizer, creatine significantly improve the stability of formulation containing EDTA/Rongalite
- The addition of creatinine as the third stability does not offer noticeable further stability improvement to EDTA/monothiolglycerol, EDTA/sulfite combination Three lead formulations having much better stability than the U.S. Pat. No. 10,456,355 formulation, with ~60% less degradation after 6 mon at 40° C., and with extrapolated shelf life at 24 months based on current stability trend (see FIG. 1). Formulation at 50 mg/mL has a viscosity close to water and injection time about 3 second for 2 mL fill. Addition of creatinine as the third stabilizer for EDTA/MTG and EDTA/sulfite offering no noticeable improvement based on 3 month data.

TABLE 9

| Formulation | Ingredient | Comment |
| --- | --- | --- |
| F #3 | EDTA/Rongalite | U.S. Pat. No. 10,456,355 |
| F #10 | EDTA/Rongalite/Creatinine | Improved on patented formulation |
| F #6 | EDTA/sulfite | Sulfite allergic concern |
| F #7 | EDTA/MTG | Best candidate |

TABLE 10

Total impurities at 25 ° C.:

| Time (mon) | Rongalite/EDTA | Rongalite/EDTA/Creatinine | Sulfite/EDTA | MTG/EDTA |
| --- | --- | --- | --- | --- |
| 0 | 0.00% | 0.00% | 0.09% | 0.00% |
| 3 | 0.20% | 0.09% | 0.04% | 0.06% |
| 6 | 0.61% | 0.12% | 0.21% | 0.12% |

TABLE 11

| Ingredients | Function | Composition per 1 mL | Composition per unit dose, 2 mL | FDA inactive ingredient database limit |
| --- | --- | --- | --- | --- |
| Hydrocortisone sodium phosphate | Active ingredient | 67.1 mg (50 mg hydrocortisone) | 134.2 mg (100 mg hydrocortisone) | — |
| Monobasic sodium phosphate anhydrous | Buffer agent | 1.0 mg | 2.0 mg | 1.2% w/v, IM |
| Dibasic sodium phosphate anhydrous | Buffer agent | 10.9 mg | 21.8 mg | 1.75% w/v, IM |
| Disodium edetate | Chelating agent | 0.2 mg | 0.4 mg | 10% w/v, IM |
| Monothioglycerol | Antioxidant | 5.0 mg | 10.0 mg | 0.5% w/v, IM |
| Sodium hydroxide/HCl | pH adjustor | Q.S pH (appr 8.0) | Q.S pH (appr 8.0) | — |
| Water | Solvent | Q.S. to 1 mL | Q.S. to 1 mL | — |

Figure 3A:
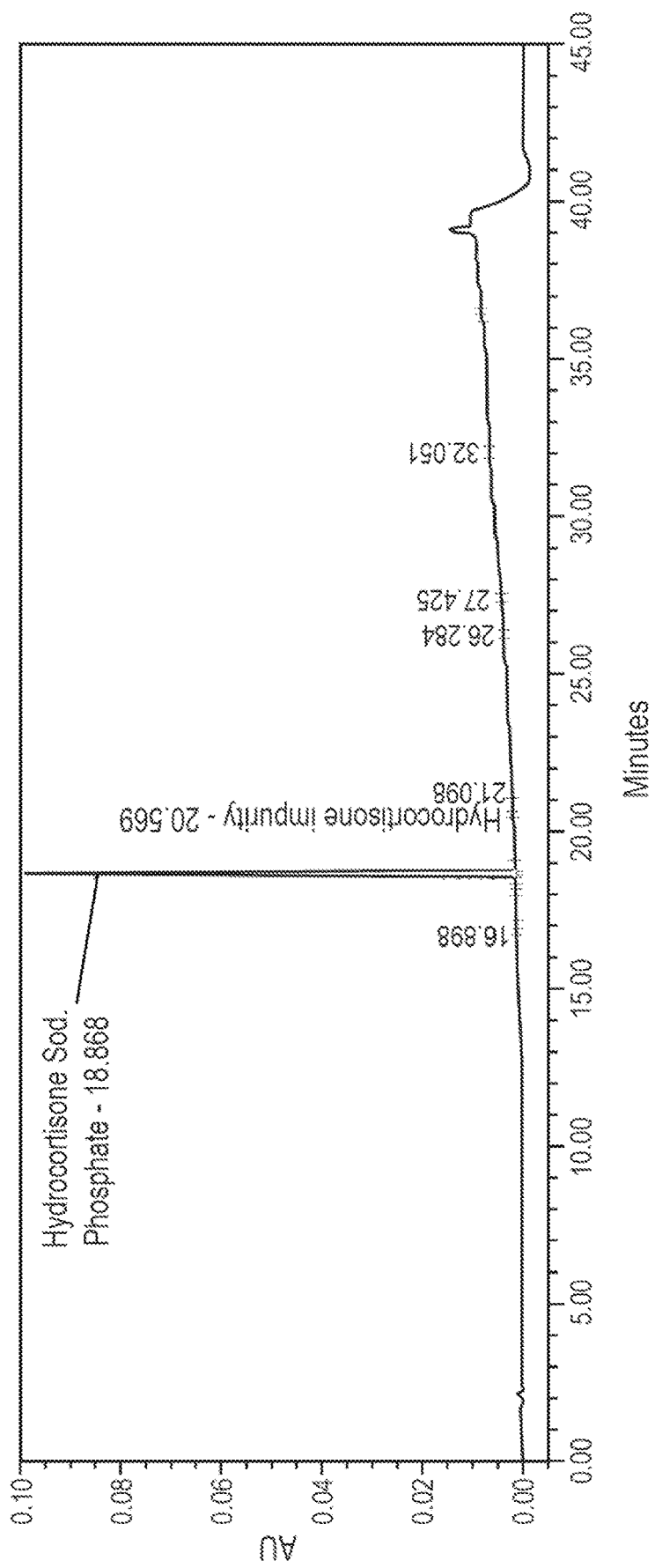
FIG. 3A illustrates the acid hydrolysis of HCP using 0.1 N HCl.
Figure 3B:
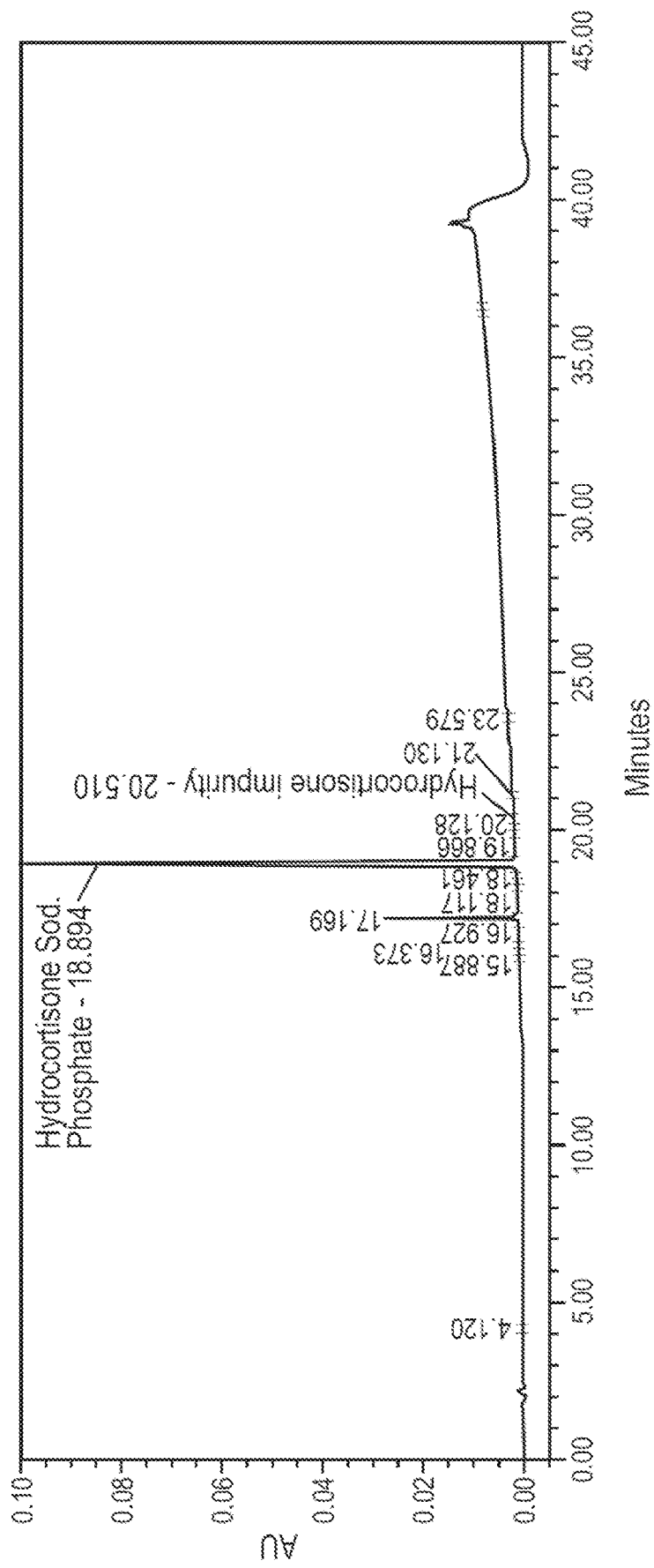
FIG. 3B illustrates alkali hydrolysis of HCP using 0.1 N NaOH.
Figure 3C:
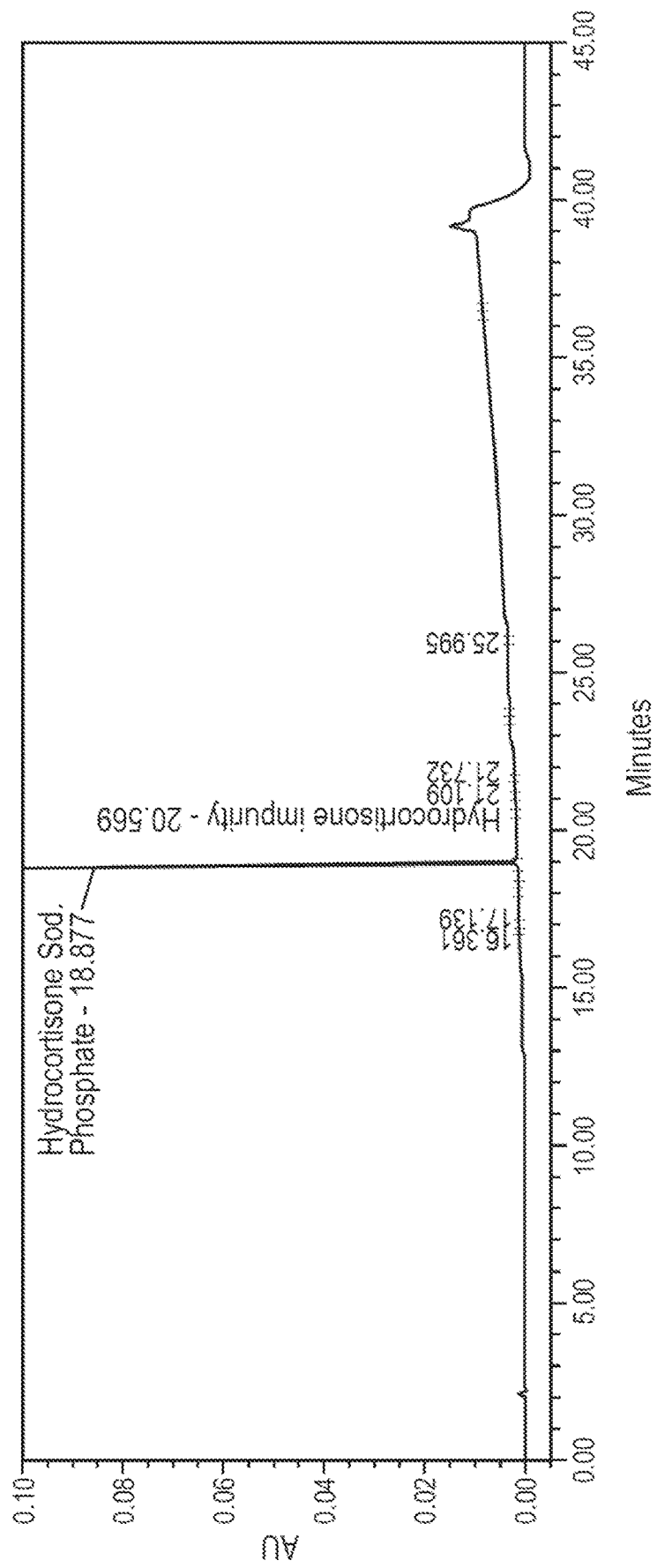
FIG. 3C illustrates the thermal degradation of HCP using dry heat.

To develop this method, Hydrocortisone sodium phosphate API was kept under stress conditions. These stress conditions included treatment with 0.1 N HCl, 0.1 N NaOH and dry heat. This was performed to investigate the nature of API and its compatibility with the stress conditions. It also helped generate degradation products to assess the specificity of the HPLC method under development. Information on degradation products and the conditions used to generate them was used to optimize the method for better resolution of such degradation products on chromatogram. FIGS. 3A-3C show chromatograms of HCP under stress conditions.

Forced degradation of HCP under 3 different stress conditions resulted in formation of Hydrocortisone, other common degradants. The proportions in which the degradants formed depended on the stress condition. Stress studies performed on the API were done for qualitative purpose only.

Preparation of HCP prototype formulations.

Following Tables 12 to 26 contain actual composition of HCP prototype formulations prepared for this study. Each Table also has values for density for each formulation prepared. Density has been calculated using gravimetry in the flask used to prepare formulation.

TABLE 12

Composition of HCP Formulation #1
Description: Drug concentration: 13.42%, pH 7.0

| Ingredient | Amount w/v | Amount/50 mL | Actual amount |
| --- | --- | --- | --- |
| Hydrocortisone sodium phosphate (w/v) | 13.42% | 6.71 g | 6.7110 g |
| Monobasic sodium phosphate anhydrous | 0.1% | 50 mg | 50.3 mg |
| Dibasic sodium phosphate anhydrous | 1.09% | 545 mg | 545.4 mg |
| Disodium EDTA | 0.02% | 10 mg | 10.1 mg |
| Sodium formaldehyde sulfoxylate | 0.2% | 100 mg | 102.2 mg |
| Sodium hydroxide/HCl | q.s. to pH 7.0 | q.s. to pH 7.0 | 7.08 |
| Water | q.s. to 1 mL | q.s. to 50 mL | q.s. to 50 mL |

Density: 1.0602 g/mL

TABLE 13

Composition of HCP Formulation #2
Description: Drug concentration: 13.42%, pH 7.5

| Ingredient | Amount w/v | Amount/50 mL | Actual amount |
| --- | --- | --- | --- |
| Hydrocortisone sodium phosphate (w/v) | 13.42% | 6.71 g | 6.7100 g |

TABLE 13-continued

Composition of HCP Formulation #2
Description: Drug concentration: 13.42%, pH 7.5

| Ingredient | Amount w/v | Amount/50 mL | Actual amount |
|---|---|---|---|
| Monobasic sodium phosphate anhydrous | 0.1% | 50 mg | 50.0 mg |
| Dibasic sodium phosphate anhydrous | 1.09% | 545 mg | 545.1 mg |
| Disodium EDTA | 0.02% | 10 mg | 9.8 mg |
| Sodium formaldehyde sulfoxylate | 0.2% | 100 mg | 100.1 mg |
| Sodium hydroxide/HCl | q.s. to pH 7.5 | q.s. to pH 7.5 | 7.55 |
| Water | q.s. to 1 mL | q.s. to 50 mL | q.s. to 50 mL |

Density: 1.0587 g/mL

TABLE 14

Composition of HCP Formulation #3
Description: Drug concentration: 13.42%, pH 8.0

| Ingredient | Amount w/v | Amount/50 mL | Actual amount |
|---|---|---|---|
| Hydrocortisone sodium phosphate (w/v) | 13.42% | 6.71 g | 6.7102 g |
| Monobasic sodium phosphate anhydrous | 0.1% | 50 mg | 50.9 mg |
| Dibasic sodium phosphate anhydrous | 1.09% | 545 mg | 545.6 mg |
| Disodium EDTA | 0.02% | 10 mg | 10.0 mg |
| Sodium formaldehyde sulfoxylate | 0.2% | 100 mg | 102.0 mg |
| Sodium hydroxide/HCl | q.s. to pH 8.0 | q.s. to pH 8.0 | 8.03 |
| Water | q.s. to 1 mL | q.s. to 50 mL | q.s. to 50 mL |

Density: 1.0597 g/mL

TABLE 15

Composition of HCP Formulation #4
Description: Drug concentration: 13.42%, pH 8.5

| Ingredient | Amount w/v | Amount/50 mL | Actual amount |
|---|---|---|---|
| Hydrocortisone sodium phosphate (w/v) | 13.42% | 6.71 g | 6.7107 g |
| Monobasic sodium phosphate anhydrous | 0.1% | 50 mg | 50.7 mg |
| Dibasic sodium phosphate anhydrous | 1.09% | 545 mg | 544.9 mg |
| Disodium EDTA | 0.02% | 10 mg | 10.4 mg |
| Sodium formaldehyde sulfoxylate | 0.2% | 100 mg | 99.9 mg |
| Sodium hydroxide/HCl | q.s. to pH 8.5 | q.s. to pH 8.5 | 8.50 |
| Water | q.s. to 1 mL | q.s. to 50 mL | q.s. to 50 mL |

Density: 1.0602

TABLE 16

Composition of HCP Formulation #5
Description: Drug concentration: 6.71%, pH 8.0

| Ingredient | Amount w/v | Amount/50 mL | Actual amount |
|---|---|---|---|
| Hydrocortisone sodium phosphate (w/v) | 6.71% | 3.355 g | 3.3556 g |
| Monobasic sodium phosphate anhydrous | 0.1% | 50 mg | 50.2 mg |
| Dibasic sodium phosphate anhydrous | 1.09% | 545 mg | 544.9 mg |
| Disodium EDTA | 0.02% | 10 mg | 9.9 mg |
| Sodium formaldehyde sulfoxylate | 0.2% | 100 mg | 100.7 mg |

TABLE 16-continued

Composition of HCP Formulation #5
Description: Drug concentration: 6.71%, pH 8.0

| Ingredient | Amount w/v | Amount/50 mL | Actual amount |
|---|---|---|---|
| Sodium hydroxide/HCl | q.s. to pH 8.0 | q.s. to pH 8.0 | 8.03 |
| Water | q.s. to 1 mL | q.s. to 50 mL | q.s. to 50 mL |

Density: 1.0329 g/mL

TABLE 17

Composition of HCP Formulation #6
Description: Drug concentration: 13.42%, pH 8.0, Effect of Sodium sulfite

| Ingredient | Amount w/v | Amount/50 mL | Actual amount |
|---|---|---|---|
| Hydrocortisone sodium phosphate (w/v) | 13.42% | 6.71 g | 6.7107 g |
| Monobasic sodium phosphate anhydrous | 0.1% | 50 mg | 50.4 mg |
| Dibasic sodium phosphate anhydrous | 1.09% | 545 mg | 545.2 mg |
| Disodium EDTA | 0.02% | 10 mg | 10.0 mg |
| Sodium sulfite | 0.2% | 100 mg | 100.0 mg |
| Sodium hydroxide/HCl | q.s. to pH 8.0 | q.s. to pH 8.0 | 8.04 |
| Water | q.s. to 1 mL | q.s. to 50 mL | q.s. to 50 mL |

Density: 1.0584 g/mL

TABLE 18

Composition of HCP Formulation #7
Description: Drug concentration: 13.42%, pH 8.0, Effect of Monothioglycerol

| Ingredient | Amount w/v | Amount/ 50 mL | Actual amount |
|---|---|---|---|
| Hydrocortisone sodium phosphate (w/v) | 13.42% | 6.71 g | 6.7100 g |
| Monobasic sodium phosphate anhydrous | 0.1% | 50 mg | 50.5 mg |
| Dibasic sodium phosphate anhydrous | 1.09% | 545 mg | 545.2 mg |
| Disodium EDTA | 0.02% | 10 mg | 10.3 mg |
| Monothioglycerol | 0.5% | 250 mg | 256.6 mg |
| Sodium hydroxide/HCl | q.s. to pH 8.0 | q.s. to pH 8.0 | 8.15 |
| Water | q.s. to 1 mL | q.s. to 50 mL | q.s. to 50 mL |

Density: 1.0600 g/mL

TABLE 19

Composition of HCP Formulation #8
Description: Drug concentration: 13.42%, pH 8.0, Effect of Ascorbic Acid.

| Ingredient | Amount w/v | Amount/200 ml | Actual amount |
|---|---|---|---|
| Hydrocortisone sodium phosphate (w/v) | 13.42% | 26.84 g | 26.838 g |
| Monobasic sodium phosphate anhydrous | 0.1% | 200 mg | 200.1 mg |
| Dibasic sodium phosphate anhydrous | 1.09% | 2.180 g | 2.1806 g |
| Disodium EDTA | 0.02% | 40 mg | 40.0 mg |
| Ascorbic acid | 0.2% | 400 mg | 400.2 mg |
| Sodium hydroxide/HCl | q.s. to pH 8.0 | q.s. to pH 8.0 | 7.98 |
| Water | q.s. to 1 mL | q.s. to 200 mL | q.s. to 200 mL |

Density: 1.0598 g/mL

Syringes of HCP Formulation #8 was divided into 3 sublots HCP F #8A, HCP F #8B and HCP F #8C.

HCP F #8A syringes were kept unpouched.

HCP F #8B3 syringes were pouched with Nitrogen purging.

HCP F #8C syringes were pouched with 2 Oxygen scavengers (no Nitrogen purging).

TABLE 20

Composition of HCP Formulation #9
Description: Drug concentration: 13.42%, pH 8.0, Effect of Methoinine.

| Ingredient | Amount w/v | Amount/ 50 mL | Actual amount |
|---|---|---|---|
| Hydrocortisone sodium phosphate (w/v) | 13.42% | 6.71 g | 6.7113 g |
| Monobasic sodium phosphate anhydrous | 0.1% | 50 mg | 50.0 mg |
| Dibasic sodium phosphate anhydrous | 1.09% | 545 mg | 545.0 mg |
| Disodium EDTA | 0.02% | 10 mg | 10.2 mg |
| Methionine | 0.05% | 25 mg | 25.1 mg |
| Sodium hydroxide/HCl | q.s. to pH 8.0 | q.s. to pH 8.0 | 8.14 |
| Water | q.s. to 1 mL | q.s. to 50 mL | q.s. to 50 mL |

Density: 1.0592 g/mL

TABLE 21

Composition of HCP Formulation #10
Description: Drug concentration: 13.42%, pH 8.0, Effect of Creatinine.

| Ingredient | Amount w/v | Amount/ 50 mL | Actual amount |
|---|---|---|---|
| Hydrocortisone sodium phosphate (w/v) | 13.42% | 6.71 g | 6.7109 g |
| Monobasic sodium phosphate anhydrous | 0.1% | 50 mg | 50.2 mg |
| Dibasic sodium phosphate anhydrous | 1.09% | 545 mg | 545.5 mg |
| Disodium EDTA | 0.02% | 10 mg | 10.0 mg |
| Sodium formaldehyde sulfoxylate | 0.2% | 100 mg | 101.0 mg |
| Creatinine | 0.8% | 400 mg | 400.2 mg |
| Sodium hydroxide/HCl | q.s. to pH 8.0 | q.s. to pH 8.0 | 8.09 |
| Water | q.s. to 1 mL | q.s. to 50 mL | q.s. to 50 mL |

Density: 1.0610 g/mL

TABLE 22

Composition of HCP Formulation #11
Description: Drug concentration: 13.42%, pH 8.0, Effect of Niacinamide.

| Ingredient | Amount w/v | Amount/ 50 mL | Actual amount |
|---|---|---|---|
| Hydrocortisone sodium phosphate (w/v) | 13.42% | 6.71 g | 6.7107 g |
| Monobasic sodium phosphate anhydrous | 0.1% | 50 mg | 50.0 mg |
| Dibasic sodium phosphate anhydrous | 1.09% | 545 mg | 545.2 mg |
| Disodium EDTA | 0.02% | 10 mg | 10.4 mg |
| Sodium formaldehyde sulfoxylate | 0.2% | 100 mg | 100.9 mg |
| Niacinamide | 2.5% | 1.25 g | 1.2504 g |
| Sodium hydroxide/HCl | q.s. to pH 8.0 | q.s. to pH 8.0 | 7.98 |
| Water | q.s. to 1 mL | q.s. to 50 mL | q.s. to 50 mL |

Density: 1.0655 g/mL

TABLE 23

Composition of HCP Formulation #12
Description: Drug concentration: 13.42%, pH 8.0, Effect of 5% HP-β-cyclodextrin.

| Ingredient | Amount w/v | Amount/50 mL | Actual amount |
|---|---|---|---|
| Hydrocortisone sodium phosphate (w/v) | 13.42% | 6.71 g | 6.7106 g |
| Monobasic sodium phosphate anhydrous | 0.1% | 50 mg | 50.0 mg |
| Dibasic sodium phosphate anhydrous | 1.09% | 545 mg | 545.2 mg |
| Disodium EDTA | 0.02% | 10 mg | 9.9 mg |
| Sodium formaldehyde sulfoxylate | 0.2% | 100 mg | 100.9 mg |
| HP-β-cyclodextrin | 5.0% | 2.5 g | 2.5002 g |
| Sodium hydroxide/HCl | q.s. to pH 8.0 | q.s. to pH 8.0 | 8.06 |
| Water | q.s. to 1 mL | q.s. to 50 mL | q.s. to 50 mL |

Density: 1.0749 g/mL

TABLE 24

Composition of HCP Formulation #13
Description: Drug concentration: 13.42%, pH 8.0, Effect of 10% HP-β-cyclodextrin.

| Ingredient | Amount w/v | Amount/50 mL | Actual amount |
|---|---|---|---|
| Hydrocortisone sodium phosphate (w/v) | 13.42% | 6.71 g | 6.7098 g |
| Monobasic sodium phosphate anhydrous | 0.1% | 50 mg | 50.1 mg |
| Dibasic sodium phosphate anhydrous | 1.09% | 545 mg | 544.8 mg |
| Disodium EDTA | 0.02% | 10 mg | 10.3 mg |
| Sodium formaldehyde sulfoxylate | 0.2% | 100 mg | 100.9 mg |
| HP-β-cyclodextrin | 10.0% | 5.0 g | 5.0007 g |
| Sodium hydroxide/HCl | q.s. to pH 8.0 | q.s. to pH 8.0 | 7.98 |
| Water | q.s. to 1 mL | q.s. to 50 mL | q.s. to 50 mL |

Density: 1.0883 g/mL

TABLE 25

Composition of HCP Formulation #14
Description: Drug concentration: 13.42%, pH 8.0, Effect of Lactbionic acid.

| Ingredient | Amount w/v | Amount/50 mL | Actual amount |
|---|---|---|---|
| Hydrocortisone sodium phosphate (w/v) | 13.42% | 6.71 g | 6.7100 g |
| Monobasic sodium phosphate anhydrous | 0.1% | 50 mg | 49.9 mg |
| Dibasic sodium phosphate anhydrous | 1.09% | 545 mg | 545.3 mg |
| Disodium EDTA | 0.02% | 10 mg | 9.8 mg |
| Sodium formaldehyde sulfoxylate | 0.2% | 100 mg | 101.8 mg |
| Lactobionic Acid | 0.2% | 100 mg | 100.4 mg |
| Sodium hydroxide/HCl | q.s. to pH 8.0 | q.s. to pH 8.0 | 8.04 |
| Water | q.s. to 1 mL | q.s. to 50 mL | q.s. to 50 mL |

Density: 1.0607 g/mL

TABLE 26

Composition of HCP Formulation #15 (Previously HCP F#3)
Description: Drug concentration: 13.42%, pH 8.0.

| Ingredient | Amount w/v | Amount 200 mL | Actual amount |
|---|---|---|---|
| Hydrocortisone sodium phosphate (w/v) | 13.42% | 26.840 g | 26.838 g |
| Monobasic sodium phosphate anhydrous | 0.1% | 200 mg | 200.3 mg |
| Dibasic sodium phosphate anhydrous | 1.09% | 2.180 g | 2.1806 g |
| Disodium EDTA | 0.02% | 40 mg | 40.3 mg |
| Sodium formaldehyde sulfoxylate | 0.2% | 400 mg | 402.0 mg |
| Sodium hydroxide/ HCl | q.s to pH 8.0 | q.s to pH 8.0 | 7.98 |
| Water | q.s to 1 mL | q.s to 200 mL | q.s to 200 mL |

Density: 1.0603 g/mL

Syringes of HCP Formulation #15 was divided into 3 sublots HCP F #15A, HCP F #15B and HCP F #15C.

HCP F #15A syringes were kept unpouched.

HCP F #15B syringes were pouched with Nitrogen purging.

HCP F #15C syringes were pouched with 2 Oxygen scavengers (no Nitrogen purging).

Stability data for HCP prototype formulations.

Following Tables 27 to 45 contain stability profile for HCP formulations 1 to 15 up to 6 month storage at 25° C. and 40° C. It has data on % assay, % peak area of HCP, % area of known impurity Hydrocortisone and other unknown impurities. Please note that the reporting threshold for Hydrocortisone impurity have been kept as 0.01% as it is a major degradant.

For other impurities, it has been kept as 0.05% on chromatogram. Once the identification and qualification these unknown impurities is completed, a suitable identification threshold and qualification threshold can be used in future studies.

Stability data on following 4 unknown impurities have been kept in the table according to their formation. The sum of total other unknown impurities, which are lower in amounts have been taken into account when % peak area of HCP was calculated. Following formulas can be used to calculate impurities.

Sum of total impurities=100−% peak area of HCP

Sum of total unknown imp=100−(% peak of HCP+% peak of Hydrocortisone imp)

Sum of other unknown imp=100−(sum of % peak of HCP,Hydrocortisone & imp 1 to 4)

Impurity 1 in the stability data tables has been identified as the peak of a degradation product that elutes at 5.00 minutes on chromatogram. The relative retention time for this impurity is 0.26. This impurity was observed during the alkali hydrolysis of HCP using 0.1N NaOH during method development. This impurity was also prevalent from early stages of the accelerated stability condition (40° C.) in formulations that had Sodium formaldehyde sulfoxylate in their composition as an antioxidant.

Impurity 2 in the stability data tables has been identified as the peak of a degradation product that elutes at 15.07 minutes on chromatogram. The relative retention time for this impurity is 0.79. This impurity was not observed during forced degradation of HCP in method development.

Impurity 3 in the stability data tables has been identified as the peak of a degradation product that elutes at 17.25 minutes on chromatogram. The relative retention time for this impurity is 0.91. This impurity was observed during the alkali hydrolysis of HCP using 0.1 N NaOH during method development.

Impurity 4 in the stability data tables has been identified as the peak of a degradation product that elutes at 23.64 minutes on chromatogram. The relative retention time for this impurity is 1.24. This impurity was observed during the thermal degradation of HCP using dry heat during method development.

Amounts of these 4 unknown impurities are more in formulations compared to those of other unknown impurities. Further investigation should be done on such unknown impurities to reduce the risk of their formation in future formulations.

TABLE 27

Stability profile of HCP Formulation #1
Description: Drug concentration: 13.42%, pH 7.0

| Duration | % Assay | % Impurity 1 RRT 0.26 | % Impurity 2 RRT 0.79 | % Impurity 3 RRT 0.91 | % Impurity 4 RRT 1.24 | % Hydrocortisone RRT 1.09 | % Peak area | pH of formulation |
|---|---|---|---|---|---|---|---|---|
| Storage conditions: 25° C. | | | | | | | | |
| Initial | 101.27 | — | — | — | | 0.0 | 100.0 | 7.08 |
| 3M | 97.53 | — | — | — | 0.16 | 0.18 | 99.6 | 7.08 |
| 6M | 95.30 | — | — | — | 0.28 | 0.28 | 99.2 | 7.04 |
| 12M | | | | | | | | |
| 18M | | | | | | | | |
| 24M | | | | | | | | |
| Storage conditions: 40° C. | | | | | | | | |
| Initial | 101.27 | | | | | 0.0 | 100.0 | 7.08 |
| 1M | 100.64 | | | | 0.21 | 0.70 | 98.3 | 7.05 |
| 2M | 91.53 | 0.13 | 0.11 | 0.05 | 0.93 | 0.87 | 96.5 | 6.99 |
| 3M | 89.06 | 0.24 | 0.14 | 0.06 | 1.50 | 0.92 | 94.9 | 7.10 |
| 6M | 80.32 | 0.63 | 0.23 | 0.14 | 3.42 | 1.40 | 89.6 | 7.04 |

TABLE 28

Stability profile of HCP Formulation #2
Description: concentration: 13.42%, pH 7.5

Storage condition: 25° C.

| Duration | % Assay | % Impurity 1 RRT 0.26 | % Impurity 2 RRT 0.79 | % Impurity 3 RRT 0.91 | % Impurity 4 RRT 1.24 | % Hydrocortisone RRT 1.09 | % Peak area | pH of formulation |
|---|---|---|---|---|---|---|---|---|
| Initial | 100.85 | — | — | — | — | 0.0 | 100.0 | 7.61 |
| 3M | 98.53 | — | — | — | 0.07 | 0.08 | 99.8 | 7.56 |
| 8M | 95.80 | — | 0.08 | — | 0.10 | 0.10 | 99.5 | 7.51 |
| 9M | | | | | | | | |
| 12M | | | | | | | | |
| 18M | | | | | | | | |
| 24M | | | | | | | | |

Storage condition: 40° C.

| Duration | % Assay | % Impurity 1 RRT 0.26 | % Impurity 2 RRT 0.79 | % Impurity 3 RRT 0.91 | % Impurity 4 RRT 1.24 | % Hydrocortisone RRT 1.09 | % Peak area | pH of formulation |
|---|---|---|---|---|---|---|---|---|
| Initial | 100 85 | — | — | — | — | 0.0 | 100.0 | 7.61 |
| 1M | 95.49 | — | 0.13 | 0.11 | 0.13 | 0.31 | 98.9 | 7.52 |
| 2M | 95.21 | 0.27 | 0.22 | 0.09 | 0.44 | 0.30 | 97.7 | 7.50 |
| 3M | 92.30 | 0.45 | 0.24 | 0.16 | 0.55 | 0.25 | 97.4 | 7.54 |
| 6M | 86.72 | 1.36 | 0.41 | 0.22 | 1.36 | 0.41 | 94.1 | 7.44 |

TABLE 29

Stability profile of HCP Formulation
Description: Drug concentration: 13.42%, pH 8.0

Storage condition: 25° C.

| Duration | % Assay | % Impurity 1 RRT 0.26 | % Impurity 2 RRT 0.79 | % Impurity 3 RRT 0.91 | % Impurity 4 RRT 1.24 | % Hydrocortisone RRT 1.09 | % Peak area | pH of formulation |
|---|---|---|---|---|---|---|---|---|
| Initial | 100.62 | — | — | — | — | 0.0 | 100.0 | 8.17 |
| 3M | 95.08 | — | 0.10 | — | — | 0.04 | 99.8 | 7.97 |
| 6M | 95.84 | 0.14 | 0.16 | — | 0.05 | 0.05 | 99.4 | 7.88 |
| 9M | | | | | | | | |
| 12M | | | | | | | | |
| 18M | | | | | | | | |
| 24M | | | | | | | | |

Storage condition: 40° C.

| Duration | % Assay | % Impurity 1 RRT 0.26 | % Impurity 2 RRT 0.79 | % Impurity 3 RRT 0.91 | % Impurity 4 RRT 1.24 | % Hydrocortisone RRT 1.09 | % Peak area | pH of formulation |
|---|---|---|---|---|---|---|---|---|
| Initial | 100.62 | — | — | — | — | 0.0 | 100.0 | 8.17 |
| 1M | 96.17 | — | 0.25 | 0.10 | 0.16 | 0.11 | 99.0 | 8.05 |
| 2M | 95.58 | 0.72 | 0.36 | 0.18 | 0.21 | 0.14 | 97.7 | 7.89 |
| 9M | 92.89 | 1.13 | 0.47 | 0.25 | 0.35 | 0.13 | 96.9 | 7.86 |
| 6M | 85.66 | 2.30 | 0.57 | 0.45 | 0.75 | 0.16 | 94.3 | 7.75 |

TABLE 30

Stability profile of HCP Formulation #4
Description: Drug concentration: 13.42%, pH 8.5

Storage condition: 25° C.

| Duration | % Assay | % Impurity 1 RRT 0.26 | % Impurity 2 RRT 0.79 | % Impurity 3 RRT 0.91 | % Impurity 4 RRT 1.24 | % Hydrocortisone RRT 1.09 | % Peak area | pH of formulation |
|---|---|---|---|---|---|---|---|---|
| Initial | 100.41 | — | — | — | — | 0.0 | 100.0 | 8.54 |
| 3M | 95.95 | — | 0.14 | — | — | 0.04 | 99.7 | 8.30 |
| 6M | 95.36 | 0.19 | 0.23 | — | 0.06 | 0.03 | 99.3 | 8.06 |
| 9M | | | | | | | | |
| 12M | | | | | | | | |
| 18M | | | | | | | | |
| 24M | | | | | | | | |

Storage condition: 40° C.

| Duration | % Assay | % Impurity 1 RRT 0.26 | % Impurity 2 RRT 0.79 | % Impurity 3 RRT 0.91 | % Impurity 4 RRT 1.24 | % Hydrocortisone RRT 1.09 | % Peak area | pH of formulation |
|---|---|---|---|---|---|---|---|---|
| Initial | 100.41 | — | — | — | — | 0.0 | 100.0 | 8.54 |
| 1M | 96.64 | — | 0.91 | 0.18 | 0.10 | 0.08 | 99.0 | 8.27 |
| 2M | 94.39 | 0.80 | 0.44 | 0.21 | 0.12 | 0.08 | 98.0 | 8.07 |
| 3M | 92.66 | 1.20 | 0.52 | 0.30 | 0.28 | 0.08 | 97.2 | 8.08 |
| 6M | 88.67 | 2.42 | 0.63 | 0.55 | 0.58 | 0.12 | 94.4 | 7.88 |

TABLE 31

Stability profile of HCP Formulation #5
Description: Drug concentration: 6.71%, pH 8.0

Storage conditions 25° C.

| Duration | % Assay | % Impurity 1 RRT 0.26 | % Impurity 2 RRT 0.79 | % Impurity 3 RRT 0.91 | % Impurity 4 RRT 1.24 | % Hydrocortisone RRT 1.09 | % Peak area | pH of formulation |
|---|---|---|---|---|---|---|---|---|
| Initial | 99.63 | — | — | — | — | 0.0 | 100.0 | 8.02 |
| 3M | 88.39 | — | 0.12 | — | — | 0.06 | 99.7 | 7.99 |
| 6M | 92.41 | 0.12 | 0.19 | — | 0.06 | 0.10 | 99.3 | 7.76 |
| 8M | | | | | | | | |
| 12M | | | | | | | | |
| 18M | | | | | | | | |
| 24M | | | | | | | | |

Storage conditions 40° C.

| Duration | % Assay | % Impurity 1 RRT 0.26 | % Impurity 2 RRT 0.79 | % Impurity 3 RRT 0.91 | % Impurity 4 RRT 1.24 | % Hydrocortisone RRT 1.09 | % Peak area | pH of formulation |
|---|---|---|---|---|---|---|---|---|
| Initial | 99.63 | — | — | — | — | 0.0 | 100.0 | 8.02 |
| 1M | 91.10 | — | 0.28 | 0.10 | 0.10 | 0.16 | 98.0 | 7.88 |
| 2M | 88.86 | 0.93 | 0.55 | 0.16 | 0.23 | 0.20 | 97.5 | 7 79 |
| 3M | 87.26 | 1.37 | 0.71 | 0.22 | 0.42 | 0.17 | 96.3 | 7.78 |
| 6M | 79.67 | 3.11 | 1.16 | 0.35 | 0.84 | 0.22 | 92.6 | 7.64 |

TABLE 32

Stability profile of HCP Formulation #6
Description: Drug concentration: 13.4256, pH 8.0,
Effect of Sodium sulfite Storage condition: 25° C.

| Duration | % Assay | % Impurity 1 RRT 0.26 | % Impurity 2 RRT 0.79 | % Impurity 3 RRT 0.91 | % Impurity 4 RRT 1.24 | % Hydrocortisone RRT 1.09 | % Peak area | pH of formulation |
|---|---|---|---|---|---|---|---|---|
| Initial | 103.37 | — | — | — | — | 0.0 | 99.9 | 8.34 |
| 3M | 101.28 | — | — | — | — | 0.00 | 99.9 | 8.50 |
| 6M | 99.59 | — | — | 0.07 | 0.06 | 0.02 | 99.8 | 8.40 |
| 9M | | | | | | | | |
| 12M | | | | | | | | |
| 18M | | | | | | | | |
| 24M | | | | | | | | |

Storage condition: 40° C.

| Duration | % Assay | % Impurity 1 RRT 0.26 | % Impurity 2 RRT 0.79 | % Impurity 3 RRT 0.91 | % Impurity 4 RRT 1.24 | % Hydrocortisone RRT 1.09 | % Peak area | pH of formulation |
|---|---|---|---|---|---|---|---|---|
| Initial | 103.37 | — | — | — | — | 0.0 | 99.9 | 8.34 |
| 1M | 100.02 | — | — | 0.29 | — | 0.07 | 99.5 | 8.44 |
| 2M | 99.71 | — | — | 0.45 | 0.13 | 0.07 | 90.2 | 8.41 |
| 3M | 99.46 | — | — | 0.75 | 0.19 | 0.07 | 98.9 | 8.47 |
| 6M | 95.26 | 0.06 | — | 1.16 | 0.26 | 0.06 | 98.2 | 8.46 |

TABLE 33

Stability profile of HCP Formulation #7
Description: Drug concentration: 13.42%, pH 8.0, Effect of Monothioglycerol Storage condition: 25° C.

| Duration | % Assay | % Impurity 1 RRT 0.26 | % Impurity 2 RRT 0.79 | % Impurity 3 RRT 0.91 | % Impurity 4 RRT 1.24 | % Hydrocortisone RRT 1.09 | % Peak area | pH of formulation |
|---|---|---|---|---|---|---|---|---|
| Initial | 103.06 | — | — | — | — | 0.0 | 100.0 | 8.56 |
| 3M | 98.87 | — | — | 0.05 | — | 0.00 | 99.9 | 8.65 |
| 6M | 99.58 | — | — | 0.08 | — | 0.03 | 99.9 | 8.58 |
| 9M | | | | | | | | |
| 12M | | | | | | | | |
| 18M | | | | | | | | |
| 24M | | | | | | | | |

Storage condition: 40° C.

| Duration | % Assay | % Impurity 1 RRT 0.26 | % Impurity 2 RRT 0.79 | % Impurity 3 RRT 0.91 | % Impurity 4 RRT 1.24 | % Hydrocortisone RRT 1.09 | % Peak area | pH of formulation |
|---|---|---|---|---|---|---|---|---|
| Initial | 103.06 | — | — | — | — | 0.0 | 100.0 | 8.56 |
| 1M | 100.27 | — | — | 0.27 | — | 0.07 | 99.7 | 8.59 |
| 2M | 101.01 | — | — | 0.51 | — | 0.10 | 99.3 | 8.51 |
| 3M | 99.27 | — | — | 0.84 | — | 0.12 | 98.9 | 8.49 |
| 6M | 07.99 | — | — | 1.39 | — | 0.12 | 98.2 | 8.58 |

TABLE 34

Stability profile of HCP Formulation #8A
Description: Drug concentration: 13.42%, pH 8.0, Effect of Ascorbic acid and unpouched sample Storage condition: 25° C.

| Duration | % Assay | % Impurity 1 RRT 0.26 | % Impurity 2 RRT 0.79 | % Impurity 3 RRT 0.91 | % Impurity 4 RRT 1.24 | % Hydrocortisone RRT 1.09 | % Peak area | pH of formulation |
|---|---|---|---|---|---|---|---|---|
| Initial | 99.92 | — | — | — | — | 0.0 | 100.0 | 8.37 |
| 3M | 99.94 | — | — | — | 0.05 | 0.04 | 99.9 | 8.08 |
| 6M | 99.40 | — | — | 0.04 | 0.08 | 0.05 | 99.8 | 7.96 |
| 9M | | | | | | | | |
| 12M | | | | | | | | |
| 18M | | | | | | | | |
| 24M | | | | | | | | |

Storage condition: 40° C.

| Duration | % Assay | % Impurity 1 RRT 0.26 | % Impurity 2 RRT 0.79 | % Impurity 3 RRT 0.91 | % Impurity 4 RRT 1.24 | % Hydrocortisone RRT 1.09 | % Peak area | pH of formulation |
|---|---|---|---|---|---|---|---|---|
| Initial | 99.92 | — | — | — | — | 0.0 | 100.0 | 8.37 |
| 1M | 98.04 | — | — | 0.13 | — | 0.10 | 99.6 | 8.19 |
| 2M | 99.84 | — | — | 0.16 | 0.15 | 0.14 | 99.5 | 7.94 |
| 3M | 99.41 | — | — | 0.28 | 0.29 | 0.24 | 99.1 | 7.88 |
| 6M | 95.40 | — | — | 0.46 | 0.71 | 0.46 | 97.9 | 7.72 |

TABLE 35

Stability profile of HCP Formulation #8B
Description: Drug concentration: 13.42%, pH 8.0, Effect of
Ascorbic acid and pouched with Nitrogen purging Storage condition: 25° C.

| Duration | % Assay | % Impurity 1 RRT 0.26 | % Impurity 2 RRT 0.79 | % Impurity 3 RRT 0.91 | % Impurity 4 RRT 1.24 | % Hydrocortisone RRT 1.09 | % Peak area | pH of formulation |
|---|---|---|---|---|---|---|---|---|
| Initial | 99.93 | — | — | — | — | 0.0 | 100.0 | 8.37 |
| 3M | 100.16 | — | — | — | 0.07 | 0.04 | 99.8 | 7.97 |
| 6M | 98.25 | — | — | 0.03 | 0.10 | 0.06 | 99.8 | 7.82 |
| 9M | | | | | | | | |
| 12M | | | | | | | | |
| 18M | | | | | | | | |
| 24M | | | | | | | | |

Storage condition: 40° C.

| Duration | % Assay | % Impurity 1 RRT 0.26 | % Impurity 2 RRT 0.79 | % Impurity 3 RRT 0.91 | % Impurity 4 RRT 1.24 | % Hydrocortisone RRT 1.09 | % Peak area | pH of formulation |
|---|---|---|---|---|---|---|---|---|
| Initial | 98.92 | — | — | — | — | 0.0 | 100.0 | 8.37 |
| 1M | 99.74 | — | — | 0.11 | 0.11 | 0.10 | 99.5 | 8.47 |
| 2M | 99.63 | — | — | 0.18 | 0.17 | 0.16 | 99.4 | 7.94 |
| 3M | 99.55 | — | — | 0.25 | 0.28 | 0.22 | 99.1 | 7.90 |
| 6M | 98.84 | — | — | 0.45 | 0.70 | 0.44 | 98.0 | 7.72 |

TABLE 36

Stability profile of HCP Formulation #8C
Description: Drug concentration: 13.42%, pH 8.0, Effect of Ascorbic acid and pouched with 2 Oxygen scavengers.

Storage condition: 25° C.

| Duration | % Assay | % Impurity 1 RRT 0.26 | % Impurity 2 RRT 0.79 | % Impurity 3 RRT 0.91 | % Impurity 4 RRT 1.24 | % Hydrocortisone RRT 1.09 | % Peak area | pH of formulation |
|---|---|---|---|---|---|---|---|---|
| Initial | 99.92 | — | — | — | — | 0.0 | 100.0 | 8.37 |
| 3M | 101.20 | — | — | — | 0.05 | 0.04 | 99.9 | 8.12 |
| 6M | 100.06 | — | — | 0.03 | 0.07 | 0.05 | 99.9 | 7.89 |
| 9M | | | | | | | | |
| 12M | | | | | | | | |
| 16M | | | | | | | | |
| 24M | | | | | | | | |

Storage condition: 40° C.

| Duration | % Assay | % Impurity 1 RRT 0.26 | % Impurity 2 RRT 0.79 | % Impurity 3 RRT 0.91 | % Impurity 4 RRT 1.24 | % Hydrocortisone RRT 1.09 | % Peak area | pH of formulation |
|---|---|---|---|---|---|---|---|---|
| Initial | 99.92 | — | — | — | — | 0.0 | 100.0 | 8.37 |
| 1M | 99.73 | — | — | 0.11 | — | 0.10 | 99.8 | 8.06 |
| 2M | 99.96 | — | — | 0.23 | 0.18 | 0.15 | 99.4 | 8.03 |
| 3M | 100.11 | — | — | 0.37 | 0.30 | 0.21 | 99.0 | 8.00 |
| 6M | 97.27 | — | — | 0.55 | 0.58 | 0.31 | 98.3 | 7.93 |

TABLE 37

Stability profile of HCP Formulation #9
Description: Drug concentration: 13.42%, pH 8.0, Effect of Methoinine.

Storage Condition: 25° C.

| Duration | % Assay | % Impurity 1 RRT 0.26 | % Impurity 2 RRT 0.79 | % Impurity 3 RRT 0.91 | % Impurity 4 RRT 1.24 | % Hydrocortisone RRT 1.09 | % Peak area | pH of formulation |
|---|---|---|---|---|---|---|---|---|
| Initial | 102.86 | — | — | — | — | 0.0 | 100.0 | 8.61 |
| 3M | 97.89 | 0.05 | — | 0.04 | 0.06 | 0.00 | 99.7 | 8.38 |
| 6M | 98.37 | 0.07 | — | 0.06 | 0.08 | 0.02 | 99.6 | 8.26 |
| 9M | | | | | | | | |
| 12M | | | | | | | | |
| 18M | | | | | | | | |
| 24M | | | | | | | | |

Storage Condition: 40° C.

| Duration | % Assay | % Impurity 1 RRT 0.26 | % Impurity 2 RRT 0.79 | % Impurity 3 RRT 0.91 | % Impurity 4 RRT 1.24 | % Hydrocortisone RRT 1.09 | % Peak area | pH of formulation |
|---|---|---|---|---|---|---|---|---|
| Initial | 102.86 | — | — | — | — | 0.0 | 100.0 | 8.61 |
| 1M | 96.11 | — | — | 0.22 | 0.34 | 0.05 | 99.4 | 8.19 |
| 2M | 99.09 | 0.05 | — | 0.39 | 0.14 | 0.07 | 99.0 | 8.29 |
| 3M | 97.52 | 0.08 | — | 0.56 | 0.24 | 0.08 | 98.7 | 8.29 |
| 6M | 95.08 | 0.07 | — | 0.95 | 0.42 | 0.10 | 97.6 | 8.16 |

TABLE 38

Stability profile of HCP Formulation #10
Description: Drug concentration 13.42%, pH 8.0, Effect of Creatinine Storage condition: 25° C.

| Duration | % Assay | % Impurity 1 RRT 0.26 | % Impurity 2 RRT 0.79 | % Impurity 3 RRT 0.91 | % Impurity 4 RRT 1.24 | % Hydrocortisone RRT 1.09 | % Peak area | pH of formulation |
|---|---|---|---|---|---|---|---|---|
| Initial | 103.32 | — | — | — | — | 0.0 | 100.0 | 8.11 |
| 3M | 95.68 | — | 0.03 | — | — | 0.04 | 99.9 | 8.01 |
| 6M | 93.95 | — | 0.05 | — | — | 0.03 | 99.9 | 7.95 |
| 9M | | | | | | | | |
| 12M | | | | | | | | |
| 18M | | | | | | | | |
| 24M | | | | | | | | |

Storage condition: 40° C.

| Duration | % Assay | % Impurity 1 RRT 0.26 | % Impurity 2 RRT 0.79 | % Impurity 3 RRT 0.91 | % Impurity 4 RRT 1.24 | % Hydrocortisone RRT 1.09 | % Peak area | pH of formulation |
|---|---|---|---|---|---|---|---|---|
| Initial | 103.32 | — | — | — | — | 0.0 | 100.0 | 8.11 |
| 1M | 91.71 | 0.07 | 0.08 | 0.08 | — | 0.09 | 99.6 | 8.05 |
| 2M | 101.45 | 0.11 | 0.10 | 0.11 | — | 0.09 | 99.5 | 7.82 |
| 3M | 93.59 | 0.27 | 0.13 | 0.17 | 0.07 | 0.12 | 98.8 | 7.85 |
| 6M | 90.78 | 0.44 | 0.14 | 0.30 | 0.16 | 0.13 | 97.8 | 7.75 |

TABLE 39

Stability profile of HCP Formulation #11
Description: Drug concentration 13.42%, pH 8.0, Effect of Niacinamide.

Storage condition: 25° C.

| Duration | % Assay | % Impurity 1 RRT 0.26 | % Impurity 2 RRT 0.79 | % Impurity 3 RRT 0.91 | % Impurity 4 RRT 1.24 | % Hydrocortisone RRT 1.09 | % Peak area | pH of formulation |
|---|---|---|---|---|---|---|---|---|
| Initial | 100.15 | — | — | — | — | 00 | 100.0 | 8.11 |
| 3M | 95.69 | — | — | — | — | 0.05 | 99.9 | 8.01 |
| 6M | 93.72 | — | 0.06 | — | — | 0.05 | 99.8 | 7.95 |
| 9M | | | | | | | | |
| 12M | | | | | | | | |
| 18M | | | | | | | | |
| 24M | | | | | | | | |

Storage condition: 40° C.

| Duration | % Assay | % Impurity 1 RRT 0.26 | % Impurity 2 RRT 0.79 | % Impurity 3 RRT 0.91 | % Impurity 4 RRT 1.24 | % Hydrocortisone RRT 1.09 | % Peak area | pH of formulation |
|---|---|---|---|---|---|---|---|---|
| Initial | 100.15 | — | — | — | — | 0.0 | 100.0 | 7.95 |
| 1M | 92.79 | 0.14 | 0.15 | 0.07 | — | 0.15 | 99.4 | 7.95 |
| 2M | 94.22 | 0.33 | 0.20 | 0.13 | 0.19 | 0.16 | 98.8 | 7.77 |
| 3M | 91.85 | 0.76 | 0.33 | 0.14 | 0.40 | 0.16 | 97.5 | 7.86 |
| 6M | 88.89 | 1.09 | 0.38 | 0.32 | 0.69 | 0.16 | 96.2 | 7.78 |

TABLE 40

Stability profile of HCP Formulation #12
Description: Drug concentration: 13.42%, pH 8.0, Effect of 5% HP-8-cyclodextrin Storage condition: 25° C.

| Duration | % Assay | % Impurity 1 RRT 0.26 | % Impurity 2 RRT 0.79 | % Impurity 3 RRT 0.91 | % Impurity 4 RRT 1.24 | % Hydrocortisone RRT 1.09 | % Peak area | pH of formulation |
| --- | --- | --- | --- | --- | --- | --- | --- | --- |
| Initial | 100.99 | — | — | — | — | — | 100.0 | 8.1 |
| 3M | 98.38 | — | 0.08 | — | — | 0.05 | 99.8 | 8.04 |
| 6M | 94.96 | — | 0.16 | — | 0.04 | 0.05 | 99.5 | 7.92 |
| 9M | | | | | | | | |
| 12M | | | | | | | | |
| 18M | | | | | | | | |
| 24M | | | | | | | | |

Storage condition: 40° C.

| Duration | % Assay | % Impurity 1 RRT 0.26 | % Impurity 2 RRT 0.79 | % Impurity 3 RRT 0.91 | % Impurity 4 RRT 1.24 | % Hydrocortisone RRT 1.09 | % Peak area | pH of formulation |
| --- | --- | --- | --- | --- | --- | --- | --- | --- |
| Initial | 100.99 | — | — | — | — | 0.0 | 100.0 | 8.1 |
| 1M | 91.91 | 0.17 | 0.18 | 0.07 | — | 0.10 | 99.3 | 7.98 |
| 2M | 94.04 | 0.43 | 0.30 | 0.14 | 0.14 | 0.13 | 98.6 | 7.82 |
| 3M | 92.70 | 0.84 | 0.41 | 0.21 | 0.30 | 0.15 | 97.5 | 7.85 |
| 6M | 87.37 | 1.81 | 0.61 | 0.33 | 0.63 | 0.14 | 95.0 | 7.79 |

TABLE 41

Stability profile of HCP Formulation #13
Description: Drug concentration 13.42 %, pH 8.0. Effect of 10% HP-8-cyclodextrin.

Storage condition: 25° C.

| Duration | % Assay | % Impurity 1 RRT 0.26 | % Impurity 2 RRT 0.79 | % Impurity 3 RRT 0.91 | % Impurity 4 RRT 1.24 | % Hydrocortisone RRT 1.09 | % Peak area | pH of formulation |
| --- | --- | --- | --- | --- | --- | --- | --- | --- |
| Initial | 99.99 | — | — | — | — | 0.0 | 100.0 | 8.01 |
| 3M | 96.97 | — | 0.09 | — | — | 0.05 | 99.8 | 8.00 |
| 6M | 96.41 | 0.08 | 0.15 | — | — | 0.06 | 99.5 | 7.90 |
| 9M | | | | | | | | |
| 18M | | | | | | | | |
| 18M | | | | | | | | |
| 24M | | | | | | | | |

Storage condition: 40° C.

| Duration | % Assay | % Impurity 1 RRT 0.26 | % Impurity 2 RRT 0.79 | % Impurity 3 RRT 0.91 | % Impurity 4 RRT 1.24 | % Hydrocortisone RRT 1.09 | % Peak area | pH of formulation |
| --- | --- | --- | --- | --- | --- | --- | --- | --- |
| Initial | 99.99 | — | — | — | — | 0.0 | 100.0 | 8.01 |
| 1M | 94.62 | 0.15 | 0.19 | 0.08 | — | 0.13 | 99.2 | 8.02 |
| 2M | 94.66 | 0.36 | 0.27 | 0.12 | 0.12 | 0.13 | 98.8 | 7.79 |
| 3M | 92.40 | 0.88 | 0.44 | 0.20 | 0.30 | 0.15 | 97.4 | 7.90 |
| 6M | 88.55 | 1.54 | 0.56 | 0.30 | 0.58 | 0.14 | 95.5 | 7.78 |

TABLE 42

Stability profile of HCP Formulation #14
Description: Drug concentration: 13.42%, pH 8.0, Effect of Lacthionic acid.

Storage condition: 25° C.

| Duration | % Assay | % Impurity 1 RRT 0.26 | % Impurity 2 RRT 0.79 | % Impurity 3 RRT 0.91 | % Impurity 4 RRT 1.24 | % Hydrocortisone RRT 1.09 | % Peak area | pH of formulation |
|---|---|---|---|---|---|---|---|---|
| Initial | 100.34 | — | — | — | — | 0.0 | 100.0 | 8.04 |
| 3M | 96.09 | — | 0.08 | — | — | 0.05 | 99.8 | 8.00 |
| 8M | 94.21 | 0.10 | 0.16 | — | 0.05 | 0.05 | 99.5 | 7.87 |
| 9M | | | | | | | | |
| 12M | | | | | | | | |
| 18M | | | | | | | | |
| 24M | | | | | | | | |

Storage condition: 40° C.

| Duration | % Assay | % Impurity 1 RRT 0.26 | % Impurity 2 RRT 0.79 | % Impurity 3 RRT 0.91 | % Impurity 4 RRT 1.24 | % Hydrocortisone RRT 1.09 | % Peak area | pH of formulation |
|---|---|---|---|---|---|---|---|---|
| Initial | 100.34 | — | — | — | — | 0.0 | 100.0 | 8.04 |
| 1M | 94.32 | 0.14 | 0.20 | 0.06 | — | 0.10 | 99.4 | 8.02 |
| 2M | 95.79 | 0.40 | 0.28 | 0.11 | 0.12 | 0.13 | 98.8 | 7.81 |
| 3M | 94.83 | 0.82 | 0.40 | 0.17 | 0.29 | 0.13 | 97.7 | 7.88 |
| 6M | 88.85 | 1.67 | 0.54 | 0.30 | 0.62 | 0.13 | 95.4 | 7.79 |

TABLE 43

Stability profile of HCP Formulation #15A
Description: Drug concentration: 13.42%, pH 8.0, unpouched sample.
Storage condition: 26° C.

| Duration | % Assay | % Impurity 1 RRT 0.26 | % Impurity 2 RRT 0.79 | % Impurity 3 RRT 0.91 | % Impurity 4 RRT 1.24 | % Hydrocortisone RRT 1.09 | % Peak area | pH of formulation |
|---|---|---|---|---|---|---|---|---|
| Initial | 102.24 | — | — | — | — | 0.0 | 100.0 | 7.98 |
| 3M | 95.80 | — | 0.09 | — | — | 0.04 | 99.8 | 7.90 |
| 6M | 94.80 | 0.12 | 0.16 | — | 0.06 | 0.05 | 98.4 | 7.87 |
| 9M | | | | | | | | |
| 12M | | | | | | | | |
| 18M | | | | | | | | |
| 24M | | | | | | | | |

Storage condition: 40° C.

| Duration | % Assay | % Impurity 1 RRT 0.26 | % Impurity 2 RRT 0.79 | % Impurity 3 RRT 0.91 | % Impurity 4 RRT 1.24 | % Hydrocortisone RRT 1.09 | % Peak area | pH of formulation |
|---|---|---|---|---|---|---|---|---|
| Initial | 102.24 | — | — | — | — | 0.0 | 100.0 | 7.98 |
| 1M | 93.50 | 0.34 | 0.26 | 0.11 | 0.08 | 0.13 | 98.8 | 7.94 |
| 2M | 93.67 | 0.98 | 0.44 | 0.22 | 0.33 | 0.15 | 97.4 | 7.90 |
| 3M | 91.42 | 1.11 | 0.46 | 0.23 | 0.40 | 0.15 | 96.9 | 7.81 |
| 6M | 87.07 | 2.06 | 0.58 | 0.38 | 0.72 | 0.16 | 94.7 | 7.79 |

TABLE 44

Stability profile of HCP Formulation #15B
Description: Drug concentration: 13.42%, pH 8.0, pouched with Nitrogen purging.
Storage condition: 25° C.

| Duration | % Assay | % Impurity 1 RRT 0.26 | % Impurity 2 RRT 0.79 | % Impurity 3 RRT 0.91 | % Impurity 4 RRT 1.24 | % Hydrocortisone RRT 1.09 | % Peak area | pH of formulation |
|---|---|---|---|---|---|---|---|---|
| Initial | 102.24 | — | — | — | — | 0.0 | 100.0 | 7.98 |
| 3M | 96.23 | — | 0.08 | — | — | 0.04 | 99.8 | 7.88 |
| 6M | 95.36 | 0.13 | 0.17 | — | 0.06 | 0.05 | 99.4 | 7.85 |
| 9M | | | | | | | | |
| 12M | | | | | | | | |
| 18M | | | | | | | | |
| 24M | | | | | | | | |

Storage condition: 40° C.

| Duration | % Assay | % Impurity 1 RRT 0.26 | % Impurity 2 RRT 0.79 | % Impurity 3 RRT 0.91 | % Impurity 4 RRT 1.24 | % Hydrocortisone RRT 1.09 | % Peak area | pH of formulation |
|---|---|---|---|---|---|---|---|---|
| Initial | 102.24 | — | — | — | — | 0.0 | 100.0 | 7.98 |
| 1M | 94.57 | 0.21 | 0.20 | 0.05 | 0.03 | 0.11 | 99.2 | 7.93 |
| 2M | 95.28 | 0.83 | 0.41 | 0.18 | 0.28 | 0.13 | 97.7 | 7.94 |
| 3M | 91.77 | 0.89 | 0.44 | 0.21 | 0.34 | 0.15 | 97.4 | 7.83 |
| 6M | 88.69 | 1.88 | 0.54 | 0.35 | 0.65 | 0.16 | 95.1 | 7.84 |

TABLE 45

Stability profile of HCP Formulation #15C.
Description: Drug concentration: 13.42%, pH 8.0, pouched with 2 Oxygen scavengers.
Storage condition: 25° C.

| Duration | % Assay | % Impurity 1 RRT 0.26 | % Impurity 2 RRT 0.79 | % Impurity 3 RRT 0.91 | % Impurity 4 RRT 1.24 | % Hydrocortisone RRT 1.09 | % Peak area | pH of formulation |
|---|---|---|---|---|---|---|---|---|
| Initial | 102.24 | — | — | — | — | 0.0 | 100.0 | 7.98 |
| 3M | 93.75 | — | 0.07 | — | — | 0.05 | 99.9 | 7.85 |
| 6M | 94.81 | 0.07 | .012 | — | — | 0.07 | 99.6 | 7.75 |
| 9M | | | | | | | | |
| 12M | | | | | | | | |
| 18M | | | | | | | | |
| 24M | | | | | | | | |

Storage condition: 40° C.

| Duration | % Assay | % Impurity 1 RRT 0.26 | % Impurity 2 RRT 0.79 | % Impurity 3 RRT 0.91 | % Impurity 4 RRT 1.24 | % Hydrocortisone RRT 1.09 | % Peak area | pH of formulation |
|---|---|---|---|---|---|---|---|---|
| Initial | 102.24 | — | — | — | — | 0.0 | 100.0 | 7.98 |
| 1M | 94.04 | 0.20 | 0.20 | 0.07 | 0.02 | 0.12 | 99.2 | 7.98 |
| 2M | 94.34 | 0.58 | 0.27 | 0.19 | 0.21 | 0.24 | 98.2 | 7.96 |
| 3M | 92.25 | 0.57 | 0.27 | 0.21 | 0.26 | 0.27 | 98.2 | 7.82 |
| 6M | 90.92 | 1.02 | 0.24 | 0.37 | 0.66 | 0.39 | 96.7 | 7.81 |

TABLE 46

Summary of all HCP formulations after 6M of storage at 25° C. and 40° C.

| Form, # | pH | Drug conc. | Antioxidant or solublizing agent | Packing type | % Assay value of HCP 25° C. | % Assay value of HCP 40° C. |
|---|---|---|---|---|---|---|
| 1 | 7.0 | 13.42 | None | — | 95.30 | 80.32 |
| 2 | 7.5 | 13.42 | None | — | 95.80 | 86.72 |
| 3 | 8.0 | 13.42 | None | — | 95.84 | 85.66 |
| 4 | 8.5 | 13.42 | None | — | 95.36 | 88.67 |
| 5 | 8.0 | 6.71 | None | — | 92.41 | 79.67 |
| 6 | 8.0 | 13.42 | Sodium Sulfite | — | 99.59 | 95.26 |
| 7 | 8.0 | 13.42 | Monothioglycerol | — | 99.58 | 97.99 |
| 8A | 8.0 | 13.42 | Ascorbic acid | Unpouched | 99.40 | 95.40 |
| 8B | 8.0 | 13.42 | Ascorbic acid | $N_2$ purging | 98.25 | 98.84 |
| 8C | 8.0 | 13.42 | Ascorbic acid | $O_2$ | 100.06 | 97.27 |

TABLE 46-continued

Summary of all HCP formulations after 6M of storage at 25° C. and 40° C.

| Form, # | Drug pH | conc. | Antioxidant or solublizing agent | Packing type | % Assay value of HCP 25° C. | 40° C. |
|---|---|---|---|---|---|---|
| 9 | 8.0 | 13.42 | Methionine | — | 98.37 | 95.08 |
| 10 | 8.0 | 13.42 | Creatinine | — | 93.95 | 90.78 |
| 11 | 8.0 | 13.42 | Niacinamide | — | 93.72 | 88.89 |
| 12 | 8.0 | 13.42 | 5% HP-β-CD | — | 94.96 | 87.37 |
| 13 | 8.0 | 13.42 | 10% HP-β-CD | — | 95.41 | 88.55 |
| 14 | 8.0 | 13.42 | Lactobionic acid | — | 94.21 | 88.85 |
| 15A | 8.0 | 13.42 | None | Unpouched | 94.80 | 87.07 |
| 15B | 8.0 | 13.42 | None | N$_2$ purging | 95.35 | 86.69 |
| 15C | 8.0 | 13.42 | None | O$_2$ scavenger | 94.81 | 90.92 |

Without wishing to be bound by any particular theory, and after stability analysis of all HCP formulations for 6 months of storage at 25° C. and 40° C., HCP F #7 seems to be the most stable formulation. It contains 0.5% w/v Monothioglycerol as an antioxidant.

Monothioglycerol is a liquid excipient.

Example 2: Exemplar Hydrocortisone Injection Formulation

| Ingredients | Function | Composition per 1 mL | Composition per unit dose, 2 mL | FDA inactive ingredient database limit |
|---|---|---|---|---|
| Hydrocortisone sodium phosphate | Active ingredient | 67.1 mg (50 mg hydrocortisone) | 134.2 mg (100 mg hydrocortisone) | — |
| Monobasic sodium phosphate anhydrous | Buffer agent | 1.0 mg | 2.0 mg | 1.2% w/v, IM |
| Dibasic sodium phosphate anhydrous | Buffer agent | 10.9 mg | 21.8 mg | 1.75% w/v, IM |
| Disodium edetate | Chelating agent | 0.2 mg | 0.4 mg | 10% w/v, IM |
| Monothioglycerol | Antioxidant | 5.0 mg | 10.0 mg | 0.5% w/v, IM |
| Sodium hydroxide/HCl | pH adjustor | Q.S. pH (appr 8.0) | Q.S pH (appr 8.0) | — |
| Water | Solvent | Q.S. to 1 mL | Q.S. to 1 mL | — |

Example 3: Stability Data for Example Formulations to Evaluate Alternative Antioxidants

| | Total Impurities (% area), 40° C. | | | | |
|---|---|---|---|---|---|
| Time (mon) | F#3, EDTA/ Rongalite | F#6, EDTA/ sulfite | F#7, EDTA/ MTG | F#8, EDTA/ ascorbic acid | F#9, EDTA/ methionine |
| 0 | 0.00% | 0.09% | 0.00% | 0.00% | 0.00% |
| 1 | 0.97% | 0.53% | 0.35% | 0.42% | 0.50% |
| 2 | 2.14% | 0.77% | 0.74% | 0.52% | 0.98% |
| 3 | 3.05% | 1.07% | 1.13% | 0.93% | 1.31% |
| 6 | 5.72% | 1.80% | 1.78% | 2.08% | 2.42% |

Figure 4:
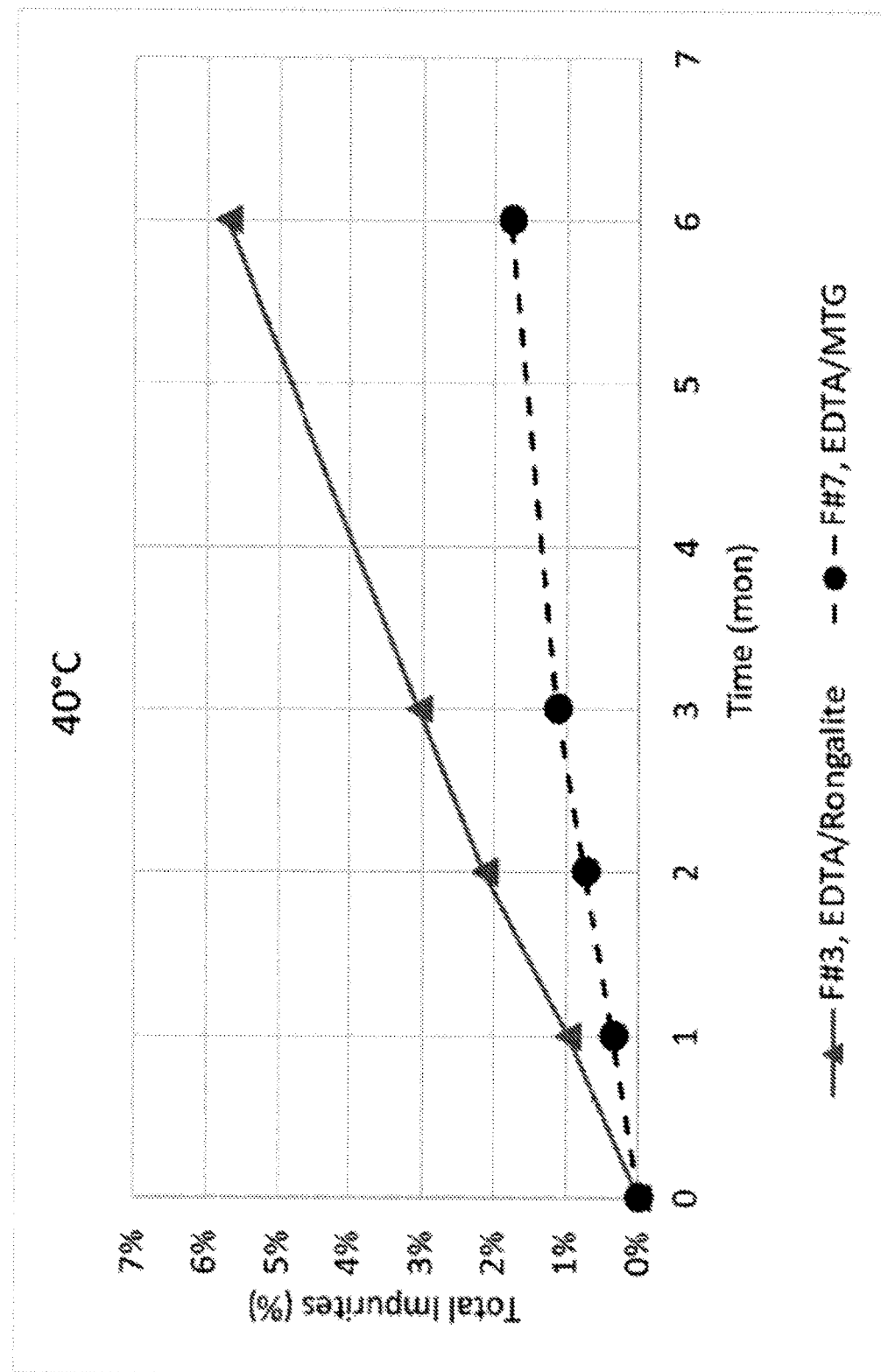
FIG. 4 illustrates the stability of two formulations (#3 and #7) over 6 months.

Also as shown in FIG. 4 which illustrates the stability of two formulations (#3 and #7) over 6 months.

| | Total Impurities (% area), 25° C. | | | | |
|---|---|---|---|---|---|
| Time (mon) | F#3, EDTA/ Rongalite | F#6, EDTA/ sulfite | F#7, EDTA/ MTG | F#8, EDTA/ ascorbic acid | F#9, EDTA/ methionine |
| 0 | 0.00% | 0.09% | 0.00% | 0.00% | 0.00% |
| 3 | 0.20% | 0.04% | 0.06% | 0.15% | 0.31% |
| 6 | 0.61% | 0.21% | 0.12% | 0.17% | 0.42% |

Stability Data for Example Formulations to the Third Additive Creatinine

| | Total Impurities (% area), 40° C. | |
|---|---|---|
| Time (mon) | F#3, EDTA/ Rongalite | F#10, EDTA/ Rongalite/Creatinine |
| 0 | 0.00% | 0.00% |
| 1 | 0.97% | 0.38% |
| 2 | 2.14% | 0.48% |

-continued

| | Total Impurities (% area), 40° C. | |
|---|---|---|
| Time (mon) | F#3, EDTA/ Rongalite | F#10, EDTA/ Rongalite/Creatinine |
| 3 | 3.05% | 1.20% |
| 6 | 5.72% | 2.22% |

Figure 5:
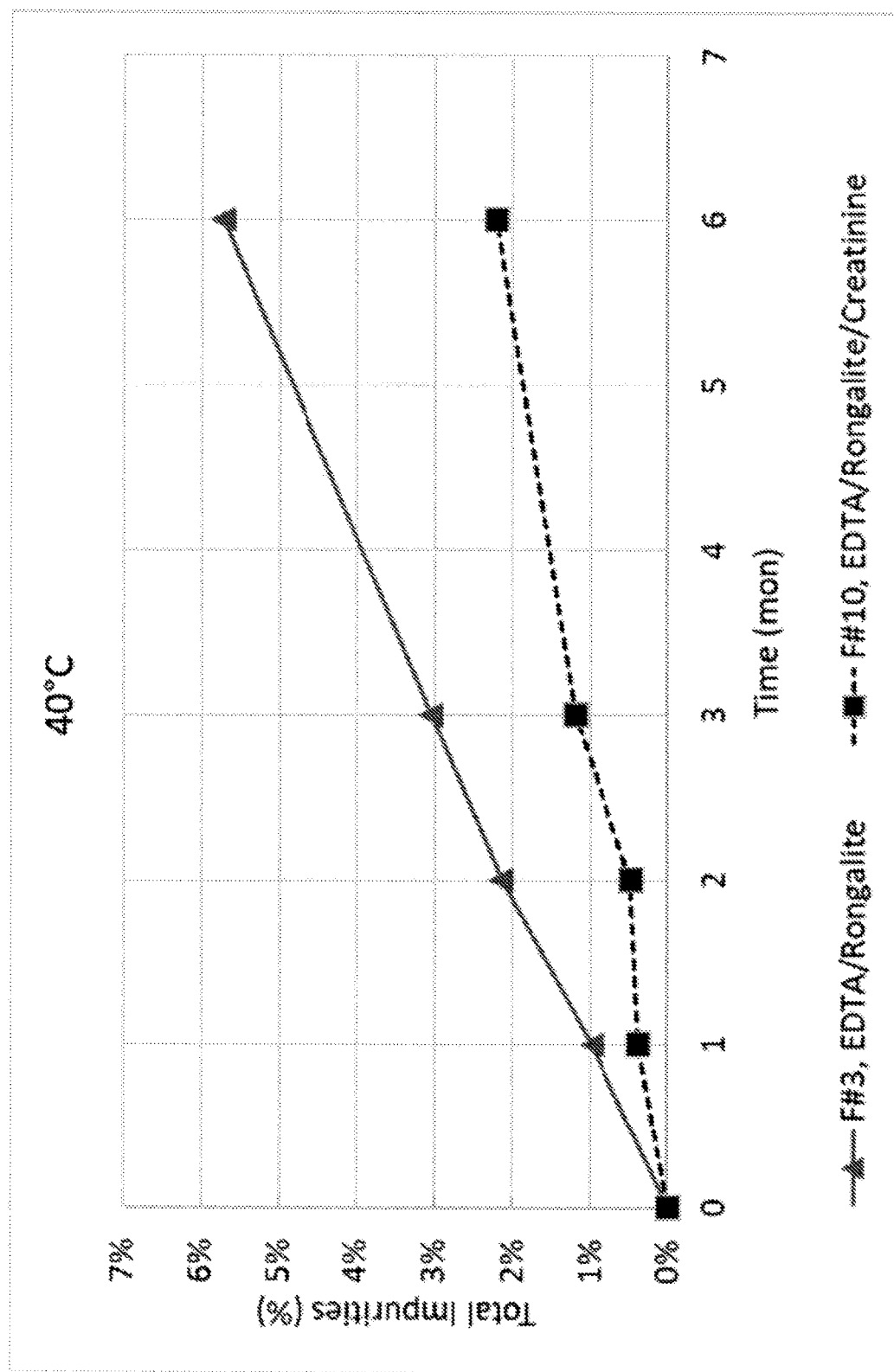
FIG. 5 illustrates the stability of two formulations (#3 and #10) over 6 months.
Figure 6:
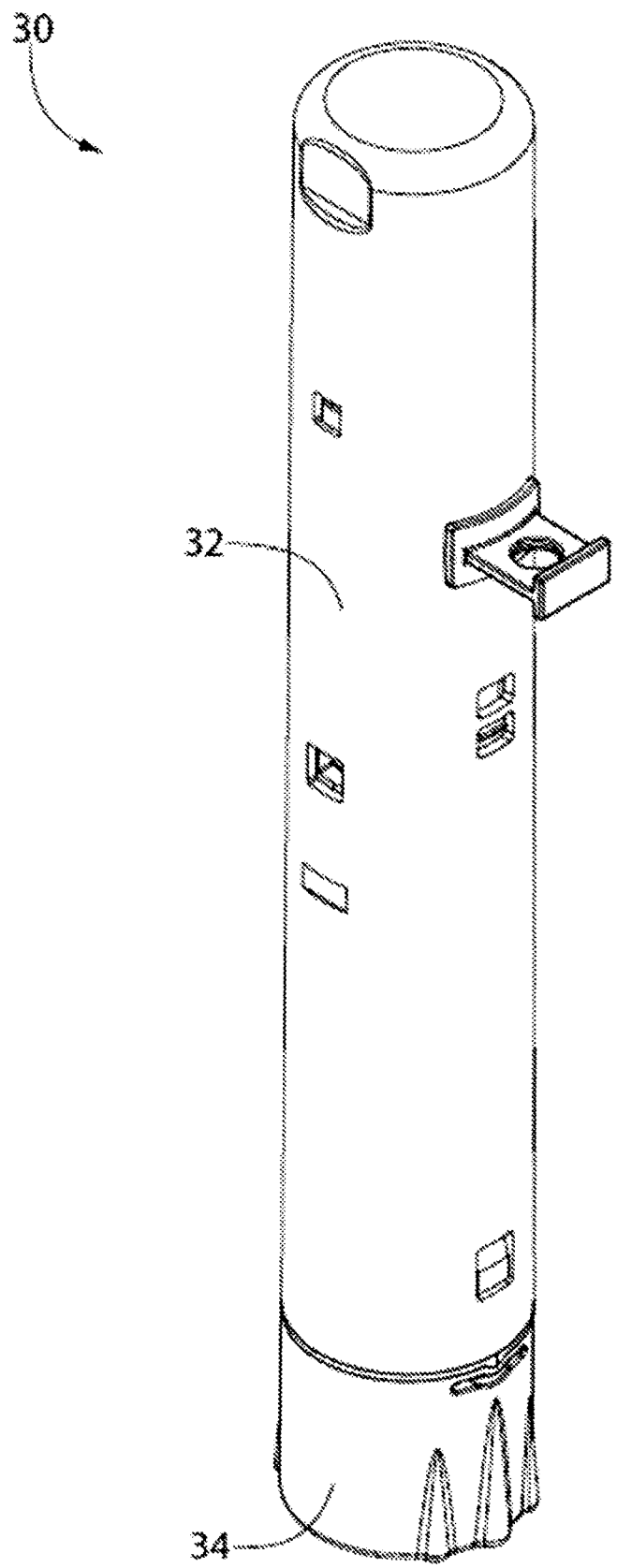
FIG. 6 is a perspective view of an injector in accordance with an exemplary embodiment of the present invention.
Figure 7:
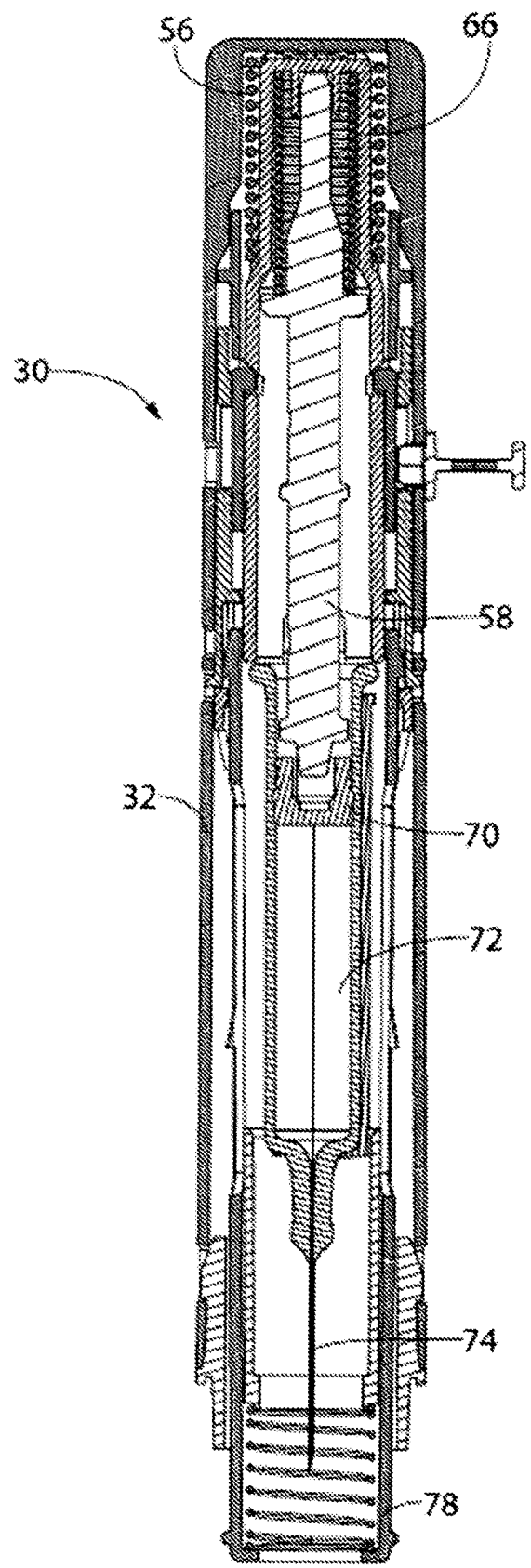
FIG. 7 is a sectional view of the injector of FIG. 6.

FIG. 5 illustrates the stability of two formulations #3 and #10) over 6 months.

| | Total Impurities (% area), 25° C. | |
|---|---|---|
| Time (mon) | F#3, EDTA/ Rongalite | F#10, EDTA/ Rongalite/ Creatinine |
| 0 | 0.00% | 0.00% |
| 3 | 0.20% | 0.09% |
| 6 | 0.61% | 0.12% |

Example 4: Formulation Concentrations

| Formulation: Component | Equivalent to: 50 mg/ml hydrocortisone | | Equivalent to: 100 mg/ml hydrocortisone | | Equivalent to: 100 mg/ml hydrocortisone | | Equivalent to: 100 mg/ml hydrocortisone | |
|---|---|---|---|---|---|---|---|---|
| Hydrocortisone sodium phosphate | 67.1 mg | 6.71% | 134.2 mg | 13.42% | 6710.0 mg | 13.42% | 2,013.0 g | 13.42% |
| Monobasic sodium phosphate | 1.0 mg | 0.10% | 1.0 mg | 0.10% | 50.0 mg | 0.10% | 19.5 g[(1)] | 0.13%[(1)] |
| Dibasic sodium phosphate | 10.9 mg | 1.09% | 10.9 mg | 1.09% | 545.0 mg | 1.09% | 205.5 g[(2)] | 1.37%[(2)] |
| Disodium EDTA | 0.2 mg | 0.02% | 0.2 mg | 0.02% | 10.0 mg | 0.02% | 3.0 g | 0.02% |
| Monothioglycerol | 5.0 mg | 0.50% | 5.0 mg | 0.50% | 250.0 mg | 0.50% | 75.0 g | 0.50% |
| Sodium hydroxide | | | | | | | | |
| Water (Q. S.) | 1 mL | | 1 mL | | 50 mL | | 15,900.0 g[(3)] | |

[(1)] Monobasic sodium phosphate dihydrate
[(2)] Dibasic sodium phosphate dihydrate
[(3)] Equivalent to 15 Liter

| Analysis | Release (Time zero) limits | Stability acceptance limits | Time (months) 0 | Time (months) 3 | Time (months) 6 |
|---|---|---|---|---|---|
| Appearance & pH | | | | | |
| Appearance of Solution | Clear colorless to yellowish solution in a 2.25 mL glass syringe with grey stopper | Clear colorless to yellowish solution in a 2.25 mL glass syringe with grey stopper | Clear colorless to yellowish solution in a 2.25 mL glass syringe with grey stopper | Clear colorless to yellowish solution in a 2.25 mL glass syringe with grey stopper | Clear colorless to yellowish solution in a 2.25 mL glass syringe with grey stopper |
| pH | 7.5-8.5 | 7.5-8.5 | 8.0 | 8.0 | 8.0 |
| Assay & Impurities | | | | | |
| Assay of Hydrocortisone Sodium Phosphate | 127.5-140.9 (mg/mL) | 120.8-147.6 (mg/mL) | 137.2 | 139.0 | 136.6 |
| Assay of Hydrocortisone Equivalent | 95-105% of label claim | 90-110% of label claim | 102.2 | 103.6 | 101.8 |
| Specified Impurity, % | | | | | |
| Hydrocortisone | ≤0.5% | ≤2.0% | <0.05% | <0.05% | 0.05% |
| RRT 0.91 | ≤0.1% | ≤0.5% | <0.05% | <0.05% | <0.05% |
| Single Unspecified Impurity, % | | | | | |
| RRT 0.23 | ≤0.1% | ≤0.2% | — | 0.05% | 0.07% |
| RRT 1.03 | ≤0.1% | ≤0.2% | 0.05% | <0.05% | <0.05% |
| RRT 1.16 | ≤0.1% | <0.2% | — | — | 0.05% |
| Sum of Impurities, % | ≤1.0% | ≤3.0% | 0.05% | 0.05% | 0.16% |
| Sub-Visible Particles | | | | | |
| ≥10 μm | ≤6000 part. Per container | ≤6000 part. Per container | 433 | 95 | 200 |
| ≥25 μm | ≤600 part. Per container | ≤600 part. Per container | 4 | 1 | 2 |
| Uniformity of dosage | | | | | |
| Volume in container | 1.0-1.2 mL Individual delivered volume (mL): To be reported | 1.0-1.2 mL Individual delivered volume (mL): To be reported | Complies, 1.) 1.5 2.) 1.05 3.) 1.05 4.) 1.05 5.) 1.05 | Complies, 1.) 1.06 2.) 1.06 3.) 1.05 4.) 1.07 5.) 1.06 | To be added |
| Uniformity of dosage units | Acceptance value (AV) for 10 dosage units ≤ 15.0, if AV > 15.0, test the next 20 dosage units, AV for 30 dosage units ≤ 15.0, No individual content of any dosage unit is less than [0.75 M] or more than | Acceptance value (AV) for 10 dosage units ≤ 15.0, if AV > 15.0, test the next 20 dosage units, AV for 30 dosage units ≤ 15.0, No individual content of any dosage unit is less than [0.75 M] or moret han | Complies after first step, Acceptance value = 2.0, Average Volume = 1.05 mL | Complies after first step, Acceptance value = 3.1, Average Volume = 1.05 mL | To be added |

-continued

| Analysis | Release (Time zero) limits | Stability acceptance limits | Time (months) 0 | Time (months) 3 | Time (months) 6 |
|---|---|---|---|---|---|
| | [1.25 M], Average volume: To be reported. | [1.25 M], Average volume: To be reported. Microbiological tests | | | |
| Sterility | Sterile | Sterile | Sterile | Not tested | Not tested |
| Bacterial Endotoxins | ≤1.25 EU/mg hydrocortisone | ≤1.25 EU/mg hydrocortisone | ≤1.25 EU/mg hydrocortisone | Not tested | Not tested |

Example 6

One unknown impurity peak (RRT·0.91) in hydrocortisone phosphate product was purified via preparative HPLC and characterized by LCMS, HPLC and NMR. Its structure was tentatively proposed as phosphate migration isomer of hydrocortisone phosphate.

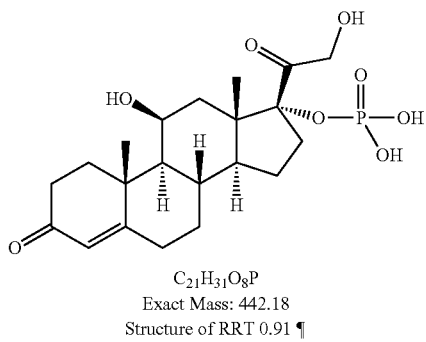

$C_{21}H_{31}O_8P$
Exact Mass: 442.18
Structure of RRT 0.91 ¶

Example 7: Formulation of the Disclosure

| Ingredients | Function | Amount (%) | Amount per 1 mL |
|---|---|---|---|
| Hydrocortisone sodium phosphate | Active ingredient | 13.42% w/v | 134.2 mg* |
| Monobasic sodium phosphate anhydrous | Buffer agent | 0.1% w/v | 1.0 mg |
| Dibasic sodium phosphate anhydrous | Buffer agent | 1.09% w/v | 10.9 mg |
| Disodium EDTA, dihydrate | Chelating agent | 0.02% w/v | 0.20 mg |
| Monothioglycerol | Antioxidant | 0.50%-2.5% w/v | 5.0-25 mg |
| Sodium hydroxide/HCl | pH adjuster | Q.S pH (approx. 8.0) | Q.S pH (approx. 8.0) |
| Water | Solvent | Q.S to 100% | Q.S to 1 mL |

*100 mg hydrocortisone equivalent

Without wishing to be bound by any particular theory, it is believed that the concentration of monothioglycerol decrease over the shelf life of formulation. In some embodiments, the levels of monothioglycerol drops to about 60% of the original level in about 6 months at room temperature. Although not wishing to be limited by theory, it is anticipated that, over the course of storage (e.g., without limitation, after 12 or 18 months), the level of monothioglycerol may, in some embodiments, fall to ~0%. Without wishing to be bound by any particular theory, it is believed that a decrease in monothioglycerol levels may lead to an increase in hydrocortisone (HCT) related impurities. Monothioglycerol is an antioxidant and thus, without wishing to be bound by any particular theory, it is believed that as long as there is some amount of monothioglycerol left in the formulation, it is going to protect HCT from getting oxidized. Therefore, in some embodiments, the initial formulation (before storage) is formulated to comprise greater than 0.5% w/v monothioglycerol.

In one embodiment, the formulation of Example 7 has improved stability compared to formulations wherein monothioglycerol is replaced with Rongalite, creatinine, or a combination thereof. In one embodiment, the formulation of Example 7 demonstrates about 60% less degradation after 6 months at 40° C. than formulations comprising Rongalite. In one embodiment, the formulation of Example 7 is expected to have shelf life of about 24 months.

Example 8: Impurity Specifications

The table below provides the organic impurity specifications for a hydrocortisone sodium phosphate formulation disclosed herein. Without wishing to be bound by any particular theory, it is believed that the impurities should stay below this level over the course of storage (either at room temperature or elevated temperature). In some embodiments, the impurities should stay below this level for up to 24 months of storage.

| Impurity | Level |
|---|---|
| Hydrocortisone | ≤2.0% |
| Individual specified | ≤0.5% |
| Individual unspecified | ≤0.2% |
| Total Impurity | ≤3.0% |

Example 9: Pharmacokinetic Data

Pharmacokinetic (PK) data of a formulation of Example 7 demonstrates that the formulation disclosed herein is biocomparable to a hydrocortisone reference listed drug (Solu-Cortef). Solu-Cortef is a powder formulation lacking an antioxidant while comprising hydrocortisone sodium succinate, anhydrous monobasic sodium phosphate, and dried dibasic sodium phosphate, which is reconstituted in sterile water. The formulation disclosed herein achieved a higher area under the curve (AUC), and the maximum (or peak) serum concentration that achieved by hydrocortisone after administration ($C_{max}$) occurred sooner.

Without wishing to be bound by any particular theory, and given that, in some embodiments, hydrocortisone is administered for the treatment of an acute event, these results demonstrate that the instant formulation is better at treating such an event, particularly since the data shows that a patient would be nowhere near to receiving the maximal therapeutic dose or an "unsafe" concentration. Specifically, the formulation disclosed herein provides a higher dose of hydrocortisone to the patient in the acute setting. This additional amount of hydrocortisone, as compared with the reference listed drug, may provide additional hydrocortisone that could help during an acute event and may aid the patient in avoiding an adrenal crisis. In one embodiment, the disclosed formulations will be used in an emergency-use/rescue auto-injector device for the treatment of AAI (Acute Adrenal Insufficiency) in subjects with primary or secondary adrenal insufficiency. This therapy is indicated when oral therapy is not feasible for use including the management of PAI (Primary Adrenal Insufficiency) or SAI (Secondary Adrenal Insufficiency), congenital adrenal hyperplasia.

Therefore, while 90% CI for the ratio of a formulation disclosed herein (ATRS-2001) and Reference (Solu-Cortef) for $AUC_{0-tlast}$ and $AUC_{0-inf}$ was higher than the FDA accepted limits of 80-125%, the disclosed formulation could be beneficial for administration to subjects suffering an acute event. The point estimates of $C_{max}$ fell within the criteria (80-125) while the upper limits were outside of the range, demonstrating that the disclosed formulation could be preferable for treating acute events/conditions, such as acute adrenal insufficiency.

$AUC_{0-tlast}$

| 90% Confidence Interval of Geometric Mean Ratio (T/R) | | | |
|---|---|---|---|
| | Lower Limit | Point Estimate | Upper Limit |
| | $AuC_{0-tlast}$ | | |
| 90% CI for Ratio | 1.224252 | 1.282081 | 1.342641 |
| | $AUC_{0-inf}$ | | |
| 90% CI for Ratio | 1.225703 | 1.286723 | 1.35078 |
| | $C_{max}$ | | |
| 90% CI for Ratio | 1.090687 | 1.158084 | 1.229646 |

Graphical PK Results

Figure 12:
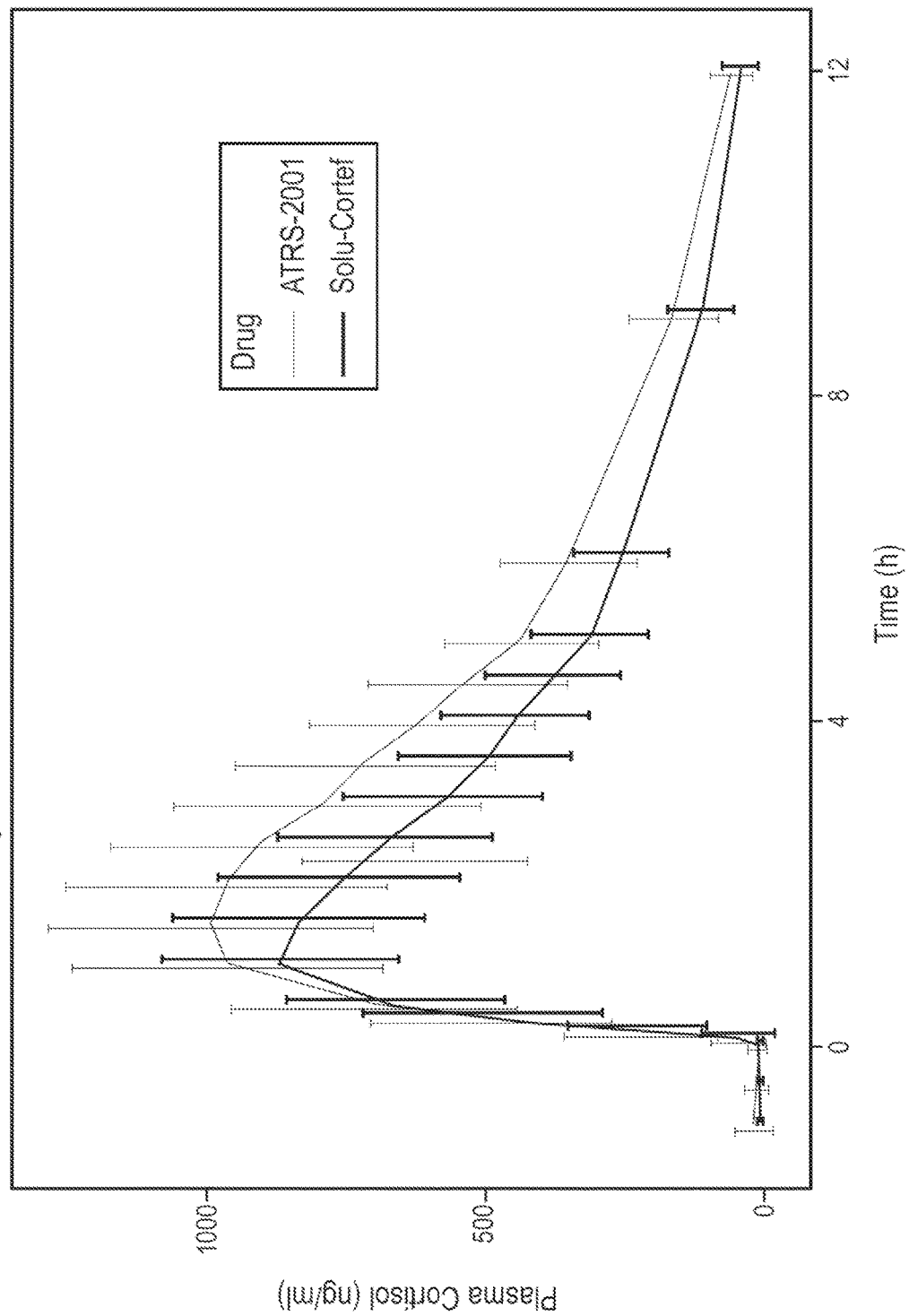
FIGS. 12 and 13 depict cortisol plasma concentration curves for a formulation disclosed herein (ATRS-2001) and Solu-Cortef.
Figure 13:
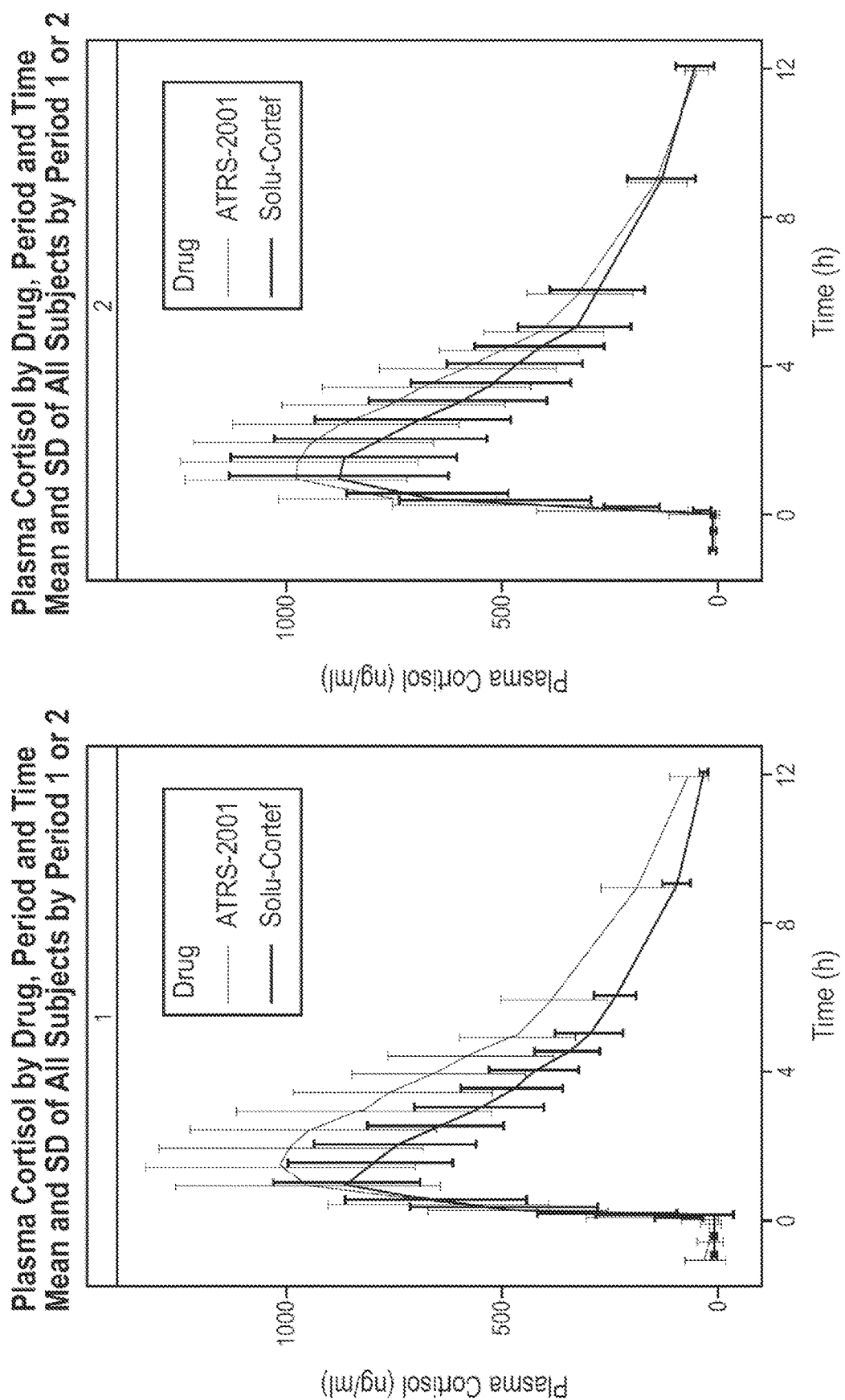

The cortisol plasma concentration curves for the formulation disclosed herein and Solu-Cortef are similar but there are consistently higher plasma levels of cortisol for the formulation disclosed herein both on average and for both periods (FIGS. 12 and 13).

PK Analysis

Pharmacokinetic parameters for each subject and period were estimated to include $C_{max}$, $T_{max}$, $T_{1/2}$, Vp, Vss, CL, $AUC_{0-inf}$, $AUC_{0-tlast}$, $\lambda_z$, and other standard NCA parameters in the R package "Ubiquity" and "PKNCA" which have been validated against WinNonLin. Summaries will be appended to the report.

The parameters of $C_{max}$, $AUC_{0-inf}$, $AUC_{0-tlast}$, and $T_{max}$ were analyzed in the R package "BE" which uses the SAS PROC GLM method of least squares to fit general linear models.

AUClast

Figure 14:
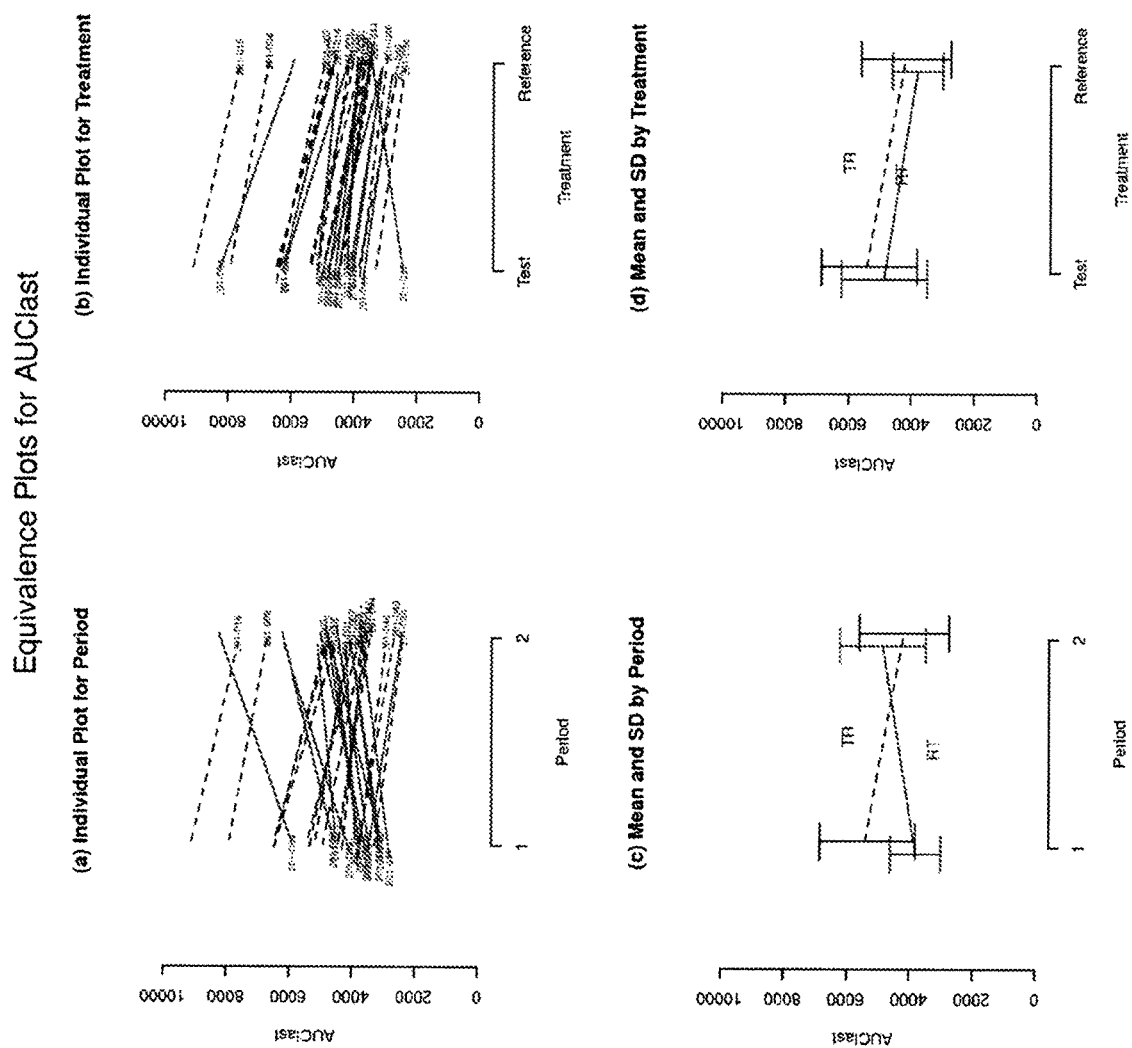
FIG. 14 provides equivalence plots for $AUC_{last}$.
Figure 15:
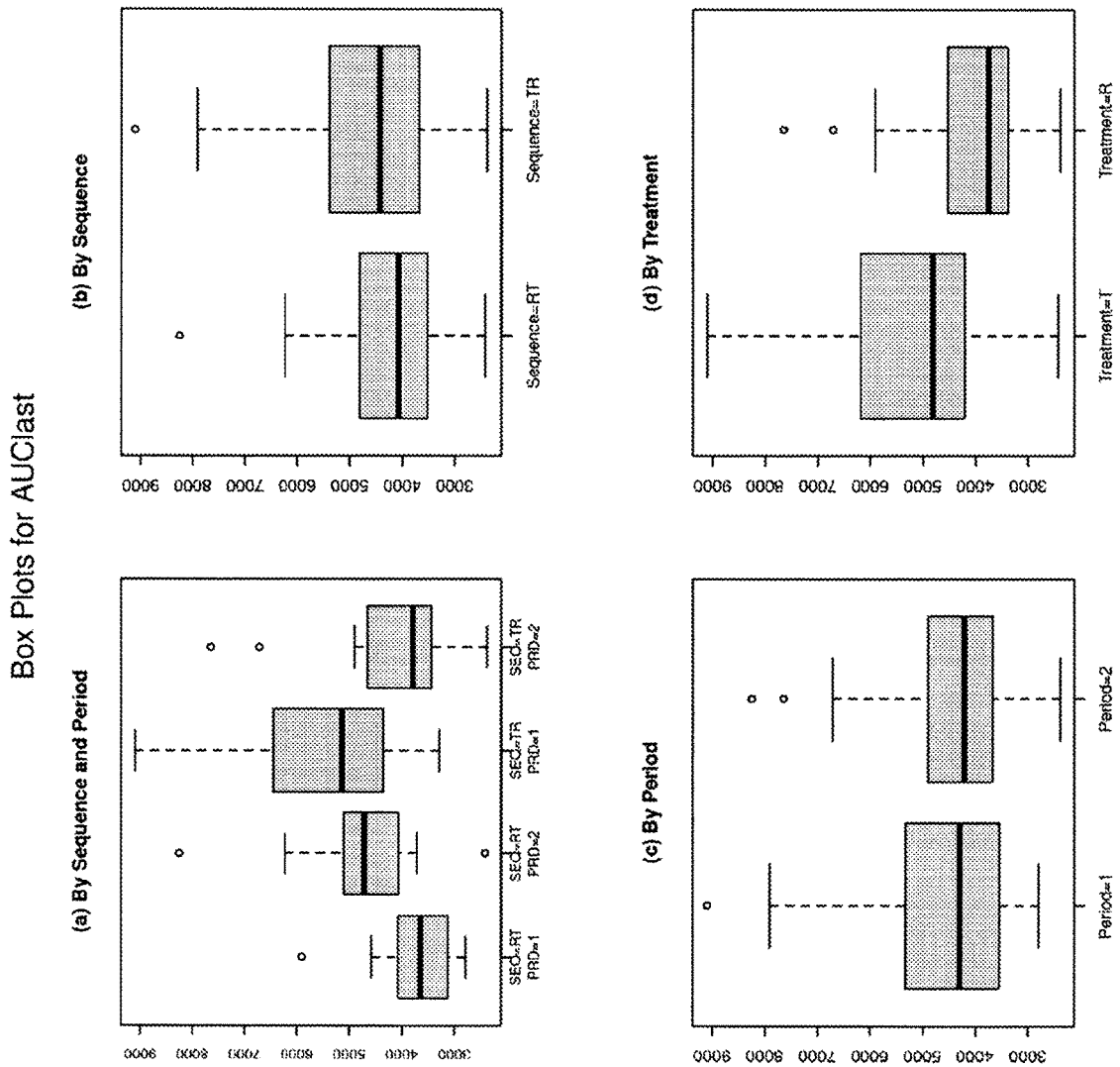
FIG. 15 provides box plots for $AUC_{last}$.

FIGS. 14 and 15 provide equivalence plots and box plots for $AUC_{last}$, respectively.

| $'Analysis of Variance (log scale)' | | | | | |
|---|---|---|---|---|---|
| | Sum of Sq | Df | Mean Sq | F value | p(>F) |
| SUBJECT | 3.8683 | 28 | 0.13816 | 12.9918 | 0.00000 |
| GROUP | 0.1078 | 1 | 0.10779 | 0.7739 | 0.38677 |
| SUBJECT(GROUP) | 3.7606 | 27 | 0.13928 | 13.0976 | 0.00000 |
| PERIOD | 0.0063 | 1 | 0.00626 | 0.5883 | 0.44971 |
| DRUG | 0.8942 | 1 | 0.89423 | 84.0918 | 0.00000 |
| ERROR | 0.2871 | 27 | 0.01063 | | |
| TOTAL | 5.0622 | 57 | | | |

| $'Between Subject Within Subject Variability' | | |
|---|---|---|
| | Between Subject | Within Subject |
| Variance Estimate | 0.06432289 | 0.010634 |
| Coefficient of Variation, CV(%) | 25.77531411 | 10.339603 |

| $'Least Square Means (geometric mean)' | | |
|---|---|---|
| | Reference Drug | Test Drug |
| Geometric Means | 3853.737 | 4940.804 |

| '$90% Confidence Interval of Geometric Mean Ratio (T/R)' | | |
|---|---|---|
| | Lower Limit | Point Estimate | Upper Limit |
| 90% CI for Ratio | 1.224252 | 1.282081 | 1.342641 |

| $'Sample Size' | | |
|---|---|---|
| | True Ratio = 1 True | Ratio = Point Estimate |
| 80% Power Sample Size | 3 | Inf |

AUCinf

Figure 16:
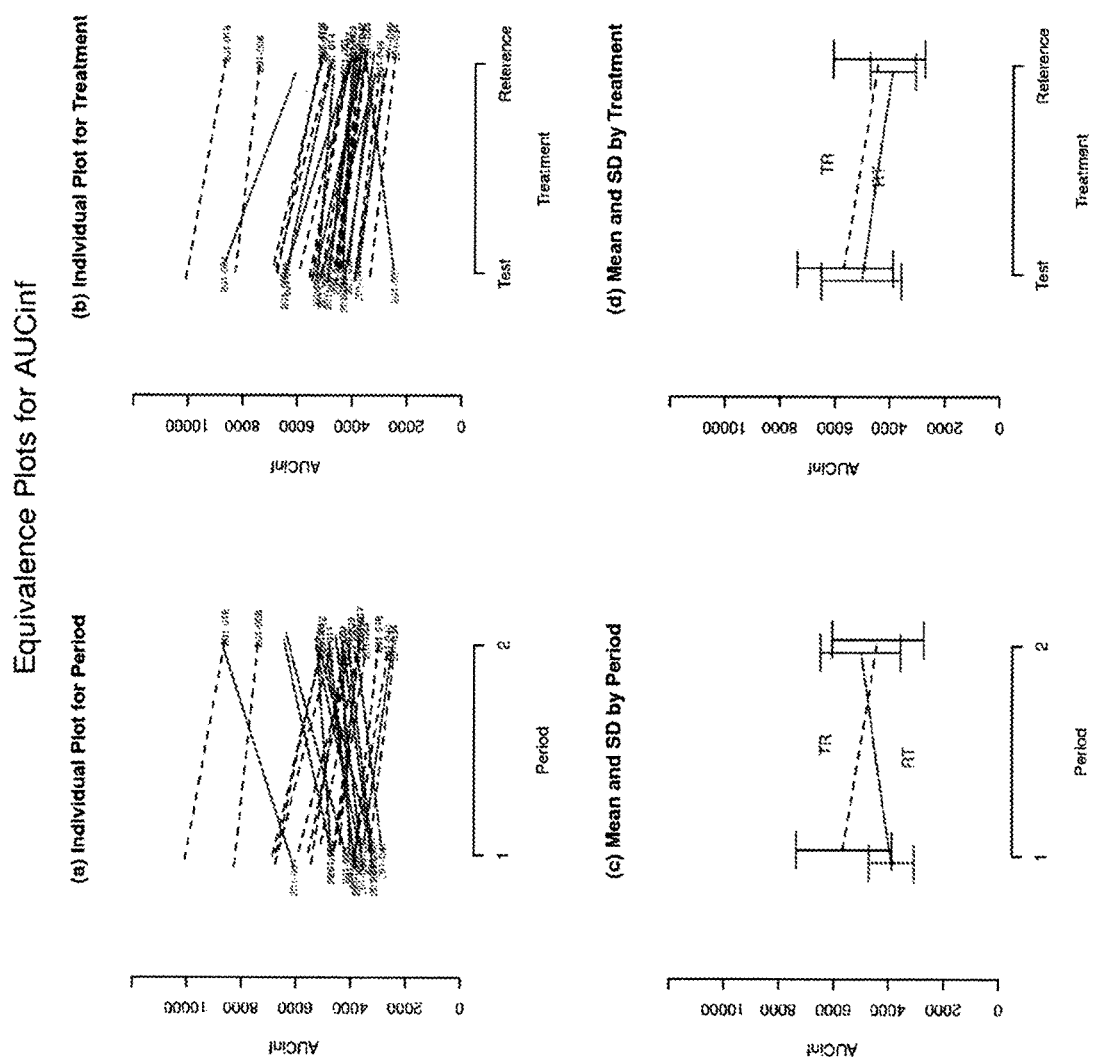
FIG. 16 provides equivalence plots for $AUC_{inf}$.
Figure 17:
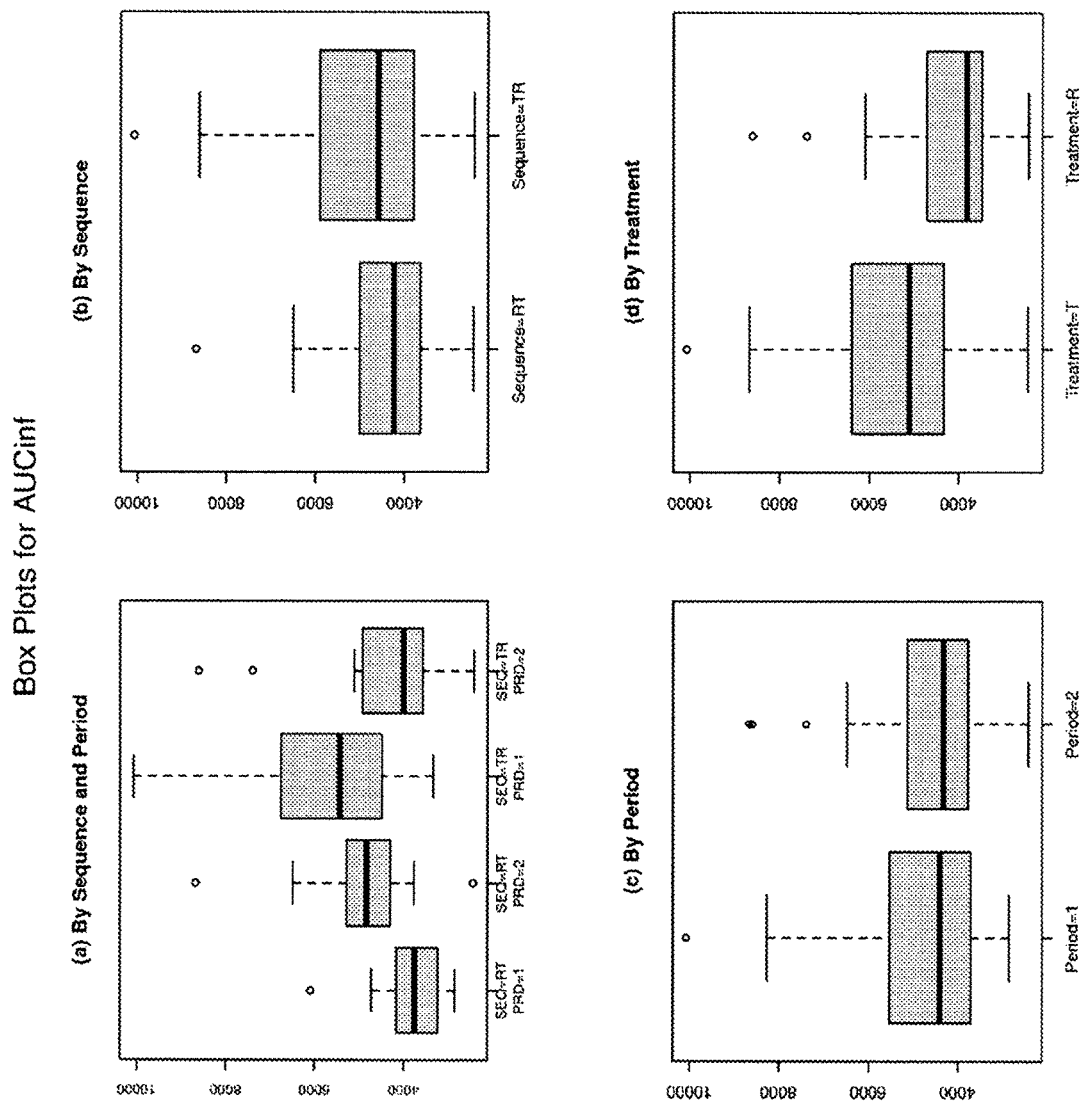
FIG. 17 provides box plots for $AUC_{inf}$.

FIGS. 16 and 17 provide equivalence plots and box plots for $AUC_{inf}$, respectively.

| $'Analysis of Variance (log scale)' | | | | | |
|---|---|---|---|---|---|
| | Sum of Sq | Df | Mean Sq | F value | p(>F) |
| SUBJECT | 4.3446 | 28 | 0.15516 | 13.1685 | 0.00000 |
| GROUP | 0.1446 | 1 | 0.14458 | 0.9294 | 0.34357 |
| SUBJECT(GROUP) | 4.2000 | 27 | 0.15556 | 13.2018 | 0.00000 |
| PERIOD | 0.0049 | 1 | 0.00485 | 0.4117 | 0.52649 |
| DRUG | 0.9204 | 1 | 0.92043 | 78.1154 | 0.00000 |
| ERROR | 0.3181 | 27 | 0.01178 | | |
| TOTAL | 5.5937 | 57 | | | |

| $'Between and Within Subject Variability' | | |
|---|---|---|
| | Between Subject | Within Subject |
| Variance Estimate | 0.07188676 | 0.01178299 |
| Coefficient of Variation, CV(%) | 27.30085196 | 10.88700194 |

| $'Least Square Means (geometric mean)' | | |
|---|---|---|
| | Reference Drug | Test Drug |
| Geometric Means | 3992.025 | 5136.63 |

| $'90% Confidence Interval of Geometric Mean Ratio (T/R)' | | | |
|---|---|---|---|
| | Lower Limit | Point Estimate | Upper Limit |
| 90% CI for Ratio | 1.225703 | 1.286723 | 1.35078 |

| $'Sample Size' | | |
|---|---|---|
| | True Ratio = 1 | True Ratio = Point Estimate |
| 80% Power Sample Size | 4 | Inf |

Cmax

Figure 18:
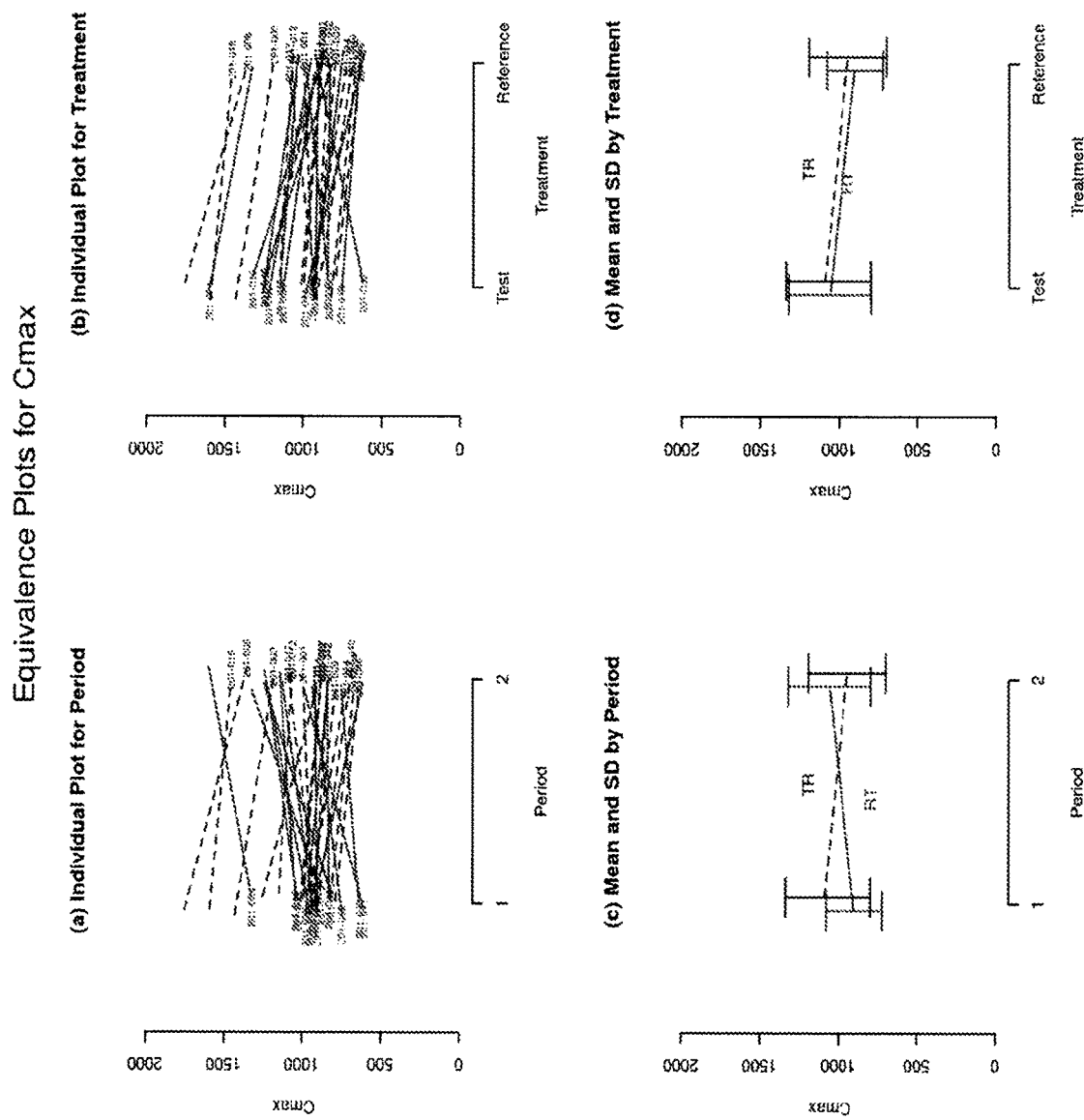
FIG. 18 provides equivalence plots for $C_{max}$.
Figure 19:
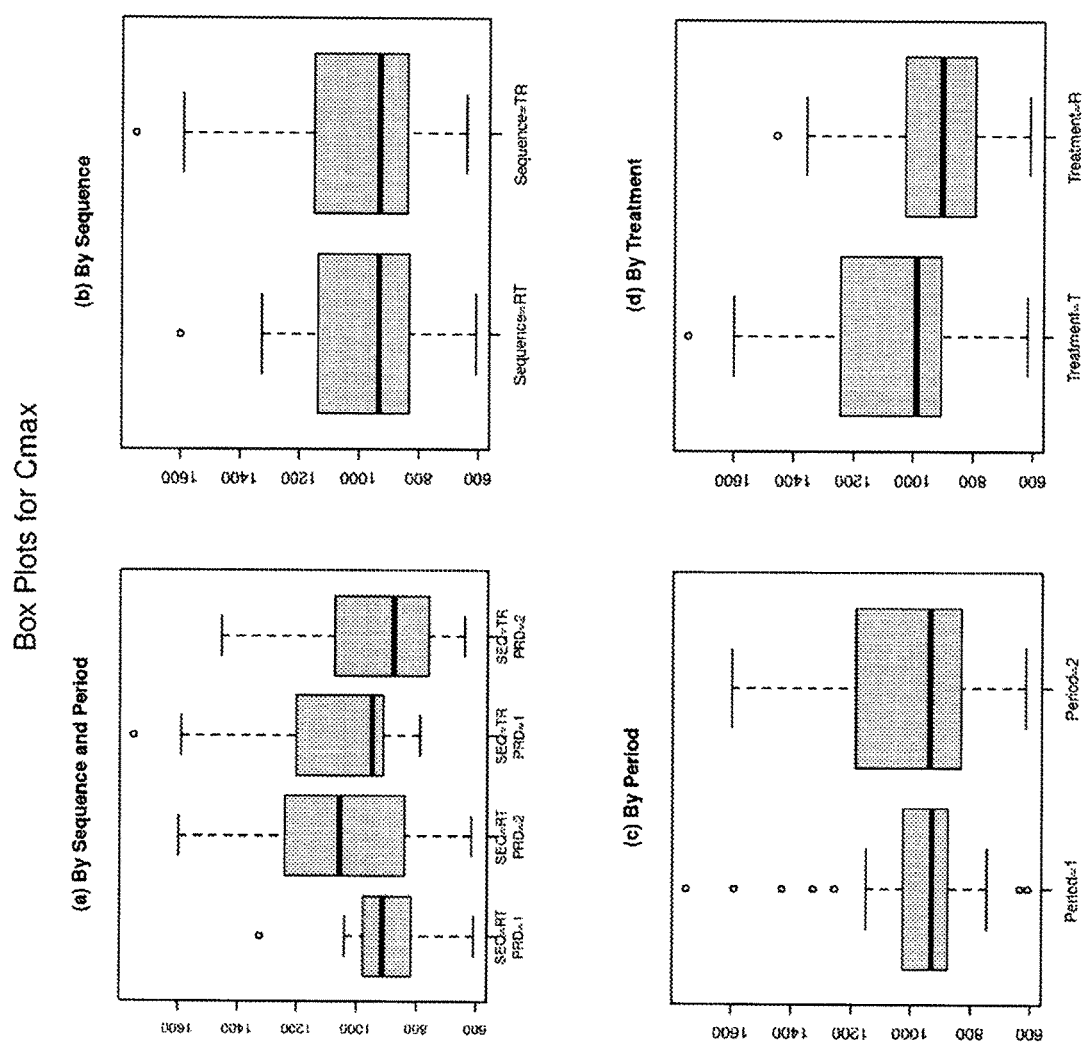
FIG. 19 provides box plots for $C_{max}$.

FIGS. 18 and 19 provide equivalence plots and box plots for $C_{max}$, respectively.

| $'Analysis of Variance (log scale)' | | | | | |
|---|---|---|---|---|---|
| | Sum of Sq | Df | Mean Sq | F value | p(>F) |
| SUBJECT | 2.6095 | 28 | 0.093197 | 5.1929 | 0.00003 |
| GROUP | 0.0157 | 1 | 0.015673 | 0.1631 | 0.68946 |
| SUBJECT (GROUP) | 2.5938 | 27 | 0.096068 | 5.3529 | 0.00002 |
| PERIOD | 0.0002 | 1 | 0.000174 | 0.0097 | 0.92222 |
| DRUG | 0.3120 | 1 | 0.311967 | 17.3828 | 0.00028 |
| ERROR | 0.4846 | 27 | 0.017947 | | |
| TOTAL | 3.4061 | 57 | | | |

| $'Between and Within Subject Variability' | | |
|---|---|---|
| | Between Subject | Within Subject |
| Variance Estimate | 0.03906065 | 0.01794683 |
| Coefficient of Variation, CV(%) | 19.95834372 | 13.45691087 |

-continued

| $'Least Square Means (geometric mean)' | | |
|---|---|---|
| | Reference Drug | Test Drug |
| Geometric Means | 899.802 | 1042.046 |

| $'90% Confidence Interval of Geometric Mean Ratio (T/R)' | | | |
|---|---|---|---|
| | Lower Limit | Point Estimate | Upper Limit |
| 90% CI for Ratio | 1.090687 | 1.158084 | 1.229646 |

| $'Sample Size' | | |
|---|---|---|
| | True Ratio = 1 True | Ratio = Point Estimate |
| 80% Power Sample Size | 4 | Inf |

Tmax

Figure 20:
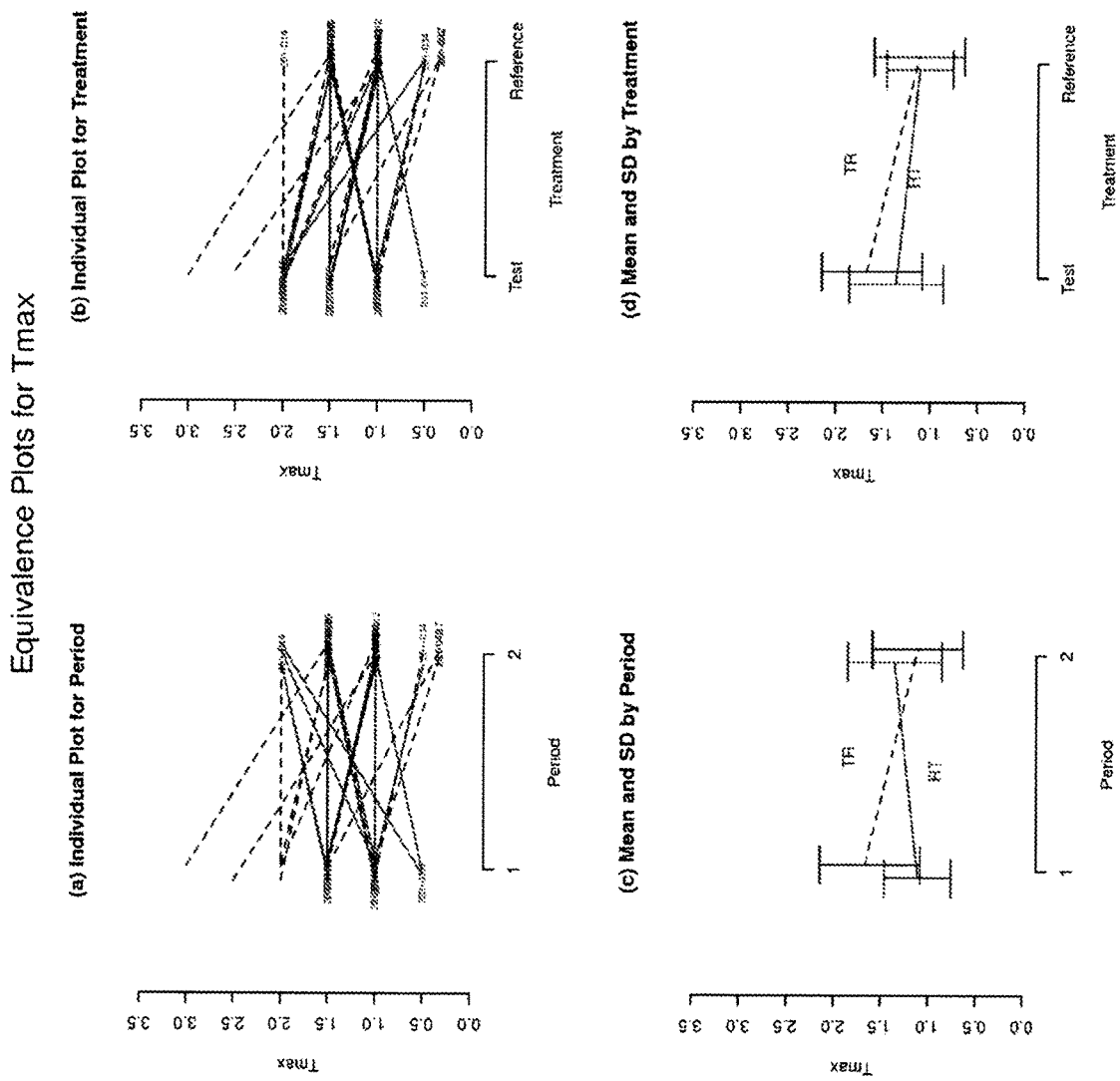
FIG. 20 provides equivalence plots for $T_{max}$.
Figure 21:
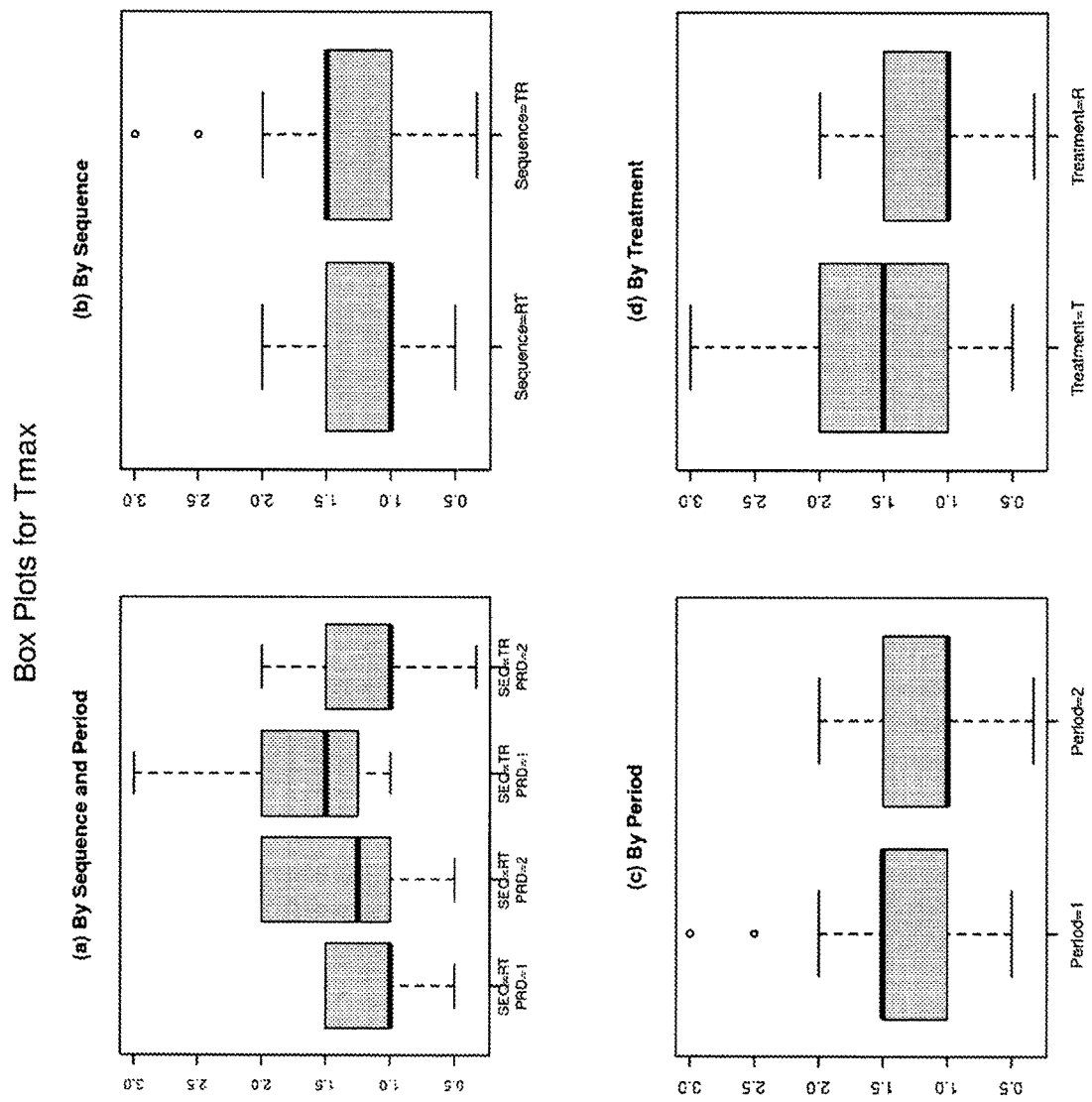
FIG. 21 provides box plots for $T_{max}$.

FIGS. 20 and 21 provide equivalence plots and box plots for $T_{max}$, respectively.

| $'Wilcoxon Signed-Rank Test' p-value |
|---|
| 1.174593e−05 |

| $'Hodges-Lehmann Estimate' | | | |
|---|---|---|---|
| | Lower Limit | Point Estimate | Upper Limit |
| 90% Confidence Interval | 0.2500 | 0.5000 | 0.5000 |
| 90% Confidence Interval(%) | 122.5407 | 145.0814 | 145.0814 |

Example 10: A Phase 1, Randomized, Two-Period, Single-Dose Crossover Study to Compare Pharmacokinetics and Safety of ATRS-1902 to Solu-Cortef Background Patients with adrenal insufficiency (AI) are at risk for acute AI (AAI) and adrenal crisis (AC). Patients with AI may experience stressful situations (eg, illness with fever, vomiting, surgical procedures) that increase physiologic demand for cortisol. When this occurs, The Endocrine Society recommends increasing the oral hydrocortisone (HCT) dose or injecting 100 mg of IM HCT when oral therapy is not feasible. Extra HCT is essential to avoid progression to severe AAI or AC. A prefilled HCT autoinjector (ATRS-1902) has been developed to provide IM HCT without reconstitution. This trial was conducted to assess the PK and the relative bioavailability and bioequivalence of ATRS-1902 compared to Solu-Cortef.

Methods

In this phase 1, randomized, open-label trial, healthy human adults received a single dose of ATRS-1902 (100 mg IM HCT sodium phosphate via prefilled syringe) and Solu-Cortef (100 mg IM HCT sodium succinate via needle and syringe). Patients were randomized 1:1 to one of two treatment sequences (ATRS-1902 or Solu-Cortef), where the first treatment was given in Period 1 and the second treatment was given after crossover to Period 2. Prior to dosing, patients underwent a dexamethasone suppression test for adrenocortical suppression. Dosing between treatment periods was separated by an approximately 5-day washout period. Patients were evaluated for TEAEs as well as PK parameters including $AUC_{0-inf}$, $AUC_{0-t}$, residual area, $C_{max}$, $K_{el}$, $T_{1/2\ el}$, and $T_{max}$.

Results

Figure 29:
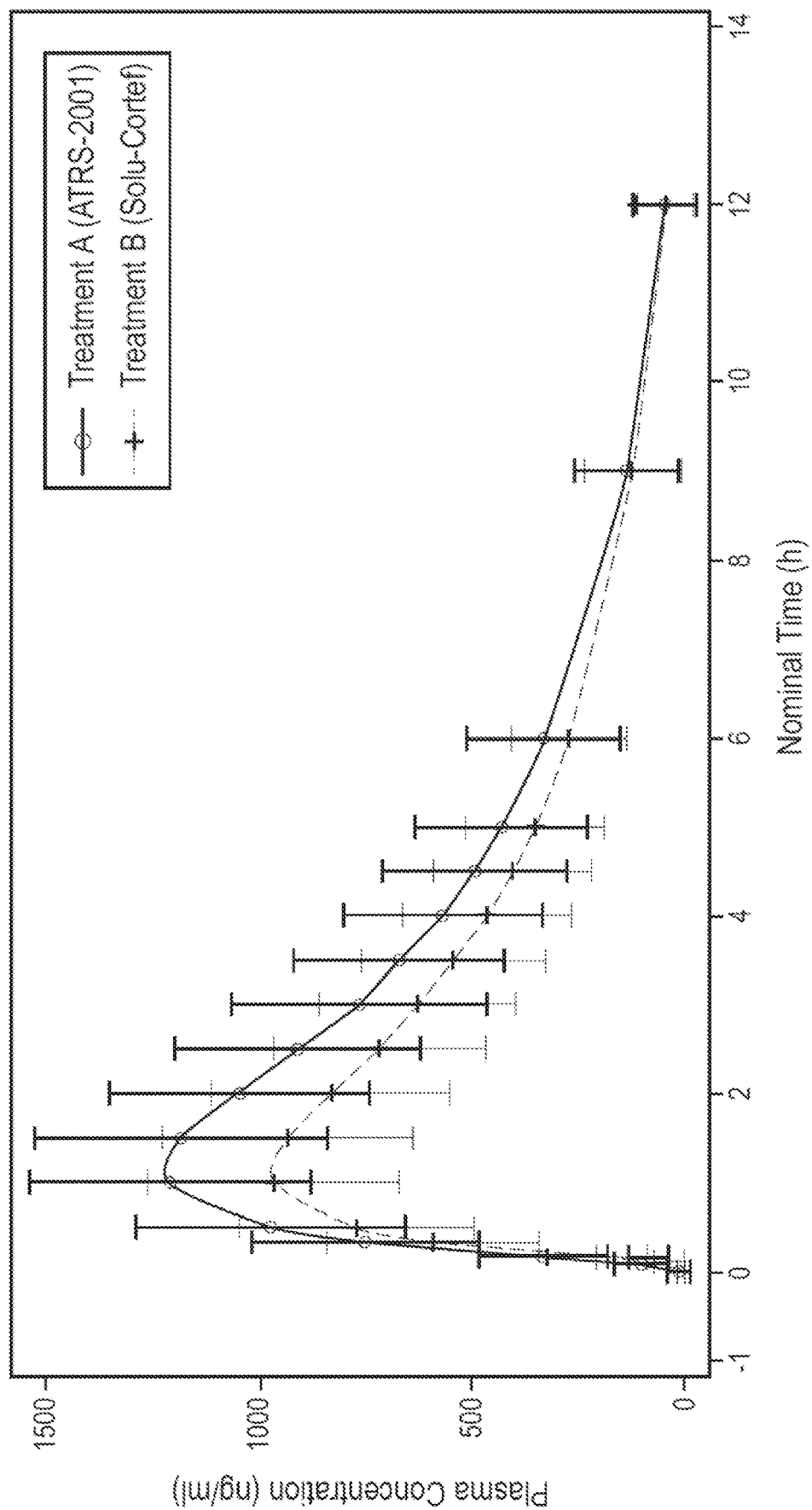
FIG. 29 is a chart of mean (±SD) baseline-corrected cortisol plasma concentrations (linear scale) of ATRS-1902 compared to Solu-Cortef.

Fifty-six patients received at least 1 dose of ATRS-1902 and Solu-Cortef. Patients were median (range) age 40 (18-59) y, and 50% (28/56) were female. For patients receiving ATRS-1902 and Solu-Cortef, mean $AUC_{0-inf}$ was 5539.62 and 4530.69 h*ng/mL, respectively, and mean $AUC_{0-t}$ was 5320.05 and 4329.14 h*ng/mL, respectively. Mean $C_{max}$ was 1249.22 and 1006.64 ng/mL for patients receiving ATRS-1902 and Solu-Cortef, respectively. For patients receiving ATRS-1902 and Solu-Cortef, the median (range) $T_{max}$ was 1.0 (0.0-2.5) and 1.0 (0.5-2.5) h, respectively, and the mean $T_{1/2\ el}$ was 1.98 and 2.18 h, respectively. The mean residual area values were 2.79% and 3.14% for ATRS-1902 and Solu-Cortef, respectively. These results are summarized in a chart of the percent compared to the reference listed drug (FIG. 29). Overall, the most commonly reported TEAEs for patients receiving ATRS-1902 and Solu-Cortef, respectively, were headache (4 vs 3 patients), muscle spasms (2 vs 0 patients), and nausea (0 vs 2 patients). No deaths or serious AEs were reported.

CONCLUSIONS

In this trial, ATRS-1902 exhibited a slightly higher exposure compared to Solu-Cortef. ATRS-1902 and Solu-Cortef demonstrated similar safety profiles, and all AEs were consistent with HCT therapy. Overall, ATRS-1902 produced acceptable safety and PK properties. ATRS-1902 provides simple administration of HCT in important clinical situations. ATRS-1902 provides an increase in exposure of HCT as compared with the reference listed drug (Solu-Cortef), in times where patients are likely to need further doses of HCT to avoid adrenal crisis and hospitalization. Therefore, ATRS-1902 may offer the unexpected benefit of additional and necessary cortisol during critical stress situations (as compared with the reference listed drug).

Example 11: Hydrocortisone Sodium Phosphate Injection

Components of the Drug Product, Hydrocortisone Sodium Phosphate Injection

Hydrocortisone Sodium Phosphate Injection is available in a drug/device combination product, as a ready to use prefilled syringe (PFS) for administration with a pressure-assisted autoinjector (AI) device for intramuscular administration. The PFS contains a sterile clear colorless to yellow solution in a single 1.0 mL dose to yield a final delivered dose equivalent to 100 mg of hydrocortisone.

The final drug/device presentation includes a PFS filled with 1.0 mL hydrocortisone sodium phosphate at a concentration of 134.2 mg/mL (equivalent to 100 mg of hydrocortisone) in a buffered aqueous solution containing disodium edetate dihydrate as a chelating agent and monothioglycerol as an antioxidant. The single use AI delivers the labeled dose contained in the PFS. The PFS is composed of a USP Type I clear glass syringe barrel with a fixed stainless-steel needle, a needle shield, and a plunger stopper.

Drug Substance, Hydrocortisone Sodium Phosphate

The Drug Substance (DS) Hydrocortisone Sodium Phosphate (HSP) is a sodium salt of phosphate ester of hydrocortisone. The high-water solubility of HSP enables the development of aqueous injectable solutions. The DS meets the requirements of USP monograph, "Hydrocortisone sodium phosphate, USP," except for loss on drying (LOD) specification, instead the Karl Fischer method is used to test water content which meets the British Pharmacopoeia specification. This is because the crystalline form obtained through the manufacturing process is a crystalline hydrate. To meet the USP LOD specification of NMT 5%, the manufacturing process would need to involve a lyophilization step which leads to the formation of an amorphous form of HSP. As such, amorphous hydrocortisone sodium phosphate drug substance is highly hygroscopic as demonstrated by data presented in Table 47.

TABLE 47

Room temperature stability of crystalline as compared to amorphous drug substance

| Test | Time 0 | Time 3 mo. | Time 6 mo. |
|---|---|---|---|
| Crystalline Hydrocortisone Sodium Phosphate | | | |
| Total Impurities | 0.00% | 0.06% | 0.00% |
| Assay | 100.9% | 101.4% | 99.5% |
| Amorphous Hydrocortisone Sodium Phosphate | | | |
| Total Impurities | 0.20% | 1.1% | 1.5% |
| Assay | 97.8% | 99.0% | 96.5% |

Hydrocortisone Sodium Phosphate (HSP) Injection is supplied as an Autoinjector (AI) that contains a single use prefilled syringe with 1 mL sterile, non-pyrogenic, clear colorless to yellow solution of HSP at a concentration of 134.2 mg/mL to yield a delivered dose equivalent to 100 mg of hydrocortisone through intramuscular injection.

Drug Product

Formulation Development

Hydrocortisone Sodium Phosphate (HSP) is sodium salt of phosphate ester of hydrocortisone. Its molecular formula is $C_{21}H_{29}Na_2O_8P$ and its molecular weight is 486.4 g/mol. Formulation development of HSP is based on the prior knowledge of two injectable formulations previously approved by the FDA, namely, Hydrocortone® (approved in 1960) and Solu-Cortef®.

Hydrocortisone sodium phosphate injectable drug, including Merck's Hydrocortone®, are no longer available in the US. Pharmacia and Upjohn's hydrocortisone sodium succinate for injection (Solu-Cortef, NDA 009866) is the only other hydrocortisone injection product currently approved for use in the US. The active ingredient in this formulation is the sodium succinate ester of the hydrocortisone. Because of its poor aqueous stability, the formulation is a lyophilized powder for injection. The formulation composition of the four available Solu-Cortef presentations is in Table 48.

TABLE 48

Formulation composition of Solu-Cortef®

| Ingredient | 100 mg Each 2 mL contains when mixed | 250 mg Each 2 mL contains when mixed | 500 mg Each 4 mL contains when mixed | 1000 mg Each 8 mL contains when mixed |
|---|---|---|---|---|
| Hydrocortisone sodium succinate | Eq. to 100 mg base | Eq. to 250 mg base | Eq. to 500 mg base | Eq. to 1000 mg base |
| Monobasic sodium phosphate anhydrous | 0.8 mg | 2 mg | 4 mg | 8 mg |
| Dibasic sodium phosphate dried | 8.73 mg | 21.8 mg | 44 mg | 87.32 mg |

Solu-Cortef was use as the Reference Listed rug as it is currently the only other approved hydrocortisone ester product in the US which is listed as RLD and RS (Reference Standard).

Analysis of Solu-Cortef (Reference Listed Drug) One lot of Solu-Cortef, the RLD, was analyzed for pH, density, assay, and total withdrawal and deliverable volume. Five Solu-Cortef Act-O-Vials, 100 mg hydrocortisone in 2 mL, NDC: 00009-0825-01 were prepared as per the instructions in the package insert and analyzed for pH, density, and the assay. The density of the hydrocortisone drug solution was determined to be 1.02075 g/mL and the mean pH value of Solu-Cortef injection was observed to be 7.48. Each vial was analyzed for assay in duplicate and the results are provided in Table 49,

TABLE 49

Assay values of Solu-Cortef injection

| Sample Name | Practical Conc. (mg/mL) | Theoretical conc (mg/mL) | Percent assay | % Peak Area |
|---|---|---|---|---|
| Solu-Cortef 1/1 | 52.28 | 50.00 | 104.57 | 95.44 |
| Solu-Cortef 1/2 | 51.99 | 50.00 | 103.98 | 95.75 |
| Solu-Cortef 2/1 | 52.01 | 50.00 | 104.03 | 95.52 |
| Solu-Cortef 2/2 | 51.77 | 50.00 | 103.54 | 94.89 |
| Solu-Cortef 3/1 | 52.24 | 50.00 | 104.47 | 95.96 |
| Solu-Cortef 3/2 | 52.09 | 50.00 | 104.18 | 96.23 |
| Solu-Cortef 4/1 | 50.92 | 50.00 | 101.83 | 96.18 |
| Solu-Cortef 4/2 | 52.69 | 50.00 | 105.39 | 96.20 |
| Solu-Cortef 5/1 | 50.89 | 50.00 | 101.79 | 95.72 |
| Solu-Cortef 5/2 | 51.00 | 50.00 | 101.99 | 95.96 |
| Mean | 51.79 ± 0.63 | 50.00 | 103.58 ± 1.27 | 95.79 ± 0.42 |

The average drug concentration in the five vials was observed to be 51.79±0.63 mg/mL (on hydrocortisone basis). The label claim is 100 mg in 2 mL or 50 mg per mL of drug solution. Based on this, the mean % assay value was observed to be 103.583±0.27%. For the withdrawable and the deliverable volume, three vials were weighed and then reconstituted following the instructions in the package insert. The solution was then withdrawn using a 3 mL syringe with 18G*1½(1.2 mm*40 mm) needle (pre-weighed). The withdrawable weight was calculated by weight difference of the syringe with and without solution. The withdrawable volume was then calculated based on the density of the solution. The delivered volume was similarly calculated by measuring the weight of solution that is delivered from the syringe. The results of this study are presented in Table 50.

TABLE 50

Total withdrawable and deliverable volume from Solu-Cortef vials

| Procedure Step | Sample #1 (g) | Sample #2 (g) | Sample #3 (g) | Mean |
|---|---|---|---|---|
| Weight of vial + Product + Cap (As Is) | 16.4084 | 16.5683 | 16.4505 | 16.48 |
| Weight of syringe + needle (w/o shield) | 3.6251 | 3.6391 | 3.6122 | 3.63 |
| Weight of vial + product + cap (As is w/o small cap) # | 16.3764 | 16.5384 | 16.4206 | 16.45 |
| Weight of empty glass vial + stopper + cap | 18.9911 | 18.8598 | 19.0465 | 18.97 |
| Weight of syringe + needle + entire product | 5.7658 | 5.7794 | 5.6916 | 5.75 |
| Weight of syringe + needle + entire product w/o air bubble | 5.7489 | 5.7664 | 5.6662 | 5.73 |
| Weight of product in the syringe | 2.1238 | 2.1273 | 2.0540 | 2.10 |
| Withdrawable Volume (mL) | 2.08 | 2.08 | 2.01 | 2.05 |
| Weight of injected product in the autoclaved glass vial + stopper + cap | 2.0021 | 1.9903 | 1.9386 | 1.98 |
| Deliverable Volume (mL) | 1.96 | 1.94 | 1.90 | 1.93 |

The following Quality Target Product Profile (QTPP) (Table 51) was developed as a prospective summary of the decided quality, safety, and efficacy characteristics of the drug product and forms the basis for the development of the CQAs, CPPs, and control strategy.

TABLE 51

Quality target product profile of hydrocortisone sodium phosphate injection

| Quality Element | Target |
|---|---|
| Intended Use | For the treatment of primary or secondary adrenocortical insufficiency when oral therapy is not feasible |
| Route of Administration | Intramuscular Injection |
| Dosage Form | Sterile Solution |
| Dose | 100 mg hydrocortisone equivalent |
| Deliverable Volume | 1 mL |
| Primary Container Closure Configuration | 2.25 mL Glass syringe with a 25-G, 1-inch needle and a rubber plunger stopper |
| Secondary Container Closure Configuration | Pressure assisted spring powered, single use, disposable auto-injector device |
| Shelf-Life | 24 months or longer at Room Temperature storage. |
| Drug Product Quality Requirement | Meets pharmacopeial requirements for injectable dosage forms and product specific quality requirements |

Effect of pH on the Stability of HSP Under Accelerated Storage Conditions (40° C.)

Figure 22:
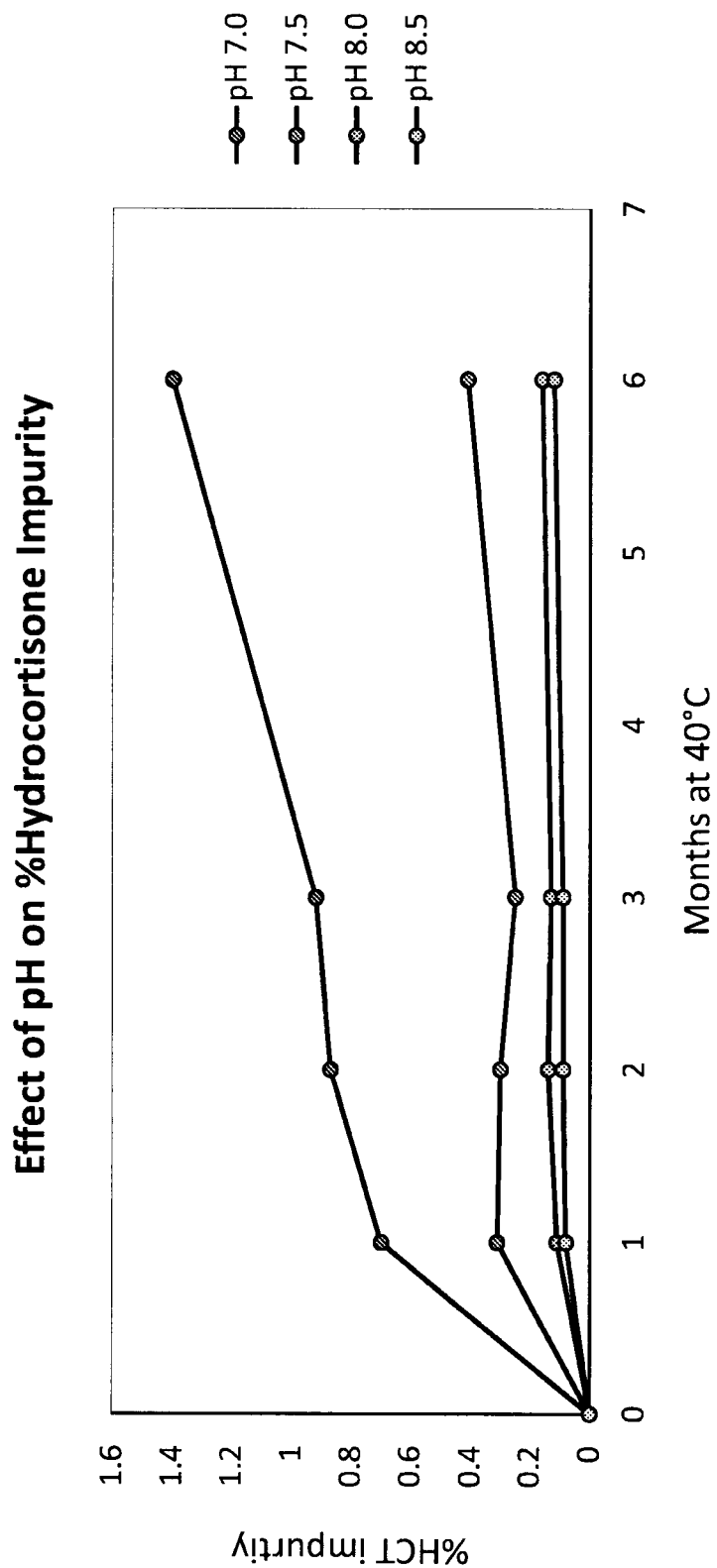
FIG. 22 is a chart demonstrating the effect of pH on the hydrocortisone impurity formation under accelerated storage conditions.

As shown in FIG. 22, the level of the main hydrolytic impurity i.e. hydrocortisone increases as the pH of the formulation decreases under accelerated storage condition of 40° C. HSP is prone to general acid-catalyzed hydrolysis at pH<7.5. pH is a Critical Quality Attribute (CQA) which needs to be controlled within pH 7.5 to 8.5.

Effect of Concentration and Solubilizers on Hydrocortisone Sodium Phosphate

The formation of hydrocortisone was primarily dependent on the pH of the formulations. Within the pH range studied (pH 7.0-8.5), the level of hydrocortisone impurity was well below 2.0% at the 6 M timepoint, and no precipitation was observed in any of the formulations, regardless of HSP concentration. Therefore, the use of solubilizers in the HSP formulation is not necessary as long as the pH (>pH 7.5) of the formulation is controlled over the shelf-life.

Physicochemical and Biological Properties

In addition to the formulation development work described above, characterization studies were carried out on the selected batches in an effort to confirm the overall physicochemical and biological properties of the drug product. The temperature cycling study is described below:

The purpose of the study is to evaluate effects of stress temperature cycling on the product in its final container closure configuration, simulating the high and low temperature variations that may be encountered during shipping and handling. The study was performed on the final container closure configuration, i.e., Hydrocortisone sodium phosphate injection solution in naked syringes (PFS) and syringes with Hydrocortisone sodium phosphate injection solution assembled into auto injectors (AI) packaged into cartons with 3 autoinjectors per carton. All samples were stored horizontally throughout the study.

The study was carried out using the PFS from one of the registration batches (Y0175) and assembled Auto Injectors from lot 12555. Temperature cycling was preformed according to Table 52 below. The reference samples were stored at room temperature protected from light. All samples were analyzed at the end of Cycle 3.

TABLE 52

Temperature sampling plan

| Temperature | Storage space | Storage time (h) | | |
|---|---|---|---|---|
| −20° C. ± 5° C. | Freezer | 24 h | 72 h | 24 h |
| 40° C. ± 3° C. | Climate chamber | 24 h | 24 h | 24 h |
| | | Cycle 1 | Cycle 2 | Cycle 3 |

After the temperature cycling, appearance of all samples was Clear colorless to yellowish solution (Table 53). Assay and impurity results of the two batches were within specifications, as well as subvisible particle measurement, pH and delivered volume. In addition, no significant stopper movement was observed, with the stopper position measurement. It can be concluded that the product can withstand a repeated (3 times) exposure to −20° C. and 40° C. for at least 1 day each, with no detectable product changes as measured by validated test methods.

TABLE 53

Results for temperature cycling study

| | | Test | | | |
|---|---|---|---|---|---|
| | Stability Acceptance Limits | Reference PFS | Cycled PFS | Reference AI | Cycled AI |
| Appearance | PFS: Clear colorless to yellowish solution in a 2.25 mL glass syringe with grey stopper<br>AI: Clear colorless to yellowish solution in a prefilled, single use autoinjector | Clear colorless to yellowish solution in a 2.25 mL glass syringe with grey stopper | Clear colorless to yellowish solution in a 2.25 mL glass syringe with grey stopper | Clear colorless to yellowish solution in a prefilled, single use autoinjector | Clear colorless to yellowish solution in a prefilled, single use autoinjector |
| Color | Report result | GY6 | GY5 | GY5 | GY5 |
| pH | 7.5-8.5 | 7.9 | 8.0 | 8.0 | 8.0 |
| Assay & impurities | | | | | |
| Assay of Hydrocortisone Sodium Phosphate | 120.8-147.6 (mg/mL) | 137.0 | 137.5 | 137.3 | 137.3 |
| Assay of Hydrocortisone Equivalent | 90-110% of label claim | 102.1 | 102.4 | 102.3 | 102.3 |
| Specified impurity, % | | | | | |
| Hydrocortisone | ≤2.0% | ND | ND | ND | ND |
| RRT 0.91 | ≤0.5% | ND | ND | ND | ND |
| Sum of impurities | ≤3.0% | 0.08 | 0.08 | 0.08 | 0.08 |
| EDTA | | | | | |
| Assay of disodium EDTA dihydrate, mg/mL | Report result | 0.14 | 0.14 | 0.13 | 0.12 |
| Subvisible particles | | | | | |
| ≥10 μm | ≤6000 particles. per container | 26 | 11 | 131 | 46 |
| ≥2 μm | ≤600 particles. per container | 0 | 0 | 0 | 0 |
| Microbiological testing | | | | | |
| Sterility | Sterile | Sterile | Sterile | Not tested | Not tested |
| Uniformity of dosage | | | | | |
| Delivered volume | 1.0-1.2 mL<br>Individual delivered volume (mL): To be reported | Complies,<br>1.) 1.07<br>2.) 1.07<br>3.) 1.07<br>4.) 1.07<br>5.) 1.07 | Complies,<br>1.) 1.08<br>2.) 1.07<br>3.) 1.07<br>4.) 1.08<br>5.) 1.08 | Not tested | Not tested |
| Uniformity of dosage units | Acceptance value (AV) for 10 dosage units ≤15.0<br>If AV >15.0, test the next 20 dosage units:<br>AV for 30 dosage units ≤15.0<br>No individual content of any dosage unit is less than [0.75M] or more than [1.25M]<br>Average volume: To be reported [1] | Complies after first step,<br>AV = 1.9<br>Average volume = 1.07 mL | Complies after first step,<br>AV = 0.6<br>Average volume = 1.08 mL | Not tested | Not tested |
| Plunger position | | | | | |
| Plunger position | Report result | Avg: 26.3 mm<br>Min-max: 25.9-26.6 mm<br>RSD: 1.0 % | Avg: 26.3<br>Min-max: 25.9-26.7 mm<br>RSD: 1.0 % | Not tested | Not tested |

Container Closure System

Container and Closure System Components

The PFS container closure system for HSP Injection, assembled into an autoinjector (AAI) includes syringe, plunger stopper, and autoinjector sub-assemblies, as described in Table 54. The syringe contains a 2.25 mL syringe barrel made of siliconized USP Type I borosilicate glass and a fixed siliconized stainless steel needle protected with a rigid needle shield (RNS). The syringe complies with USP<660> requirements for Type I glass containers for parenteral preparations. The syringe is supplied pre-cleaned and sterilized, as described in DMF 021723 held by Nuova Ompi. S.r.l. The plunger stopper is composed of chlorobutyl as the elastomer type and meets the requirements for Type I closures as outlined in <381>. The stopper is supplied prewashed and sterilized, as described in DMF 011648, DMF 030048, and DMF 020880 held by West Pharmaceutical Services, Inc. The syringe and the plunger stopper serve as the primary packaging components, which have product contact with the HSP Injection.

TABLE 54

Container/closure and delivery system for hydrocortisone sodium phosphate

| Component | Description/Material | Supplier |
|---|---|---|
| Syringe | Ompi Article #7600001.9073, Syringe EZ-Fill 2.25 mL, 25G 1" 3B, RNS 4800GS, NEST100 | Nuova Ompi S.r.l. |
| Plunger Stopper | West Pharma Item # 10149660, ART 2345 4432/50 GRY B2-40 WESTAR RU(US) | West Pharmaceutical Services, Inc |
| Autoinjector | Single-use disposable, spring powered (non-product contact) | Antares Pharma Minnetonka Operations Facility (APMOF). |

Medical Device

HSP Injection is administered using a single use autoinjector device that is disposed after injection and requires no cleaning, maintenance, or reprocessing. The autoinjector device provides a spring powered needle-based intramuscular injection of HSP. The drug product can be either self-injected by a patient or by a caregiver. The device offers protection from accidental needle sticks post injection. The autoinjector device does not need any preparation before injection, such as filling, reconstitution, or dose dialing. The delivery volume is not adjustable by the end user. The autoinjector has no fluid path and does not come in contact with the HSP injection solution contained in the syringe. Therefore, the autoinjector is not sterilized. APMOF manufactures the autoinjector. There is no contact between the autoinjector and the drug product.

Secondary Packaging for the Combination Product—Cardboard Carton

One (1) commercial packaging configuration will be available: a paperboard shelf carton containing 3 autoinjectors.

Container Closure System Leachables and Extractables

Analytical Evaluation Threshold (AET)

Per USP <1664>"Assessment of Drug Product Leachables Associated with Pharmaceutical Packaging/Delivery Systems", Analytical Evaluation Threshold (AET) is the threshold at or above which a leachable should be characterized and reported for toxicological assessment. Thus, AET must be defined prior to extractable/leachable studies. The AET can be mathematically derived from the Safety Concern Threshold (SCT) based on the dosing parameters of the drug product. For organic compounds, a Safety Concern Threshold (SCT) of 5 µg/day is selected based on the following rationales:

(1) The SCT for an individual irritant or sensitizer per Product Quality Research Institute (PQRI) is 5 µg/day.

(2) For acute use for which the Duration of Treatment is not expected to be more than 30 days, the SCT per ICH M7(R1) is 120 µg/day for an individual and multiple genotoxic impurities.

Thus, the SCT of 5 µg/day is a lower threshold than the ICH M7 thresholds even if the more stringent threshold of the total impurities is used for comparison, unless there are more than 24 genotoxic impurities with at least 5 µg/day, which seems quite unlikely. Based on the maximum dosing regimen (1 dose/day), the SCT can be converted to an AET as follows (using 1 dose/day and 1 dose/component):

$$AET(\mu g/component) = 5(\mu g/day) \times \frac{1 \text{ day}}{1 \text{ dose}} \times \frac{1 \text{ dose}}{1 \text{ component}} = 5 \ \mu g/component$$

OR $$AET(\mu g/mL) = 5(\mu g/day) \times \frac{1 \text{ day}}{1 \text{ dose}} \times \frac{1 \text{ dose}}{1 \text{ mL}} = 5 \ \mu g/mL$$

For elemental impurities, since currently there is no universal SCT available for metals, the AET is set at 1 ng/mL, the detection limit of the instrument. Elemental metals below 1 ng/mL will be reported as not detected.

Controlled Extraction Study

The primary packaging components evaluated in the controlled extraction study (CES) included syringe/needle assemblies, needle shields, and plunger stoppers. The CES is summarized in Table 55.

TABLE 55

Summary of controlled extraction studies for all syringe components

| Packaging Components | Target Extractables | Analysis Methodology | Extraction Solvent |
|---|---|---|---|
| All[1] | Volatile organic Semi-volatile organic | HS/GC-MS[2] D/GC/MS[3] | Dry heat at 80° C. pH 3 citrate buffer, buffer 50% isopropyl alcohol pH 10 phosphate |
| Syringe assemblies | Non-volatile organic Metals | LC/UV/MS[4] ICP/MS[5] | ~2% nitric acid |

[1] Including syringe barrels, needles, needle shields and stoppers
[2] HS/GC-MS = headspace gas chromatography/mass spectrometry
[3] Di/GC/MS = direct injection (Di) GC/MS
[4] LC/UV/MS = liquid chromatography LC/UV/MS
[5] ICP/MS = Inductively coupled plasma/mass spectrometry Leachable Screening Based on Aged Drug Product An aged PFS sample (Lot HCP #28) based on the identical formulation as proposed drug product that had been stored at 40° C. for 6 months was used for leachable screening. The aged PFS sample was tested by using the same methodologies used in the CES, and the results are summarized in Table 56.

TABLE 56

Summary of leachable screening studies

| Category of Leachable | Method | Leachable found in the Aged Sample Leachable | mg/ Syringe | Source of Leachable Per CES[1] |
|---|---|---|---|---|
| Volatile organic | HS/GC-MS | 2-Propanol | 0.04 | Needle shield |
| Semi-volatile organic | Di/GC/MS | Tetrahydro-2-furanmethanol or Tetrahydrofurfuryl alcohol (THFM) | 0.53 | Needle shield Glass barrel |
|  |  | 3-Methyl-1-oxaspiro[4.5]decan-2-one (MOSDO) | 0.03 | Needle shield Glass barrel |
|  |  | Dodecanoic acid | 0.06 | Stopper, needle shield |

TABLE 56-continued

Summary of leachable screening studies

| Category of Leachable | Method | Leachable found in the Aged Sample | | Source of Leachable Per CES[1] |
|---|---|---|---|---|
| | | Leachable | mg/ Syringe | |
| Non-volatile organic | LC/UV/MS | Dodecanoic acid | 2.58 | Stopper, needle shield |
| Metals | ICP/MS | None [2] | None [2] | None [2] |

[1]Source identified by matching the leachable results from the aged sample to extractable in the CES
[2] Metal impurities observed in the aged sample were the one which are already detected in the bulk control sample.

Development and Validation of Leachable Methods

A GC with flame-ionization detection (FID) method (M22448) was developed for testing the potential target leachables, THFM and MOSDO. Because MOSDO is not commercially available, a structurally similar compound, 1-Oxaspiro[4.5]decan-2-one (OSDO) was used as a surrogate for method development and validation. MOSDO is monitored via a Relative Retention Time (RRT) of 1.005 versus (vs.) OSDO. Acetophenone (ACET), Tetrahydrofurfuryl methacrylate (THFMA), and Diphenyl ether (DPE) are common leachables found in a typical PFS system. Although ACET, THFMA, and DPE were not found in the aged sample, they are also included for monitoring and screening purposes on stability. The practical quantitation limit (PQL) of M22448 is 1 mg/syringe, five times lower than the AET.

There was only one non-volatile leachable, i.e., dodecanoic acid (~2.5 mg/syringe, Table 56) in the aged sample during the leachable screening study. Dodecanoic acid is a major component of dietary triglycerides such as coconut oil and a common food ingredient. Its SCT and AET is likely much higher than 5 mg/day and 5 mg/syringe, respectively. Therefore, a method specific for dodecanoic acid was not developed for the leachable stability study. Instead, a universal LC-MS screening method (M22182) was developed to monitor potential non-volatile leachables, including dodecanoic acid on stability for precautionary reasons. A surrogate compound, Irganox 245 is used to demonstrate the method feasibility including a reporting limit (i.e., detection limit) of 1 mg/syringe. Dodecanoic acid is monitored via RRT of 0.78 vs. Irganox 245. Similarly, other unknown potential non-volatile leachables are monitored via RRT vs. Irganox 245.

Irganox 245 is used as the surrogate standard in M22182 because it is detected in all three detection channels, including UV, Electrospray Ionization (ESI)(−) and ESI(+), and it has similar response in at least one of the three detection channels compared to common leachable/extractable compounds, which makes it an ideal surrogate standard for quantitation when authentic standards are not available for general screening purpose:
- Irganox 245 contains the same phenolic moiety as typical stopper extractables such as butylated hydroxytoluene (BHT) and Irganox 1010. Thus, Irganox 245, BHT and Irganox 1010 have similar UV chromophore and UV response.
- The response of Irganox 245 in the ESI negative mode is comparable to that of typical extractable long chain fatty acids including dodecanoic acid.
- There was only one volatile leachable, isopropanol (2-propanol), found in the aged sample. However, the level of isopropanol found in the aged sample (0.04 mg/syringe, or 0.04 ppm, Table 56) was 105 times below the 5000 ppm limit per ICH Q3C(R6) in which isopropanol is a Class 3 residual solvent with a low toxic potential. Thus, isopropanol was not selected as a potential leachable to be monitored in the leachable stability study.

Summary Leachable Stability Results

Leachable stability results are summarized in Table 57. The three primary stability batches were manufactured in August-September of 2021. The stability samples were stored at ambient prior to the leachable stability start in April of 2022 (approximately 8 months). No detectable (i.e., <1 mg/syringe) leachables were observed for up to 14 months (including the 8 months at ambient and 6 months at 25° C./60% RH in the stability chamber). Leachable stability study will be continued through 36 months.

TABLE 57

Summary of leachable stability results

| | | | µg/syringe | | |
|---|---|---|---|---|---|
| Time/Storage Condition | | Leachable | Batch Y0173 | Batch Y0175 | Batch Y0184 |
| Initial | Semi-volatile | THFM | ND | ND | ND |
| | | ACET | ND | ND | ND |
| | | THFMA | ND | ND | ND |
| | | DPE | ND | ND | ND |
| | | MOSDO | ND | ND | ND |
| | | Unknown | ND | ND | ND |
| | Non-volatile | Dodecanoic Acid | ND | ND | ND |
| | | Unknown | ND | ND | ND |
| 6 months at 25° C./ 60% RH | Semi-volatile | THFM | ND | ND | ND |
| | | ACET | ND | ND | ND |
| | | THEMA | ND | ND | ND |
| | | DPE | ND | ND | ND |
| | | MOSDO | ND | ND | ND |
| | | Unknown | ND | ND | ND |
| | Non-volatile | Dodecanoic Acid | ND | ND | ND |
| | | Unknown | ND | ND | ND |

ND = Not Detected (i.e., <Reporting limit);
Reporting limits: Semi-volatile leachables = 1 µg/syringe;
Non-volatile leachables = 0.1 µg/syringe (UV channel), 1 µg/g (MS channels)

Specification for Excipients

The excipients used in the manufacture of Hydrocortisone Sodium Phosphate Injection are tested and released in accordance with the specifications and test methods described in the referenced pharmacopoeia from Table 58.

TABLE 58

Specifications for compendial excipients

| Excipient | Compendial Standard |
|---|---|
| Sodium dihydrogen phosphate dihydrate | USP |
| Disodium hydrogen phosphate dihydrate | USP |
| Disodium edetate dihydrate | USP |
| Monothioglycerol | NF |
| Sodium hydroxide | NF |
| Water for Injection | USP |

An additional test for Bacterial Endotoxins (BET) and Microbial limit test (TAMC and TYMC) beyond those described in the USP monographs was performed for following excipients as shown in Table 59. BET and Microbial Limit tests for Sodium Hydroxide were not required as it is a strong base.

TABLE 59

Additional test beyond that described in the Pharmacopoeia

| Excipient | Acceptance Criteria | | | |
|---|---|---|---|---|
| | Bacterial Endotoxins USP <85> | Total Aerobic Microbial Count (TAMC) USP <61> | Total Combined Yeasts and Molds Count (TYMC) USP <61> | |
| Sodium dihydrogen phosphate dihydrate | ≤1.35 EU/mg | ≤1000 CFU/g | Not Tested | |
| Disodium hydrogen phosphate dihydrate | ≤0.0025 EU/mg | ≤100 CFU/g | Not Tested | |
| Disodium edetate dihydrate | ≤0.2 EU/mg | ≤100 CFU/g | Not Tested | |
| Monothioglycerol | ≤1.35 EU/mg | ≤1000 CFU/g | ≤100 CFU/g | |

Justification of Specifications for Excipients

In addition to the tests stipulated in the United States Pharmacopeia—National Formulary (USP-NF), all excipients other than sodium hydroxide which is a strong base, were also tested for bacterial endotoxins (BET) per USP <85> to ensure appropriate control of BET for the parenteral product. Theoretically, the maximal allowable BET limit per dose for all excipients ($BET_{excipients}$) can be estimated as follows:

- The BET limit for the drug product (DP) is 1.25 EU/mg of hydrocortisone, for a total limit of BET per daily dose ($BET_{DP}$) of 125 EU.
- The BET limit for the drug substance (DS) is 0.75 EU/mg of hydrocortisone, and the maximal total limit of BET per daily dose ($BET_{DS}$) is 75 EU.
- The BET limit for syringe ($BET_{Syringe}$) and for stopper ($BET_{Stopper}$) is 0.25 EU/syringe and 1 EU/stopper, respectively.
- The maximal BET limit per dose for all excipients can be calculated below:

$$BET_{excipients} = BET_{DP} - (BET_{DS} + BET_{Syringe} + BET_{Stopper}) = 48.75 \text{ EU/Dose}.$$

The maximal total contribution of BET from all excipients based on the BET specification limits is 8.6 EU/Dose, which is much lower than 73.75 EU/Dose allowed by the DP acceptance criteria as calculated above. Thus, the acceptance criteria for all excipients are justified and shown in Table 60.

TABLE 60

The maximal total contribution of BET from all excipients

| Ingredients | Quantity per unit dose (1 mL) | Bacterial Endotoxins Limit (EU/mg) | Max Contribution of BET to Drug Product (EU/Dose) |
|---|---|---|---|
| Sodium dihydrogen phosphate dihydrate | 1.3 mg | 1.35 EU/mg | 1.755 |
| Disodium hydrogen phosphate dihydrate | 13.7 mg | 0.0025 EU/mg | 0.034 |
| Disodium edetate dihydrate | 0.2 mg | 0.2 EU/mg | 0.040 |
| Monothioglycerol | 5 mg | 1.35 EU/mg | 6.750 |
| Sodium hydroxide | Q.S pH (approximately 8.0) | 0[1] | 0 |
| Total | | | 8.6 |

[1]No BET since it is a strong base

Additionally, microbial limit tests were performed to ensure appropriate control of microbials in excipients for the parenteral product. The maximal total contribution of microbials from all excipients is 826 CFU/100 mL (Table 61).

During the manufacture of the DP, the bulk solution which contains the DS and other excipients was made and then filtered through a 0.22 µm, bioburden reduction filter. Theoretically, the DS is the major source of microbials since its maximal microbial contribution (11,000 CFU/100 mL) is much higher than the maximal microbial contribution from all excipients combined (i.e., 826 CFU/100 mL). Approximately 12,000 CFU/100 mL total maximal microbial contribution can be readily removed/reduced by a typical sterile bioburden reduction filter to meet the In-Process Control (IPC) bioburden specification limit of no more than 10 CFU/100 mL. The IPC bioburden results for all three registration batches were 0 CFU/100 mL after the bioburden reduction filtration.

TABLE 61

The maximal total contribution of microbial from all excipients

| Ingredients | Quantity per unit dose (1 mL) | TAMC Limit (CFU/g) | Max TAMC per 100 mL (CFU/100 mL) | TYMC Limit (CFU/g) | Max TYMC per 100 mL (CFU/100 mL) |
|---|---|---|---|---|---|
| Sodium dihydrogen phosphate dihydrate | 1.3 mg | 1000 | 137 | NT | 0 |
| Disodium hydrogen phosphate dihydrate | 13.7 mg | 100 | 137 | NT | 0 |
| Disodium edetate dihydrate | 0.2 mg | 100 | 2 | NT | 0 |
| Monothioglycerol | 5 mg | 1000 | 500 | 100 | 50 |
| Sodium hydroxide | Q.S to pH 8 | 0[1] | 0 | 0[1] | 0 |
| Total | | | 776 | | 50 |
| Total Microbials | | | | | 826 |

[1]No microbials since it is a strong base; NT: Not Tested

Specification for HSP Injection

The testing for the proposed single-use final (drug/device) combination product, Hydrocortisone Sodium Phosphate (HSP) Injection, was carried out both on the prefilled syringes (PFS) and the assembled autoinjector (AAI). The PFS was tested for drug product identification and attributes associated with potency, purity, and safety. The specifications for the PFS are shown in Table 62. The AAI was tested for the attributes associated with device performance for drug product delivery, and the results are shown in Table 63.

TABLE 62

Specifications for Hydrocortisone Sodium Phosphate Injection Prefilled Syringes, 134.2 mg/mL, equivalent to 100 mg/mL of hydrocortisone

| Test | Acceptance Criteria | Method |
|---|---|---|
| Appearance | Clear colorless to yellowish solution in a 2.25 mL glass syringe with grey stopper | Visual |
| Color of Solution | Report Results | Ph. Eur.2.2.2. Method 1 |
| Identification by UV[1] | The UV spectrum of the hydrocortisone sodium phosphate peak in the chromatogram of a sample preparation corresponds to that of the standard preparation | QE-499[2]/ TMS-0989 |
| Identification by HPLC Retention Time[1] | The retention time of the Hydrocortisone Sodium Phosphate peak in the chromatogram of a sample preparation corresponds to that of the standard preparation | QE-499[2]/ TMS-0989 |
| pH | pH 7.5-8.5 | USP <791> |
| Particulate Matter | ≥10 μm: ≤ 6000/syringe<br>≥25 μm: ≤ 600/syringe | USP <788> Method 1 |
| Hydrocortisone Sodium Phosphate Assay | 127.5-140.9 (mg/mL)/95.0-105.0% (release)<br>120.8-147.6 (mg/mL)/90.0-110.0% (shelf-life) | QE-499[2]/ TMS-0989 |
| Hydrocortisone Equivalent Assay | 95.0-105.0 (mg/mL)/95.0-105.0% of label claim (release)<br>90.0-110.0 (mg/mL)/90.0-110.0% of label claim (shelf-life) | QE-499[2]/ TMS-0989 |
| Monothioglycerol (MTG)[1] | 3.5-5.5 mg/mL (70-110%) | TMS - 1031 |
| Ethylenediaminetetraacetic Acid (EDTA)[1] | 0.1-0.22 mg/mL (50-110%) | QE - 516 |
| Sterility | No evidence of microbial growth | USP <71> |
| Bacterial Endotoxins (BET) | 1.25 EU/mg Hydrocortisone | USP <85> |
| Volume in Container[1] | 1.00-1.20 mL | USP <1>/ M22269 |
| Uniformity of Dosage Units - Weight variation[1] | Acceptance value (AV) for 10 dosage units ≤15.0<br>If AV > 15.0, test the next 20 dosage units: AV for 30 dosage units ≤ 15.0<br>No individual content of any dosage unit is less than [0.75 M] or more than [1.25 M] | USP <905> |

[1] Release testing only
[2] QE-499 and TMS-0989 are the same method (used at different sites)

TABLE 63

Hydrocortisone Sodium Phosphate Injection Combination Product (assembled autoinjector) specification, 134.2 mg/mL, equivalent to 100 mg/mL of hydrocortisone - release only

| Test | Acceptance Criteria | Method |
|---|---|---|
| Appearance | Clear, colorless to yellowish solution in a prefilled, single dose autoinjector. | Visual |
| Uniformity of Dosage Units - Weight variation | Acceptance value (AV) for 10 dosage units <= 15.0<br>If AV > 15.0, test the next 20 dosage units:<br>AV for 30 dosage units £ 15.0<br>No individual content of any dosage unit is less than [0.75M] or more than [1.25M] | USP <905> |
| Functionality Test | | A. PPD Method |
| A. Delivered Volume | A. 1.00-1.20 mL | Number M22269 (USP <1>) |
| B Ejection Time | B <10 seconds | B. PPD Method Number M22269 |
| C. Trigger Force | C ≤8.5 lbf (pounds force) | C. PPD Method Number M22269 |
| D. Exposed Needle Length | D. 20-26 mm | |
| E. Safety Cap Removal Torque | E. ≤11 in-lbs (inch-pounds) | D. PPD Method Number M22269 |

TABLE 63-continued

Hydrocortisone Sodium Phosphate Injection Combination Product (assembled autoinjector) specification, 134.2 mg/mL, equivalent to 100 mg/mL of hydrocortisone - release only

| Test | Acceptance Criteria | Method |
|---|---|---|
| F. Attribute Tests[1] | F. Per methods | E. PPD Method Number M22432<br>F. PPD Method Number M22433 |

[1] Attribute tests include verifying the needle is hidden before injection, the viewing window is clear and the AAI is ready to inject, the needle shield is removed with the cap, the AAI triggers, the AAI delivers the drug, the viewing window is occluded at the end of injection and the passive sharps injury protection feature engages.

Batch Analysis

The batch analysis results for the three registration batches of Hydrocortisone Sodium Phosphate (HSP) Injection pre-filled syringes (PFS) are summarized in Table 64. The release testing of the functional attributes for the AAI are summarized in Table 65.

TABLE 64

Batch Analysis for PFS registration batches of Hydrocortisone Sodium Phosphate Injection Prefilled Syringes, 134.2 mg/mL, equivalent to 100 mg/mL of hydrocortisone

| Test | Release Acceptance Criteria | Results Batch Y0173 | Batch Y0175 | Batch Y0184 |
|---|---|---|---|---|
| Appearance | Clear colorless to yellowish solution in a 2.25 mL glass syringe with grey stopper | Conforms | Conforms | Conforms |
| Identification by UV[1] | The UV spectrum of the hydrocortisone sodium phosphate peak in the chromatogram of a sample preparation corresponds to that of the standard preparation | Complies | Complies | Complies |
| Identification by HPLC Retention Time[1] | The retention time of the Hydrocortisone Sodium Phosphate peak in the chromatogram of a sample preparation corresponds to that of the standard preparation | Complies | Complies | Complies |
| Particulate Matter | ≥10 μm: ≤6000/syringe | 815 | 177 | 231 |
|  | >25 μm: ≤600/syringe | 3 | 2 | 2 |
| pH | pH 7.5-8.5 | pH 8.0 | pH 8.0 | pH 8.0 |
| Hydrocortisone Sodium Phosphate Assay | 127.5-140.9 (mg/mL) (95.0-105.0% of label claim) | 137.8 mg/ml | 135.9 mg/mL | 140.0 mg/mL |
| Hydrocortisone Equivalent Assay | 95.0-105.0 (mg/mL) (95.0-105.0% of label claim) | 102.7% | 101.3% | 104.3% |
| Sterility | Sterile | Sterile | Sterile | Sterile |
| Monothioglycerol[1] [3] | 3.5-5.5 mg/mL | 3.55 mg/mL | 3.60 mg/ml | 3.60 mg/ml |
| Ethylenediaminetetraacetic Acid[1] [4] | 0.1-0.22 mg/mL | 0.14 mg/mL | 0.13 mg/mL | 0.13 mg/mL |
| Color of Solution[5] | Report Results | GY6[6] | GY6 | GY6 |
| Bacterial Endotoxins | ≤1.25 EU/mg Hydrocortisone | <0.63 EU/mg Hydrocortisone (beginning, middle and end) | <0.63 EU/mg Hydrocortisone (beginning, middle and end) | <0.63 EU/mg Hydrocortisone (beginning, middle and end) |
| Volume in Container (mL)[1] | 1.00-1.20 | 1.07 | 1.07 | 1.08 |
| Uniformity of Dosage Units - Weight variation[1] | Acceptance value (AV) for 10 dosage units £ 15.0 If AV > 15.0, test the next 20 dosage units: AV for 30 dosage units £ 15.0 No individual content of any dosage unit is less than [0.75M] or more than [1.25M] | Conform | Conform | Conform |

[1] Release testing only
[3] Monothioglycerol (MTG) was not tested at release as the validated MTG method was not yet available. The results shown are from 8-month stability samples stored at 25° C./60% RH Horizontal orientation).
[4] Ethylenediaminetetraacetic Acid (EDTA) was not tested at release in Sept of 2021 because a validated EDTA method was not available. The initial testing of EDTA was based on 6-month stability samples stored at 25° C./60% RH tested in March, 2022. The test results for samples stored at the Horizontal orientation were used.
[5] Color of Solution was not included in the release specifications initially. The initial stability testing results were included. Refer to
[6] GY is defined as greenish-yellow.
ND = Not detected (below LOD).

TABLE 65

Batch Analysis for AAI registration batches of Hydrocortisone Sodium Phosphate
Injection, 134.2 mg/mL, equivalent to 100 mg/mL of hydrocortisone

| Test | Release Acceptance Criteria | Results Batch I2553 | Batch I2554 | Batch I2555 |
|---|---|---|---|---|
| Appearance[1] | Clear, colorless to yellowish solution in a prefilled, single dose autoinjector. | Conform | Conform | Conform |
| Uniformity of Dosage Units - Weight variation[1] | Acceptance value (AV) for 10 dosage units £ 15.0 If AV > 15.0, test the next 20 dosage units: AV for 30 dosage units £ 15.0 No individual content of any dosage unit is less than [0.75 M] or more than [1.25 M] Functionality tests | Conform | Conform | Conform |
| Delivered Volume | 1.00-1.20 mL | 1.05-1.09 mL | 1.06-1.09 mL | 1.06-1.09 mL |
| Ejection Time | <10 seconds | 2 seconds | 2 seconds | 3 seconds |
| Trigger Force | ≤8.5 lbf (pounds force) | 6.4 lbf | 6 lbf | 6 lbf |
| Exposed Needle Length | 20-26 mm | 23-24 mm | 22-24 mm | 22-24 mm |
| Safety Cap Removal Torque | ≤11 in-lbs (inch-pounds) | 2 in-lbs | 2 in-lbs | 2 in-lbs |
| Attribute Tests[2] | Per methods[1] | Pass | Pass | Pass |

[1]Initial stability results are used
[2]Attribute tests include verifying the needle is hidden before injection, the viewing window is clear and the AAI is ready to inject, the needle shield is removed with the cap, the AAI triggers, the AAI delivers the drug, the viewing window is occluded at the end of injection and the passive sharps injury protection feature engages.
ND = not detected, detection limit = 0.015%

Justification of HSP Injection Combination Product Specifications

The Hydrocortisone Sodium Phosphate (HSP) Injection combination product was tested in two stages. The prefilled syringe (PFS) containing sterile HSP Injection was tested for identification (ID) and attributes associated with potency and patient safety. The assembled autoinjector (AAI) was tested for the attributes associated with delivery device performance for drug delivery.

Tests for physicochemical and microbiological (PCM) Critical Quality Attributes (CQAs) for HSP Injection Drug Product (DP) are designed to fulfill the requirements stipulated in ICHQ6A, USP <1>, and HSP Injection USP Monograph. All PCM tests will be performed on the HSP Injection PFS for the following reasons:

- The autoinjector (AI) has no direct contact with the HSP DP solution contained in the PFS. Consequently, the AI does not alter the PCM attributes as further explained in Table 66. Comparison of the release testing results of the three primary stability batches confirmed that assembly of the PFS into the autoinjector did not change the PCM attributes.
- The AI is not a barrier to temperature, humidity, and oxygen. When stored in the stability chamber, the HSP DP in PFS with or without the AI are subject to the identical environmental conditions including temperature, humidity, and exposure to oxygen. AI has no impacts on product stability in fact AI may provide better light protection.

TABLE 66

Autoinjector does not impact PCM attributes

| PCM Attributes | Autoinjector (AI) does not |
|---|---|
| Assay & Impurities | facilitate or inhibit degradation change concentration of the active & impurities |
| pH | add (H⁺) or (OH⁻) ions |
| Particulate Matters | add or remove particles |
| Bacterial Endotoxin | add or remove endotoxin |
| Sterility | add or remove microbial organisms strengthen or weaken the integrity of primary container closure (i.e., PFS) |

PCM = physicochemical and microbiological; PFS = prefilled syringe

As indicated in the Table 66, the AAI was not tested on stability. There is no requirement for AAI testing at stability because the materials it is composed of do not change over time. The AI components are made of plastics and metals. Once tested and verified at release, the functionality of the AI should not change over time unless the AI components relevant to the functions deform. It is known that the rate of deformation is a function of material properties, applied structural stress, exposure time and exposure temperature. Deformation is most significant at a temperature near the melting point of the material but is negligible at a temperature much below the melting point. The melting points of the plastics and metals used in the autoinjector are significantly higher than the room temperature.

Therefore, these AI components are not expected to deform when stored under ambient temperature within a relatively short period of time of 2 years (i.e., the proposed shelf life). Consequently, all functional attributes are not expected to change over time at the long-term condition. Testing has been completed on AI units exposed to accelerated aging per ASTM F1980-21 for a representative shelf-life of 2 years. This data supports that AI functional attributes don't change over shelf life of the product. This justification is further supported by the stability results from the registration batches, which show that all functional attributes including delivered volume, ejection time, exposed needle length, trigger force, and cap removal torque remained nearly constant at the long-term condition. Therefore, the AI functional attributes were only tested at release but not on stability for the post-approval commercial batches.

Appearance

Acceptance Criteria (PFS): Clear, colorless to yellowish solution in a 2.25 mL glass syringe with grey stopper.

Acceptance Criteria (AAI): Clear, colorless to yellowish solution in a prefilled, single dose autoinjector.

The purpose of this test was to evaluate the appearance of the DP. Dissolution of HSP Drug Substance (DS) in aqueous solution resulted in a clear, colorless to yellowish colored solution.

Color of Solution

Acceptance Criteria: Report Result

The European Pharmacopeia (EP) method, Ph. Eur. 2.2.2., Method 1 will be used to evaluate the color of the solution against a set of color standards should the solution not to be colorless.

Identification by HPLC

Acceptance Criteria:

UV: The UV spectrum of the hydrocortisone sodium phosphate peak in the chromatogram of a sample preparation corresponds to that of the standard preparation.

HPLC Retention Time: The retention time of the Hydrocortisone Sodium Phosphate peak in the chromatogram of a sample preparation corresponds to that of the standard preparation.

The purpose of this RP-HPLC test was to confirm identification (ID) of HSP in the DP based on both HPLC retention time and UV spectrum. For a positive ID, both acceptance criteria cited above must be met.

The HPLC retention time requirement was based on the unique characteristic hydrophobic behavior of HSP under defined chromatographic conditions and was compared to that of the reference standard. The identification was confirmed by HPLC using the sample preparation and chromatographic conditions described in Method QE-499, which was also used for HSP assay and analysis of organic impurities. Specificity studies showed that there are no diluent peaks and no interference from HSP degradation products that eluted at the retention time of HSP under the method chromatographic conditions. The retention time for the HSP peak in the DP was specific to the DS and is therefore appropriate for identification.

The UV spectrum of HSP was also specific and unique. ID was confirmed upon comparison to the reference standard. The combination of UV spectrum and HPLC retention time provides two orthogonal methods for confirmation of identity. ID testing was performed only for release.

Hydrocortisone Sodium Phosphate Assay

Acceptance Criteria for Hydrocortisone Equivalent

Shelf-life: 90.0% to 110.0% of label claim

Release: 95.0% to 105.0% of label claim pH

Acceptance Criteria: pH 7.5-8.5

Particulate Matter

Acceptance Criteria:

≥10 μm: Max 6000 particles/syringe

≥25 μm: Max 600 particles/syringe

The purpose of this test was to ensure compliance with USP <1> Injections, and ICH guidelines Q6A for parenteral products, which stipulate to include a test procedure and acceptance criteria for evaluation of Particulate Matter. Per USP <788>, Particulate Matter in Injections, Method I (Light Obscuration Particle Count Test) was selected for the aqueous based Hydrocortisone Sodium Phosphate Injection. The USP recommended acceptance criteria, as shown above, were adopted.

Monothioglycerol

Acceptance Criteria: 3.5-5.5 mg/mL (release only)

Monothioglycerol (MTG) was used as an antioxidant. The nominal concentration of MTG is 5 mg/mL. As the end of shelf-life (i.e., 24 months) MTG results were not available for the three primary stability batches, the aged development batches (i.e., Formulations 7A through 7F) and Batch Y0011 were tested for MTG.

For Formulations 7A and 7D with a starting MTG level of 2.5 mg/mL, no MTG was detected at 27 months. Thus, it is likely that at 24 months, the MTG level was approaching zero for these two batches. It was noted that the nominal concentration of HSP in the development batches 7A through 7F was 67 mg/mL, which is 50% of the HSP concentration in the proposed formulation. The oxygen concentration in the PFS should be the same regardless of the HSP concentration. Obviously, when the HSP concentration is lower, the ratio of the oxygen versus HSP is higher. Therefore, formulation with 67 mg/mL of HSP, compared to 134 mg/mL of HSP, represents the worst-case scenario in terms of oxidation.

For Formulations 7B and 7C (with a starting MTG level of 5 mg/mL), the MTG level was approximately 30% at 27 months implying that the MTG level was likely ≥30% at 24 months. For Batch Y0011 (with a starting MTG level of 5 mg/mL), the MTG level was 48% at 22 months.

For the formulation with a starting MTG level of 10 mg/mL, the MTG level was >60% at 27 months implying that the MTG level was likely ≥60% at 24 months.

In summary, when the starting MTG level ranged from 2.5 mg/mL to 5 mg/mL, at the end of the proposed shelf-life (i.e., 24 months), while the MTG level may range from approaching zero to approximately 30%, oxidation was effectively suppressed. The higher limit of MTG (5.5 mg/mL or 110%) was to account for potential manufacturing variation, whereas the lower limit (3.5 mg/mL or 70%) was to account for both potential manufacturing variation and potential loss of MTG acting as an antioxidant during manufacturing.

Ethylenediaminetetraacetic Acid

Acceptance Criteria: 0.10-0.22 mg/mL (release only)

Ethylenediaminetetraacetic Acid (EDTA) is a chelating agent which scavenges catalytic or transition metal ions (e.g., $Fe^{3+}$, $Cu^{2+}$, and $Ni^{2+}$) that that may be present in the manufacturing process, and hence prevents potential catalytic oxidation of the drug product. However, after manufacturing, any potential catalytic metal ions from the manufacturing equipment or the starting materials should be completely scavenged by EDTA, and there are no free catalytic metal ions in the drug product for the following two reasons:

(1) There is no possible mechanism to generate any catalytic metal ions from any formulation ingredients.

(2) It is known that there are no leachable metals from the primary container closure in typical aqueous prefilled syringe systems, and this is no exception for the HSP injection PFS. Leachable metals were not found in an aged PFS batch after storage at 40° C. for 6 months.

Because there are no catalytic metal ions in the drug product after manufacturing, the presence (or lack thereof) of EDTA should not impact the stability, safety and efficacy of the drug product. Therefore, only release acceptance criterion is proposed. The higher limit (0.22 mg/mL or 110%) is to account for potential manufacturing variation, whereas the lower limit (0.10 mg/mL or 50%) is to account for the decrease in the EDTA level due to the chelation with the metal ions that may be present in the manufacturing process.

Bacterial Endotoxin

Acceptance Criteria: 1.25 EU/mg hydrocortisone

The purpose of this test was to ensure compliance with ICH guidelines Q6A for parenteral products, which stipulates to include a test procedure and acceptance criterion for evaluation of endotoxins. The USP <85>, Bacterial Endotoxin turbidimetric method, was used to perform this test and has been validated and qualified as suitable for use for release and stability testing of Hydrocortisone Sodium Phosphate Injection. The NMT 1.25 EU/mg hydrocortisone limit per the USP monograph was adopted. This limit is nearly three times the 3.5 EU/mg hydrocortisone limit recommended per USP <85> based on the pyrogenic response threshold (NMT 5 EU/kg/hr) and a patient weight of 70 Kg.

Sterility

Acceptance Criteria: Media must not exhibit growth

The purpose of this test was to ensure compliance with USP<1>, Injections, and ICH guidelines Q6A for parenteral products, which stipulate to include a test procedure and acceptance criterion for evaluation of sterility. A validated method based on USP <71> was used. This validation was performed to ensure that any bacteriostatic and fungistatic activity inherent to the test solutions did not affect the reliability of the test and that the procedure to be used is suitable for its intended use.

Uniformity of Dosage Units—Release Testing Only

Acceptance Criteria:

Acceptance value (AV) for 10 dosage units ≤15.0

If AV >15.0, test the next 20 units, AV for 30 dosage units ≤15.0, and no individual content of any dosage unit is less than [0.75 M] or more than [1.25 M]

The purpose of this test was to ensure compliance with ICH guidelines Q6A for parenteral products, which stipulates to include a test procedure and acceptance criteria for evaluation of uniformity of dosage units. The test procedure and acceptance criteria of USP <905>, Uniformity of Dosage Units, were adopted. Since the HSP DP is a solution in unit-dose containers, weight variation is utilized according to USP <905>. This test was performed at release on both PFS and AAI.

Volume in Container (Delivered Volume)

Acceptance Criteria: 1.00-1.20 mL for Pre-Filled Syringe (PFS) and assembled autoinjector (AAI) Final Combination Product.

The purpose of this test was to verify the delivered volume of the parenteral preparation, as per current USP <1>. The lower limit (1.00 mL) was based on the requirements per USP <1> that the delivered volume be no less than the label volume (i.e., 1 mL). The upper limit (1.20 mL) is based on the maximal target fill volume (1.11 mL) and potential manufacturing variation. Volume in Container was tested at release only to ensure that appropriate volume was filled in the PFS.

Residual Solvents

The HSP DP complies with USP<467> general chapter for residual solvents per Option 1—Cumulative Approach via Control of Raw Materials. Thus, no additional testing for residual solvents is required for the HSP DP.

Elemental Impurities

Elemental impurities (EIs) in the HSP DP were determined by using Inductively Coupled Plasma Mass Spectrometry (ICP-MS) methods for the two potential EI sources (manufacturing and container closure components) per ICH Q3D. For the DS and the excipients, the elemental impurities statement/Risk Assessment from the respective vendors were considered to calculate the maximum daily exposure of the EIs.

The EI test results (usually in concentration, e.g., ug/mL or ug/g) are converted to daily exposure (ug/day) based on the maximal dose of 134.2 mg/day or maximal dose volume of 1 mL/day, and the results of maximal daily exposure are shown in Table 70. The results for any given EI were not more than (NMT) 0.1 ug/day for any one of the four potential sources, and NMT 0.2 ug/day for the total of the four potential sources (Table 70). The risk of EI is evaluated based on the Margin of Exposure (MOE) which is the ratio of the Permitted Daily Exposure (PDE) per ICH Q3D to the maximal total daily exposure. As shown in Table 67, the MOEs ranges from 222 to 75,000, indicating that there is no risk of EIs in the drug product and therefore, the test for Elemental Impurities was excluded from the finished drug product testing.

TABLE 67

Risk assessment of elemental impurities in Hydrocortisone Sodium Phosphate Injection

| | | | Max Daily Exposure (µg/day) | | | | | |
|---|---|---|---|---|---|---|---|---|
| EI | Class | ICH Q3D Parenteral PDE (µg/day) | Drug Substance[1] | Excipients[4] | Leachable Manufacturing Equipment[5] | Leachable Container Closure System[5][6] | Total | Margin of Exposure (MOE)[7] |
| As | 1 | 15 | <0.007 | <0.0003 | <0.001 | <0.001 | <0.009 | 1667 |
| Cd | 1 | 6.0 | <0.007 | <0.0001 | <0.001 | <0.001 | <0.009 | 222 |
| Hg | 1 | 4.0 | <0.004 | <0.0001 | <0.001 | <0.001 | <0.006 | 500 |
| Pb | 1 | 5.0 | <0.007 | <0.0025 | <0.001 | <0.001 | <0.012 | 417 |
| Co | 2A | 5.0 | <0.007 | NT[3] | <0.001 | <0.001 | <0.009 | 556 |
| Mo | 2A | 180 | NT[2] | NT[3] | <0.001 | <0.001 | <0.002 | 750000 |
| Se | 2A | 85 | NT[2] | <0.00003 | <0.001 | <0.001 | <0.002 | 40000 |
| V | 2A | 12 | <0.02 | NT[3] | <0.001 | <0.001 | <0.022 | 455 |
| Ag | 2B | 35 | NT[2] | NT[3] | <0.001 | <0.001 | <0.002 | 5000 |
| Au | 2B | 130 | NT[2] | NT[3] | <0.001 | <0.001 | <0.002 | 50000 |
| Ir | 2B | 10 | NT[2] | NT[3] | <0.001 | <0.001 | <0.002 | 5000 |
| Os | 2B | 10 | NT[2] | NT[3] | <0.001 | <0.001 | <0.002 | 5000 |
| Pd | 2B | 10 | NT[2] | NT[3] | <0.001 | <0.001 | <0.002 | 5000 |
| Pt | 2B | 10 | NT[2] | NT[3] | <0.001 | <0.001 | <0.002 | 5000 |
| Rh | 2B | 10 | NT[2] | NT[3] | <0.001 | <0.001 | <0.002 | 5000 |
| Ru | 2B | 10 | NT[2] | NT[3] | <0.001 | <0.001 | <0.002 | 5000 |
| Tl | 2B | 8.0 | NT[2] | NT[3] | <0.001 | <0.001 | <0.002 | 4000 |
| Ba | 3 | 1300 | NT[2] | NT[3] | <0.001 | <0.001 | <0.002 | 350000 |

TABLE 67-continued

Risk assessment of elemental impurities in Hydrocortisone Sodium Phosphate Injection

| EI | Class | ICH Q3D Parenteral PDE (µg/day) | Max Daily Exposure (µg/day) | | | | | Margin of Exposure (MOE)[7] |
|---|---|---|---|---|---|---|---|---|
| | | | Drug Substance[1] | Excipients[4] | Leachable Manufacturing Equipment[5] | Leachable Container Closure System[5][6] | Total | |
| Cr | 3 | 1100 | NT[2] | NT[3] | 0.017 | <0.001 | <0.018 | 61111 |
| Cu | 3 | 130 | 0.0737 | NT[3] | <0.001 | 0.053 | <0.128 | 2344 |
| Li | 3 | 390 | <0.07 | NT[3] | 0.016 | <0.001 | <0.087 | 2874 |
| Ni | 3 | 60 | <0.02 | NT[3] | 0.004 | <0.001 | <0.025 | 800 |
| Sb | 3 | 600 | <0.07 | NT[3] | <0.001 | <0.001 | <0.072 | 1250 |
| Sn | 3 | 640 | NT[2] | NT[3] | <0.001 | <0.001 | <0.002 | 300000 |

ND = Not Detected;
NT = Not Tested
[1]Daily Exposure = Concentration of EI X 0.134 g, where 0.134 g is the maximal daily dose, and the Concentration of EI (in ppm, or µg/g)
[2]Though these EIs were not tested, the risk of these EIs is minimal because these elemental metals are not expected to be present at levels exceeding the PDEs based on the DS EI Risk assessment
[3]Though these EIs were not tested, Class 1-3 elements are not likely to be present above the ICHQ3D option 1 limit.
[4]Max Daily Exposure = Concentration of EI X amount of excipient in 1 mL of the drug product. 1 mL is the maximal daily dose volume.
[5]Daily Exposure = Concentration of EI X 1.0 mL, where 1.0 mL is the approximate volume of the TE Injection in a single dose, in which the detection limit was 1 ng/ml.
[6]Aged PFS stored at 40° C./75% RH for 6 months were used for leachable studies.
[7]Margin of Exposure = PDE/Maximal Total Daily Exposure The risk assessment for the presence of nitrosamine in the Drug product was conducted based on the nitrosamine declaration from the excipient and the container closure component vendors, as well as a risk assessment conducted by the DS manufacturer and the DP manufacturing facility. The risk evaluation considered the following factors:
1. Use of any nitrosating agent in the presence of any secondary/tertiary amines
2. Introduction of Nitrosamine during the manufacturing process
3. Use of any recovery/recycled material
4. Probability of cross contamination
5. Primary packaging materials.

There is no risk of presence of nitrosamines in Hydrocortisone sodium phosphate injection per the following summary:
1. There are no amines, nitrite, nitrate, or nitrosamines in the drug substance, excipient, Water for injection and components (syringe barrel, stopper, and needle shield)
2. Formation of nitrosamines (e.g., from nitrite sale and amines), which requires acidic condition, is negligible-based HSP DP formulation pH of 8.0
3. No risk of potential contamination of nitrosamines or formation of nitrosamines in the drug product manufacturing process and from drug product manufacturing equipment. Therefore, the test for Nitrosamine was not included as part of HSP DP testing.

Delivered Volume (Dose Accuracy)
Acceptance Criteria: No less than 1.00 mL and no greater than 1.20 mL
The autoinjector must deliver the labeled volume of drug product to deliver drug to the target injection site.

Ejection (Injection) Time
Acceptance Criteria: <10.0 seconds
Drug delivery time of less than 10 seconds. This was within the range of existing products currently on the market.

Exposed Needle Length
Acceptance Criteria: 23+/−3 mm.
For a patient to receive an adequate dose of HSP, the needle must fully penetrate the tissue superior to the muscle and penetrate the muscle of interest. In most patients, a needle length of 20-26 mm will accomplish this task. In the United States, the average adult (>18 years of age) is likely to fall into one of 3 categories, healthy weight, overweight, and obese, with few patients falling into the underweight and morbidly obese categories. Each of these categories will impact the thickness of the sub-cutaneous fat layer causing a variation in the thickness of tissue above the muscle layer of the thigh. Furthermore, differences in tissue thickness above the muscle layer may vary depending on if the patient is male or female. It appears based on literature available, under all body mass and gender conditions, the thickness of supra-muscular tissue (skin+fat) is likely to range between 2.25 mm-21.75 mm in males and 4.0 mm-28.3 mm in females. As might be expected, the thickness is highly dependent on BMI status.

There is a small subset of patients with the highest BMIs where it is possible the HSP product may not be able to fully penetrate the muscle and deliver the intramuscular dose. In patients with BMIs >40 (morbidly obese), consultation with a physician is recommended to see if the patient's skin and subcutaneous tissue is thicker than the 20-26 mm needle length included in the HSP product.

Trigger (Activation) Force
Acceptance Criteria: ≤8.5 lbF (pounds-force)
Based on a DTI study of strength data, 8.5 lbf is achievable by the average 6- to 10-year-old adolescent when pushing with one hand. Therefore, the specification as set should be achievable by the intended patient population (patients and caregivers <18 years of age). This activation force specification is similar to other products on the market.

Safety Cap Removal Torque
Acceptance Criteria: ≤11 in-lbs (inch-pounds)
Similar to other autoinjectors on the market and based on a DTI study of strength data. 11 in-lbs is achievable by the average 6- to 10-year-old female adolescent when twisting a knob or removing a similar sized jar lid with one hand. Therefore, the specification as set should be achievable by the intended patient population (patients and caregivers <18 years of age).

Attribute Functionality

Attribute tests included verifying the needle was hidden before injection, the viewing window was clear and the Assembled Autoinjector (AAI) was ready to inject, the needle shield was removed with the cap, the AAI triggered, the AAI delivered the drug, the viewing window was occluded at the end of injection and the passive sharps injury protection feature engaged.

Acceptance Criteria: Report Results

Each of these functions must occur to allow the AI to deliver the dose to the targeted injection site. The window occlusion at the end of injection provides a visual cue to the user that the device has been triggered and the full dose has been delivered. The activation of the passive sharps injury protection feature is a safety feature designed to prevent accidental needle sticks from a used needle.

Container Closure System

The proposed Drug Product (DP) are supplied as a single-use prefilled syringe (PFS) containing sterile hydrocortisone sodium phosphate (HSP) solution for intramuscular administration of a fixed volume of 1.0 mL yielding final delivered doses of 100 mg hydrocortisone (equivalent to 132.4 mg hydrocortisone sodium phosphate). Pre-filled syringes containing the final DP are then assembled into autoinjectors, which is the final presented product.

Primary Container Closure

The primary container closure system Hydrocortisone Sodium Phosphate (HSP) drug product (DP) solution includes standard packaging components for injection drug products. The HSP DP was aseptically filled into a USP clear Type I borosilicate glass, siliconized 2.25 mL syringe barrel fitted with a fixed siliconized stainless steel needle protected with a latex-free rigid needle shield. The syringe was supplied pre-washed, sterilized, and siliconized by the manufacturer, Nuova Ompi S.r.l (Ompi). The closure consists of a latex-free grey chlorobutyl elastomer plunger stopper which is supplied pre-washed, siliconized, and sterilized by the manufacturer, West Pharmaceutical Services, Inc. A detailed summary of the primary container closure system and manufacturer information is included in Table.

TABLE 68

Hydrocortisone Sodium Phosphate primary container closure system

| Component | Material | Size | Manufacturer |
|---|---|---|---|
| Syringe | | | |
| Syringe Barrel | USP Clear Type I borosilicate glass, siliconized | 2.25 mL syringe barrel | Nuova OMPI S.r.l |
| Needle Rigid Needle Shield (RNS) | Stainless steel, siliconized Internal part: Polyisoprene, latex-free. External part: Polypropylene, transparent. | 25 G × 1 inch | |
| Plunger Stopper | 4432/50 Gray elastomer (chlorobutyl), USP Type I closure, latex-free, siliconized, B2-40 coating, FluroTec | 1-3 mL | West Pharmaceutical Services, Inc. |

Syringe Barrel with Needle and Needle Shield

Figure 23:
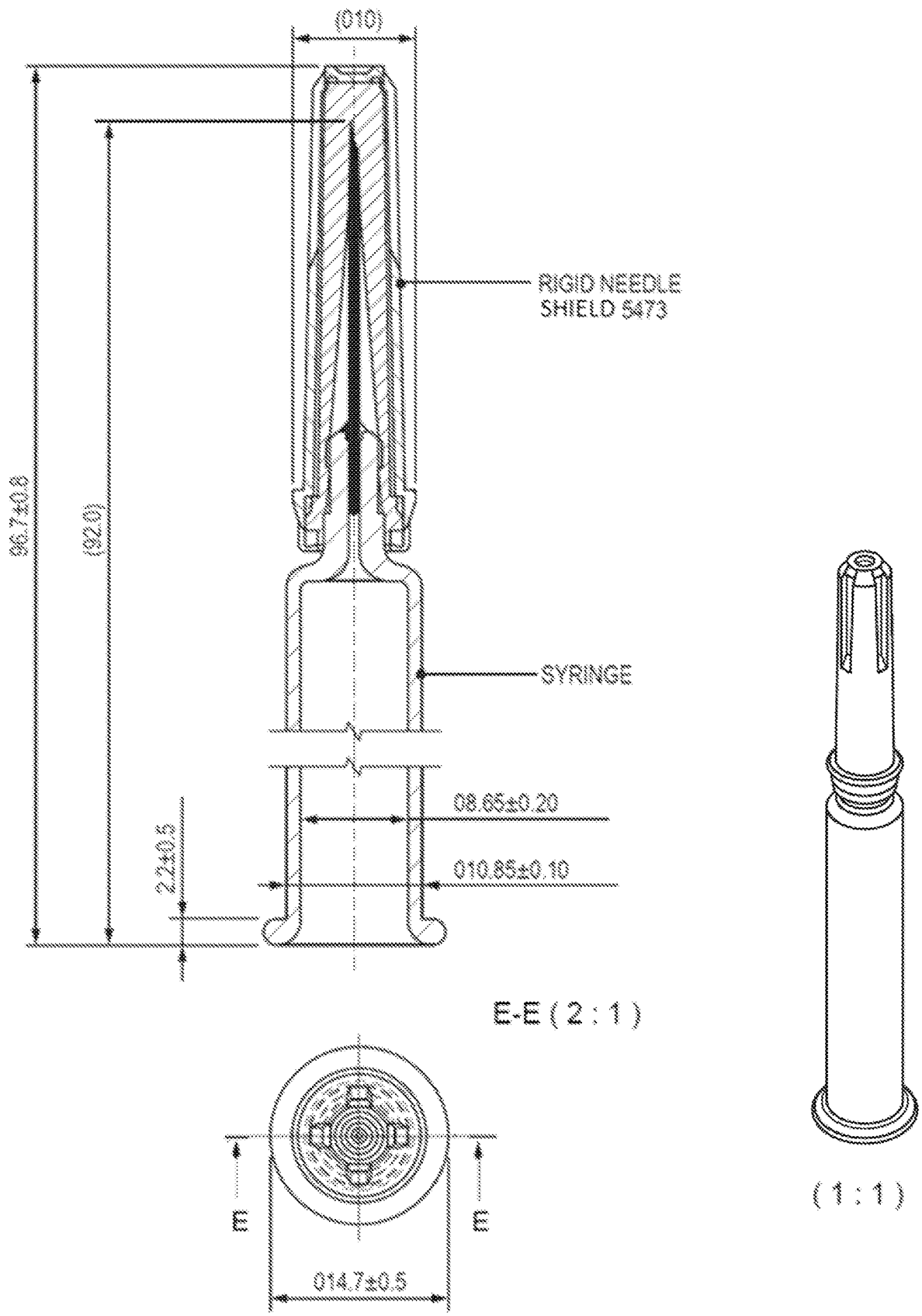
FIG. 23 is a drawing of the sterile 2.25 ml glass syringe

The syringe was supplied as a single unit consisting of the glass barrel, the fixed stainless steel needle, and rigid needle shield. The borosilicate glass met the requirements of USP<660> for Type I glass containers for parenteral preparations. The sterile 2.25 mL glass syringe barrel was supplied by Nuova OMPI S.r.l (FIG. 23).

Plunger Stopper

The siliconized gray chlorobutyl elastomer plunger stopper met the requirements for Type I closures as outlined in the USP<381> (Table 69).

TABLE 69

Acceptance criteria of plunger stopper

| Test | Analytical Procedure | Acceptance Criteria |
|---|---|---|
| Identification by IR-spectrum | USP<197> | Conform to reference spectrum of rubber code 4432/50 |
| Appearance of solution - Determination of turbidity | USP<381> | ≤6 NTU (Nephelometric Turbidity Units) |
| Appearance of solution - Determination of color | USP<381> | Solution S not more intensely colored than the Color Standard |
| Acidity or alkalinity | USP<381> | ≤0.3 mL of 0.01N NaOH to produce blue color, or ≤0.8 mL of 0.01N HCl to produce yellow color, or no titration is required |

TABLE 69-continued

Acceptance criteria of plunger stopper

| Test | Analytical Procedure | Acceptance Criteria |
|---|---|---|
| Absorbance | USP<381> | ≤0.2 for the absorbance between 220 nm to 360 nm |
| Reducing substances | USP<381> | ≤3.0 mL for the difference between the titration volumes |
| Heavy metals | USP<381> | ≤2 ppm for Solution S |
| Extractable zinc | USP<381> | ≤5 ppm for Solution S |
| Ammonium | USP<381> | ≤2 ppm for Solution S |
| Volatile sulfides | USP<381> | Any black stain on the paper produced by the test solution is not more intense than that produced by the control substance |
| Bacterial endotoxins | USP <85> | ≤1 EU/stopper |
| Sterility | USP <71> | Sterile |

Autoinjector

The Vai™ autoinjector (VAT) is an automated drug delivery device for the intramuscular administration of Hydrocortisone sodium phosphate (1 ml via a pre-filled syringe). It is a pre-assembled, pre-filled, single dose, spring-powered, disposable drug delivery device that may be used by the subject, partners/spouses, immediate family members, and bystanders such as a school nurse, or other health professionals.

Features include the ability to deliver 1 mL (100 mg) of drug product in less than 10 seconds intramuscularly to the anterolateral thigh musculature. A viewing window enables visualization of the contained drug product. A visual indicator alerts the user that the drug has been delivered. The AI device is designed to enable injection through clothing if required and includes several safety features to avoid accidental triggering of the device. The device has no fluid path and does not come in contact with the drug contained in the pre-filled syringe.

It utilizes the primary container closure of a 2.25 ml, glass syringe with a 25 gauge, 25.4 mm (1") staked needle, and a rigid needle shield. Injection is accomplished by pushing the device against the injection site with the needle guard held against the injection site. Following the injection, the device is removed from the injection site and the needle guard automatically extends over the needle and locks out to prevent further exposure of the needle. The delivery volume is fixed by syringe fill volume and cannot be adjusted by the end user.

The Vai™ autoinjector does not require preparation before injection such as filling, reconstitution, or dose-dialing. The device is designed for single dose and is discarded after injection, requiring no cleaning, maintenance, or reprocessing. The autoinjector and components thereof are described in International Patent Application No. PCT/US2019/036178 (International Publication No. WO 2019/237082) filed Dec. 19, 2019 and U.S. patent application Ser. No. 16/435,450 (Publication No. U.S. 2019/0374717) filed Jun. 7, 2019, each of which applications is incorporated by reference herein in its entirety.

Figure 24:
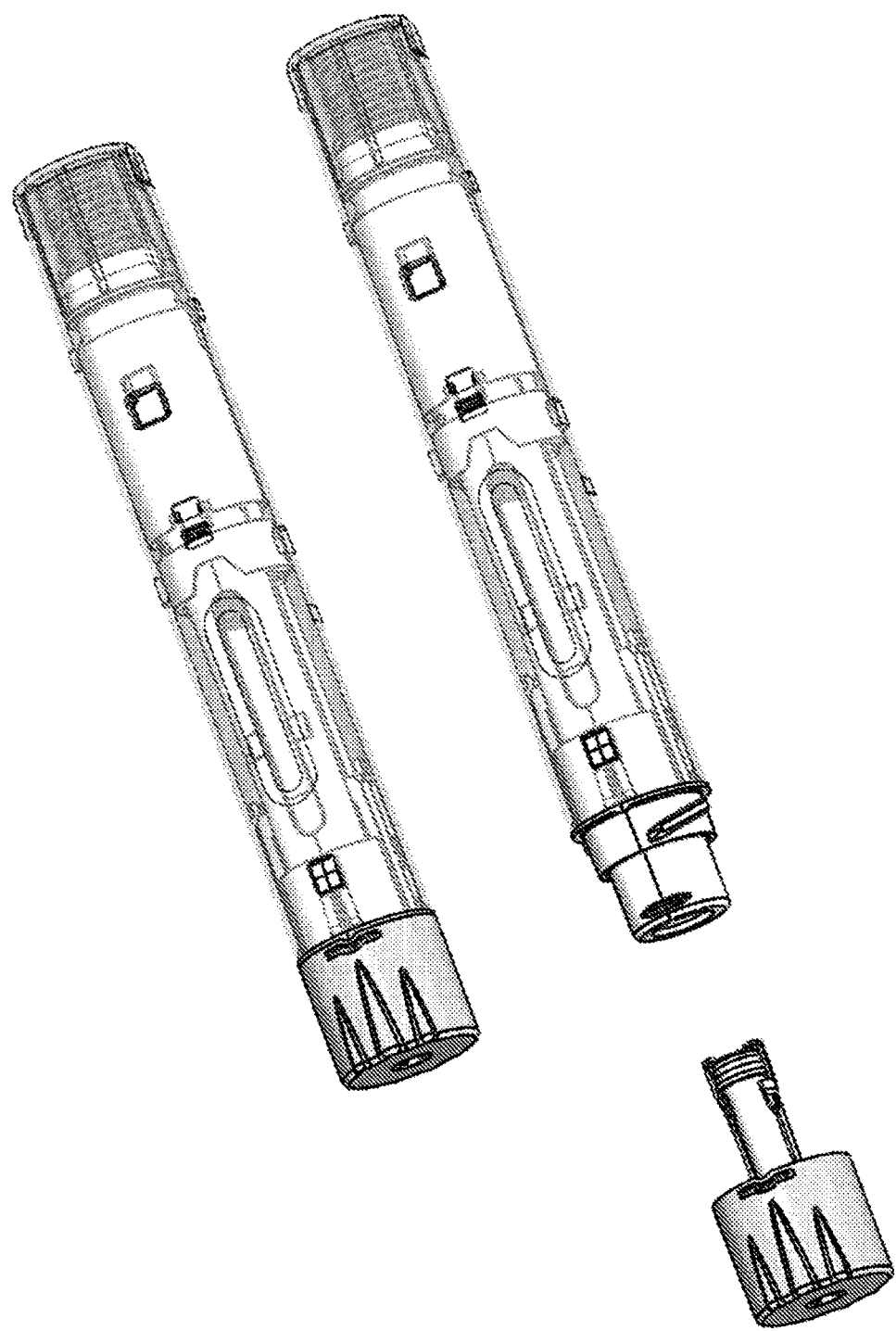
FIG. 24 is a representative model of the auto-injector assembly.
Figure 25:
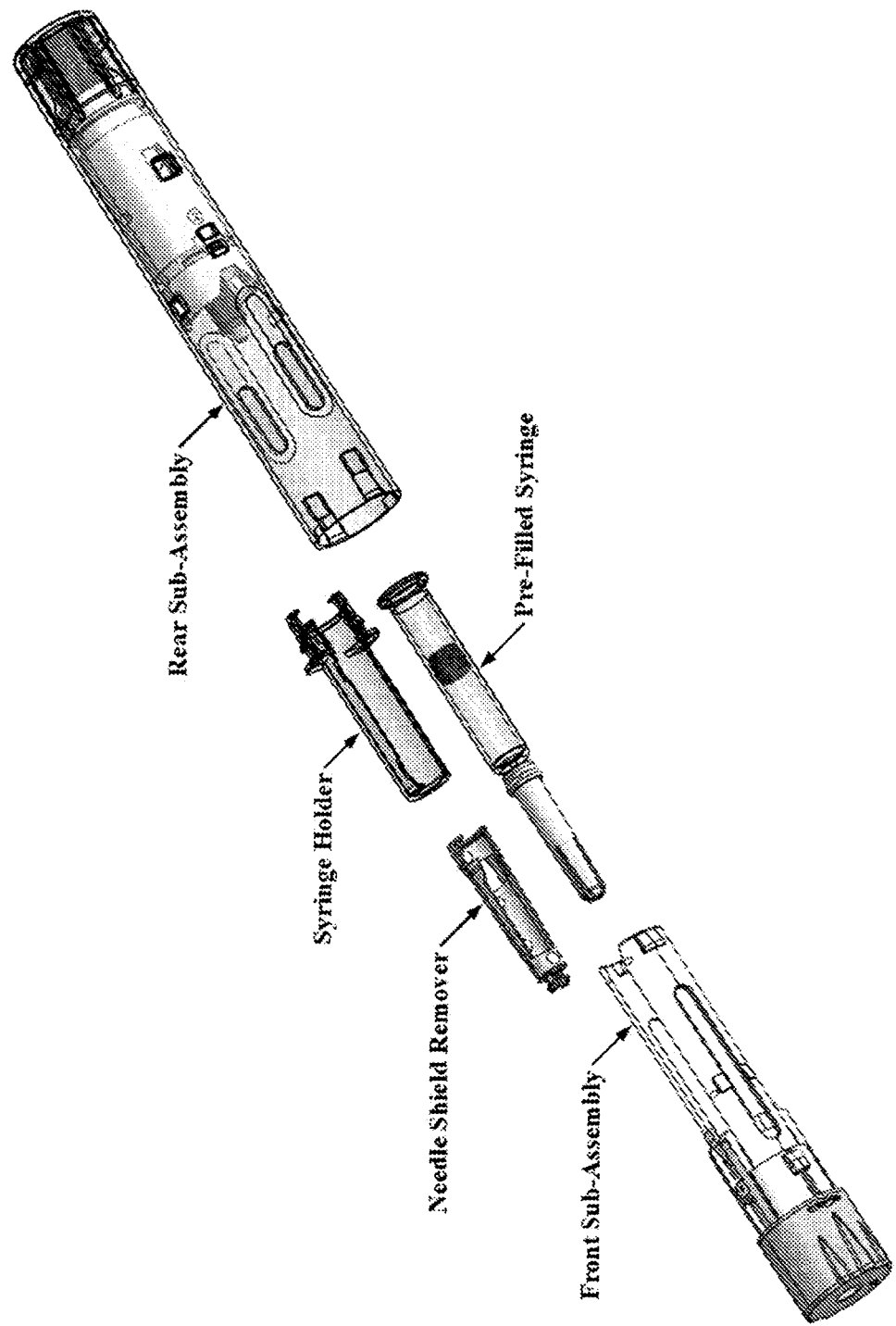
FIG. 25 is a representative model of the auto-injector assembly—assembly view.
Figure 26:
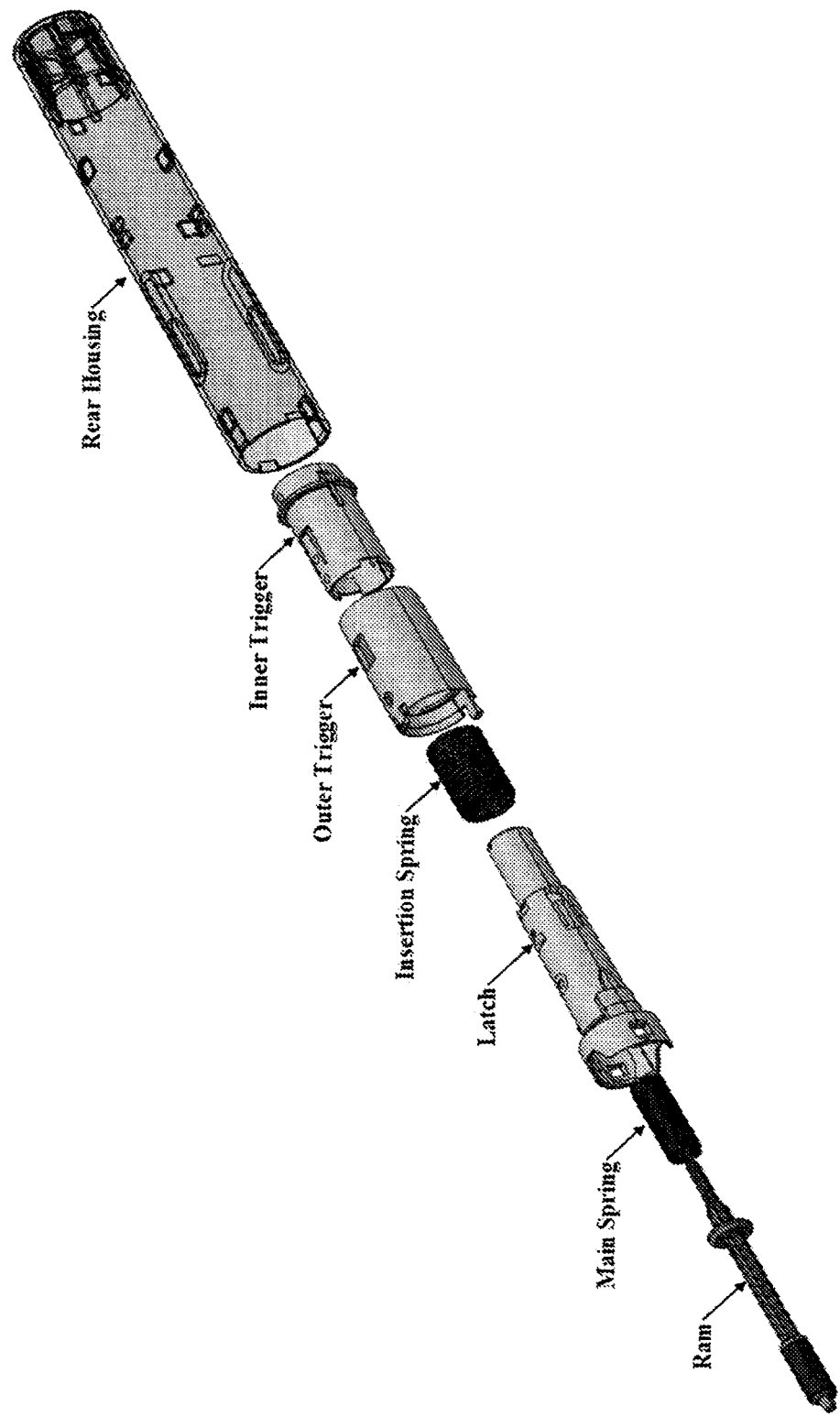
FIG. 26 is an exploded view drawing of the rear subassembly.
Figure 27:
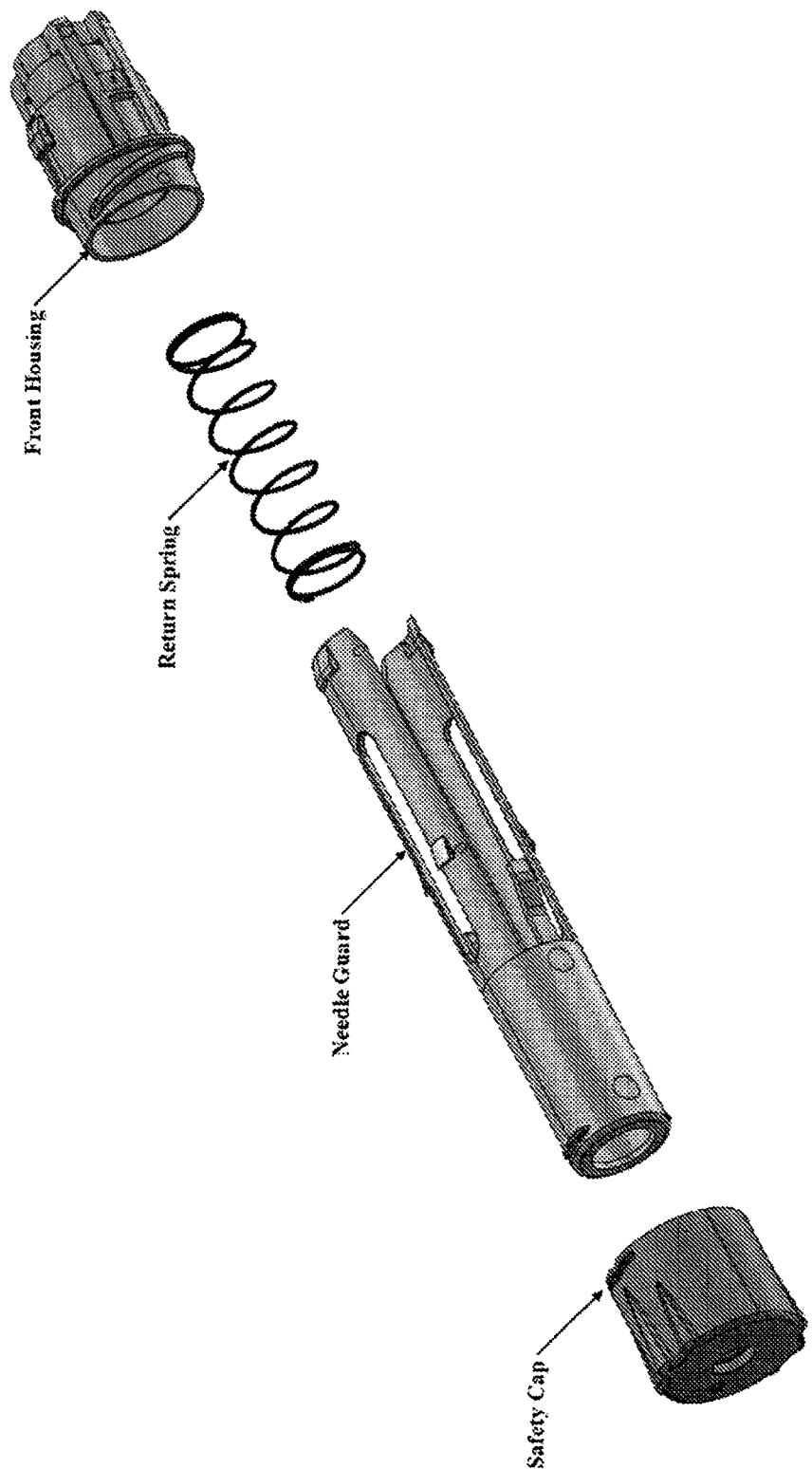
FIG. 27 is an exploded view drawing of the front subassembly.

Front sub-assemblies, rear sub-assemblies, needle shield remover, and syringe holder components were assembled into the autoinjector for testing and release of the sub-assemblies. The representative autoinjector assembly is provided in FIGS. 24 and 25. Sub-assembly drawings are included in FIGS. 26 and 27.

TABLE 70

Specification for the Autoinjector - front sub-assembly and rear sub-assembly

| Test | Methods | Acceptance Criteria |
|---|---|---|
| Kind, Count, Condition | Visual | Part number and quantity match documentation<br>No damage |
| Functionality<br><br>assembled devices)<br>(Performed on | Attribute<br><br>Variable Tests and | Pre-Triggering Attribute Inspection<br><br>1 Safety cap present and aligned<br>2. Viewing Window unobstructed<br>3. Needle Shield is removed by safety cap<br>4 AI triggered when needleguard retracted<br>5. Auto injector delivered the Syringe contents following activation; needle pathway was not obstructed, and Syringe did not shatter upon impact<br>6. Viewing window begins to occlude at the point of activation<br>Functionality Test<br><br>1. Safety Cap torque 7 in-lbs maximum<br>2. Trigger Force - 8.5 lbs maximum<br>3. Ejection Time (delivery time) - Delivers drug in less than 10 Seconds<br>4. Delivered Volume 1.00-1.20 mL<br>5. Exposed Needle Length 20-26 mm<br>6. Needlleguard lockout override force 17 lbs maximum |

TABLE 70-continued

Specification for the Autoinjector - front sub-assembly and rear sub-assembly

| Test | Methods | Acceptance Criteria |
|---|---|---|
| | | Post Triggering Attribute Inspection |
| | | 1. Viewing window is completely occluded by the orange Ram following the injection; full contents of the syringe is delivered |
| | | 2. The Needle Guard re-extended after Needle removal from the injection site and device locked out |
| | | 3. Overall cosmetic appearance acceptable |

Stability Summary and Conclusion

Stability Studies

Description of Registration Batches. Table 71 lists the information of the primary stability batches for both the Hydrocortisone Sodium Phosphate (HSP) Injection prefilled syringes (PFS) and the HSP Injection Assembled Autoinjector (AAI). The batch size of the PFS registration batches was the same as the proposed production PFS batch size of 30 Liters (L), which typically yield approximately 23,000-25,000 units of PFS' based on an approximate 85% yield. The maximal AAI production batch size is approximately 23,000 units if the entire 30 L PFS batch is assembled into the AAI based on an approximate 90% of assembly yield.

Thus, the batch size of the primary stability AAI batches represents approximately one fifth of the AAI production batch size (see Table 71).

Stability Protocols

Stability protocols, including storage conditions and test intervals, were established in accordance with the current ICH guidelines. A summary of the stability protocol for the PFS is provided in Table 72. The PFS samples, with no additional packaging, were stored in two orientations: horizontal and upright (needle tip up). A summary of the stability protocol for the AAI for the physicochemical (PC) related attributes is provided in Table 73. For the AAI stability studies, three units of AAI were packaged in one carton and all AAI samples were stored in the horizontal position.

TABLE 71

Description of registration batches

| Drug Batch # Substance | PFS | | | | AAI Batch | | | | | |
|---|---|---|---|---|---|---|---|---|---|---|
| | Batch # | Date Manufactured | Batch Size | Stability Start Date | Batch # | Date Manufactured | Size (# of Unit) | Stability Start Date | Stability Attributes | Use of the Batch |
| U3181/020020 | Y0173 | Aug. 24, 2021 | 30 L[1] | Sep. 10, 2021 | I2554 (Y0173-AI1) | Dec. 15, 2021 | ~4218 | Feb. 10, 2022 | Functionality tests[2] | Primary Stability/ Registration |
| | | | | | | | | Feb. 23, 2022 | Functionality tests[3] PC[4] | |
| U3181/020020 | Y0175 | Aug. 26, 2021 | 30 L | Sep. 10, 2021 | I2555 (Y0175-AI1 | Jan. 10, 2022 | ~4215 | Feb. 10, 2022 | Functionality tests[2] | Primary Stability/ Registration |
| | | | | | | | | Feb. 23, 2022 | Functionality tests[3] PC[4] | |
| U3181/020030 | Y0184 | Sep. 3, 2021 | 30 L | Sep. 10, 2021 | I2553 (Y0184-AI1) | Dec. 1, 2021 | ~4866 | Dec. 30, 2021 | Functionality tests[2] | Clinical Study ATRS-2001-20-001 & Primary Stability/Registration |
| | | | | | | | | Feb. 23, 2022 | Functionality tests[3] PC[4] | |

[1] 30 L yielded approximately 23,000 PFS
[2] Functionality tests for 25° C./60% RH
[3] Functionality tests for 40° C./75% RH
[4] PC = physicochemical attributes

TABLE 72

Stability protocol for prefilled syringe for the registration batches

| Condition | | 25° C./60% RH | | | | | | | | 30° C./65% RH [1] | | | 40° C./75% RH | |
|---|---|---|---|---|---|---|---|---|---|---|---|---|---|---|
| Duration (Month) | Initial | 3 | 6 | 9 | 12 | 18 | 24 | 30 | 36 | 6 | 9 | 12 | 3 | 6 |
| Appearance | X | X | X | X | X | X | X | X | X | X | X | X | X | X |
| Color | X | X | X | X | X | X | X | X | X | X | X | X | X | X |
| pH | X | X | X | X | X | X | X | X | X | X | X | X | X | X |
| Assay | X | X | X | X | X | X | X | X | X | X | X | X | X | X |
| Organic Impurities | X | X | X | X | X | X | X | X | X | X | X | X | X | X |
| Sub-visible Particles | X | X | X | X | X | X | X | X | X | X | X | X | X | X |
| EDTA[2] | NT | NT | X | X | X | X | X | X | X | X | X | X | NT | X |
| MTG[3] | X(8)[3] | X(11)[3] | NT | NT | X[4] | X | X | X | X | NT | NT | X | NT | X |
| Bacteria Endotoxins | X | NT | NT | NT | X | X | X | X | X | NT | NT | X | NT | X |
| Sterility | X | NT | NT | NT | X | X | X | X | X | NT | NT | X | NT | X |
| Volume in Container | X | X | X | X | X | X | X | X | X | X | X | X | X | X |
| Break loose and glide force | X | NT | NT | X | X | NT | X | NT | X | NT | NT | X | NT | X |

X = Required Test
NT = Not Tested
EDTA = Ethylenediamine Tetra-acetic Acid;
MTG = Monothioglycerol
[1] Optional, which will be performed only if significant changes are observed in the 40° C./75 RH storage condition
[2] The initial and 3-month data was not available as validated Ethylenediamine Tetraacetic Acid (EDTA) method was not available when the batch was made.
[3] Stability started in May 2022, approximately 8 months after the Date of Manufacturing (DOM) in September of 2021 because a validated MTG method was not available until then. Thus, the actual age of the sample is the Month in the stability chamber + 8 months, as shown in the number of the parentheses
[4] Sample stored at 25° C./60% RH was pulled at 14 months for MTG testing

TABLE 73

Stability protocol for AAI for the registration batches

| Condition | | 25° C./60% RH | | | | | | | | 30° C./65% RH[1] | | | 40° C./75% RH | | |
|---|---|---|---|---|---|---|---|---|---|---|---|---|---|---|---|
| Duration (Month) | Initial | 3 | 6 | 9 | 12 | 18 | 24 | 30 | 36 | 6 | 9 | 12 | 1[2] | 3 | 6 |
| Appearance | X | X | X | X | X | X | X | X | X | X | X | X | X | X | X |
| Color of Solution | X | X | X | X | NT | X | X | X | NT | X | X | X | X | X | X |
| pH | X | X | X | X | X | X | X | X | X | X | X | X | X | X | X |
| Assay | X | X | X | X | X | X | X | X | X | X | X | X | X | X | X |
| Organic Impurities | X | X | X | X | X | X | X | X | X | X | X | X | X | X | X |
| Sub-visible Particles | X | X | X | X | X | X | X | X | X | X | X | X | X | X | X |
| EDTA[3] | NT | X | X | X | X | X | X | X | X | X | X | X | X | X | X |
| MTG[3,4] | NT | NT | NT | X | X | NT | X | NT | X | NT | NT | NT | NT | NT | X |
| Volume in Container | X | X | X | X | X | X | X | X | X | X | X | X | X | X | X |
| Uniformity of Dosage Unit | X | X | X | X | X | X | X | X | X | X | X | X | X | X | X |
| Ejection Time[5] | X | NT | X | X | X | NT | X | NT | X | NT | NT | NT | NT | X | X |
| Exposed Needle Length[5] | X | NT | X | X | X | NT | X | NT | X | NT | NT | NT | NT | X | X |
| Trigger Force[5] | X | NT | X | X | X | NT | X | NT | X | NT | NT | NT | NT | X | X |
| Cap Removal Torque[5] | X | NT | X | X | X | NT | X | NT | X | NT | NT | NT | NT | X | X |

X = Required Test
NT = Not Tested
EDTA = Ethylenediamine Tetra-acetic Acid
MTG = Monothioglycerol
[1] Optional, which will be performed only if significant changes are observed in the 40° C./75% RH storage condition
[2] Only for Batch I2553
[3] The initial data was not available because a validated EDTA method was not available.
[4] The data through 6 months was not available because a validated MTG method was not available.
[5] Tested at 11 months, instead of 9 months for Batch I2253

Summary of Stability Results for Physicochemical and Microbiological Attributes

The following physicochemical and microbiological (PCM) attributes were evaluated on the primary stability batches: appearance, color, assay, organic impurities, pH, particulate matter (sub-visible particles), monothioglycerol (MTG), ethylenediamine tetraacetic acid (EDTA), bacterial endotoxin (BET), and sterility.

The stability results of all PCM attributes from storage up to 12 months at 25° C./60% RH, up to 12 months at 30° C./60% RH, and up to 6 months at 40° C./75% RH are summarized below.

The level of the hydrocortisone impurity increased with time and the storage temperature (Tables 74 and 75). The impurity level for the hydrocortisone impurity after storage at 25° C./60% RH for 12 months was <0.1% with total impurities in the formulation <0.6%. The impurity level for the hydrocortisone impurity after storage at 40° C./75% RH for 6 months was <0.3% with total impurities in the formulation <1.1%. The level of the antioxidant MTG decreased with time (Tables 76 and 77). The level of EDTA decreased with time and temperature (Tables 78 and 79).

Except organic impurities, MTG, and EDTA, all the other PCM attributes including appearance, color, assay, pH, particulate matter, bacterial endotoxin, and sterility exhibited no significant change from the initial and no clear stability trend throughout the stability as shown in Tables 80 and 81 for the assay. It is noted that since the total impurities (≤1.2%) was smaller than the typical assay variability (~2%), no clear decreasing trend with time in assay was observed. There was no impact of sample orientation on stability.

A comparison of the stability results in PFS and AAI confirmed that assembly of the PFS into the autoinjector did not impact stability. However, because the AAI stability started approximately 5 to 6 months after the start of the PFS stability, the level of organic impurities was slightly higher and the level of MTG and EDTA slightly lower in the AAI compared to the PFS for the same storage duration at the same storage condition. All PCM attributes met the proposed acceptance criteria and no significant change was observed at the accelerated condition.

TABLE 74

Summary of stability results for Hydrocortisone in PFS

| | | % Hydrocortisone Acceptance Criteria: ≤1.0% | | | | | |
|---|---|---|---|---|---|---|---|
| | | Batch Y0173 | | Batch Y0175 | | Batch Y0184 | |
| Storage Condition | Storage Duration (Month) | Horizontal | Upright | Horizontal | Upright | Horizontal | Upright |
| | Initial | <0.05 | | <0.05 | | <0.05 | |
| | 3 | <0.05 | <0.05 | <0.05 | <0.05 | <0.05 | <0.05 |
| 25° C./ | 6 | <0.05 | <0.05 | <0.05 | <0.05 | <0.05 | <0.05 |
| 60% RH | 9 | <0.05 | <0.05 | <0.05 | <0.05 | 0.05 | <0.05 |
| | 12 | 0.05 | 0.05 | 0.05 | 0.05 | 0.06 | 0.06 |
| 30° C./ | 6 | 0.06 | 0.06 | 0.06 | 0.06 | 0.07 | 0.07 |
| 65% RH | 9 | 0.09 | 0.09 | 0.09 | 0.09 | 0.09 | 0.09 |
| | 12 | 0.10 | 0.10 | 0.10 | 0.10 | 0.11 | 0.10 |
| 40° C./ | 3 | 0.12 | 0.11 | 0.13 | 0.12 | 0.13 | 0.13 |
| 75% RH | 6 | 0.18 | 0.18 | 0.20 | 0.20 | 0.20 | 0.20 |

TABLE 75

Summary of stability results for Hydrocortisone in AAI

| Storage Condition | Storage Duration (Month) | % Hydrocortisone Acceptance Criteria: ≤1.0% | | |
|---|---|---|---|---|
| | | Batch I2554 | Batch I2555 | Batch I2553 |
| | Initial | <0.05 | <0.05 | <0.05 |
| 25° C./ | 3 | <0.05 | <0.05 | <0.05 |
| 60% RH | 6 | <0.05 | <0.05 | <0.05 |
| | 9 | <0.05 | <0.05 | 0.05 |
| 30° C./ | 6 | 0.06 | 0.06 | 0.07 |
| 65% RH | 9 | 0.07 | 0.07 | 0.08 |
| 40° C./ | 1 | NT | NT | 0.07 |
| 75% RH | 3 | 0.14 | 0.14 | 0.15 |
| | 6 | 0.19 | 0.19 | 0.20 |

TABLE 76

Summary of stability results for MTG in PFS

| | | MTG: mg/mL (%) Acceptance Criteria: ≤ Report Results | | | | | |
|---|---|---|---|---|---|---|---|
| | | Batch Y0173 | | Batch Y0175 | | Batch Y0184 | |
| Storage Condition | Storage Duration (M) | Horizontal | Upright | Horizontal | Inverted | Horizontal | Inverted |
| 25° C./ | 0 (8)[1] | 3.65 (71%) | 3.50 (70%) | 3.60 (72%) | 3.60 (72%) | 3.60 (72%) | 3.48 (70%) |
| 60% RH | 3 (11)[1] | 3.12 (62%) | 3.20 (64%) | 3.30 (66%) | 3.38 (68%) | 3.18 (64%) | 3.09 (62%) |
| | 14 | 1.51 (30%) | 1.80 (36%) | 2.27 (45%) | 1.61 (32%) | 1.75 (35%) | 1.13 (23) |

TABLE 76-continued

Summary of stability results for MTG in PFS

| | | MTG: mg/mL (%) Acceptance Criteria: ≤ Report Results | | | | | |
|---|---|---|---|---|---|---|---|
| Storage Condition | Storage Duration (M) | Batch Y0173 | | Batch Y0175 | | Batch Y0184 | |
| | | Horizontal | Upright | Horizontal | Inverted | Horizontal | Inverted |
| 30° C./ 65% RH | 12 | 2.20 (44%) | 2.00 (40%) | 2.57 (51%) | 1.81 (36%) | 2.08 (42%) | 2.16 (43%) |
| 40° C./ 75% RH | 6 | 2.21 (42%) | 1.82 (36%) | 2.38 (48%) | 2.08 (42%) | 2.29 (46%) | NT |

[1]The number in the parenthesis under the Storage Duration (M) Column represents the actual age of the sample in month from the date of manufacturing

TABLE 77

Summary of stability results for MTG in AAI

| Storage Condition | Storage Duration (M) | MTG: mg/mL (%) Acceptance Criteria: Report Results | | |
|---|---|---|---|---|
| | | Batch I2554 | Batch I2555 | Batch I2553 |
| 25° C./ 75% RH | 9 | 3.06 (61%) | 2.75 (55%) | 2.44 (49%) |
| 40° C./ 75% RH | 6 | 2.03 (41%) | 2.42 (48%) | 2.07 (41%) |

TABLE 78

Summary of stability results for EDTA in PFS

| | | EDTA (mg/mL) | | | | | |
|---|---|---|---|---|---|---|---|
| Storage Condition | Storage Duration (M) | Batch Y0173 | | Batch Y0175 | | Batch Y0184 | |
| | | Horizontal | Upright | Horizontal | Upright | Horizontal | Upright |
| 25° C./ 60% RH | 6 | 0.13 | NT | 0.12 | NT | 0.12 | NT |
| | 9 | 0.10 | 0.08 | 0.10 | 0.09 | 0.09 | 0.08 |
| | 12 | 0.08 | 0.07 | 0.07 | 0.08 | 0.09 | 0.08 |
| 30° C./ 65% RH | 6 | 0.11 | NT | 0.10 | NT | 0.11 | NT |
| | 9 | 0.09 | 0.09 | 0.09 | 0.09 | 0.08 | 0.07 |
| | 12 | 0.08 | 0.08 | 0.08 | 0.09 | 0.07 | 0.06 |
| 40° C./ 75% RH | 6 | 0.11 | NT | 0.09 | NT | 0.10 | NT |

NT = not tested

TABLE 79

Summary of stability results for EDTA in AAI

| Storage Condition | Storage Duration (M) | EDTA (mg/mL) | | |
|---|---|---|---|---|
| | | Batch I2554 | Batch I2555 | Batch I2553 |
| 25° C./ 60% RH | 3 | 0.11 | 0.13 | 0.11 |
| | 6 | 0.11 | 0.12 | 0.10 |
| | 9 | 0.10 | 0.11 | 0.10 |
| 30° C./ 65% RH | 6 | 0.10 | 0.10 | 0.09 |
| | 9 | 0.11 | 0.10 | 0.10 |
| 40° C./ 75% RH | 3 | 0.10 | 0.10 | 0.09 |
| | 6 | 0.09 | 0.10 | 0.08 |

TABLE 80

Summary of assay in PFS

| | | % Assay of Hydrocortisone Equivalent Acceptance Criteria: 90.0-110.0% | | | | | |
|---|---|---|---|---|---|---|---|
| | | Batch Y0173 | | Batch Y0175 | | Batch Y0184 | |
| Storage Condition | Storage Duration (Month) | Horizontal | Upright | Horizontal | Inverted | Horizontal | Inverted |
| | Initial | 102.7 | | 101.3 | | 104.3 | |
| 25° C./ 60% RH | 3 | 101.5 | 101.8 | 102.1 | 102.3 | 105.3 | 105.3 |
| | 6 | 102.6 | 102.8 | 102.8 | 102.8 | 104.5 | 104.5 |
| | 9 | 102.3 | 102.4 | 102.2 | 102.0 | 104.2 | 104.2 |
| | 12 | 101.6 | 101.7 | 101.8 | 101.5 | 104.6 | 104.6 |
| 30° C./ 65% RH | 6 | 102.6 | 102.6 | 103.0 | 102.4 | 104.2 | 104.3 |
| | 9 | 102.3 | 101.7 | 102.3 | 101.8 | 104.1 | 103.9 |
| | 12 | 101.6 | 101.3 | 101.1 | 101.2 | 104.8 | 103.6 |
| 40° C./ 75% RH | 3 | 102.1 | 101.9 | 102.4 | 103.2 | 104.8 | 104.9 |
| | 6 | 101.9 | 102.0 | 102.0 | 101.5 | 103.9 | 103.5 |

TABLE 81

Summary of assay in AAI

| | | % Assay of Hydrocortisone Equivalent Acceptance Criteria: 90.0-110.0% | | |
|---|---|---|---|---|
| Storage Condition | Storage Duration (M) | Batch I2554 | Batch I2555 | Batch I2553 |
| | Initial | 102.9 | 102.2 | 103.7 |
| 25° C./ 60% RH | 3 | 102.0 | 102.5 | 104.2 |
| | 6 | 102.2 | 102.4 | 103.2 |
| | 9 | 101.7 | 102.0 | 103.9 |
| 30° C./ 65% RH | 6 | 101.9 | 102.1 | 103.6 |
| | 9 | 101.4 | 101.4 | 103.5 |
| 40° C./ 75% RH | 1 | NT | NT | 104.1 |
| | 3 | 101.9 | 101.7 | 103.9 |
| | 6 | 101.4 | 101.0 | 103.2 |

Impurities

Organic Impurities Structural formulae and substance names of potential synthesis or degradant impurities of hydrocortisone sodium phosphate are listed in Table 82. Hydrocortisone, the starting material for the drug substance is the only impurity in the drug substance. In addition, hydrocortisone is a potential degradation product of the drug substance through hydrolysis. An assessment concluded that the starting material Hydrocortisone has a high purity and all impurities are less than 0.05% or not detected, thus these impurities do not impact the impurity profile of hydrocortisone sodium phosphate.

Residual Solvents

Solvents used in the manufacture of hydrocoritisone sodium phosphate include: tetrahydrofuran (Class 2) as a reaction solvent, ethanol (Class 3) as a crystallizing solvent, and methanol (Class 2) as a crystallizing solvent. These three solvents were routinely tested using validated in-house GC-head space methods. The limits were set based on ICH Q3C: Impurities: Guideline for Residual Solvents and Maintenance of Note for Guidance for Residual Solvents, less than 720 ppm for tetrahydrofuran, less than 3000 ppm for methanol, less than 5000 ppm for ethanol. Test results for the three solvents in three validation batches are provided in Table 83.

Methylene chloride is an ICH class 2 solvent, which is present in the starting material and thus based on the guideline CPMP/QWP/450/03, Annex 1, methylene chloride is not included in the specifications of the drug substance because it has been demonstrated that its content in three consecutive industrial scale batches (validation batches) is below 10% of the ICH limit for each solvent.

TABLE 82

IUPAC name, code, classification, and source of Hydrocortisone Sodium Phosphate related impurities

| Chemical Name | Code # | Chemical Structure | Process/ Degradation Impurity | Source/mechanism | Limit |
|---|---|---|---|---|---|
| Hydrocortisone/ 11β,17,21-trihydroxypregn-4-ene-3,20-dione | I0701-01 | (structure) | Process and potential degradation impurity | This impurity is the starting material. It remains in the final drug substance due to an incomplete reaction. Hydrocortisone purges in the crystallization stage of Hydrocortisone sodium phosphate. | NMT 1.0% |

TABLE 83

Residual solvent results for three drug substance validation batches

| Residual solvent | Origin | ICH limits (ppm) | Validation batch No. | | |
|---|---|---|---|---|---|
| | | | U3181/0 20010 | U3181/0 20020 | U3181/0 20030 |
| Tetrahydrofuran | Process | <720 | <LOQ (72 ppm) | <LOQ (72 ppm) | <LOQ (72 ppm) |
| Methanol | Process & Starting material | <3000 | 342 ppm | 220 ppm | 355 ppm |
| Ethanol | Process | <5000 | 392 ppm | 1067 ppm | 381 ppm |
| Methylene Chloride | Starting material | <600 | <LOD (9 ppm) | <LOD (9 ppm) | <LOD (9 ppm) |

During the manufacturing process of Hydrocortisone Sodium Phosphate, methanol and ethanol are used as solvents. These solvents could be potential sources of the class 1 solvent benzene. Benzene is tested in methanol and ethanol prior to the synthesis of the drug substance. Nevertheless, the three validation batches of Hydrocortisone sodium phosphate were analyzed to demonstrate absence of this class 1 solvent (Table 84).

TABLE 84

Residual solvent results for three drug substance validation batches

| Residual solvent | ICH limits (ppm) | Validation batch No. | | |
|---|---|---|---|---|
| | | U3181/0 20010 | U3181/0 20020 | U3181/0 20030 |
| Benzene | <2 | <LOD (0.06 ppm) | <LOD (0.06 ppm) | <LOD (0.06 ppm) |

Inorganic Impurities

Inorganic impurities, including phosphate and chloride ions, were controlled by using tests described in USP monograph for Hydrocortisone Sodium Phosphate with a limit of not more than (NMT) 1.0%, and 1.00%, respectively.

Genotoxic Impurities

A genotoxicity assessment was performed and provided the following conclusions: hydrocortisone sodium phosphate is not a genotoxic product and all of the related impurities to hydrocortisone sodium phosphate have been assigned as ICH M7-class 5 compounds which are treated as non-mutagenic compounds to be limited according to ICH Q3A guidelines.

Elemental Impurities

The potential elemental impurities that may arise from several sources have been analyzed on three manufacturing batches. Elements evaluated were Class 1 (As, Cd, Hg and Pb), Class 2A (Co, Ni and V) and class 3 (Li, Sb and Cu). The route of administration chosen was parenteral administration. Absence of all of them was demonstrated (below 30% of limit for Option 1).

Drug Product Batch Analysis

Two lots of Hydrocortisone Sodium Phosphate drug substance (DS) were used to make three primary stability batches of the drug product (DP). The release testing results are summarized in Table 85, based on the certificate of analyses.

TABLE 85

Batch results for Hydrocortisone Sodium Phosphate Drug Substance

| TEST | | ACCEPTANCE CRITERIA | Results | | | |
|---|---|---|---|---|---|---|
| | | | U3181/020020 | 3725701-3725702 | U3181/020030 | 3758501-3758502 |
| Description | | White to light yellow powder | Conform | Conform | Conform | Conform |
| Identification | TLC/UV/HPLC | According to reference standard | Conform | Conform* | Conform | Conform* |
| Sodium and Phosphate | | Positive | Conform | NT | Conform | NT |
| Phosphate ions | | ≤1.0% | 0.1% | NT | 0.2% | NT |
| Chloride (as NaCl) | | ≤1.00% | 0.08% | NT | 0.02% | NT |
| Specific rotation (dried basis) | | +121° to +129° (10 mg/mL, buffer, 25° C.) | +121° | NT | +125° | NT |
| pH | | 7.5-10.5 (0.5%, water) | 8.6 | NT | 8.2 | NT |
| Free hydrocortisone | | ≤1.0% | <1.0% | NT | <1.0% | NT |
| Water | | ≤10.0% | 8.4% | 8.6% | 8.5% | 8.6% |
| Assay HPLC (anhydrous basis) | | 96.0-102.0% | 100.1% | 101.7% | 100.1% | 100.2% |
| Organic Impurities (HPLC) | Hydrocortisone | ≤0.5% | <0.05% | not detected | <0.05% | not detected |
| | Unknown | ≤0.10% | <0.05% | not detected | <0.05% | not detected |
| | Total | ≤1.0% | 0.00% | not detected | 0.00% | not detected |
| Residual Solvents | Tetrahydrofuran | <720 ppm | <LOQ[(1)] | NT | <LOQ[(1)] | NT |
| | Methanol | <3000 ppm | 220 ppm | NT | 355 ppm | NT |
| | Ethanol | <5000 ppm | 1067 ppm | NT | 181 ppm | NT |
| Microbial Limits | | TAMC ≤1000 cfu/g | TAMC = 1 cfu/g | TAMC: <1 CFU/g | TAMC = 1 cfu/g | TAMC: <1 CFU/g |
| | | TYMC ≤100 cfu/g | TYMC = 0 cfu/g | TYMC: <1 CFU/g | TYMC = 2 cfu/g | TYMC: <1 CFU/g |
| Bacterial Endotoxins | | ≤0.75 EU/mg | <0.75 EU/mg | <0.03 EU/mg | <0.75 EU/mg | <0.03 EU/mg |

Figure 28:
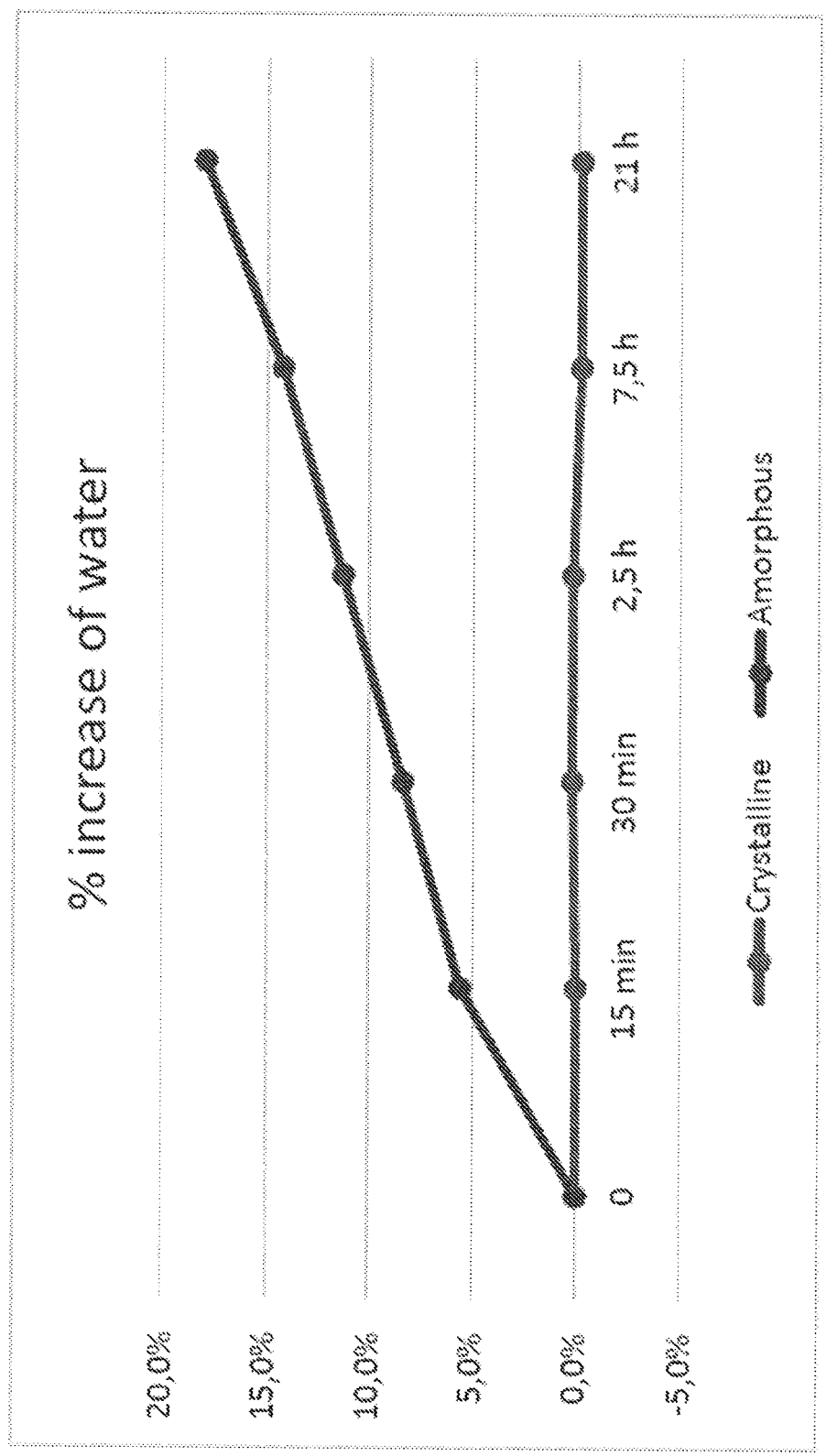
FIG. 28 is chart demonstrating the increase in water content of the amorphous form compared to that of the crystalline hydrate.

[(1)]LOQ = 73 ppm
NT = Not Tested by, accepted the results from tested COAs
*Identification test was performed by UV and HPLC methods The water content test method utilizes the British Pharmacopoiea (BP) HSP monograph semi-micro water content method instead of the less specific USP HSP monograph water content Loss on Drying method. In addition, the water content acceptance criteria utilizes the BP HSP monograph acceptance criteria of ≤10.0% which is based on the characteristics of this drug substance. This is because the crystalline form obtained through the manufacturing process is a crystalline hydrate. To meet the USP LOD specification of NMT 5%, the manufacturing process would need to involve a lyophilization step which leads to the formation of an amorphous form of HSP. As such, amorphous hydrocortisone sodium phosphate drug substance is highly hygroscopic (See FIG. 28) and not stable as compared to crystalline form as demonstrated by data presented in Table 47. Therefore, the water content of the desired polymorphic form (crystalline) of drug substance is measured through Karl-Fischer titration and not through LOD method as recommended by USP monograph.

The stability of the crystalline product manufactured is guaranteed both in terms of purity and water content. For these reasons, the manufacturing process of Hydrocortisone Sodium Phosphate (with a water content specification of NMT 10%) was validated.

While certain embodiments of the present invention have been described and/or exemplified above, various other embodiments will be apparent to those skilled in the art from the foregoing disclosure. The present invention is, therefore, not limited to the particular embodiments described and/or exemplified, but is capable of considerable variation and modification without departure from the scope and spirit of the appended claims.

The invention claimed is:

1. A method of treating a disease, condition, or disorder alleviated by administering hydrocortisone or hydrocortisone sodium phosphate to a patient in need thereof, the method comprising administering to the patient a therapeutically effective amount of 1.0 mL of an aqueous pharmaceutical formulation consisting essentially of:
    from 127 to 141 mg/mL hydrocortisone sodium phosphate,
    from 3.5 to 5.5 mg/mL monothioglycerol,
    from 0.5 to 2.5 mg/mL monobasic sodium phosphate,
    from 5 to 25 mg/mL dibasic sodium phosphate,
    from 0.1 to 1 mg/mL disodium EDTA, and
    water;
    wherein the therapeutically effective amount results in an in vivo plasma profile for hydrocortisone in the patient that includes a mean area under the curve from a dosing time 0 extrapolated to infinite time ($AUC_{0\text{-}inf}$) of about 5,500 to 5,575 h*ng/mL.

2. The method of claim 1, wherein the therapeutically effective amount is administered intravenously or intramuscularly.

3. The method of claim 1, wherein the therapeutically effective amount results in an in vivo plasma profile for hydrocortisone in the patient that includes a mean area under the curve from a dosing time 0 to time t ($AUC_{0\text{-}t}$) of about 5,275 to 5,375 h*ng/mL, wherein t is about 12 hours.

4. The method of claim 1, wherein the therapeutically effective amount results in a maximum serum concentration ($C_{max}$) of hydrocortisone in the patient that is between about 800 to 1600 ng/mL.

5. The method of claim 1, wherein the therapeutically effective amount results in a hydrocortisone median time to peak concentration ($T_{max}$) in the patient about 0.5 to 1.5 hours after administration.

6. The method of claim 1, wherein hydrocortisone is eliminated from the patient with a mean elimination half-life ($T_{1/2el}$) of about 1.8 to 2.1 hours.

7. The method of claim 1, wherein, after administration to the patient, the aqueous pharmaceutical formulation provides one or more of higher exposure, higher area under the curve (AUC), higher maximum serum concentration ($C_{max}$), or faster maximum serum concentration ($C_{max}$) than a hydrocortisone reference formulation, wherein the hydrocortisone reference formulation comprises about 67 mg/mL hydrocortisone sodium succinate, about 4.4 mg/mL dibasic sodium phosphate, about 0.4 mg/mL monobasic sodium phosphate, and water, and about 2.0 mL of the hydrocortisone reference formulation is administered to the patient.

8. The method of claim 7, wherein the aqueous pharmaceutical formulation provides a higher area under the curve (AUC) after administration to the patient compared to the hydrocortisone reference formulation.

9. The method of claim 7, wherein the aqueous pharmaceutical formulation provides a higher maximum serum concentration ($C_{max}$) after administration to the patient compared to the hydrocortisone reference formulation.

10. The method of claim 7, wherein the aqueous pharmaceutical formulation provides a maximum serum concentration ($C_{max}$) after administration to the patient faster than the hydrocortisone reference formulation.

11. The method of claim 7, wherein the hydrocortisone reference formulation is administered intravenously or intramuscularly to a patient.

12. The method of claim 7, wherein the hydrocortisone reference formulation does not comprise an antioxidant.

13. The method of claim 1, wherein the disease, condition, or disorder is selected from adrenal insufficiency, acute adrenal insufficiency, primary adrenal insufficiency, secondary adrenal insufficiency, or adrenal crisis.

14. A method of preventing an adrenal crisis and/or an acute adrenal insufficiency in a patient with adrenal insufficiency, the method comprising administering to the patient a therapeutically effective amount of 1.0 mL of an aqueous pharmaceutical formulation consisting essentially of:
    from 127 to 141 mg/mL hydrocortisone sodium phosphate,
    from 3.5 to 5.5 mg/mL monothioglycerol,
    from 0.5 to 2.5 mg/mL monobasic sodium phosphate,
    from 5 to 25 mg/mL dibasic sodium phosphate,
    from 0.1 to 1 mg/mL disodium EDTA, and
    water;
    wherein the therapeutically effective amount results in an in vivo plasma profile for hydrocortisone in the patient that includes a mean area under the curve from a dosing time 0 extrapolated to infinite time ($AUC_{0\text{-}inf}$) of about 5,500 to 5,575 h*ng/mL.

15. The method of claim 14, wherein the therapeutically effective amount provides one or more of a maximum serum concentration ($C_{max}$) of hydrocortisone between about 800 to 1600 ng/mL, a hydrocortisone median time to peak concentration ($T_{max}$) of about 0.5 to about 1.5 hours, and/or a mean elimination half-life ($T_{1/2el}$) of about 1.8 to about 2.1 hours.

* * * * *